US011482301B2

(12) United States Patent
Antysheva et al.

(10) Patent No.: US 11,482,301 B2
(45) Date of Patent: Oct. 25, 2022

(54) GENE EXPRESSION ANALYSIS TECHNIQUES USING GENE RANKINGS AND STATISTICAL MODELS FOR IDENTIFYING BIOLOGICAL SAMPLE CHARACTERISTICS

(71) Applicant: BostonGene Corporation, Waltham, MA (US)

(72) Inventors: Zoia Antysheva, Moscow (RU); Viktor Svekolkin, Ulyanovsk (RU); Nikita Kotlov, Limassol (CY); Anton Karelin, Chelyabinsk (RU); Ekaterina Postovalova, Waltham, MA (US)

(73) Assignee: BostonGene Corporation, Waltham, MA (US)

( * ) Notice: Subject to any disclaimer, the term of this patent is extended or adjusted under 35 U.S.C. 154(b) by 0 days.

(21) Appl. No.: 17/113,008

(22) Filed: Dec. 5, 2020

(65) Prior Publication Data

US 2021/0174899 A1    Jun. 10, 2021

Related U.S. Application Data

(60) Provisional application No. 63/060,512, filed on Aug. 3, 2020, provisional application No. 62/943,976, filed on Dec. 5, 2019.

(51) Int. Cl.
*G16B 25/10* (2019.01)
*G16B 40/00* (2019.01)
*G16B 5/20* (2019.01)

(52) U.S. Cl.
CPC ............... *G16B 25/10* (2019.02); *G16B 5/20* (2019.02); *G16B 40/00* (2019.02)

(58) Field of Classification Search
None
See application file for complete search history.

(56) References Cited

U.S. PATENT DOCUMENTS

| 2013/0172203 | A1 | 7/2013 | Yeatman et al. |
| 2017/0233827 | A1 | 8/2017 | Moffitt et al. |
| 2020/0199671 | A1 | 6/2020 | Pan et al. |
| 2020/0365268 | A1 | 11/2020 | Michuda et al. |

OTHER PUBLICATIONS

Karim, Md Rezaul, et al. "OncoNetExplainer: explainable predictions of cancer types based on gene expression data." 2019 IEEE 19th International Conference on Bioinformatics and Bioengineering (BIBE). IEEE, 2019.*
Golub, Todd R., et al. "Molecular classification of cancer: class discovery and class prediction by gene expression monitoring." science 286.5439 (1999): 531-537.*
Khan, Javed, et al. "Classification and diagnostic prediction of cancers using gene expression profiling and artificial neural networks " Nature medicine 7.6 (2001): 673-679.*
Singh, Dinesh, et al. "Gene expression correlates of clinical prostate cancer behavior." Cancer cell 1.2 (2002): 203-209.*
[No Author Listed], Non-Hodgkin Lymphoma-Complete. National Cancer Institute Center for Cancer Research. Feb. 20, 2020:2 pages. https://ocg.cancer.gov/programs/cgci/projects/non-hodgkin-lymphoma [last accessed Jan. 19, 2021].
Alizadeh et al., Distinct types of diffuse large B-cell lymphoma identified by gene expression profiling. Nature. Feb. 3, 2000;403(6769):503-11.
Bray et al., Near-optimal RNA-Seq quantification. Nature Biotechnology. May 2016;34(5):525-527.
Chakravarthy et al., Human papillomavirus drives tumor development throughout the head and neck: improved prognosis is associated with an immune response largely restricted to the oropharynx. Journal of Clinical Oncology. Dec. 1, 2016;34(34):4132-4141.
Chapuy et al., Molecular subtypes of diffuse large B cell lymphoma are associated with distinct pathogenic mechanisms and outcomes. Nature medicine. May 2018;24(5):679-90.
Chevrier et al., An immune atlas of clear cell renal cell carcinoma. Cell. May 4, 2017;169(4):736-49.
Ciavarella et al., Dissection of DLBCL microenvironment provides a gene expression-based predictor of survival applicable to formalin-fixed paraffin-embedded tissue. Annals of Oncology. Dec. 1, 2018;29(12):2363-70.
Clozel et al., Mechanism-based epigenetic chemosensitization therapy of diffuse large B-cell lymphoma. Cancer discovery. Sep. 2013;3(9):1002-19.
Dave et al., Molecular Diagnosis of Burkitt's Lymphoma. National Cancer Institute Center for Cancer Research. 2006:1 page. https://llmpp.nih.gov/BL/ [last accessed Jan. 19, 2021].
Ennishi et al., Double-hit gene expression signature defines a distinct subgroup of germinal center B-cell-like diffuse large B-cell lymphoma. Journal of Clinical Oncology. Jan. 20, 2019;37(3):190.
Frontzek et al., Novel insights into the pathogenesis of molecular subtypes of diffuse large B-cell lymphoma and their clinical implications. Expert Review of Clinical Pharmacology. Nov. 2, 2019;12(11):1059-67.
Jais et al., The expression of 16 genes related to the cell of origin and immune response predicts survival in elderly patients with diffuse large B-cell lymphoma treated with CHOP and rituximab. Leukemia. Oct. 2008;22(10):1917-24.
Loeffler-Wirth et al., A modular transcriptome map of mature B cell lymphomas. Genome medicine. Dec. 2019;11(1):27.

(Continued)

*Primary Examiner* — G Steven Vanni
(74) *Attorney, Agent, or Firm* — Wolf, Greenfield & Sacks, P.C.

(57) ABSTRACT

Techniques for determining one or more characteristics of a biological sample using rankings of gene expression levels in expression data obtained using one or more sequencing platforms is described. The techniques may include obtaining expression data for a biological sample of a subject. The techniques further include ranking genes in a set of genes based on their expression levels in the expression data to obtain a gene ranking and determining using the gene ranking and a statistical model, one or more characteristics of the biological sample.

33 Claims, 44 Drawing Sheets

(56) References Cited

OTHER PUBLICATIONS

Monti et al., Molecular profiling of diffuse large B cell lymphoma reveals a novel disease subtype with brisk host inflammatory response and distinct genetic feamres. Blood. 2005;105(5):1851-61.
Nicholas et al., Tumor microenvironment (TME)-driven immune suppression in B cell malignancy. Biochimica et Biophysica Acta (BBA)-Molecular Cell Research. Mar. 1, 2016;1863(3):471-82.
Pasqualucci et al., The genetic landscape of diffuse large B-cell lymphoma. Seminars in hematology. Apr. 1, 2015;52(2):67-76.
Racle et al., Simultaneous enumeration of cancer and immune cell types from bulk tumor gene expression data. Elife. Nov. 13, 2017;6:e26476.
Rashid et al., Purity Independent Subtyping of Tumors (PurIST), A Clinically Robust, Single-sample Classifier for Tumor Subtyping in Pancreatic Cancer. Clinical Cancer Research. Jan. 1, 2020;26(1):82-92.
Reddy et al., Genetic and functional drivers of diffuse large B cell lymphoma. Cell. Oct. 5, 2017;171(2):481-94.
Santiago et al., Changes in Tumor Immune Micro-Environment in Diffuse Large B-Cell Lymphoma (DLBCL): A Comparative Study of Relapsed Versus Diagnostic DLBCL. Blood. Nov. 13, 2019;134:3968.
Schmitz et al., Genetics and pathogenesis of diffuse large B-cell lymphoma. New England Journal of Medicine. Apr. 12, 2018;378(15):1396-407.
Sotiriou et al., Gene expression profiling in breast cancer: understanding the molecular basis of histologic grade to improve prognosis. Journal of the National Cancer Institute. Feb. 15, 2006;98(4):262-72.
Vose et al., Project International peripheral T-cell and natural killer/T-cell lymphoma study: pathology findings and clinical outcomes, International T-Cell Lymphoma. Journal of clinical oncology. Sep. 1, 2008;26(25):4124-30.
Wright et al., A gene expression-based method to diagnose clinically distinct subgroups of diffuse large B cell lymphoma. Proceedings of the National Academy of Sciences of the United States of America. Aug. 19, 2003;100( 17):9991-6.
Wright et al., A Probabilistic Classification Tool for Genetic Subtypes of Diffuse Large B Cell Lymphoma with Therapeutic Implications. Cancer Cell. Apr. 13, 2020;37(4):551-68.
International Search Report and Written Opinion for International Application No. PCT/US2020/063503 dated Mar. 18, 2021.
Afsari et al., Rank discriminants for predicting phenotypes from RNA expression. ArXiv preprint arXiv:1401.1490v3. Nov. 21, 2014;3:1-24.
Leek, The tspair package for finding top scoring pair classifiers in R. Bioinformatics. May 1, 2009;25(9):1203-4.
Patil et al., Test set bias affects reproducibility of gene signatures. Bioinformatics. Jul. 15, 2015;31(14):2318-23.
Rashid et al., Modeling Between-Study Heterogeneity for Improved Reproducibility in Gene Signature Selection and Clinical Prediction. ArXiv preprint arXiv:1708.05508v2. Mar. 26, 2019;2:1-32.
Dong et al., A survey on ensemble learning. Frontiers of Computer Science. Apr. 2020;14(2):241-58.
Sagi et al., Ensemble learning: A survey. Wiley Interdisciplinary Reviews: Data Mining and Knowledge Discovery. Jul. 2018;8(4):e1249.
Yang et al., A review of ensemble methods in bioinformatics. Current Bioinformatics. Dec. 1, 2010;5(4):296-308.
International Preliminary Report on Patentability for International Application No. PCT/US2020/063503 dated Jun. 16, 2022.
International Search Report and Written Opinion for International Application No. PCT/US2021/061923 dated Mar. 21, 2022.

* cited by examiner

GENE EXPRESSION ANALYSIS TECHNIQUES USING GENE RANKINGS AND STATISTICAL MODELS FOR IDENTIFYING BIOLOGICAL SAMPLE CHARACTERISTICS

RELATED APPLICATIONS

This application claims the benefit under 35 U.S.C. § 119(e) of U.S. Provisional Patent Application Ser. No. 62/943,976, filed Dec. 5, 2019, titled "MACHINE LEARNING TECHNIQUES FOR GENE EXPRESSION ANALYSIS" and U.S. Provisional Patent Application Ser. No. 63/060,512, filed Aug. 3, 2020, titled "MACHINE LEARNING TECHNIQUES FOR DETERMINING PERIPHERAL T-CELL LYMPHOMA (PTCL) SUBTYPE USING GENE EXPRESSION DATA", the entire contents of each of which are incorporated by reference herein.

FIELD

Aspects of the technology described herein relate to determining characteristics of a biological sample obtained from a subject known to have, suspected of having, or at risk of having cancer by sequencing the biological sample using one or multiple sequencing platforms and analyzing the resulting gene expression data using machine learning techniques. In particular, the technology described herein involves using gene expression data from one or multiple sequencing platforms to determine characteristics of the biological sample, such as tissue of origin and cancer grade.

BACKGROUND

Characteristics of a biological cell may relate to the expression levels of certain genes. For example, a cancerous cell may have some genes upregulated and other genes downregulated relative to a normal, healthy cell. This relationship between cell characteristics and gene expression levels may be utilized in analyzing gene expression data for biological cells, such as data obtained using a gene expression microarray or by performing next generation sequencing, to determine characteristics of the biological cells.

SUMMARY

Some embodiments are directed to a computer-implemented method, comprising using at least one computer hardware processor to perform: obtaining expression data obtained at least in part by sequencing a biological sample of a subject having, suspected of having or at risk of having cancer, the expression data comprising expression levels for a plurality of genes, the plurality of genes comprising a set of genes; ranking at least some genes in the set of genes, based on their expression levels in the expression data to obtain a gene ranking; and determining, using the gene ranking and a statistical model trained using training data indicating a plurality of gene rankings of at least some of the genes in the set of genes obtained, at least one characteristic of the biological sample, wherein each of the plurality of gene rankings is obtained based on respective expression levels for the at least some genes in the set of genes.

The at least one characteristic may be selected from cancer grade for cells in the biological sample (e.g., breast cancer grade, kidney clear cell cancer grade, lung adenocarcinoma grade), tissue of origin for cells in the biological sample (e.g., lung, pancreas, stomach, colon, liver, bladder, kidney, thyroid, lymph nodes, adrenal gland, skin, breast, ovary, prostrate, or cell of origin in a tissue such as e.g. germinal center B-cell (GCB) or activated B-cell (ABC)), histological information (tissue type, such as e.g. adenocarcinoma, squamous cell carcinoma, carcinoma, cystadenocarcinoma, sarcoma, and glioma) for cells in the biological sample, and cancer subtype (e.g. PTCL subtype such as, anaplastic large cell lymphoma (ALCL), angioimmunoblastic T-cell lymphoma (AITL), natural killer/T-cell lymphoma (NKTCL), and adult T-cell leukemia/lymphoma (ATLL)), viral status (e.g., HPV status, such as HPV-positive or HPV-negative for head and neck squamous cell carcinoma) for cells in the biological sample.

In some embodiments, the at least one characteristic of the biological sample is a physiological characteristic of cells in the biological sample or a tissue from which the cells originate. In some embodiments, the at least one characteristic is selected from cancer grade for cells in the biological sample, tissue of origin for cells in the biological sample, tissue type for cells in the biological sample, and cancer subtype for cells in the biological sample.

In some embodiments, the method further comprises performing sequencing of the biological sample using a gene expression microarray prior to obtaining the expression data. In some embodiments, the method further comprises performing next generation sequencing of the biological sample prior to obtaining the expression data.

In some embodiments, the at least one characteristic includes cancer grade for cells in the biological sample. In some embodiments, the at least one characteristic includes tissue of origin for cells in the biological sample.

In some embodiments, the subject has, is suspected of having, or is at risk of having breast cancer. In some embodiments, the set of genes is selected from the group of genes listed in Table 1. In some embodiments, the set of genes comprises at least 3 genes selected from the group of genes listed in Table 1. In some embodiments, the set of genes comprises at least 5 genes selected from the group of genes listed in Table 1. In some embodiments, the set of genes comprises at least 10 genes selected from the group of genes listed in Table 1. In some embodiments, the set of genes comprises at least 20 genes selected from the group of genes listed in Table 1.

In some embodiments, the subject has, is suspected of having, or is at risk of having kidney cancer. In some embodiments, the subject has, is suspected of having, or is at risk of having clear cell kidney cancer. In some embodiments, the set of genes is selected from the group of genes listed in Table 2. In some embodiments, the set of genes comprises at least 3 genes selected from the group of genes listed in Table 2. In some embodiments, the set of genes comprises at least 5 genes selected from the group of genes listed in Table 2. In some embodiments, the set of genes comprises at least 10 genes selected from the group of genes listed in Table 2. In some embodiments, the set of genes comprises at least 20 genes selected from the group of genes listed in Table 2.

In some embodiments, the subject has, is suspected of having, or is at risk of having lymphoma. In some embodiments, the set of genes is selected from the group of genes listed in Table 3. In some embodiments, the set of genes comprises at least 3 genes selected from the group of genes listed in Table 3. In some embodiments, the set of genes comprises at least 5 genes selected from the group of genes listed in Table 3. In some embodiments, the set of genes comprises at least 10 genes selected from the group of genes listed in Table 3. In some embodiments, the set of genes comprises at least 20 genes selected from the group of genes listed in Table 3.

In some embodiments, the subject has, is suspected of having, or is at risk of having head and neck squamous cell carcinoma. In some embodiments, the set of genes is selected from the group of genes listed in Table 6. In some embodiments, the set of genes comprises at least 10 genes selected from the group of genes listed in Table 6.

In some embodiments, the at least one characteristic includes human papillomavirus status for cells in a biological sample. In some embodiments, the set of genes is selected from the group of genes listed in Table 8. In some embodiments, the set of genes comprises at least 10 genes selected from the group of genes listed in Table 8.

In some embodiments, the method further comprises ranking at least some genes in a second set of genes based on their expression levels in the expression data to obtain a second gene ranking; and determining, using the second gene ranking and a second statistical model trained using second training data indicating a plurality of rankings for the at least some of the genes in the second set of genes, at least one second characteristic of the biological sample.

In some embodiments, the at least one second characteristic includes cancer grade for cells in the biological sample. In some embodiments, the at least one second characteristic includes tissue of origin for cells in the biological sample.

In some embodiments, determining the gene ranking comprises determining a relative rank for each gene in the set of genes based on the expression levels. In some embodiments, determining the at least one characteristic further comprises providing the gene ranking as input to the statistical model and obtaining an output indicating the at least one characteristic. In some embodiments, the statistical model comprises a gradient boosted decision tree classifier. In some embodiments, the statistical model comprises a classifier selected from the group consisting of: a gradient boosted decision tree classifier, a decision tree classifier, a gradient boosted classifier, a random forest classifier, a clustering-based classifier, a Bayesian classifier, a Bayesian network classifier, a neural network classifier, a kernel-based classifier, and a support vector machine classifier.

In some embodiments, the set of genes includes at least 5 genes. In some embodiments, the set of genes consists of 5-50 genes. In some embodiments, the set of genes consists of 5-300 genes.

In some embodiments, the method further comprises presenting, to a user, an indication of the at least one characteristic. In some embodiments, presenting the indication of the at least one characteristic further comprises displaying the at least one characteristic to the user in a graphical user interface (GUI).

In some embodiments, the at least one characteristic includes cancer grade for cells in the biological sample, and the cancer grade is selected from the group consisting of Grade 1, Grade 2, Grade 3, Grade 4, and Grade 5. In some embodiments, the at least one characteristic includes tissue of origin for cells in the biological sample, and the tissue of origin is selected from the group consisting of lung tissue, pancreas tissue, stomach tissue, colon tissue, liver tissue, bladder tissue, kidney tissue, thyroid tissue, lymph node tissue, adrenal gland tissue, skin tissue, breast tissue, ovary tissue, prostate tissue, urothelial tissue, cervical tissue, esophagus tissue, brain tissue, soft tissue, connective tissue, head tissue, and neck tissue. In some embodiments, the at least one characteristic includes tissue type for cells in the biological sample, and the tissue type is selected from the group consisting of adenocarcinoma, squamous cell carcinoma, carcinoma, cystadenocarcinoma, sarcoma, and glioma.

In some embodiments, the at least one characteristic includes human papillomavirus (HPV) status for cells in the biological sample, and wherein the set of genes includes at least 5 genes selected from the group of genes listed in Table 8. In some embodiments, the at least one characteristic includes a subtype of peripheral T-cell lymphoma (PTCL) for cells in the biological sample, and wherein the set of genes includes at least 5 genes selected from the group of genes listed in Table 10. In some embodiments, the subtype of PTCL is selected from the group consisting of: anaplastic large cell lymphoma (ALCL), angioimmunoblastic T-cell lymphoma (AITL), natural killer/T-cell lymphoma (NKTCL), and adult T-cell leukemia/lymphoma (ATLL).

In some embodiments, the subject has, is suspected of having, or is at risk of having breast cancer, and wherein the set of genes comprises at least 5 genes selected from the group of genes listed in Table 1. In some embodiments, the set of genes comprises at least 10 genes selected from the group of genes listed in Table 1. In some embodiments, the subject has, is suspected of having, or is at risk of having kidney cancer, and wherein the set of genes comprises at least 5 genes selected from the group of genes listed in Table 2. In some embodiments, the subject has, is suspected of having, or is at risk of having lymphoma, and wherein the set of genes comprises at least 5 genes selected from the group of genes listed in Table 3. In some embodiments, the subject has, is suspected of having, or is at risk of having Diffuse Large B-Cell Lymphoma (DLBCL), the set of genes comprises at least 10 genes selected from the group of genes listed in Table 3, and the at least one characteristic is a cell of origin selected from the group consisting of germinal center B-cell (GCB) and activated B-cell (ABC). In some embodiments, the subject has, is suspected of having, or is at risk of having lung adenocarcinoma, and wherein the set of genes comprises at least 5 genes selected from the group of genes listed in Table 6.

In some embodiments, the at least one characteristic is selected from the group consisting of cancer grade for cells in the biological sample, tissue of origin for cells in the biological sample, tissue type for cells in the biological sample, and cancer subtype for cells in the biological sample.

In some embodiments, determining the at least one characteristic further comprises providing the gene ranking as an input to the statistical model and obtaining an output indicating the at least one characteristic. In some embodiments, the at least one characteristic is selected from the group consisting of cancer grade for cells in the biological sample, tissue of origin for cells in the biological sample, tissue type for cells in the biological sample, and cancer subtype for cells in the biological sample.

In some embodiments, the subject has, is suspected of having, or is at risk of having head and neck squamous cell carcinoma, and wherein the set of genes comprises at least 5 genes selected from the group of genes listed in Table 8. In some embodiments, the set of genes comprises at least 10 genes selected from the group of genes listed in Table 8.

In some embodiments, the at least one characteristic includes human papillomavirus (HPV) status for cells in a biological sample. In some embodiments, the at least one characteristic includes a subtype of peripheral T-cell lymphoma (PTCL) for cells in the biological sample, and wherein the set of genes includes at least 5 genes selected from the group of genes listed in Table 10. In some embodiments, the set of genes comprises at least 10 genes selected from the groups of genes listed in Table 10. In some embodiments, the subtype of PTCL is selected from the group consisting of: anaplastic large cell lymphoma (ALCL), angioimmunoblastic T-cell lymphoma (AITL), natural killer/T-cell lymphoma (NKTCL), and adult T-cell leukemia/lymphoma (ATLL).

Some embodiments are directed to a system comprising: at least one hardware processor; and at least one non-transitory computer-readable storage medium storing processor-executable instructions that, when executed by the at least one hardware processor, cause the at least one hardware processor to perform a method. The method comprises obtaining expression data obtained at least in part by sequencing a biological sample of a subject having, suspected of having or at risk of having cancer, the expression data comprising expression levels for a plurality of genes, the plurality of genes comprising a set of genes; ranking at least some genes in the set of genes, based on their expression levels in the expression data to obtain a gene ranking; and determining, using the gene ranking and a statistical model trained using training data indicating a plurality of gene rankings of at least some of the genes in the set of genes obtained, at least one characteristic of the biological sample, wherein each of the plurality of gene rankings is obtained based on respective expression levels for the at least some genes in the set of genes.

Some embodiments are directed to at least one non-transitory computer-readable storage medium storing processor-executable instructions that, when executed by at least one hardware processor, cause the at least one hardware processor to perform: obtaining expression data obtained at least in part by sequencing a biological sample of a subject having, suspected of having or at risk of having cancer, the expression data comprising expression levels for a plurality of genes, the plurality of genes comprising a set of genes; ranking at least some genes in the set of genes, based on their expression levels in the expression data to obtain a gene ranking; and determining, using the gene ranking and a statistical model trained using training data indicating a plurality of gene rankings of at least some of the genes in the set of genes obtained, at least one characteristic of the biological sample, wherein each of the plurality of gene rankings is obtained based on respective expression levels for the at least some genes in the set of genes.

Some embodiments are directed to a method, comprising using at least one computer hardware processor to perform: obtaining expression data for cells in a biological sample of a subject having, suspected of having, or at risk of having cancer; ranking at least some genes in at least one set of genes based on their expression levels in the expression data to obtain at least one gene ranking; and determining, using the at least one gene ranking and at least one statistical model trained using training data indicating a plurality of rankings for at least some genes in the at least one set of genes, tissue of origin for at least some of the cells in the biological sample, wherein each of the plurality of gene rankings is obtained based on respective expression levels for the at least some genes in the at least one set of genes.

In some embodiments, the expression data was obtained using a gene expression microarray. In some embodiments, the expression data was obtained by performing next generation sequencing. In some embodiments, the tissue of origin is selected from the group consisting of lung tissue, pancreas tissue, stomach tissue, colon tissue, liver tissue, bladder tissue, kidney tissue, thyroid tissue, lymph node tissue, adrenal gland tissue, skin tissue, breast tissue, ovary tissue, prostate tissue, urothelial tissue, cervical tissue, esophagus tissue, brain tissue, soft tissue, connective tissue, head tissue, and neck tissue.

In some embodiments, determining, using the at least one gene ranking and the at least one statistical model, tissue type for at least some of the cells in the biological sample. In some embodiments, the tissue type is selected from the group consisting of adenocarcinoma, squamous cell carcinoma, carcinoma, cystadenocarcinoma, sarcoma, and glioma. In some embodiments, a combination of the tissue of origin and the tissue type is selected from the group consisting of lung adenocarcinoma, lung squamous cell carcinoma, melanoma, breast carcinoma, colorectal adenocarcinoma, ovarian serous cystadenocarcinoma, phenochromocytoma, bladder urothelial carcinoma, cervical squamous cell carcinoma, glioblastoma multiforme, head squamous cell carcinoma, neck squamous cell carcinoma, kidney renal clear cell carcinoma, kidney renal papillary cell carcinoma, liver hepatocellular carcinoma, lung adenocarcinoma, pancreatic adenocarcinoma, paraganglioma, prostate adenocarcinoma, sarcoma, stomach adenocarcinoma, thyroid carcinoma, and uterine corpus endometrial carcinoma.

In some embodiments, the subject has, is suspected of having, or is at risk of having lymphoma. In some embodiments, the subject has, is suspected of having, or is at risk of having Diffuse Large B-Cell Lymphoma (DLBCL). In some embodiments, the tissue of origin is a cell of origin selected from the group consisting of germinal center B-cell (GCB) and activated B-cell (ABC). In some embodiments, a set of genes of the at least one set of genes is selected from the group of genes listed in Table 3. In some embodiments, a set of genes of the at least one set of genes comprises at least 3 genes selected from the group of genes listed in Table 3. In some embodiments, a set of genes of the at least one set of genes comprises at least 5 genes selected from the group of genes listed in Table 3. In some embodiments, a set of genes of the at least one set of genes comprises at least 10 genes selected from the group of genes listed in Table 3.

In some embodiments, a set of genes of the at least one set of genes includes at least 5 genes. In some embodiments, a set of genes of the at least one set of genes consists of 5-100 genes. In some embodiments, a set of genes of the at least one set of genes consists of 10-200 genes. In some embodiments, a set of genes of the at least one set of genes consists of 20-100 genes. In some embodiments, a set of genes of the at least one set of genes consists of 50-100 genes.

In some embodiments, the expression data includes values, each representing an expression level for a gene in the at least one set of genes, and determining a gene ranking of the at least one gene ranking comprises determining a relative rank for each gene in one of the at least one set of genes based on the values. In some embodiments, determining the at least one characteristic further comprises using the at least one gene ranking as an input to the at least one statistical model and obtaining an output indicating the tissue of origin.

In some embodiments, the at least one statistical model comprises a gradient boosted decision tree classifier. In some embodiments, the at least one statistical model comprises at least one classifier selected from the group consisting of: a gradient boosted decision tree classifier, a decision tree classifier, a gradient boosted classifier, a random forest classifier, a clustering-based classifier, a Bayesian classifier, a Bayesian network classifier, a neural network classifier, a kernel-based classifier, and a support vector machine classifier.

In some embodiments, the at least one set of genes comprises a first set of genes associated with predicting a first type of tissue and a second set of genes associated with predicting a second type of tissue.

Some embodiments are directed to a system comprising: at least one hardware processor; and at least one non-transitory computer-readable storage medium storing processor-executable instructions that, when executed by the at least one hardware processor, cause the at least one hardware processor to perform a method. The method comprises obtaining expression data for cells in a biological sample of a subject having, suspected of having, or at risk of having cancer; ranking at least some genes in at least one set of genes based on their expression levels in the expression data to obtain at least one gene ranking; and determining, using the at least one gene ranking and at least one statistical model trained using training data indicating a plurality of rankings for at least some genes in the at least one set of genes, tissue of origin for at least some of the cells in the biological sample, wherein each of the plurality of gene rankings is obtained based on respective expression levels for the at least some genes in the at least one set of genes.

Some embodiments are directed to at least one non-transitory computer-readable storage medium storing processor-executable instructions that, when executed by at least one hardware processor, cause the at least one hardware processor to perform: obtaining expression data for cells in a biological sample of a subject having, suspected of having, or at risk of having cancer; ranking at least some genes in at least one set of genes based on their expression levels in the expression data to obtain at least one gene ranking; and determining, using the at least one gene ranking and at least one statistical model trained using training data indicating a plurality of rankings for at least some genes in the at least one set of genes, tissue of origin for at least some of the cells in the biological sample, wherein each of the plurality of gene rankings is obtained based on respective expression levels for the at least some genes in the at least one set of genes.

Some embodiments are directed to a method, comprising using at least one computer hardware processor to perform: obtaining expression data for cells in a biological sample of a subject having, suspected of having, or at risk of having cancer; ranking at least some genes in a set of genes based on their expression levels in the expression data to obtain a gene ranking; and determining, using the gene ranking and a statistical model trained using training data indicating a plurality of rankings for at least some genes in the set of genes, cancer grade for at least some of the cells in the biological sample, wherein each of the plurality of gene rankings is obtained based on respective expression levels for the at least some genes in the set of genes.

In some embodiments, the expression data was obtained using a gene expression microarray. In some embodiments, the expression data was obtained by performing next generation sequencing. In some embodiments, the cancer grade is selected from the group consisting of at least Grade 1, Grade 2, and Grade 3. In some embodiments, the cancer grade is selected from the group consisting of at least Grade 1, Grade 2, Grade 3, and Grade 4. In some embodiments, the cancer grade is selected from the group consisting of Grade 1, Grade 2, Grade 3, Grade 4, and Grade 5.

In some embodiments, the subject has, is suspected of having, or is at risk of having breast cancer. In some embodiments, the set of genes is selected from the group of genes listed in Table 1. In some embodiments, the set of genes comprises at least 3 genes selected from the group of genes listed in Table 1. In some embodiments, the set of genes comprises at least 5 genes selected from the group of genes listed in Table 1. In some embodiments, the set of genes comprises at least 10 genes selected from the group of genes listed in Table 1.

In some embodiments, the subject has, is suspected of having, or is at risk of having kidney cancer. In some embodiments, the subject has, is suspected of having, or is at risk of having clear cell kidney cancer. In some embodiments, the set of genes is selected from the group of genes listed in Table 2. In some embodiments, the set of genes comprises at least 3 genes selected from the group of genes listed in Table 2. In some embodiments, the set of genes comprises at least 5 genes selected from the group of genes listed in Table 2. In some embodiments, the set of genes comprises at least 10 genes selected from the group of genes listed in Table 2.

In some embodiments, the subject has, is suspected of having, or is at risk of having lung adenocarcinoma. In some embodiments, the set of genes is selected from the group of genes listed in Table 6. In some embodiments, the set of genes comprises at least 10 genes selected from the group of genes listed in Table 6. In some embodiments, the set of genes includes at least 50 genes. In some embodiments, the set of genes consists of 10-100 genes. In some embodiments, the set of genes consists of 10-30 genes.

In some embodiments, the expression data includes values, each representing an expression level for a gene in the set of genes, and determining the gene ranking comprises determining a relative rank for each gene in the set of genes based on the values. In some embodiments, determining that at least one characteristic further comprises using the gene ranking as an input to the statistical model and obtaining an output indicating the cancer grade.

In some embodiments, the statistical model comprises a gradient boosted decision tree classifier. In some embodiments, the statistical model comprises a classifier selected from the group consisting of: a gradient boosted decision tree classifier, a decision tree classifier, a gradient boosted classifier, a random forest classifier, a clustering-based classifier, a Bayesian classifier, a Bayesian network classifier, a neural network classifier, a kernel-based classifier, and a support vector machine classifier.

Some embodiments are directed to a system comprising: at least one hardware processor; and at least one non-transitory computer-readable storage medium storing processor-executable instructions that, when executed by the at least one hardware processor, cause the at least one hardware processor to perform a method. The method comprises obtaining expression data for cells in a biological sample of a subject having, suspected of having, or at risk of having cancer; ranking at least some genes in a set of genes based on their expression levels in the expression data to obtain a gene ranking; and determining, using the gene ranking and a statistical model trained using training data indicating a plurality of rankings for at least some genes in the set of genes, cancer grade for at least some of the cells in the biological sample, wherein each of the plurality of gene rankings is obtained based on respective expression levels for the at least some genes in the set of genes.

Some embodiments are directed to at least one non-transitory computer-readable storage medium storing processor-executable instructions that, when executed by at least one hardware processor, cause the at least one hardware processor to perform: obtaining expression data for cells in a biological sample of a subject having, suspected of having, or at risk of having cancer; ranking at least some genes in a set of genes based on their expression levels in the expression data to obtain a gene ranking; and determining, using the gene ranking and a statistical model trained using training data indicating a plurality of rankings for at least some genes in the set of genes, cancer grade for at least some of the cells in the biological sample, wherein each of the plurality of gene rankings is obtained based on respective expression levels for the at least some genes in the set of genes.

Some embodiments are directed to a method, comprising using at least one computer hardware processor to perform using at least one computer hardware processor to perform: obtaining expression data for cells in a biological sample of a subject having, suspected of having, or at risk of having cancer; ranking at least some genes in at least one set of genes based on their expression levels in the expression data to obtain at least one gene ranking; and determining, using the at least one gene ranking and at least one statistical model, a subtype of peripheral T-cell lymphoma (PTCL) for at least some of the cells in the biological sample.

In some embodiments, the at least one statistical model was trained using training data indicating a plurality of rankings of expression levels for at least some genes in the at least one set of genes. In some embodiments, each of the plurality of gene rankings is obtained based on respective expression levels for the at least some genes in the at least one set of genes.

In some embodiments, the expression data was obtained using a gene expression microarray. In some embodiments, the expression data was obtained by performing next generation sequencing. In some embodiments, the expression data was obtained using a hybridization-based expression assay.

In some embodiments, the subtype of PTCL is selected from the group consisting of: anaplastic large cell lymphoma (ALCL), angioimmunoblastic T-cell lymphoma (AITL), natural killer/T-cell lymphoma (NKTCL), and adult T-cell leukemia/lymphoma (ATLL). In some embodiments, the subtype of PTCL is selected from the group consisting of: Peripheral T-Cell Lymphoma, Not Otherwise Specified (PTCL-NOS), anaplastic large cell lymphoma (ALCL), angioimmunoblastic T-cell lymphoma (AITL), cutaneous T-cell lymphoma (CTCL), Natural killer/T-cell lymphoma (NKTCL), Sezary syndrome, adult T-cell leukemia/lymphoma (ATLL), enteropathy-type T-cell lymphoma, nasal NK/T-cell lymphoma, hepatosplenic gamma-delta T-cell lymphoma, T-cell lymphomas of Follicular T-cell (TFH) origin, T-cell lymphomas of the gastrointestinal tract, and cutaneous T-cell lymphomas.

In some embodiments, a set of genes of the at least one set of genes is selected from the group of genes listed in Table 10. In some embodiments, a set of genes of the at least one set of genes comprises at least 3 genes selected from the group of genes listed in Table 10. In some embodiments, a set of genes of the at least one set of genes comprises at least 5 genes selected from the group of genes listed in Table 10. In some embodiments, a set of genes of the at least one set of genes comprises at least 10 genes selected from the group of genes listed in Table 10. In some embodiments, a set of genes of the at least one set of genes comprises at least 50 genes selected from the group of genes listed in Table 10.

In some embodiments, a set of genes of the at least one set of genes includes at least one up-regulated in AITL gene. In some embodiments, a set of genes of the at least one set of genes includes at least one down-regulated in AITL gene. In some embodiments, a set of genes of the at least one set of genes includes at least one MF profile gene.

In some embodiments, the subject has, is suspected of having, or is at risk of having lymphoma. In some embodiments, the subject has, is suspected of having, or is at risk of having peripheral T-cell lymphoma (PTCL).

In some embodiments, a set of genes of the at least one set of genes includes at least 5 genes. In some embodiments, a set of genes of the at least one set of genes consists of 5-100 genes. In some embodiments, a set of genes of the at least one set of genes consists of 10-200 genes. In some embodiments, a set of genes of the at least one set of genes consists of 20-100 genes. In some embodiments, a set of genes of the at least one set of genes consists of 50-100 genes.

In some embodiments, the expression data includes values, each representing an expression level for a gene in the at least one set of genes, and determining a gene ranking of the at least one gene ranking comprises determining a relative rank for each gene in one of the at least one set of genes based on the values.

In some embodiments, determining the subtype of PTCL further comprises using the at least one gene ranking as an input to the at least one statistical model and obtaining an output indicating the subtype of PTCL.

In some embodiments, the at least one statistical model comprises a gradient boosted decision tree classifier. In some embodiments, the at least one statistical model comprises at least one classifier selected from the group consisting of: a gradient boosted decision tree classifier, a decision tree classifier, a gradient boosted classifier, a random forest classifier, a clustering-based classifier, a Bayesian classifier, a Bayesian network classifier, a neural network classifier, a kernel-based classifier, and a support vector machine classifier.

In some embodiments, the at least one statistical model includes a multi-class classifier. In some embodiments, the multi-class classifier has at least four outputs each corresponding to a different subtype of PTCL. In some embodiments, the at least four outputs include a first output corresponding to anaplastic large cell lymphoma (ALCL), a second output corresponding to angioimmunoblastic T-cell lymphoma (AITL), a third output corresponding to natural killer/T-cell lymphoma (NKTCL), and a fourth output corresponding to adult T-cell leukemia/lymphoma (ATLL).

In some embodiments, the at least one statistical model comprises a plurality of classifiers corresponding to different subtypes of PTCL. In some embodiments, the plurality of classifiers includes a first classifier, a second classifier, a third classifier, and a fourth classifier, wherein the first classifier corresponds anaplastic large cell lymphoma (ALCL), a second classifier corresponds to angioimmunoblastic T-cell lymphoma (AITL), a third classifier corresponds to natural killer/T-cell lymphoma (NKTCL), and a fourth classifier corresponds to adult T-cell leukemia/lymphoma (ATLL). In some embodiments, the at least one set of genes includes a first set of genes associated with a first classifier of the plurality of classifiers and a second set of genes associated with a second classifier of the plurality of classifiers.

In some embodiments, the subject has, is suspected of having, or is at risk of having lymphoma. In some embodiments, the subject has, is suspected of having, or is at risk of having PTCL.

In some embodiments, the method further comprises presenting, to a user, an indication of the subtype of PTCL. In some embodiments, presenting the indication of the subtype of PTCL further comprises displaying the subtype of PTCL to the user in a graphical user interface (GUI).

Some embodiments are directed to a system comprising: at least one hardware processor; and at least one non-transitory computer-readable storage medium storing processor-executable instructions that, when executed by the at least one hardware processor, cause the at least one hardware processor to perform a method. The method comprises obtaining expression data for cells in a biological sample of a subject having, suspected of having, or at risk of having cancer; ranking at least some genes in at least one set of genes based on their expression levels in the expression data to obtain at least one gene ranking; and determining, using the at least one gene ranking and at least one statistical model, a subtype of peripheral T-cell lymphoma (PTCL) for at least some of the cells in the biological sample.

Some embodiments are directed to at least one non-transitory computer-readable storage medium storing processor-executable instructions that, when executed by at least one hardware processor, cause the at least one hardware processor to perform: obtaining expression data for cells in a biological sample of a subject having, suspected of having, or at risk of having cancer; ranking at least some genes in at least one set of genes based on their expression levels in the expression data to obtain at least one gene ranking; and determining, using the at least one gene ranking and at least one statistical model, a subtype of peripheral T-cell lymphoma (PTCL) for at least some of the cells in the biological sample.

BRIEF DESCRIPTION OF DRAWINGS

Various aspects and embodiments will be described with reference to the following figures. The figures are not necessarily drawn to scale.

DETAILED DESCRIPTION

Figure 1:
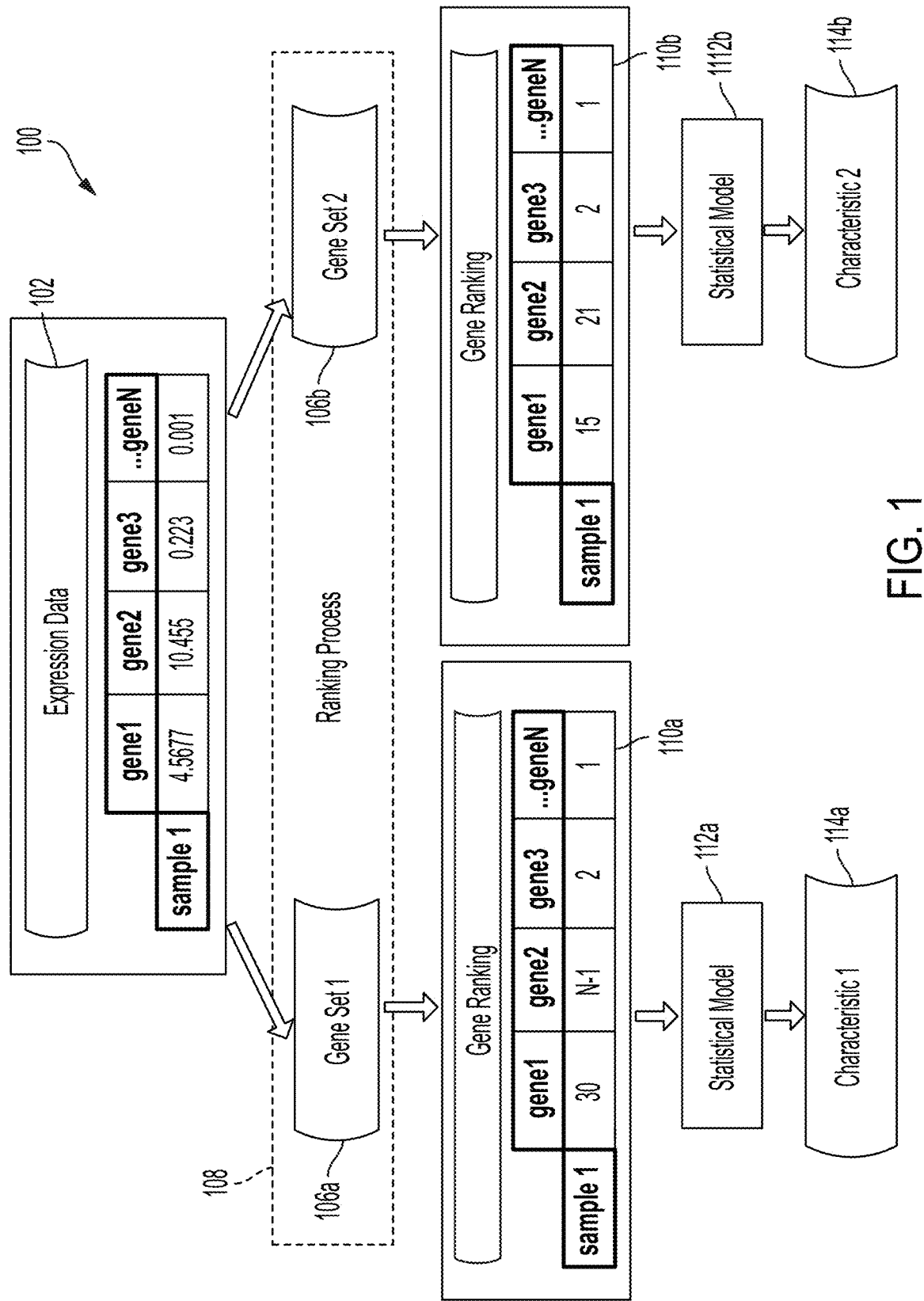
FIG. 1 is a diagram of an illustrative process for determining one or more characteristics of a biological sample based on one or more respective gene rankings for the biological sample using the machine learning techniques described herein.

Characteristics of a biological cell may relate to the expression levels of certain genes. For example, a cancerous cell may have some genes upregulated and other genes downregulated relative to a normal, healthy cell. This relationship between cell characteristics and gene expression levels may be utilized in analyzing gene expression data for biological cells. In particular, such a relationship may provide certain benefits in analyzing characteristics of biological cells that are considered histological characteristics, including tissue of origin and cancer grade, which generally relate to features of biological cells that are observed visually by a person (e.g., pathologist). In some instances, the gene expression data may provide a more consistent assessment of a certain cell characteristic than by using histological techniques, which may be subject to variation between differences in assessment among pathologists.

Large amounts of gene expression data can be obtained through different platforms, including by using a gene expression microarray and by performing next generation sequencing, and is now available or can be generated to characterize biological cells. However, the inventors have recognized that information that is derivable from these data is compromised by differences among different gene sequencing platforms which may lead to variation in gene expression data produced by the sequencing platforms, even if they are used to sequence the same biological sample. For example, microarrays and next generation sequencing (NGS) techniques, may produce gene expression data where the particular values representing gene expression levels may vary among the platforms, even if obtained from the same biological sample. This variation in the expression values across different sequencing platforms may occur because of how the expression data is obtained. The processes and devices used to obtain gene expression data using a particular type of sequencing platform (e.g., next generation sequencing, microarray) may impact the specific values for the expression levels obtained. In turn, the values for the expression levels depend on which sequencing platform was used to obtain the gene expression data. This variation may occur not only across different types of sequencing platforms, but may also occur where the different sequencing platforms are of the same type (e.g., next generation sequencing) and involve different systems (e.g., optical systems, detectors) and processes (e.g., biological sample preparation), or even the same devices in different locations (e.g., due to differences in calibration, use, environment, etc.).

The inventors have recognized that such variation in expression level values presents significant challenges in analyzing gene expression data to characterize cells, especially when using gene expression data obtained using different sequencing platforms. For some expression data, it may be a challenge to normalize the expression level values in such a way so that expression data obtained using different sequencing platforms may be analyzed using the same or similar techniques.

Conventional techniques for analyzing expression data are generally applicable only to analyzing expression data that was obtained using a single sequencing platform and to the specific conditions used in preparing and sequencing the sample. Such conventional techniques are not applicable to analyzing expression data obtained from multiple sequencing platforms, even when the sequencing platforms are of the same type (e.g., next generation sequencing, microarray). For example, conventional techniques for analyzing gene expression data may involve different data analysis pipelines for expression data obtained using different next generation sequencing devices. In addition, some conventional techniques involve implementing different data analysis pipelines depending on how the expression data was obtained even if the same sequencing device was used. For example, conventional techniques for analyzing gene expression data may differ for different sequencing conditions or different sample processing methods. As a result, conventional techniques for analyzing expression data cannot be implemented across different sequencing platforms, sample preparation techniques, and sequencing conditions. This significantly impacts the usability of gene expression data to determine characteristics of cells.

One important group of techniques for analyzing expression data include statistical models (e.g., machine learning models) that are configured to receive expression level values (or a derivative thereof) as input to produce an output of interest such as a prediction or classification. Examples of such statistical models, developed by the inventors, are provided herein. Prior to being used such statistical models are trained on training data comprising pairs of inputs/outputs. If the training data inputs include expression level values (or a derivative thereof) that comes from one type of sequencing platform, then a statistical model trained with such data will exhibit poor performance (on the task for which it is trained) when being provided with expression level values that come from another type of sequencing platform. Indeed, variation across expression level values from different sequencing platforms makes it difficult or impossible to design a single statistical model trained to perform a task using data from any one of multiple types of sequencing platforms. Instead, a separate statistical model would have to be trained for each particular sequencing platform using training data obtained for that particular sequencing platform, which is difficult because it requires training multiple models for each platform and this requires not only additional computational resources, but may simply not be possible as there may not be sufficient training data available for each type of platform.

The inventors have recognized the need for common techniques that can be used for analyzing expression data obtained across different sequencing platforms, despite differences in the type of expression level data generated by the platforms. Such techniques would ease analysis of gene expression data across different subjects, which conventional gene expression level analysis techniques would not allow. For example, techniques described herein for analyzing gene expression data may involve using the same or similar data analysis pipeline (which pipeline may include one or more statistical models, examples of which are provided herein) for expression data obtained using the same type of sequencing platform (e.g., next generation sequencing, microarray) for multiple subjects. Such a data analysis pipeline may allow for expression data to be analyzed in the same or similar manner regardless of sample processing (e.g., DNA extraction, amplification), sequencing conditions (e.g., temperature, pH), data processing (e.g., data processing for next generation sequencing, microarrays) used in obtaining the expression data.

To address some of the difficulties that arise with conventional techniques for analyzing expression data, the inventors have developed improved techniques in analyzing expression data that are independent of the sequencing platform and data processing used to obtain the expression data. In particular, the inventors have recognized that variation of the expression levels among sequencing platforms may be accounted for by using the ranking of a set of genes, rather than the specific values of the expression levels in the data, in subsequent data analysis. For example, the inventors have developed various statistical models for determining various characteristics of a biological sample (e.g., tissue of origin, cancer grade, cancer type for a tissue sample). Each such statistical model is trained to determine a respective characteristic of the biological sample using a ranking of a respective set of genes, rather than using expression levels themselves, which allows the statistical model to operate on expression data obtained from different types of sequencing platforms.

Accordingly, in some embodiments, a statistical model may be used to predict the characteristic(s) of a biological sample based on an input ranking of genes, ranked based on their respective expression levels, for a sequencing platform. Using the input ranking(s), instead of the specific values for the expression levels, allows for the same or similar data processing pipeline to be used across different expression data regardless of the specific manner in which the expression levels were obtained (e.g., regardless of which sequencing platform, sequencing conditions, sample preparation, data processing to obtain expression levels, etc.). As described herein, the statistical model may be specific to the particular characteristic being determined. A statistical model according to the techniques described here may be used to predict one or more characteristics, including cancer grade for cells in the biological sample (e.g., breast cancer grade, kidney clear cell cancer grade, lung adenocarcinoma grade), tissue of origin for cells in the biological sample (e.g., lung, pancreas, stomach, colon, liver, bladder, kidney, thyroid, lymph nodes, adrenal gland, skin, breast, ovary, prostrate, or cell of origin in a tissue such as e.g. germinal center B-cell (GCB) or activated B-cell (ABC)), histological information (tissue type, such as e.g. adenocarcinoma, squamous cell carcinoma, carcinoma, cystadenocarcinoma, sarcoma, and glioma) for cells in the biological sample, and cancer subtype (e.g. PTCL subtype such as, anaplastic large cell lymphoma (ALCL), angioimmunoblastic T-cell lymphoma (AITL), natural killer/T-cell lymphoma (NKTCL), and adult T-cell leukemia/lymphoma (ATLL)), viral status (e.g., HPV status, such as HPV-positive or HPV-negative for head and neck squamous cell carcinoma) for cells in the biological sample.

For example, in some embodiments, rankings of genes based on the gene expression levels (in a biological sample) as determined by a sequencing platform may be provided as input to a statistical model trained to predict tissue of origin for the biological sample. As another example, in some embodiments, rankings of genes based on the gene expression levels (in a biological sample) as determined by a sequencing platform may be provided as input to a statistical model trained to predict cancer grade for the biological sample. In some embodiments, the set of genes being ranked depends on the particular biological characteristic of interest. For example, one set of genes may be used for determining the tissue of origin and another set of genes may be used for determining the cancer grade.

The machine learning techniques that involve using rankings of genes as described herein are an improvement of conventional machine learning technology because they improve over conventional machine learning techniques that use gene expression values directly to analyze gene expression data. For instance, training data obtained using different sequencing platforms may be used in training the statistical models described herein because of the benefits provided by using gene rankings in allowing a common statistical model to be implemented regardless of how the expression data was generated. In contrast, conventional machine learning techniques that involve using gene expression values require individual separate statistical models depending on how the expression data was generated, such as when using different sequencing platforms, sample preparation techniques, etc.

Accordingly, the machine learning techniques described herein reduce the need for collecting training data across different sequencing platforms in order to train multiple statistical models required to analyze expression data generated in different ways. In addition, the statistical models described herein may have better performance in contrast to conventional techniques. For instance, a statistical model according to the techniques described herein can be trained using training data obtained from different sources, and thus more training data in general, which improves overall performance of the statistical model being used. In contrast, sources of training data for conventional machine learning models may be limited to a particular sequencing platform, sample preparation technique, etc. and performance may depend on the amount of training data available using a particular way of generating the expression data.

In addition, having a statistical model that is independent of the sequencing platform, sample preparation, and sequencing conditions used may make deployment and use of such a statistical model more practical. In clinical practice, data from different patients is likely to originate from multiple sources, such as expression data generated using different sample preparation techniques and sequencing platforms. As discussed above, the techniques described herein allow for the ability to handle patient data originating from these different sources in a uniform manner by using a common statistical model. The ability to analyze patient data in this way provides improvements to bioinformatics technology that depends on the number of patients represented by the patient data because a larger pool of patients can be analyzed using a common statistical model. These benefits extend to applications where bioinformatics analysis may be used, including predicting characteristic(s) of cells in a biological sample, where being able to use a larger sample size, across many patients, is beneficial.

Moreover, the machine learning techniques described herein may streamline handling of different formats for storing expression data. Different types of sequencing platforms output expression data using different data formats. As discussed herein, a ranking process is used to generate gene rankings, which are then input to a common statistical model. The ranking process may allow for expression data originating from sources that use different data formats to have a similar type of input to the statistical model. This may improve handling of expression data obtained from different sequencing platforms in comparison to conventional analysis techniques where different data processing pipelines are required for different input data formats.

Some embodiments described herein address all of the above-described issues that the inventors have recognized with determining characteristics of a biological sample using gene expression data. However, not every embodiment described herein addresses every one of these issues, and some embodiments may not address any of them. As such, it should be appreciated that embodiments of the technology described herein are not limited to addressing all or any of the above-discussed issues with determining characteristics of a biological sample using gene expression data.

Some embodiments involve obtaining gene expression data for a biological sample of a subject, ranking genes in set(s) of genes based on their expression levels in the expression data to obtain one or more gene rankings. The one or more gene rankings may be used, along with a statistical model, to determine one or more characteristics of the biological sample, including tissue of origin and cancer grade. The statistical model may be trained using rankings of expression levels for some or all genes in the set(s) of genes.

The gene ranking(s) may be obtained by ranking genes in one or more sets of genes based on their expression levels in the expression data. In some embodiments, the expression data includes values, each representing an expression level for a gene in the set(s) of genes. Determining the gene ranking(s) may involve determining a relative rank for each gene in the set(s) of genes based on the values. For example, a first gene ranking may be obtained by ranking genes in a first set of genes based on their expression levels and a second gene ranking may be obtained by ranking genes in a second set of genes based on their expression levels. In some embodiments, the first set of genes and the second set of genes may share some or all genes. Determining the one or more characteristics may involve using the first gene ranking, the second gene ranking, and the statistical model, where the statistical model is trained using training data indicating gene rankings of expression levels for some or all genes in the first set of genes and the second set of genes. Different gene sets may correspond to predicting particular characteristics of the biological sample, and a gene ranking for a specific gene set may be used to determine the characteristic associated with the gene set. For example, a gene ranking where expression levels for a gene set associated with predicting cancer grade may be used to predict cancer grade for cells in the biological sample from which the expression data is obtained.

In some embodiments, the expression data may be obtained for cells in the biological sample, where the subject has or is suspected of having cancer. In the context where tissue of origin is a characteristic being determined, the tissue of origin is for the cells in the biological sample. The tissue of origin may refer to a particular tissue type from which the cells originate, such as lung, pancreas, stomach, colon, liver, bladder, kidney, thyroid, lymph nodes, adrenal gland, skin, breast, ovary, and prostrate.

For example, some embodiments involve using a gene set for predicting tissue of origin, which may include cell of origin, for Diffuse Large B-Cell Lymphoma (DLBCL), such as germinal center B-cell (GCB) and activated B-cell (ABC). Genes in the gene set may be selected from the group consisting of: ITPKB, MYBL1, LMO2, BATF, IRF4, LRMP, CCND2, SLA, SP140, PIM1, CSTB, BCL2, TCF4, P2RX5, SPINK2, VCL, PTPN1, REL, FUT8, RPL21, PRKCB1, CSNK1E, GPR18, IGHM, ACP1, SPIB, HLA-DQA1, KRT8, FAM3C, and HLA-DMB.

In the context where cancer grade is a characteristic being determined, the cancer grade is for the cells in the biological sample. The cancer grade may refer to proliferation and differentiation characteristics of the cells in the biological sample and refer to a numerical grade that is generally determined by visual observation of cells using microscopy, such as Grade 1, Grade 2, Grade 3, and Grade 4. For example, a pathologist may examine a biopsied tissue under a microscope and determine a cancer grade for the tissue. Cancer grades generally depend on the amount of abnormality of the cells in tissue and may depend on the type cancer. For Grade 1, tumor cells and the organization of the tumor tissue appears close to normal, healthy tissue. Grade 1 tumors tend to grow and spread slowly. In contrast, cells and tissue of Grade 3 and Grade 4 tumors do not look like normal cells and tissue. Grade 3 and Grade 4 tumors tend to grow rapidly and spread faster than tumors with a lower grade. An example grading system for cancer tissue is described in American Joint Committee on Cancer *AJCC Cancer Staging Manual.* 7th ed. New York, N.Y.: Springer; 2010, which is incorporated by reference in its entirety. This grading system applies the following definitions: Grade X (GX) is an undetermined grade and applies when the grade of a tissue cannot be assessed; Grade 1 (G1) is a low grade and applies when the cells are well differentiated; Grade 2 (G2) is an intermediate grade and applies when the cells are moderately differentiated; Grade 3 (G3) is a high grade and applies when the cells are poorly differentiated; and Grade 4 (G4) is a high grade and applies when the cells are undifferentiated.

For example, some embodiments involve using a gene set for predicting breast cancer grade. Genes in the gene set may be selected from the group consisting of: UBE2C, MYBL2, PRAME, LMNB1, CXCL9, KPNA2, TPX2, PLCH1, CCL18, CDK1, MELK, CCNB2, RRM2, CCNB1, NUSAP1, SLC7A5, TYMS, GZMK, SQLE, C1orf106, CDC25B, ATAD2, QPRT, CCNA2, NEK2, IDO1, NDC80, ZWINT, ABCA12, TOP2A, TDO2, S100A8, LAMP3, MMP1, GZMB, BIRC5, TRIP13, RACGAP1, ASPM, ESRP1, MAD2L1, CENPF, CDC20, MCM4, MKI67, PBK, CKS2, KIF2C, MRPL13, TTK, BUB1, TK1, FOXM1, CEP55, EZH2, ECT2, PRC1, CENPU, CCNE2, AURKA, HMGB3, APOBEC3B, LAGE3, CDKN3, DTL, ATP6V1C1, KIAA0101, CD2, KIF11, KIF20A, CDCA8, NCAPG, CENPN, MTFR1, MCM2, DSCC1, WDR19, SEMA3G, KCND3, SETBP1, KIF13B, NR4A2, NAV3, PDZRN3, MAGI2, CACNA1D, STC2, CHAD, PDGFD, ARMCX2, FRY, AGTR1, MARCH8, ANG, ABAT, THBD, RAI2, HSPA2, ERBB4, ECHDC2, FST, EPHX2, FOSB, STARD13, ID4, FAM129A, FCGBP, LAMA2, FGFR2, PTGER3, NME5, LRRC17, OSBPL1A, ADRA2A, LRP2, C1orf115, COL4A5, DIXDC1, KIAA1324, HPN, KLF4, SCUBE2, FMO5, SORBS2, CARD10, CITED2, MUC1, BCL2, RGS5, CYBRD1, OMD, IGFBP4, LAMB2, DUSP4, PDLIM5, IRS2, and CX3CR1.

As another example, some embodiments involve using a gene set for predicting kidney clear cell cancer grade. Genes in the gene set may be selected from the group consisting of: PLTP, C1S, LY96, TSKU, TPST2, SERPINF1, SRPX2, SAA1, CTHRC1, GFPT2, CKAP4, SERPINA3, CFH, PLAU, BASP1, PTTG1, MOCOS, LEF1, SLPI, PRAME, STEAP3, LGALS2, CD44, FLNC, UBE2C, CTSK, SULF2, TMEM45A, FCGRA, PLOD2, C19orf80, PDGFRL, IGF2BP3, SLC7A5, PRRX1, RARRES1, LHFPL2, KDELR3, TRIB3, IL20RB, FBLN1, KMO, C1R, CYP1B1, KIF2A, PLAUR, CKS2, CDCP1, SFRP4, HAMP, MMP9, SLC3A1, NAT8, FRMD3, NPR3, NAT8B, BBOX1, SLC5A1, GBA3, EMCN, SLC47A1, AQP1, PCK1, UGT2A3, BHMT, FMO1, ACAA2, SLC5A8, SLC16A9, TSPAN18, SLC17A3, STK32B, MAP7, MYLIP, SLC22A12, LRP2, CD34, PODXL, ZBTB42, TEK, FBP1, and BCL2.

As another example, some embodiments involve using a gene set for predicting cancer grade for lung adenocarcinoma. Genes in the gene set may be selected from the group consisting of: AADAC, ALDOB, ANXA10, ASPM, BTNL8, CEACAM8, CENPA, CHGB, CHRNA9, COL11A1, CRABP1, F11, GGTLC1, HJURP, IGF2BP3, IHH, KCNE2, KIF14, LRRC31, MYBL2, MYOZ1, PCSK2, PI15, SCTR, SHH, SLC22A3, SLC7A5, SPOCK1, TM4SF4, TRPM8, YBX2.

Some embodiments involve using the machine learning techniques described herein to predict cell of origin for diffuse large B-cell lymphoma (DLBCL) for a biological sample. Such embodiments may involve using a gene set for predicting cell of origin, such as germinal center B-cell (GCB) and activated B-cell (ABC). Genes in the gene set may be selected from the group consisting of: ITPKB, MYBL1, LMO2, BATF, IRF4, LRMP, CCND2, SLA, SP140, PIM1, CSTB, BCL2, TCF4, P2RX5, SPINK2, VCL, PTPN1, REL, FUT8, RPL21, PRKCB1, CSNK1E, GPR18, IGHM, ACP1, SPIB, HLA-DQA1, KRT8, FAM3C, and HLA-DMB.

Some embodiments involve using the machine learning techniques described herein to predict a subtype of peripheral T-cell lymphoma (PTCL) for a biological sample. Such embodiments may involve using a gene set for predicting PTCL subtype, such as, anaplastic large cell lymphoma (ALCL), angioimmunoblastic T-cell lymphoma (AITL), natural killer/T-cell lymphoma (NKTCL), and adult T-cell leukemia/lymphoma (ATLL). Genes in the gene set may be selected from the group consisting of: EFNB2, ROBO1, S1PR3, ANK2, LPAR1, SNAP91, SOX8, RAMP3, TUBB2B, ARHGEF10, NOTCH1, ZBTB17, CCNE1, FGF18, MYCN, PTHLH, SMARCA2, WNK1, NKX2-1, CYP26A1, HPSE, CTLA4, PELI1, PRKCB, SPAST, ALS2, KIF3B, ZFYVE27, GF18, FNTB, REL, DMRT1, SLC19A2, STK3, PERP, TNFRSF8, TMOD1, BATF3, CDC14B, WDFEY3, AGT, ALK, ANXA3, BTBD11, CCNA1, DNER, GAS1, HS6ST2, IL1RAP, PCOLCE2, PDE4DIP, SLC16A3, TIAM2, TUBB6, WNT7B, SMOX, TMEM158, NLRP7, ADRB2, GALNT2, HRASLS, CD244, FASLG, KIR2DL4, LOC100287534, KLRD1, SH2D1B, KLRC2, NCAM1, CXCR5, IL6, ICOS, CD40LG, CD84, IL21, BCL6, MAF, SH2D1A, IL4, PTPN1, PIM1, ENTPD1, IRF4, CCND2, IL16, ETV6, BLNK, SH3BP5, FUT8, CCR4, GATA3, IL5, IL10, IL13, MMEITPKB, MYBL1, LRMP, KIAA0870, LMO2, CR1, LTBR, PDPN, TNFRSF1A, FCER2, ICAM1, FCGR2B, IKZF2, CCR8, TNFRSF18, IKZF4, FOXP3, IL2, TBX21, IFNG, GZMH, GNLY, EOMES, NCR1, GZMB, NKG7, FGFBP2, KLRF1, CD160, KLRK1, CD226, NCR3, TNFRSF8, BATF3, TMOD1, TMEM158, MSC, POPDC3.

Some embodiments involve using the machine learning techniques described herein to predict a viral status for a biological sample. In some embodiments the viral status is human papillomavirus (HPV) status (e.g., HPV-positive status, HPV-negative status) for a biological sample. In some embodiments, the HPV status may be determined for a subject having, suspected of having, or at risk of having head and neck squamous cell carcinoma. Genes in the gene set may be selected from the group consisting of: APOBEC3B, ATAD2, BIRC5, CCL20, CCND1, CDC45, CDC7, CDK1, CDKN2A, CDKN2C, CDKN3, CENPF, CENPN, CXCL14, DCN, DHFR, DKK3, DLGAP5, EPCAM, FANCI, FEN1, GMNN, GPX3, ID4, IGLC1, IL18, IL1R2, KIF18B, KIF20A, KIF4A, KLK13, KLK7, KLK8, KNTC1, KRT19, LAMP3, LMNB1, MCM2, MCM4, MCM5, ME1, MELK, MKI67, MLF1, MMP12, MTHFD2, NDN, NEFH, NEK2, NUP155, NUP210, NUSAP1, PDGFD, PLAGL1, PLOD2, PPP1R3C, PRIM1, PRKDC, PSIP1, RAD51AP1, RASIP1, RFC5, RNASEH2A, RPA2, RPL39L, RSRC1, RYR1, SLC35G2, SMC2, SPARCL1, STMN1, SYCP2, SYNGR3, TIMELESS, TMPO, TPX2, TRIP13, TYMS, UCP2, UPF3B, USP1, ZSCAN18.

It should be appreciated that the various aspects and embodiments described herein be used individually, all together, or in any combination of two or more, as the technology described herein is not limited in this respect.

FIG. 1 is a diagram of an illustrative processing pipeline 100 for determining one or more characteristics (e.g. tissue of origin, cancer grade, PTCL subtype) of a biological sample based on one or more respective gene rankings for the biological sample, which may include ranking genes based on their gene expression levels and using the ranking(s) and one or more statistical models to determine the one or more characteristics, in accordance with some embodiments of the technology described herein. Processing pipeline 100 may be performed on any suitable computing device(s) (e.g., a single computing device, multiple computing devices co-located in a single physical location or located in multiple physical locations remote from one another, one or more computing devices part of a cloud computing system, etc.), as aspects of the technology described herein are not limited in this respect. In some embodiments, processing pipeline 100 may be performed by a desktop computer, a laptop computer, a mobile computing device. In some embodiments, processing pipeline 100 may be performed within one or more computing devices that are part of a cloud computing environment.

As shown in FIG. 1, gene expression data 102 may be obtained for a biological sample of a subject. The subject may have, be suspected of having, or be at risk of having cancer (e.g., breast cancer, kidney cancer, clear cell kidney cancer, lymphoma). A subject having, suspected of having, or at risk of having cancer may be a subject exhibiting one or more signs or symptoms of cancer, subject that is diagnosed as having cancer, a subject that has a family history and/or a genetic predisposition to having cancer, and/or a subject that has one or more other risk factors for cancer (e.g., age, exposure to carcinogens, environmental exposure, exposure to a virus associated with a higher likelihood of developing cancer, etc.). Expression data 102 may be obtained using any suitable sequencing platform (e.g., gene expression microarray, next generation sequencing, hybridization-based expression assay), resulting in expression data (e.g., microarray data, RNAseq data, hybridization-based expression assay data) for the biological sample. Some embodiments involve performing a sequencing process of the biological sample (e.g., a gene expression microarray, next generation sequencing) prior to obtaining expression data 102. In some embodiments, obtaining gene expression data 102 may involve obtaining gene expression data 102 in silico, such as by accessing, using a computing device, expression data (e.g., expression data that has been previously obtained from a biological sample) in one or more data stores, receiving the expression data from one or more other device, or any other way. In some embodiments, obtaining gene expression data 102 may involve analyzing a biological sample (in vitro) and accessing (e.g., by a computing device, by a processor) the expression data. Further aspects relating to obtaining expression data are provided in the section titled "Obtaining Expression Data".

As shown in FIG. 1, expression data 102 includes expression level values for N different genes, "gene1", "gene2", "gene3", . . . "geneN" of "sample 1." Different sequencing platforms may be used to obtain expression data 102. In some embodiments, expression data 102 may be obtained using a gene expression microarray (e.g., by determining an amount of RNA that binds to different probes on a microarray). A gene expression microarray may detect expression of thousands of genes at a time. Expression data 102 associated with using a gene expression microarray may be associated with 1,000, at least 10,000, or at least 100,000 gene detection events. In some embodiments, expression data 102 may be obtained by performing next generation sequencing. Such expression data may be associated with obtaining sequence reads using next generation sequencing, aligning the sequencing reads to a reference (e.g., by using one or more sequence alignment algorithms), determine expression level values for certain genes based on the alignment, etc. Expression data 102 associated with performing next generation sequencing may be associated with at least 10,000, at least 100,000, at least 1,000,000, or at least 10,000,000 sequence reads. In some embodiments, expression data 102 may be obtained by using a hybridization-based expression assay (e.g., labeled probe to target a region of interest in a biological sequence). Expression data 102 associated with using a hybridization-based expression may be associated with 1,000, at least 10,000, or at least 100,000 gene detection events.

In some embodiments, expression data 102 includes RNA Seq data. In such embodiments, expression data 102 may involve obtaining RNA expression levels obtained by performing RNA sequencing. In some embodiments, expression data 102 is obtained by performing whole genome sequencing (WGS). In some embodiments, expression data 102 is obtained by performing whole exome sequencing (WES). In some embodiments, expression data 102 includes a combination of RNA Seq data and WGS data. In some embodiments, expression data 102 includes a combination of RNA Seq data and WES data.

In some embodiments, expression data 102 includes values for the N different genes, where a value represents an expression level for a particular gene. For example, first expression data 102 includes a value of 10.455 representing the expression level for gene2 and a value of 0.0001 representing the expression level for geneN, which indicates that gene2 has a higher expression level in sample 1 than geneN. As discussed above, the sequencing platform used to obtain expression data 102 may impact the specific values of the expression data and the relative values among the genes.

According to some embodiments, ranking process 108 may involve ranking genes based on their expression levels in expression data 102 to obtain gene ranking(s) 110. Ranking process 108 may involve ranking genes in a set of genes based on numerical values of their expression levels. In some embodiments, ranking process 108 may involve ranking some or all of the genes in expression data 102 to obtain gene ranking(s) 110. Different gene rankings may be obtained by ranking expression levels for different gene sets. Determining a gene ranking may involve determining a relative rank for each gene in the set of genes. As shown in FIG. 1, genes in expression data 102 may be ranked based on their expression levels using ranking process 108 for gene set 1 106a to obtain first gene ranking 110a. Similarly, genes in expression data 102 may be ranked based on their expression levels using ranking process 108 for gene set 2 106b to obtain second gene ranking 110b. Gene ranking 110a and gene ranking 110b have relative ranks for the different genes. As shown in FIG. 1, gene ranking 110a has the relative ranks of 30, N-1, 2, and 1, for gene1, gene2, gene3, and geneN, respectively, and gene ranking 110b has the relative ranks of 15, 21, 2, and 1, for gene1, gene2, gene3, and geneN, respectively. A gene ranking may include values identifying the relative ranks for genes in the gene ranking. In some embodiments, the values identifying the relative ranks may include ordinal numbers. In some embodiments, the values identifying the relative ranks may include whole numbers, such as shown in FIG. 1. In some embodiments, the values identifying the relative ranks may be used as an input (e.g., a vector of the relative ranks) to a statistical model for predicting a characteristic using the techniques described herein. In some embodiments, a gene ranking may include a sorted list of genes according to the relative ranks of the genes. In such embodiments, the sorted list of genes may be used as an input (e.g., a vector with the sorted list of genes) to a statistical model for predicting a characteristic using the techniques described herein. For example, a gene set may include gene list A=[x1, x2, x3, . . . xN−1, xN] and ranking process 108 may output a sorted list of genes [x2, x15, xN−1 . . . x1, xN] with their corresponding relative ranks as [1, 2, 3, . . . N−1, N]. The sorted list of genes [x2, x15, xN−1 . . . x1, xN] and their relative ranks [1, 2, 3, . . . N−1, N] may be used as input to a statistical model.

In some embodiments, ranking process 108 may involve ordering genes in the gene set from the lowest to highest expression level and labeling the list of genes with the rank for individual genes. For example, lowest expression level values are ordered first on the list of genes and their corresponding labels are lowest (e.g., 1, 2, 3, etc.) while the highest expression level values have corresponding higher labels. In some embodiments, ranking process 108 may involve ordering genes in descending order so that genes in the gene set are ranked from highest to lowest expression level values. In some embodiments, ranking process 108 may involve one or more pre-processing steps prior to ranking genes, including binning gene expression values, rounding gene expression values. For example, in some embodiments, gene expression values may be sorted into bins and then ranked. As another example, in some embodiments, gene expression values may be truncated and then ranked. Other pre-processing steps may be applied to the expression levels and the ranking may be performed on the pre-processed values, as aspects of the technology described herein are not limited to ranking only by sorting on the exact gene expression levels that were obtained.

In instances where a group of genes have equal or substantially similar expression level values, the genes in the group may have a common rank and a label indicating the common rank. In some embodiments, the common rank may be determined as being the average of the ranks for the genes in the group. For example, one gene in the gene set may have an expression level value of 30 and is ranked as 4 and the next genes in the ordered list have expression level values of 35, 35, and 35, which are ranked as 5, 6, and 7, respectively, then these genes are all ranked as 6 (which is the average of 5, 6, and 7). In some embodiments, a gene ranking may include two or more genes having a common rank. In some embodiments, a gene ranking where a group of genes have a common rank may include consecutive ranking labels (e.g., 1, 2, 2, 2, 3, 4, 5, etc.). In some embodiments, a gene ranking where a group of genes have a common rank may include ranking labels that skip one or more values (e.g., 1, 2, 2, 2, 5, 6, 6, 8, etc.). In some embodiments, a group of genes having equal or substantially similar expression level values may be ranked according to the minimum rank or maximum rank in the group of genes.

To determine a particular characteristic of a biological sample (e.g., tissue of origin, cancer grade, tissue type, tissue subtype, such as e.g., PTCL subtype, viral status, such as e.g., HPV status), a selected set of genes may be used in ranking process 108 to obtain gene ranking(s) 110. As shown in FIG. 1, gene set 1 106a is used to obtain gene ranking 110a, which is then used to determine characteristic 1 114a. Similarly, gene set 2 106b is used to obtain gene ranking 110b, which is then used to determine characteristic 2 114b. For example, one set of genes may be used for determining tissue of origin for the biological sample and another set of genes may be used for determining cancer grade.

The number of genes in a set of genes may be in the range of 3 to 1,000 genes, 5 to 500 genes, 5 to 200 genes, 5 to 100 genes, 3 to 50 genes, 20 to 100 genes, 50 to 100 genes, 50 to 200 genes, 50 to 300 genes, 100 to 300 genes, and 50 to 500 genes. The set of genes may include at least 3 genes, at least 5 genes, at least 10 genes, or at least 20 genes. The set of genes may consist of 5-50 genes, 5-100 genes, 20-100 genes, 50-100 genes, 5-200 genes, 5-300 genes, 10-200 genes, 50-300 genes, 5-500 genes, or 50-500 genes.

A gene ranking and a statistical model may be used to determine a particular characteristic of the biological sample. In particular, a gene ranking may be used as an input to the statistical model and an output indicating the characteristic may be obtained. To obtain different characteristics, different gene sets and different statistical models are used where determining a particular characteristic involves using a specific gene set and a statistical model trained using training data indicating rankings of expression levels for some or all genes in the set of genes. For example, statistical model 112a is specific for determining characteristic 1 114a and was trained using training data indicating rankings of expression levels for some or all of the genes in gene set 1 106a. Similarly, statistical model 112b is specific for determining characteristic 2 114b and was trained using training data indicating rankings of expression levels for some or all of the genes in gene set 2 106b. For example, statistical model 112a and gene set 1 106a may be used for determining cancer grade for cells in the biological sample and statistical model 112b and gene set 2 106b may be used for determining tissue of origin for cells in the biological sample.

The training data may include rankings of expression levels associated with multiple samples, including samples associated with the characteristic being determined using the statistical model. For example, in embodiments where the statistical model is used to predict cancer grade, the training data may include rankings of expression levels associated with samples of multiple cancer grades (e.g., Grade 1, Grade 2, Grade 3). As another example, in embodiments where the statistical model is used to predict tissue of origin, the training data may include rankings of expression levels associated with samples from multiple tissue of origins (e.g., thyroid tissue, lymph node tissue, adrenal gland tissue, skin tissue, breast tissue, ovary tissue, prostate tissue, urothelial tissue, cervical tissue, esophagus tissue, brain tissue, soft tissue, connective tissue, head tissue, and neck tissue). As another example, in embodiments where the statistical model is used to predict HPV status, the training data may include rankings of expression levels associated with samples from both HPV-positive status and HPV-negative status. As another example, in embodiments where the statistical model is used to predict PTCL subtype, the training data may include rankings of expression levels associated with samples from different PTCL subtypes (e.g., adult T-cell leukemia/lymphoma (ATLL), angioimmunoblastic T-cell lymphoma (AITL), NK/T-cell lymphoma (NKTCL), anaplastic large cell lymphoma (ALCL), and cases belong to the Not Otherwise Specified (PTCL-NOS)).

It should be appreciated that a statistical model, such as statistical model 112a and statistical model 112b, may be used determining one or more characteristics for different biological samples obtained from different subjects. In some instances, the number of subjects that may use the same statistical model may be at least 50, 100, 200, 300, 500, 1,000, 2,000, 5,000, 10,000, or more. Using the statistical model for different subjects may ease analysis of expression data across the different subjects because the same data processing pipeline may be implemented for the individual subjects.

In some embodiments, ranking process 108 may only rank genes included in a set of genes such that not all of the genes in the expression data may obtain a rank or be included in a gene ranking. In such embodiments, the ranking is specific to the set of genes and may be used as an input to statistical model 112.

In some embodiments, ranking process 108 may involve ranking all the genes in expression data 102, such that each gene has a respective rank. In such embodiments, the ranking includes genes outside the set of genes. In some embodiments, an input to a statistical model may include the ranks, determined by ranking process 108, for the set of genes. In some embodiments, an input to a statistical model may include the ranking obtained by ranking process 108 and a statistical model may selectively use the ranks for the set of genes in the ranking as part of determining the one or more characteristics.

A statistical model may involve using one or more suitable machine learning algorithms, including one or more classifiers. Examples of classifiers that a statistical model may include are a gradient boosted decision tree classifier, a decision tree classifier, a gradient boosted classifier, a random forest classifier, a clustering-based classifier, a Bayesian classifier, a Bayesian network classifier, a neural network classifier, a kernel-based classifier, and a support vector machine classifier. In some embodiments, a statistical model may involve using a gradient boosted decision tree classifier. In some embodiments, a statistical model may involve using a decision tree classifier. In some embodiments, a statistical model may involve using a gradient boosted classifier. In some embodiments, a statistical model may involve using a random forest classifier. In some embodiments, a statistical model may involve using a clustering-based classifier. In some embodiments, a statistical model may involve using a Bayesian classifier. In some embodiments, a statistical model may involve using a Bayesian network classifier. In some embodiments, a statistical model may involve using a neural network classifier. In some embodiments, a statistical model may involve using a kernel-based classifier. In some embodiments, a statistical model may involve using a support vector machine classifier.

In some embodiments, a statistical model may perform binary classification of one or more features as an output of the statistical model. For example, such a statistical model may perform classification of one or more cancer grades (e.g., Grade 1, Grade 2, Grade 3) and an output of the statistical model may include a prediction for each of the one or more cancer grades indicating whether a biological sample is categorized as being a particular cancer grade.

In some embodiments, a statistical model may involve using a machine learning algorithm that implements of a gradient boosting framework, such as a gradient boosting decision tree (GBDT) and a gradient boosted regression tree (GBRT). An example of a machine learning algorithm that implements a gradient boosting decision tree is the Light-GBM package, which is further described in Guolin Ke, Qi Meng, Thomas Finley, Taifeng Wang, Wei Chen, Weidong Ma, Qiwei Ye and Tie-Yan Liu, LightGBM: A highly efficient gradient boosting decision tree, Advances in Neural Information Processing Systems, pp. 3149-3157, 2017, which is incorporated by reference herein in its entirety. An example of a machine learning algorithm that implements a gradient boosting framework is the XGBoost package, which is further described in Tianqi Chen and Carlos Guestrin. XGBoost: A scalable tree boosting system, In Proceedings of the 22Nd ACM SIGKDD International Conference on Knowledge Discovery and Data Mining, pp. 785-794, ACM, 2016, which is incorporated by reference herein in its entirety. An example of a machine learning algorithm that implements a gradient boosted regression tree is the pGBRT package, which is further described in Stephen Tyree, Kilian Q Weinberger, Kunal Agrawal, and Jennifer Paykin, Parallel boosted regression trees for web search ranking, In Proceedings of the 20th international conference on World wide web, pp. 387-396, ACM, 2011, which is incorporated by reference herein in its entirety.

A statistical model may be trained using multiple rankings of expression levels for some or all of the genes in the set of genes. Training data may include available expression data obtained through research organizations, including the National Cancer Institute (NCI) (e.g., Gene Expression Omnibus (GEO)), National Center for Biotechnology Information (NCBI) (e.g., Sequence Reach archive (SRA)), The Cancer Genome Atlas Program (TCGA), ArrayExpress Archive of Functional Genomics Data (by the European Molecular Biology Laboratory), and International Cancer Genome Consortium.

For example, a statistical model used for determining cancer grade for breast cancer may be trained using data from Series GSE96058 available through the NCI. As another example, a statistical model used for determining cancer grade for kidney clear cell cancer may be trained using data from The Cancer Genome Atlas Kidney Renal Clear Cell Carcinoma (TCGA-KIRC) data collection. As yet another example, a statistical model used for determining tissue of origin for DLBCL (e.g., ABC, GCB) may be trained using data from one or more of Series GSE117556, Leipzig Lymphoma data set (10.1186/s13073-019-0637-7), Series GSE31312, Series GSE10846, Series GSE87371, Series GSE11318, Series GSE32918, Series GSE23501, Lymphoma/Leukemia Molecular Profiling Project (LL-MPP), and Series GSE93984. As another example, a statistical model used for determining tissue of origin and histological information (e.g., tissue type) for cancer may be trained using data from The Cancer Genome Atlas Program (TCGAP).

One characteristic that may be determined using the techniques described herein is cancer grade for cells in the biological sample. Cancer grade may include Grade 1, Grade 2, Grade 3, Grade 4, and Grade 5. It should be appreciated that some cancer grading systems may include any suitable number of grades, or other scores, and that the techniques described herein may be used for determining any number of cancer grades regardless of the cancer grading system being implemented. For example, some cancer grading systems may have a number of cancer grades in the range of 1 to 10. Another characteristic is tissue of origin for cells in the biological sample. Tissue of origin may include lung tissue, pancreas tissue, stomach tissue, colon tissue, liver tissue, bladder tissue, kidney tissue, thyroid tissue, lymph node tissue, adrenal gland tissue, skin tissue, breast tissue, ovary tissue, prostate tissue, urothelial tissue, cervical tissue, esophagus tissue, brain tissue, soft tissue, connective tissue, head tissue, and neck tissue. In some instances, tissue of origin may refer to cell of origin. For example, where the subject has, is suspected of having, or is at risk of having Diffuse Large B-Cell Lymphoma (DLBCL), the tissue of origin is a cell of origin may include germinal center B-cell (GCB) and activated B-cell (ABC).

Another characteristic is histological information for cells in the biological sample. The histological information may correspond to a determination made by a physician (e.g., pathologist) using microscopy to visually inspect the biological sample. Histological information may include a tissue type. Examples of tissue types include adenocarcinoma, squamous cell carcinoma, carcinoma, cystadenocarcinoma, sarcoma, and glioma. In some embodiments, a statistical model may output a combination of tissue of origin and histological information. The combination of tissue of origin and histological information may include lung adenocarcinoma, lung squamous cell carcinoma, melanoma, breast carcinoma, colorectal adenocarcinoma, ovarian serous cystadenocarcinoma, phenochromocytoma, bladder urothelial carcinoma, cervical squamous cell carcinoma, glioblastoma multiforme, head and neck squamous cell carcinoma, kidney renal clear cell carcinoma, kidney renal papillary cell carcinoma, liver hepatocellular carcinoma, lung adenocarcinoma, pancreatic adenocarcinoma, paraganglioma, prostate adenocarcinoma, sarcoma, stomach adenocarcinoma, thyroid carcinoma, and uterine corpus endometrial carcinoma.

A characteristic (e.g., cancer grade, tissue of origin, PTCL subtype) may be output to a user, such as a physician or clinician, by displaying the characteristic to the user in a graphical user interface (GUI), including the characteristic in a report, sending an email to the user, and/or in any other suitable way. The subject's characteristic may be used for various clinical purposes, including assessing the efficacy of a treatment for cancer, identifying a treatment for the subject, administering a treatment for the subject, determining a prognosis for the subject, and/or evaluating suitability of the subject for participating in a clinical trial. In some embodiments, the subject's characteristic may be used in identifying a treatment for the subject. For example, in embodiments where a tissue of origin is determined for cells in the biological sample, the determined tissue of origin may be used to identify a treatment for the subject associated with treating cancers of the determined tissue of origin. As yet another example, in embodiments where a cancer grade is determined for cells in the biological sample, the determined cancer grade may be used to identify a treatment for the subject associated with treating cancers having the determined cancer grade. As yet another example, in embodiments where a PTCL subtype is determined for cells in the biological sample, the determined PTCL subtype may be used to identify a treatment for the subject suitable for treating lymphomas of the determined PTCL subtype. In turn, the identified treatment may be administered.

In some embodiments, the subject's characteristic may be used for administering a treatment for the subject. For example, in embodiments where a tissue of origin is determined for cells in the biological sample, a physician may administer a treatment for the subject associated with treating cancers of the determined tissue of origin. As yet another example, in embodiments where a cancer grade is determined for cells in the biological sample, a physician may administer a treatment for the subject associated with treating cancers having the determined cancer grade. As yet another example, in embodiments where a PTCL subtype is determined for cells in the biological sample, a physician may administer a treatment for the subject suitable for treating lymphomas of the determined PTCL subtype. Further examples where characteristics of a biological sample determined using the techniques described herein are used for administering a treatment are provided in the section titled "Methods of Treatment".

In some embodiments, the subject's characteristic may be used in determining a prognosis for the subject. In embodiments where the subject has, is suspected of having, or is at risk of having cancer (e.g., kidney cancer, clear cell kidney cancer, lymphoma, head and neck squamous cell carcinoma, lung adenocarcinoma), the determined subject's characteristic may be used to determine a prognosis for the subject. For example, in embodiments, where the subject's characteristic is cancer grade, the determined cancer grade (e.g., Grade 1, Grade 2, Grade 3) may be used to determine a prognosis for the subject. Further aspects relating to other applications where characteristics of abiological sample determined using the techniques described herein are provided in the section titled "Applications".

In some embodiments, the determined characteristic of the biological sample may include cancer grade for cells in the biological sample. In such embodiments, the set of genes used to obtain agene ranking may include genes associated with biological features, expression pathways, or otherwise associated with determining cancer grade. Some embodiments involve using agene set for determining cancer grade for breast cancer. Examples of genes that may be included in such agene set are listed in Table 1, below.

TABLE 1

| Grade Classifier for Breast Cancer | | |
|---|---|---|
| Gene | NCBI Gene ID | NCBI Accession Number(s) |
| UBE2C | 11065 | NM_001281741; NM_001281742; NM_007019; NM_181799; NM_181800; NM_181801 |
| MYBL2 | 4605 | NM_001278610; NM_002466 |
| PRAME | 23532 | NM_001291715; NM_001291716; NM_006115; NM_206953; NM_206954; NM_206955; NM_206956; NM_001291717; NM_001291719; NM_001318126; NM_001318127 |
| LMNB1 | 4001 | NM_005573 |
| CXCL9 | 4283 | NM_002416 |
| KPNA2 | 3838 | NM_001320611; NM_002266 |
| TPX2 | 22974 | NM_012112; XM_011528697; XM_011528699 |
| PLCH1 | 23007 | NM_001130960; NM_001130961; NM_014996; XM_011512561; XM_017005923; XM_017005926; NM_001349251; XM_011512560; XM_011512562; XM_011512565; XM_017005925; NM_001349250; NM_001349252; XM_005247238; XM_005247239; XM_011512567; XM_017005927; XM_011512566 |
| CCL18 | 6362 | NM_002988 |
| CDK1 | 983 | NM_001320918; NM_001786; NM_033379; XM_005270303 |
| MELK | 9833 | NM_001256685; NM_001256687; NM_001256688; NM_001256689; NM_001256690; NM_001256692; NM_001256693; NM_014791; XM_011518076; XM_011518077; XM_011518078; XM_011518079; XM_011518081; XM_011518082; XM_011518083; XM_011518084 |

TABLE 1-continued

Grade Classifier for Breast Cancer

| Gene | NCBI Gene ID | NCBI Accession Number(s) |
|---|---|---|
| CCNB2 | 9133 | NM_004701 |
| RRM2 | 6241 | NM_001034; NM_001165931 |
| CCNB1 | 891 | NM_031966 |
| NUSAP1 | 51203 | NM_001243142; NM_001243143; NM_001243144; NM_001301136; NM_016359; NM_018454; XM_005254430 |
| SLC7A5 | 8140 | NM_003486 |
| TYMS | 7298 | NM_001071 |
| GZMK | 3003 | NM_002104 |
| SQLE | 6713 | NM_003129 |
| C1orf106 | 55765 | NM_001142569; NM_018265; XM_011509754; XM_011509755 |
| CDC25B | 994 | NM_001287519; NM_001287520; NM_004358; NM_021872; NM_021873; NM_001287516; NM_001287522; NM_001287518; NM_001287524 |
| ATAD2 | 29028 | NM_014109 |
| QPRT | 23475 | NM_001318249; NM_001318250; NM_014298 |
| CCNA2 | 890 | NM_001237 |
| NEK2 | 4751 | NM_001204182; NM_001204183; NM_002497; XM_005273147 |
| IDO1 | 3620 | NM_002164 |
| NDC80 | 10403 | NM_006101 |
| ZWINT | 11130 | NM_001005413; NM_007057; NM_032997 |
| ABCA12 | 26154 | NM_015657; NM_173076 |
| TOP2A | 7153 | NM_001067 |
| TDO2 | 6999 | NM_005651 |
| S100A8 | 6279 | NM_001319197; NM_001319198; NM_001319201; NM_002964 |
| LAMP3 | 27074 | NM_014398 |
| MMP1 | 4312 | NM_002421 |
| GZMB | 3002 | NM_001346011; NM_004131 |
| BIRC5 | 332 | NM_001168; NM_001012271; NM_001012270 |
| TRIP13 | 9319 | NM_004237; XM_011514163 |
| RACGAP1 | 29127 | NM_001126103; NM_001126104; NM_001319999; NM_001320000; NM_001320001; NM_001320002; NM_001320003; NM_001320004; NM_013277; XM_006719359; XM_011538238; XM_017019220; NM_001320005; NM_001320006; NM_001320007 |
| ASPM | 259266 | NM_001206846; NM_018136 |
| ESRP1 | 54845 | NM_001122827; NM_001034915; NM_001122825; NM_001122826; NM_017697; XM_005250991 |
| MAD2L1 | 4085 | NM_002358 |
| CENPF | 1063 | NM_016343; XM_017000086 |
| CDC20 | 991 | NM_001255 |
| MCM4 | 4173 | NM_005914; NM_182746 |
| MKI67 | 4288 | NM_001145966; NM_002417 |
| PBK | 55872 | NM_001278945; NM_018492; NM_001363040 |
| CKS2 | 1164 | NM_001827 |
| KIF2C | 11004 | NM_001297655; NM_001297656; NM_001297657; NM_006845 |
| MRPL13 | 28998 | NM_014078 |
| TTK | 7272 | NM_001166691; NM_003318; XM_011536099; XM_011536100 |
| BUB1 | 699 | NM_001278617; NM_004336 |
| TK1 | 7083 | NM_001346663; NM_003258 |
| FOXM1 | 2305 | NM_001243088; NM_202003; NM_202002; NM_001243089; NM_021953 |
| CEP55 | 55165 | NM_001127182; NM_018131 |
| EZH2 | 2146 | NM_004456; XM_011515884; NM_001203247; NM_001203248; NM_001203249; NM_152998 |
| ECT2 | 1894 | NM_001258315; NM_001258316; NM_018098; XM_011512514 |
| PRC1 | 9055 | NM_003981; NM_001267580 |
| CENPU | 79682 | NM_024629 |
| CCNE2 | 9134 | NM_057749; XM_011517366; NM_004702; XM_017013959; XM_017013958; NM_057735 |
| AURKA | 6790 | NM_001323303; NM_001323304; NM_001323305; NM_003600; NM_198433; NM_198434; NM_198435; NM_198436; NM_198437; XM_017028035 |
| HMGB3 | 3149 | NM_001301228; NM_001301229; NM_001301231; NM_005342 |
| APOBEC3B | 9582 | NM_001270411; NM_004900 |
| LAGE3 | 8270 | NM_006014 |
| CDKN3 | 1033 | NM_001258 |
| DTL | 51514 | NM_001286229; NM_016448 |
| ATP6V1C1 | 528 | NM_001695 |
| KIAA0101 | 9768 | NM_001029989; NM_014736 |
| CD2 | 914 | NM_001328609; NM_001767 |
| KIF11 | 3832 | NM_004523 |
| KIF20A | 10112 | NM_005733 |
| CDCA8 | 55143 | NM_001256875; NM_018101 |
| NCAPG | 64151 | NM_022346 |
| CENPN | 55839 | NM_001100624; NM_001100625; NM_001270473; NM_001270474; NM_018455; XM_006721236; XM_017023456 |

TABLE 1-continued

Grade Classifier for Breast Cancer

| Gene | NCBI Gene ID | NCBI Accession Number(s) |
|---|---|---|
| MTFR1 | 9650 | NM_014637; NM_001145838 |
| MCM2 | 4171 | NM_004526 |
| DSCC1 | 79075 | NM_024094 |
| WDR19 | 57728 | NM_001317924; NM_025132 |
| SEMA3G | 56920 | NM_020163 |
| KCND3 | 3752 | NM_172198; XM_011541425; XM_006710632; XM_011541428; NM_001378969; NM_004980; NM_001378970; XM_006710629; XM_006710631; XM_017001245; XM_011541426; XM_011541427; XM_017001244 |
| SETBP1 | 26040 | NM_001130110; NM_015559 |
| KIF13B | 23303 | NM_015254 |
| NR4A2 | 4929 | NM_006186; XM_017004219; XM_017004220; XR_001738751; XR_001738752; NM_173173; NM_173171; XM_011511246; NM_173172; XR_427087; XM_005246621; XM_006712553 |
| NAV3 | 89795 | XM_017020172; NM_001024383; NM_014903; XM_011538944 |
| PDZRN3 | 23024 | NM_001303140; NM_001303142; NM_001303139; NM_001303141; NM_015009 |
| MAGI2 | 9863 | NM_001301128; NM_012301 |
| CACNA1D | 776 | XM_005265448; NM_000720; NM_001128839; NM_001128840 |
| STC2 | 8614 | NM_003714 |
| CHAD | 1101 | NM_001267 |
| PDGFD | 80310 | NM_025208; NM_033135 |
| ARMCX2 | 9823 | NM_001282231; NM_014782; NM_177949; XM_005278109; XM_005278110; XM_005278111; XM_005278113; XM_005278114; XM_005278115; XM_005278116; XM_005278117; XM_011531071; XM_011531072; XM_017029987; XM_017029988; XM_017029989; XM_017029990; XM_017029991; XM_017029992; XM_017029993; XM_017029994; XM_017029995; XM_017029996; XM_017029997 |
| FRY | 10129 | NM_023037 |
| AGTR1 | 185 | NM_032049; NM_004835; NM_031850; NM_000685; NM_009585 |
| MARCH8 | 220972 | NM_001002266; NM_145021; XM_011539495; XM_006717704; NM_001002265; XR_246519; NM_001282866; XM_005271804; XM_011539492 |
| ANG | 283 | NM_001097577; NM_001145 |
| ABAT | 18 | NM_000663; NM_001127448; NM_020686; NM_001386602; NM_001386609; NM_001386611; NM_001386612; NM_001386613; NM_001386605; NM_001386610; NM_001386616; NM_001386601; NM_001386603; NM_001386604; NM_001386606; NM_001386615; NM_001386600; NM_001386607; NM_001386614; NM_001386608 |
| THBD | 7056 | NM_000361 |
| RAI2 | 10742 | NM_001172739; NM_001172743; NM_021785; NM_001172732; XM_006724459; XM_006724460; XM_011545439; XM_011545440; XM_011545441 |
| HSPA2 | 3306 | NM_021979 |
| ERBB4 | 2066 | NM_001042599; NM_005235; XM_005246376; XM_005246377 |
| ECHDC2 | 55268 | NM_001198962; NM_001198961; NM_018281; XM_011541722; XM_011541726; XM_017001638; XM_024448158; XM_011541719; XM_011541723; XM_024448164; XR_002957011; NM_001319958; XR_002957012; XM_011541709; XM_024448153; XM_024448157; XR_002957014; XM_011541713; XM_024448163; XM_011541715; XM_017001640; XM_024448160; XM_011541720; XM_011541727; XM_024448159; XM_024448161; XR_002957013; XM_017001639; XM_024448152 |
| FST | 10468 | NM_013409; NM_006350 |
| EPHX2 | 2053 | NM_001256482; NM_001256483; NM_001256484; NM_001979 |
| FOSB | 2354 | NM_006732; XM_005258691; NM_001114171 |
| STARD13 | 90627 | NM_178006; NM_052851; NM_001243466; NM_001243474; NM_001243476; NM_178007 |
| ID4 | 3400 | NM_001546 |
| FAM129A | 116496 | NM_052966 |
| FCGBP | 8857 | NM_003890 |
| LAMA2 | 3908 | NM_000426; NM_001079823 |
| FGFR2 | 2263 | NM_001144919; NM_023029; NM_000141; NM_001144913; NM_001144914; NM_001144915; NM_001144916; NM_001144917; NM_001144918; NM_001320654; NM_001320658; NM_022970 |
| PTGER3 | 5733 | NM_198718; NM_001126044; NM_198714; NM_198715; NM_198716; NM_198717; NM_198719 |
| NME5 | 8382 | NM_003551 |
| LRRC17 | 10234 | NM_001031692; NM_005824; XM_005250108 |
| OSBPL1A | 114876 | NM_080597; NM_018030; XM_017025533; XR_002958162; XM_006722380; XM_017025530; NM_133268; XM_017025532; XR_001753139; NM_001242508; XM_006722382; XM_017025531 |
| ADRA2A | 150 | NM_000681 |
| LRP2 | 4036 | NM_004525 |
| C1orf115 | 79762 | NM_024709 |

TABLE 1-continued

Grade Classifier for Breast Cancer

| Gene | NCBI Gene ID | NCBI Accession Number(s) |
|---|---|---|
| COL4A5 | 1287 | NM_000495; NM_033380 |
| DIXDC1 | 85458 | NM_001037954; NM_001278542; NM_033425 |
| KIAA1324 | 57535 | NM_001267048; NM_020775; XM_011541825 |
| HPN | 3249 | NM_002151; NM_182983; XM_017026732; NM_001384133; XM_017026731; NM_001375441 |
| KLF4 | 9314 | NM_001314052; NM_004235 |
| SCUBE2 | 57758 | NM_001170690; NM_001330199; NM_020974 |
| FMO5 | 2330 | NM_001461; XM_005272946; XM_005272947; XM_005272948; XM_011509350; NM_001144829; NM_001144830; XM_006711245 |
| SORBS2 | 8470 | NM_001145670; NM_001145671; NM_001145672; NM_001145673; NM_001145674; NM_001270771; NM_003603; NM_021069; XM_005263312; XM_006714390; XM_017008771 |
| CARD10 | 29775 | NM_014550 |
| CITED2 | 10370 | NM_001168389; NM_001168388; NM_006079 |
| MUC1 | 4582 | NM_001204292; NM_001204286; NM_001204291; NM_001204285; NM_001204287; NM_001204288; NM_001204289; NM_001204290; NM_001204295; NM_001204297; NM_001204296; NM_001018016; NM_001018017; NM_001044390; NM_001044391; NM_001044392; NM_001044393; NM_001204293; NM_001204294; NM_002456 |
| BCL2 | 596 | NM_000633; NM_000657 |
| RGS5 | 8490 | NM_003617; NM_001195303; NM_001254748; NM_001254749 |
| CYBRD1 | 79901 | NM_001127383; NM_001256909; NM_024843 |
| OMD | 4958 | NM_005014 |
| IGFBP4 | 3487 | NM_001552 |
| LAMB2 | 3913 | NM_002292; XM_005265127 |
| DUSP4 | 1846 | NM_001394; NM_057158; XM_011544428 |
| PDLIM5 | 10611 | NM_006457; NM_001011515; NM_001011516; NM_001256429 |
| IRS2 | 8660 | NM_003749 |
| CX3CR1 | 1524 | NM_001171171; NM_001171172; NM_001171174; NM_001337 |

Some embodiments involve using a gene set for determining cancer grade for kidney clear cell cancer. Examples of genes that may be included in such agene set are listed in Table 2, below.

TABLE 2

Grade Classifier for Kidney Clear Cell

| Gene | NCBI Gene ID | NCBI Accession Number(s) |
|---|---|---|
| PLTP | 5360 | NM_001242920; NM_001242921; NM_006227; NM_182676 |
| C1S | 716 | NM_001346850; NM_001734; NM_201442; XM_005253760 |
| LY96 | 23643 | NM_001195797; NM_015398 |
| TSKU | 25987 | NM_001258210; NM_001318477; NM_001318478; NM_001318479; NM_015516 |
| TPST2 | 8459 | NM_001008566; NM_003595 |
| SERPINF1 | 5176 | NM_001329903; NM_002615 |
| SRPX2 | 27286 | NM_014467 |
| SAA1 | 6288 | NM_000331; NM_001178006; NM_199161 |
| CTHRC1 | 115908 | NM_001256099; NM_138455 |
| GFPT2 | 9945 | NM_005110 |
| CKAP4 | 10970 | NM_006825 |
| SERPINA3 | 12 | NM_001085 |
| CFH | 3075 | NM_001014975; NM_000186 |
| PLAU | 5328 | NM_002658; NM_001145031; NM_001319191 |
| BASP1 | 10409 | NM_001271606; NM_006317 |
| PTTG1 | 9232, 10744 | NM_001282382; NM_001282383; NM_004219 |
| MOCOS | 55034 | NM_017947 |
| LEF1 | 51176 | NM_001130713; NM_001130714; NM_001166119; NM_016269 |
| SLPI | 6590 | NM_003064 |
| PRAME | 23532 | NM_001291715; NM_001291716; NM_006115; NM_206953; NM_206954; NM_206955; NM_206956; NM_001291717; NM_001291719; NM_001318126; NM_001318127 |
| STEAP3 | 55240 | NM_001008410; NM_018234; XM_006712614; XM_006712615; XM_011511403; NM_138637; NM_182915 |
| LGALS2 | 3957 | NM_006498 |
| CD44 | 960 | NM_000610; NM_001001389; NM_001001390; NM_001001391; NM_001001392; NM_001202555; NM_001202556; NM_001202557; XM_011520488 |

TABLE 2-continued

Grade Classifier for Kidney Clear Cell

| Gene | NCBI Gene ID | NCBI Accession Number(s) |
|---|---|---|
| FLNC | 2318 | NM_001127487; NM_001458 |
| UBE2C | 11065 | NM_001281741; NM_001281742; NM_007019; NM_181799; NM_181800; NM_181801 |
| CTSK | 1513 | NM_000396 |
| SULF2 | 55959 | NM_001161841; NM_018837; NM_198596; NM_001387053; XM_006723830; NM_001387051; NM_001387055; NM_001387048; NM_001387049; NM_001387054; XM_011528914; NM_001387050; NM_001387052 |
| TMEM45A | 55076 | XM_005247569; NM_018004; XM_024453614; XM_024453615; NM_001363876 |
| FCGR1A | 2209, 100132417 | NM_000566 |
| PLOD2 | 5352 | NM_000935; NM_182943 |
| C19orf80 | 55908 | NM_018687 |
| PDGFRL | 5157 | NM_006207 |
| IGF2BP3 | 10643 | NM_006547 |
| SLC7A5 | 8140 | NM_003486 |
| PRRX1 | 5396 | NM_006902; NM_022716 |
| RARRES1 | 5918 | NM_002888; NM_206963 |
| LHFPL2 | 10184 | NM_005779; XM_006714515 |
| KDELR3 | 11015 | NM_006855; NM_016657 |
| TRIB3 | 57761 | NM_001301201; XM_017027989; NM_001301188; NM_001301190; NM_001301193; NM_001301196; NM_021158 |
| IL20RB | 53833 | NM_144717 |
| FBLN1 | 2192 | NM_001996; NM_006485; NM_006486; NM_006487 |
| KMO | 8564 | NM_003679 |
| C1R | 715 | NM_001733 |
| CYP1B1 | 1545 | NM_000104 |
| KIF2A | 3796 | NM_001098511; NM_001243952; NM_004520 |
| PLAUR | 5329 | NM_001301037; NM_001005376; NM_001005377; NM_002659 |
| CKS2 | 1164 | NM_001827 |
| CDCP1 | 64866 | NM_022842; NM_178181 |
| SFRP4 | 6424 | NM_003014 |
| HAMP | 57817 | NM_021175 |
| MMP9 | 4318 | NM_004994 |
| SLC3A1 | 6519 | NM_000341; XM_011533047 |
| NAT8 | 9027, 51471 | NM_003960 |
| FRMD3 | 257019 | NM_001244959; NM_001244960; NM_001244961; NM_001244962; NM_174938 |
| NPR3 | 4883 | NM_000908; NM_001204375; NM_001204376 |
| NAT8B | 9027, 51471 | NM_016347 |
| BBOX1 | 8424 | NM_003986; NM_001376258; NM_001376259; NM_001376260; NM_001376261; XM_011520402 |
| SLC5A1 | 6523 | NM_000343; NM_001256314 |
| GBA3 | 57733 | NM_020973; NM_001128432; NM_001277225 |
| EMCN | 51705 | NM_016242; XM_011532024; NM_001159694 |
| SLC47A1 | 55244 | NM_018242 |
| AQP1 | 358 | NM_198098 |
| PCK1 | 5105 | NM_002591 |
| UGT2A3 | 79799 | NM_024743 |
| BHMT | 635 | NM_001713 |
| FMO1 | 2326 | NM_001282693; NM_002021; NM_001282692; NM_001282694 |
| ACAA2 | 10449, 648603 | NM_006111 |
| SLC5A8 | 160728 | NM_145913 |
| SLC16A9 | 220963 | NM_001323981; NM_194298; XM_017015884 |
| TSPAN18 | 90139 | NM_130783; XM_006718373; XM_011520459 |
| SLC17A3 | 10786 | NM_006632; NM_001098486 |
| STK32B | 55351 | NM_001306082; NM_018401 |
| MAP7 | 9053 | NM_001198609; NM_001198608; NM_001388350; NM_001198614; NM_001198617; NM_001198331; NM_001388336; NM_001388340; NM_001388344; NM_001388345; NM_001388347; NM_001388348; NM_001388349; XM_011536246; NM_001198616; NM_001388330; NM_001388335; NM_003980; XM_011536243; NM_001388341; NM_001388342; NM_001388343; NM_001198611; NM_001388338; NM_001388346; NM_001198615; NM_001198618; NM_001198619; NM_001388329; NM_001388334; NM_001388339; NM_001388328; NM_001388332; NM_001388337; NM_001388351; NM_001388352; NM_001388353 |
| MYLIP | 29116 | XM_005249033; NM_013262 |
| SLC22A12 | 116085 | NM_001276326; NM_001276327; NM_144585; NM_153378 |
| LRP2 | 4036 | NM_004525 |
| CD34 | 947 | NM_001025109; NM_001773 |
| PODXL | 5420 | NM_001018111; NM_005397 |

TABLE 2-continued

Grade Classifier for Kidney Clear Cell

| Gene | NCBI Gene ID | NCBI Accession Number(s) |
|---|---|---|
| ZBTB42 | 100128927 | NM_001137601; NM_001370342 |
| TEK | 7010 | NM_000459; NM_001290077; NM_001290078 |
| FBP1 | 2203 | NM_000507; NM_001127628 |
| BCL2 | 596 | NM_000633; NM_000657 |

In some embodiments, the determined characteristic of the biological sample may include tissue of origin for cells in the biological sample. In such embodiments, the set of genes used to obtain agene ranking may include genes associated with biological features, expression pathways, or otherwise associated with determining tissue of origin.

Some embodiments involve using agene set for predicting tissue of origin for Diffuse Large B-Cell Lymphoma (DLBCL), such as germinal center B-cell (GCB) and activated B-cell (ABC). Examples of genes that may be included in such agene set are listed in Table 3, below.

TABLE 3

Tissue of origin classifier for DLBCL

| Gene | NCBI Gene ID | NCBI Accession Number(s) |
|---|---|---|
| ITPKB | 3707 | NM_002221; NM_001388404; XM_017001211 |
| MYBL1 | 4603 | NM_001080416; NM_001144755; NM_001294282 |
| LMO2 | 4005 | NM_001142315; NM_001142316; NM_005574; XM_005252921; XM_017017727; XM_017017728; XM_017017729; XM_017017730; XM_017017731; XM_017017732; XM_017017733 |
| BATF | 10538 | NM_006399 |
| IRF4 | 3662 | NM_001195286; NM_002460 |
| LRMP | 4033 | NM_001204126; NM_001204127; NM_006152; NM_001366543; NM_001366544; NM_001366546; NM_001366549; NM_001366545; NR_159367; NR_159368; NM_001366541; NR_159366; NM_001366540; NM_001366542; NM_001366547; NR_159369; NM_001366548 |
| CCND2 | 894 | NM_001759 |
| SLA | 6503 | NM_001045556; NM_001045557; NM_001282964; NM_001282965; NM_006748; XM_017013739 |
| SP140 | 11262 | NM_001278452; NM_001005176; NM_001278451; NM_001278453; NM_007237 |
| PIM1 | 5292 | NM_002648; NM_001243186 |
| CSTB | 1476 | NM_000100 |
| BCL2 | 596 | NM_000633; NM_000657 |
| TCF4 | 6925 | NM_003199; XM_017025956; NM_001348220; NM_001369581; NM_001369582; NM_001369585; XM_005266749; XM_005266761; XM_017025950; NM_001083962; NM_001243235; NM_001348211; NM_001348214; NM_001369583; XM_017025951; XM_024451241; NM_001369578; NM_001243227; NM_001243231; NM_001348218; NM_001369571; NM_001369575; NM_001369586; XM_005266755; NM_006722538; XM_017025954; NM_001243230; NM_001243233; NM_001306207; NM_001306208; NM_001330604; NM_001348212; XM_005266752; NM_001243236; NM_001330605; NM_001348213; NM_001348215; NM_001348217; NM_001348219; NM_001369577; NM_001369580; XM_017025952; XM_017025953; NM_001243226; NM_001348216; NM_001369567; NM_001369569; NM_001369573; NM_001369574; NM_001369579; NM_001243228; NM_001243232; NM_001243234; NM_001369568; NM_001369570; NM_001369572; NM_001369576; NM_001369584 |
| P2RX5 | 5026 | NM_001204519; NM_001204520; NM_002561; NM_175080 |
| SPINK2 | 6691 | NM_021114; NM_001271722; NM_001271720; NM_001271718; NM_001271721 |
| VCL | 7414 | NM_003373; NM_014000 |
| PTPN1 | 5770 | NM_002827; NM_001278618 |
| REL | 5966 | NM_001291746; NM_002908 |
| FUT8 | 2530 | NM_004480; NM_178155; NM_178156 |
| RPL21 | 6144 | NM_000982 |
| PRKCB1 | 5579 | NM_002738; NM_212535 |
| CSNK1E | 1454 | NM_001289912; NM_001894; NM_152221 |
| GPR18 | 2841 | NM_001098200; NM_005292; XM_006719946 |
| IGHM | 3500, 3492, 28396, 3502, 3507, 28450, 28452 | NG_001019.6 |

TABLE 3-continued

Tissue of origin classifier for DLBCL

| Gene | NCBI Gene ID | NCBI Accession Number(s) |
|---|---|---|
| ACP1 | 52 | NM_004300; NM_007099 |
| SPIB | 6689 | NM_003121; NM_001243998; NM_001243999; NM_001244000 |
| HLA-DQA1 | 3117, 731682, 100133678 | NM_002122 |
| KRT8 | 390601, 149501, 3856 | NM_001256293; NM_002273 |
| FAM3C | 10447 | NM_001040020; NM_014888; XM_011515736; XM_011515737 |
| HLA-DMB | 3109 | NM_002118 |
| GOT2 | 2806 | NM_001286220; NM_002080 |
| PIM2 | 11040 | NM_006875 |
| PLEK | 5341 | NM_002664 |

Figure 2:
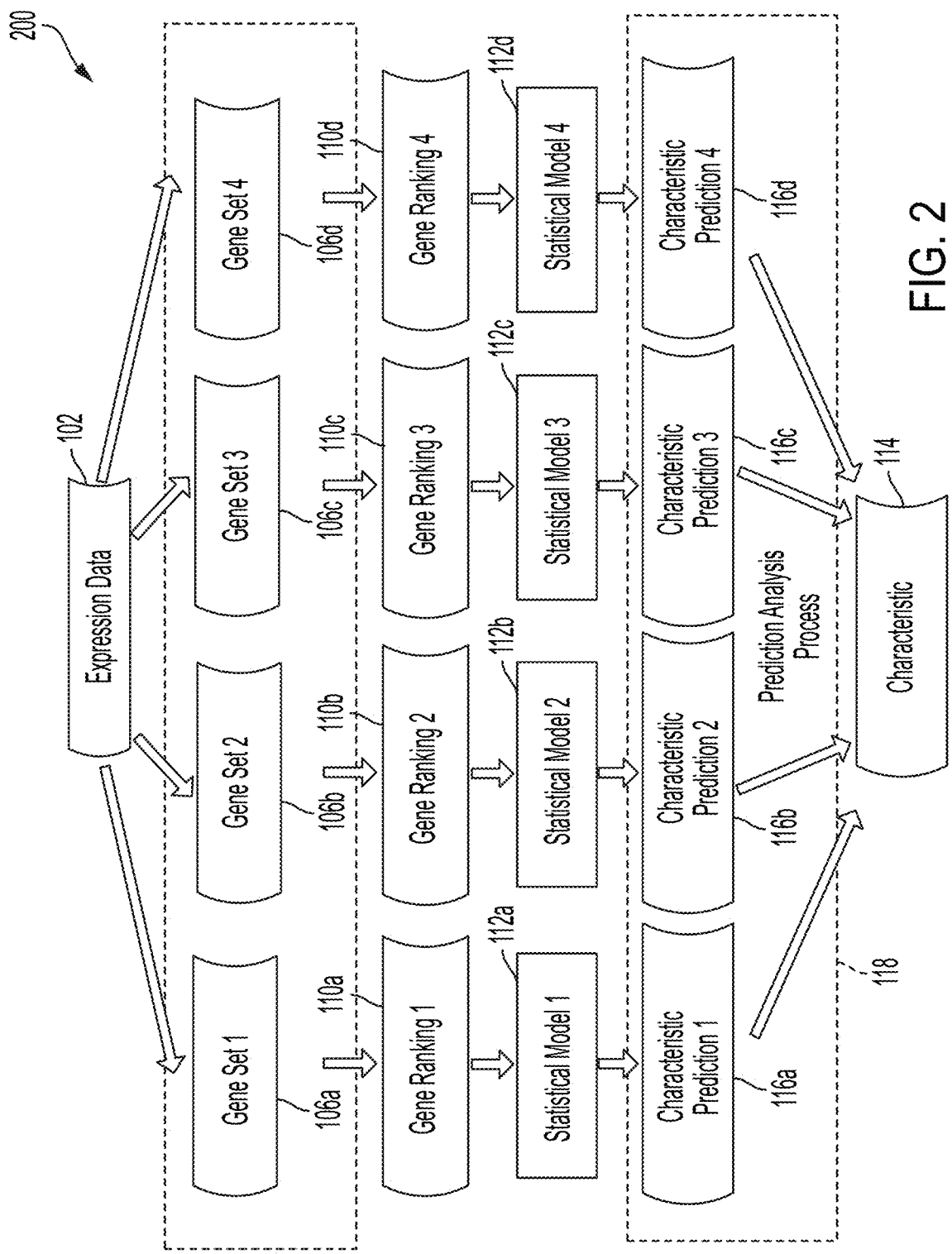
FIG. 2 is a diagram of an illustrative process for determining a characteristic of a biological sample based on using multiple statistical models to obtain multiple characteristic predictions and aggregating the characteristic predictions using the machine learning techniques described herein.

Some embodiments may involve determining a characteristic of a biological sample by using different gene sets and statistical models corresponding to the different gene sets to obtain characteristic predictions, which are used to determine the characteristic. FIG. 2 is a diagram of an illustrative processing pipeline 200 for determining a characteristic of a biological sample, which may include ranking genes based on their gene expression levels and using the rankings and statistical models to determine the characteristic, in accordance with some embodiments of the technology described herein. Processing pipeline 200 may be performed on any suitable computing device(s) (e.g., a single computing device, multiple computing devices co-located in a single physical location or located in multiple physical locations remote from one another, one or more computing devices part of a cloud computing system, etc.), as aspects of the technology described herein are not limited in this respect. In some embodiments, processing pipeline 200 may be performed by a desktop computer, a laptop computer, a mobile computing device. In some embodiments, processing pipeline 200 may be performed within one or more computing devices that are part of a cloud computing environment.

In some embodiments, gene expression data 102 is used to rank genes in different sets of genes based on their expression levels in gene expression data 102 to obtain multiple gene rankings. For example, a gene ranking may be obtained for each gene set and the gene ranking may be input to a statistical model trained using training data indicating rankings of expression levels for some or all genes in the gene set. As shown in FIG. 2, ranking process 108 may involve using expression data 102 to rank genes in different gene sets, including Gene Set 1 106a, Gene Set 2 106b, Gene Set 3 106c, and Gene Set 4 106d, to obtain Gene Ranking 1 110a, Gene Ranking 2 110b, Gene Ranking 3 110c, and Gene Ranking 4 110d, respectively. Ranking process 108 may involve ranking genes in a set of genes based on numerical values of their expression levels. Different gene rankings may be obtained by ranking expression levels for different gene sets, and each gene ranking may be input to its respective statistical model to obtain a characteristic prediction. As shown in FIG. 2, Gene Ranking 1 110a, Gene Ranking 2 110b, Gene Ranking 3 110c, and Gene Ranking 4 110d is provided as input to Statistical Model 1 112a, Statistical Model 2 112b, Statistical Model 3 112c, and Statistical Model 4 112d, respectively.

In some embodiments, the different statistical models and their respective gene sets may correspond to a particular characteristic of the biological sample. In such embodiments, each of the statistical models may output a prediction of the biological sample having a particular characteristic. In some instances, the prediction output by a statistical model may include a probability of the biological sample having the characteristic.

As shown in FIG. 2, Statistical Model 1 112a outputs Characteristic Prediction 1 116a, Statistical Model 2 112b outputs Characteristic Prediction 2 116b, Statistical Model 3 112c outputs Characteristic Prediction 3 116c, and Characteristic Prediction 4 116d outputs Characteristic Prediction 4 116d. The predictions output by the different statistical models may be analyzed using prediction analysis process 118 to determine characteristic 114 for the biological sample. Prediction analysis process 118 may involve aggregating the different predictions and selecting a particular characteristic for the biological sample from among the different characteristic predictions. In some embodiments, a characteristic prediction may include a probability that the biological sample has the particular characteristic. In such embodiments, prediction analysis process 118 may involve aggregating the probabilities for the different characteristic predictions and selecting a characteristic based on the probabilities. In some embodiments, selecting the characteristic may involve selecting the characteristic having the highest probability as being characteristic 114.

Although four gene sets and four statistical models are shown in FIG. 2, it should be appreciated that any suitable number of gene sets and corresponding statistical models may be implemented using the techniques described above in determining characteristic predictions and aggregating the characteristic predictions to obtain a characteristic of a biological sample. In some embodiments, the number of gene sets and corresponding statistical models may be in the range of 3 to 100, 3 to 70, 3 to 50, 3 to 40, 3 to 30, 5 to 50, 10 to 60, or 10 to 70.

In some embodiments, the number of gene sets and corresponding statistical models is equal to or less than the number of classes for the characteristic being predicted using processing pipeline 200. For instance, in embodiments where the characteristic being predicted is tissue of origin, the number of classes may correspond to the different types of tissue that can be determined using processing pipeline 200. Such embodiments may involve a different gene set and corresponding statistical model for each type of tissue. For example, Gene Set 1 106a and Statistical Model 1 112a may be used for generating a prediction of the biological sample being lung tissue (as Characteristic Prediction 1 116a), Gene Set 2 106b and Statistical Model 2 112b may be used for generating a prediction of the biological sample being stomach tissue (as Characteristic Prediction 2 116b), Gene Set 3 106c and Statistical Model 3 112c may be used for generating a prediction of the biological sample being liver tissue (as Characteristic Prediction 3 116c), and Gene Set 4 106d and Statistical Model 4 112d may be used for generating a prediction of the biological sample being bladder tissue (as Characteristic Prediction 4). It should be appreciated that additional gene sets and their corresponding statistical models may be implemented for different tissue types. In some embodiments, there may be 21 gene sets and corresponding statistical models, allowing processing pipeline 200 to predict 21 types of tissue.

Figure 3:
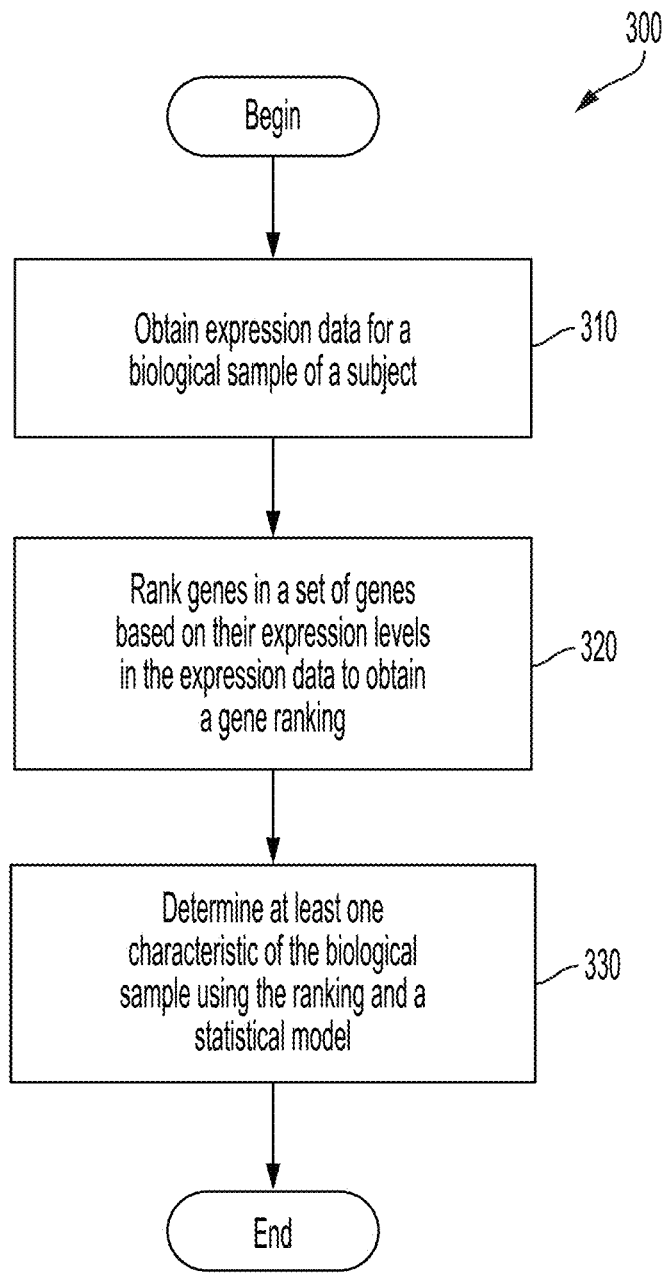
FIG. 3 is a flow chart of an illustrative process for determining a characteristic of a biological sample using a gene ranking and a statistical model, using the machine learning techniques described herein.

FIG. 3 is a flow chart of an illustrative process 300 for determining one or more characteristics of a biological sample using a gene ranking and a statistical model, in accordance with some embodiments of the technology described herein. Process 300 may be performed on any suitable computing device(s) (e.g., a single computing device, multiple computing devices co-located in a single physical location or located in multiple physical locations remote from one another, one or more computing devices part of a cloud computing system, etc.), as aspects of the technology described herein are not limited in this respect. In some embodiments, ranking process 108 and statistical model 112 may perform some or all of process 300 to determine one or more characteristics, such as characteristic(s) 114.

Process 300 begins at act 310, where expression data for a biological sample of a subject is obtained. In some embodiments, the expression data may be obtained using a gene expression microarray. In some embodiments, the expression data may be obtained by performing next generation sequencing. Some embodiments involve performing a sequencing process of the biological sample (e.g., a gene expression microarray, next generation sequencing) prior to obtaining expression data 102. In some embodiments, obtaining gene expression data 102 may involve obtaining gene expression data 102 in silico, such as by accessing, using a computing device, expression data (e.g., expression data that has been previously obtained from a biological sample) in one or more data stores, receiving the expression data from one or more other device, or any other way. In some embodiments, obtaining gene expression data 102 may involve analyzing a biological sample (in vitro) and accessing (e.g., by a computing device, a processor) the expression data. Further aspects relating to obtaining expression data are provided in the section titled "Obtaining Expression Data".

Next, process 300 proceeds to act 320, where genes in a set of genes are ranked based on their expression levels in the expression data to obtain a gene ranking, such as by using ranking process 108. The expression data may include values, each representing an expression level for a gene in the set of genes, and determining the gene ranking may involve determining a relative rank for each gene in the set of genes based on the values.

In some embodiments, the subject has, is suspected of having, or is at risk of having breast cancer. The set of genes may be selected from the group of genes listed in Table 1. The set of genes may include at least 3, 5, 10, or 20 genes selected from the group of genes listed in Table 1. In some embodiments, the set of genes may include all the genes listed in Table 1. In some embodiments, the set of genes may include 3-100 genes, 5-100 genes, 20-100 genes, 50-100 genes, 80-100 genes listed in Table 1. In some embodiments, the set of genes may include 100 or fewer genes, 80 or fewer genes, 50 or fewer genes, 20 or fewer genes listed in Table 1.

In some embodiments, the subject has, is suspected of having, or is at risk of having clear cell kidney cancer. The set of genes may be selected from the group of genes listed in Table 2. The set of genes may include at least 3, 5, 10, or 20 genes selected from the group of genes listed in Table 2. In some embodiments, the set of genes may include all the genes listed in Table 2. In some embodiments, the set of genes may include 3-80 genes, 5-80 genes, 20-80 genes, 50-80 genes, 70-80 genes listed in Table 2. In some embodiments, the set of genes may include 80 or fewer genes, 50 or fewer genes, 20 or fewer genes listed in Table 2.

In some embodiments, the subject has, is suspected of having, or is at risk of having lymphoma. The set of genes may be selected from the group of genes listed in Table 3. The set of genes may include at least 3, 5, 10, or 20 genes selected from the group of genes listed in Table 3. In some embodiments, the set of genes may include all the genes listed in Table 3. In some embodiments, the set of genes may include 3-25 genes, 5-25 genes, 10-25 genes, 20-25 genes listed in Table 3. In some embodiments, the set of genes may include 25 or fewer genes, 20 or fewer genes, 15 or fewer genes, 10 or fewer genes listed in Table 3.

Next process 300 proceeds to act 320, where one or more characteristics of the biological sample is determined using the gene ranking and a statistical model, such as statistical model 112. In some embodiments, a characteristic determined by process 300 may include cancer grade for cells in the biological sample. In some embodiments, a characteristic determined by process 300 may include tissue of origin for cells in the biological sample. The statistical model may be trained using rankings of expression levels for one or more genes in the set of genes. In some embodiments, the gene ranking may be used as an input to the statistical model to obtain an output indicating the one or more characteristics. In some embodiments, the statistical model comprises a classifier selected from the group consisting of: a gradient boosted decision tree classifier, a decision tree classifier, a gradient boosted classifier, a random forest classifier, a clustering-based classifier, a Bayesian classifier, a Bayesian network classifier, a neural network classifier, a kernel-based classifier, and a support vector machine classifier.

In some embodiments, process 300 may include ranking genes in a second set of genes based on their expression levels in the expression data to obtain a second gene ranking. The second gene ranking and a second statistical model may be used to determine one or more second characteristics of the biological sample. The second statistical model may be trained using second training data indicating rankings of expression levels for some or all of the genes in the second set of genes. The one or more second characteristics of the biological sample may be different than a characteristic determined by act 330. For example, in some embodiments, a characteristic determined by act 330 may include cancer grade for cells in the biological sample and the second characteristic may include tissue of origin for cells in the biological sample.

In some embodiments, process 300 may include outputting the one or more characteristics to a user (e.g., physician), such as by displaying the one or more characteristics to the user on a graphical user interface (GUI), including the one or more characteristics in a report, sending an email to the user, and in any other suitable way.

In some embodiments, process 300 may include administering a treatment to the subject based on the determined one or more characteristics of the biological sample. For example, in embodiments where tissue of origin is determined for cells in the biological sample, a physician may administer a treatment for the subject associated with treating cancers of the determined tissue of origin. As yet another example, in embodiments where cancer grade is determined for cells in the biological sample, a physician may administer a treatment for the subject associated with treating cancers having the determined cancer grade. Further examples where characteristics of a biological sample determined using the techniques described herein are used for administering a treatment are provided in the section titled "Methods of Treatment".

In some embodiments, process 300 may include identifying a treatment for the subject based on the determined characteristic(s) of the biological sample. For example, in embodiments where tissue of origin is determined for cells in the biological sample, the determined tissue of origin may be used to identify a treatment for the subject associated with treating cancers of the determined tissue of origin. As yet another example, in embodiments where cancer grade is determined for cells in the biological sample, the determined cancer grade may be used to identify a treatment for the subject associated with treating cancers having the determined cancer grade.

In some embodiments, process 300 may include determining a prognosis for the subject based on the determined one or more characteristics of the biological sample. For example, in embodiments where tissue of origin is determined for cells in the biological sample, the determined tissue of origin may be used to determine a prognosis for the subject associated with treating cancers of the determined tissue of origin. As yet another example, in embodiments where cancer grade is determined for cells in the biological sample, the determined cancer grade may be used to determine a prognosis for the subject associated with treating cancers having the determined cancer grade. Further aspects relating to other applications where characteristics of a biological sample determined using the techniques described herein are provided in the section titled "Applications".

Figure 4:
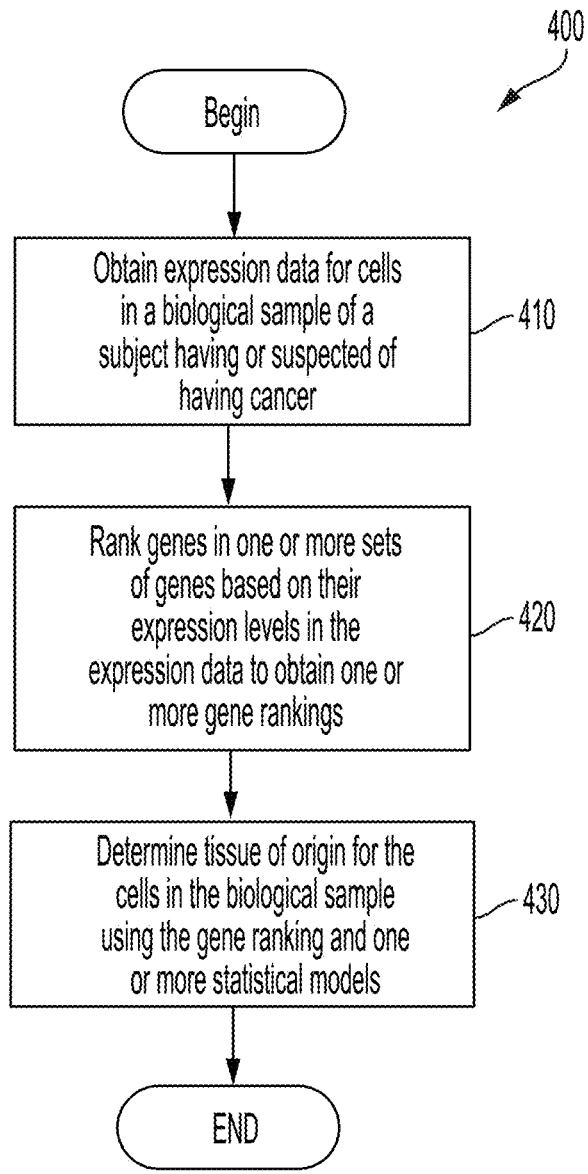
FIG. 4 is a flow chart of an illustrative process for determining tissue of origin for cells in a biological sample using the machine learning techniques described herein.

FIG. 4 is a flow chart of an illustrative process 400 for determining tissue of origin for cells in a biological sample, in accordance with some embodiments of the technology described herein. Process 400 may be performed on any suitable computing device(s) (e.g., a single computing device, multiple computing devices co-located in a single physical location or located in multiple physical locations remote from one another, one or more computing devices part of a cloud computing system, etc.), as aspects of the technology described herein are not limited in this respect. In some embodiments, ranking process 108 and statistical model 112 may perform some or all of process 400 to determine a tissue of origin.

Process 400 begins at act 410, where expression data for cells in a biological sample of a subject having, suspected of having, or is at risk of having cancer is obtained. In some embodiments, the expression data was obtained using a gene expression microarray. In some embodiments, the expression data was obtained by performing next generation sequencing. Some embodiments involve performing a sequencing process of the biological sample (e.g., a gene expression microarray, next generation sequencing) prior to obtaining expression data 102. In some embodiments, obtaining gene expression data 102 may involve obtaining gene expression data 102 in silico, such as by accessing, using a computing device, expression data (e.g., expression data that has been previously obtained from a biological sample) in one or more data stores, receiving the expression data from one or more other device, or any other way. In some embodiments, obtaining gene expression data 102 may involve analyzing a biological sample (in vitro) and accessing (e.g., by a computing device, processor) the expression data. Further aspects relating to obtaining expression data are provided in the section titled "Obtaining Expression Data".

Next, process 400 proceeds to act 420, where genes in one or more sets of genes are ranked based on their expression levels in the expression data to obtain one or more gene rankings, such as by using ranking process 108. The expression data may include values, each representing an expression level for a gene in the one or more sets of genes, and determining a gene ranking may involve determining a relative rank for each gene in a set of genes based on the values.

In some embodiments, the subject has, is suspected of having, or is at risk of having breast cancer. The set of genes may be selected from the group of genes listed in Table 1. The set of genes may include at least 3, 5, 10, or 20 genes selected from the group of genes listed in Table 1. The set of genes may consist of 5-100 genes, 10-200 genes, 20-100 genes, or 50-100 genes. In some embodiments, the set of genes may include all the genes listed in Table 1. In some embodiments, the set of genes may include 3-100 genes, 5-100 genes, 20-100 genes, 50-100 genes, 80-100 genes listed in Table 1. In some embodiments, the set of genes may include 100 or fewer genes, 80 or fewer genes, 50 or fewer genes, 20 or fewer genes listed in Table 1.

Next, process 400 proceeds to act 430, where tissue of origin for some or all of the cells in the biological sample is determined using the one or more gene rankings and one or more statistical models, such as statistical model 112. A statistical model may be trained using rankings of expression levels for some or all genes in a set of genes. Each of the gene rankings may be obtained based on respective expression levels for the one or more genes in the set of genes. In some embodiments, one or more gene rankings may be used as an input to the one or more statistical models to obtain an output indicating the tissue of origin. The tissue of origin may include lung tissue, pancreas tissue, stomach tissue, colon tissue, liver tissue, bladder tissue, kidney tissue, thyroid tissue, lymph node tissue, adrenal gland tissue, skin tissue, breast tissue, ovary tissue, prostate tissue, urothelial tissue, cervical tissue, esophagus tissue, brain tissue, soft tissue, connective tissue, head tissue, and neck tissue.

In some embodiments, the one or more statistical models comprises one or more classifiers selected from the group consisting of: a statistical model may include are a gradient boosted decision tree classifier, a decision tree classifier, a gradient boosted classifier, a random forest classifier, a clustering-based classifier, a Bayesian classifier, a Bayesian network classifier, a neural network classifier, a kernel-based classifier, and a support vector machine classifier.

In some embodiments, process 400 may further include determining, using the gene ranking and the one or more statistical models, histological information (e.g., tissue type) for at least some of the cells in the biological sample. The histological information may include adenocarcinoma, squamous cell carcinoma, carcinoma, cystadenocarcinoma, sarcoma, and glioma. A combination of the tissue of origin and the histological information may be selected from the group consisting of lung adenocarcinoma, lung squamous cell carcinoma, melanoma, breast carcinoma, colorectal adenocarcinoma, ovarian serous cystadenocarcinoma, phenochromocytoma, bladder urothelial carcinoma, cervical squamous cell carcinoma, glioblastoma multiforme, head squamous cell carcinoma, neck squamous cell carcinoma, kidney renal clear cell carcinoma, kidney renal papillary cell carcinoma, liver hepatocellular carcinoma, lung adenocarcinoma, pancreatic adenocarcinoma, paraganglioma, prostate adenocarcinoma, sarcoma, stomach adenocarcinoma, thyroid carcinoma, and uterine corpus endometrial carcinoma.

Figure 5:
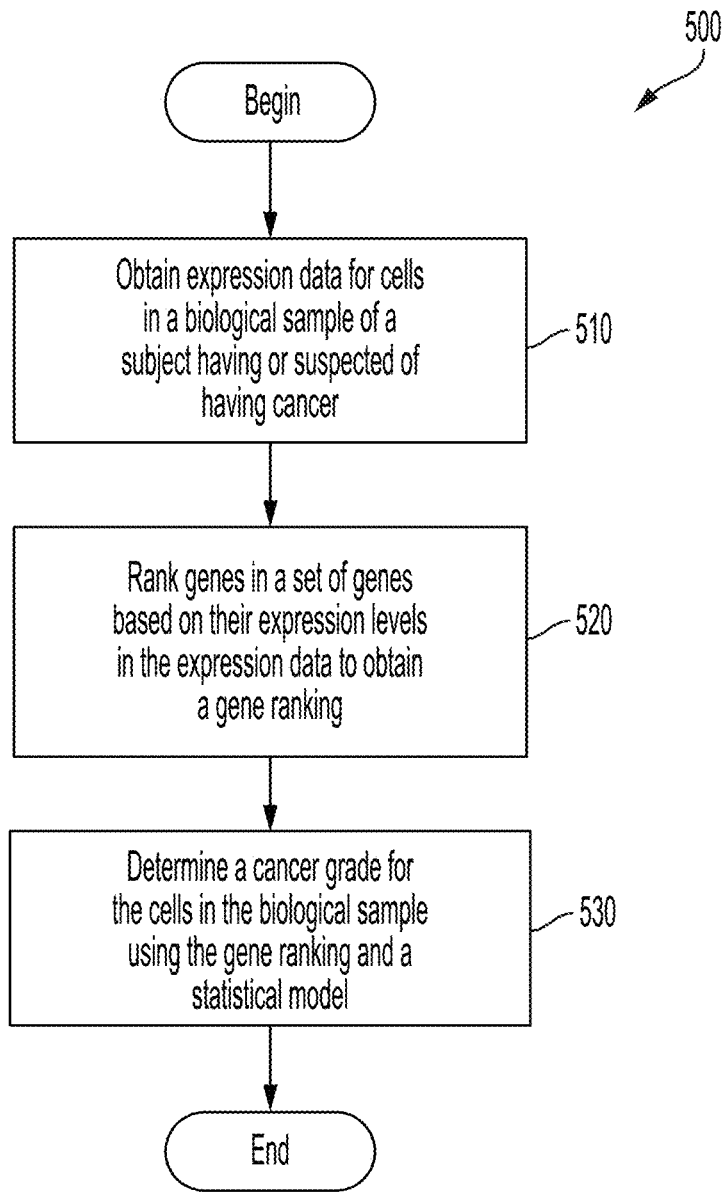
FIG. 5 is a flow chart of an illustrative process for determining cancer grade for cells in a biological sample using the machine learning techniques described herein.

FIG. 5 is a flow chart of an illustrative process 500 for determining a cancer grade for cells in a biological sample, in accordance with some embodiments of the technology described herein. Process 500 may be performed on any suitable computing device(s) (e.g., a single computing device, multiple computing devices co-located in a single physical location or located in multiple physical locations remote from one another, one or more computing devices part of a cloud computing system, etc.), as aspects of the technology described herein are not limited in this respect. In some embodiments, ranking process 108 and statistical model 112 may perform some or all of process 500 to determine a cancer grade.

Process 500 begins at act 510, where expression data for cells in a biological sample of a subject having, suspected of having, or is at risk of having cancer is obtained. In some embodiments, the expression data was obtained using a gene expression microarray. In some embodiments, the expression data was obtained by performing next generation sequencing. Some embodiments involve performing a sequencing process of the biological sample (e.g., a gene expression microarray, next generation sequencing) prior to obtaining expression data 102. In some embodiments, obtaining gene expression data 102 may involve obtaining gene expression data 102 in silico, such as by accessing, using a computing device, expression data (e.g., expression data that has been previously obtained from a biological sample) in one or more data stores, receiving the expression data from one or more other device, or any other way. In some embodiments, obtaining gene expression data 102 may involve analyzing a biological sample (in vitro) and accessing (e.g., by a computing device, processor) the expression data. Further aspects relating to obtaining expression data are provided in the section titled "Obtaining Expression Data".

Next, process 500 proceeds to act 520, where genes in a set of genes are ranked based on their expression levels in the expression data to obtain a gene ranking, such as by using ranking process 108. The expression data may include values, each representing an expression level for a gene in the set of genes, and determining the gene ranking may involve determining a relative rank for each gene in the set of genes based on the values. The set of genes may consist of 5-500 genes, 5-200 genes, 50-500 genes, or 50-300 genes.

In some embodiments, the subject has, is suspected of having, or is at risk of having breast cancer. The set of genes may be selected from the group of genes listed in Table 1. The set of genes may include at least 3, 5, 10, or 20 genes selected from the group of genes listed in Table 1. In some embodiments, the set of genes may include all the genes listed in Table 1. In some embodiments, the set of genes may include 3-100 genes, 5-100 genes, 20-100 genes, 50-100 genes, 80-100 genes listed in Table 1. In some embodiments, the set of genes may include 100 or fewer genes, 80 or fewer genes, 50 or fewer genes, 20 or fewer genes listed in Table 1.

In some embodiments, the subject has, is suspected of having, or is at risk of having clear cell kidney cancer. The set of genes may be selected from the group of genes listed in Table 2. The set of genes may include at least 3, 5, 10, or 20 genes selected from the group of genes listed in Table 2. In some embodiments, the set of genes may include 3-80 genes, 5-80 genes, 20-80 genes, 50-80 genes, 70-80 genes listed in Table 2. In some embodiments, the set of genes may include 80 or fewer genes, 50 or fewer genes, 20 or fewer genes listed in Table 2.

Next, process 500 proceeds to act 530, where cancer grade for the cells in the biological sample is determined using the gene ranking and a statistical model, such as statistical model 112. The statistical model may be trained using gene rankings of expression levels for one or more genes in the set of genes. Each of the gene rankings may be obtained based on respective expression levels for the one or more genes in the set of genes. In some embodiments, the gene ranking may be used as an input to the statistical model to obtain an output indicating the cancer grade. The cancer grade may include Grade 1, Grade 2, Grade 3, Grade 4, and Grade 5. In some embodiments, the statistical model comprises a classifier selected from the group consisting of: a gradient boosted decision tree classifier, a decision tree classifier, a gradient boosted classifier, a random forest classifier, a clustering-based classifier, a Bayesian classifier, a Bayesian network classifier, a neural network classifier, a kernel-based classifier, and a support vector machine classifier.

Figure 6A:
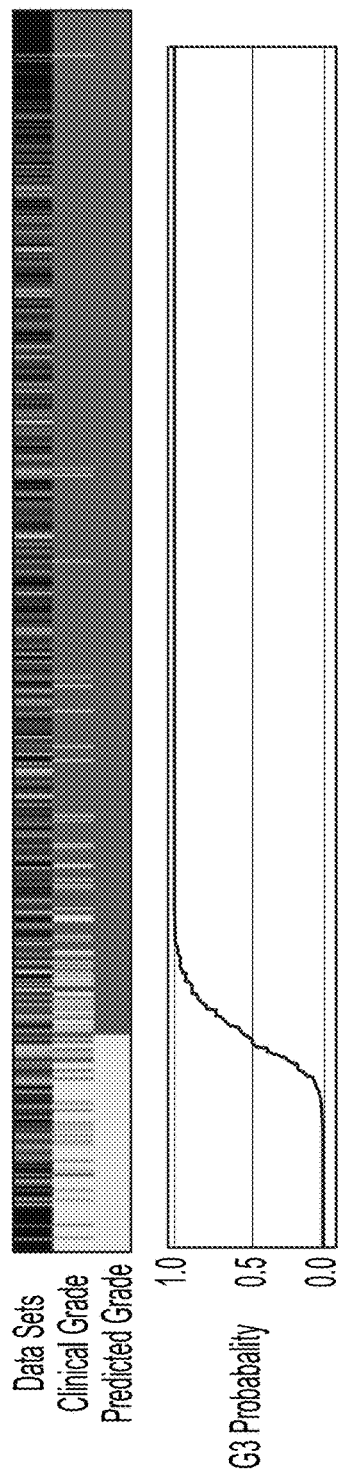
FIG. 6A shows example different data sets, associated clinical cancer grade for samples of the data sets, and predicted cancer grade obtained using the machine learning techniques described herein, for determining breast cancer grade.
Figure 6B:
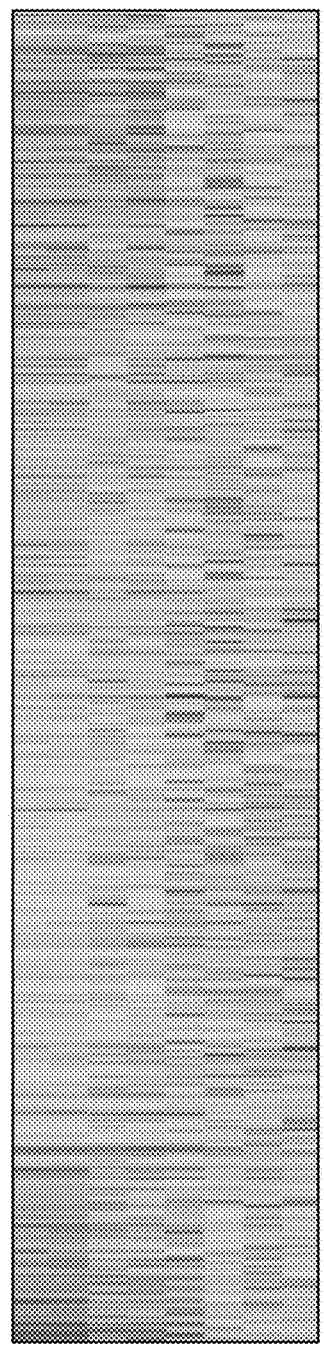
FIG. 6B shows example the enrichment signatures for different pathways, illustrating gene expression profiles associated with breast cancer Grade 1 and Grade 3.

An example of how the techniques described herein may be implemented in predicting breast cancer grade are discussed in connection with FIGS. 6A, 6B, 6C, 6D, and 7. FIG. 6A shows different data sets (data sets that vary in sample preparation, sequencing platform, data processing used to obtain expression data), associated clinical cancer grade for samples of the data sets, and predicted cancer grade obtained using the machine learning techniques described herein, for determining breast cancer grade. In particular, FIG. 6A shows different data sets (top panel) where each vertical line corresponds to a different sample, where the shading of the line corresponds to different data sets. FIG. 6A also shows the clinical grade associated with samples of the data sets, where the lighter shade indicates Grade 1 ("G1") and the darker shade indicates Grade 3 ("G3"). The clinical grade may be a determination by a physician (e.g., pathologist) using microscopy to visually inspect the samples. FIG. 6B shows the enrichment signatures for different pathways, illustrating gene expression profiles associated with breast cancer Grade 1 and Grade 3. Genes in one or more of these pathways may be used for determining breast cancer grade according to the techniques described herein. As an example, the HALLMARK_G2M_CHECKPOINT signature is shown in the top panel and has a majority of upregulated genes for the right portion of samples and a majority of downregulated genes for the left portion of samples. Other examples of pathways associated with cancer grade classification for breast cancer are in Table 4, below. In particular the different pathways that are enriched in a set of genes that are upregulated for Grade 3 ("G3") and pathways that are enriched in a set of genes that are upregulated for Grade 1 ("G1") are listed in Table 4.

TABLE 4

Grade classifier for breast cancer gene set enrichment (according to MSigDB 6.1)
Pathway enrichment

| Pathway | P-value | FDR | Genes in/all genes | Description |
|---|---|---|---|---|
| Molecular G3 upregulated | | | | |
| HALLMARK_G2M_CHECKPOINT | 1.10E−60 | 1.40E−57 | 33/200 | Genes defining early response to estrogen. |
| HALLMARK_E2F_TARGETS | 4.40E−47 | 6.10E−44 | 27/200 | Genes encoding cell cycle related targets of E2F transcription factors. |
| REACTOME_CELL_CYCLE_MITOTIC | 3.80E−35 | 5.30E−32 | 24/325 | Cell Cycle, Mitotic |
| REACTOME_CELL_CYCLE | 4.80E−34 | 6.60E−31 | 25/421 | Cell Cycle |
| HALLMARK_MITOTIC_SPINDLE | 1.80E−28 | 2.40E−25 | 18/200 | Genes important for mitotic spindle assembly. |
| PID_PLK1_PATHWAY | 6.20E−24 | 8.60E−21 | 11/46 | PLK1 signaling events |
| KEGG_CELL_CYCLE | 4.30E−20 | 5.90E−17 | 12/128 | Cell cycle |
| PID_AURORA_B_PATHWAY | 5.10E−20 | 7.00E−17 | 9/39 | Aurora B signaling |
| PID_FOXM1_PATHWAY | 6.70E−20 | 9.30E−17 | 9/40 | FOXM1 transcription factor network |
| REACTOME_DNA_REPLICATION | 1.70E−19 | 2.30E−16 | 13/192 | DNA Replication |
| REACTOME_MITOTIC_M_M_G1_PHASES | 2.20E−18 | 3.10E−15 | 12/172 | Genes involved in Mitotic M-M/G1 phases |
| REACTOME_MITOTIC_PROMETAPHASE | 3.00E−16 | 4.10E−13 | 9/87 | Mitotic Prometaphase |
| REACTOME_CELL_CYCLE_CHECKPOINTS | 1.20E−14 | 1.60E−11 | 9/124 | Cell Cycle Checkpoints |
| HALLMARK_SPERMATOGENESIS | 2.80E−14 | 3.80E−11 | 9/135 | Genes up-regulated during production of male gametes (sperm), as in spermatogenesis. |
| REACTOME_MITOTIC_G1_G1_S_PHASES | 3.20E−14 | 4.40E−11 | 9/137 | Mitotic G1-G1/S phases |
| Molecular G1 upregulated | | | | |
| NABA_MATRISOME | 9.40E−09 | 1.30E−05 | 11/1028 | Ensemble of genes encoding extracellular matrix and extracellular matrix-associated proteins |
| HALLMARK_ESTROGEN_RESPONSE_EARLY | 9.50E−09 | 1.30E−05 | 6/200 | Genes defining early response to estrogen. |
| HALLMARK_TNFA_SIGNALING_VIA_NFKB | 9.50E−09 | 1.30E−05 | 6/200 | Genes regulated by NF-kB in response to TNF (Gene ID: 7124) |
| NABA_CORE_MATRISOME | 8.40E−08 | 0.00012 | 6/275 | Ensemble of genes encoding core extracellular matrix including ECM glycoproteins, collagens and proteoglycans |
| NABA_BASEMENT_MEMBRANES | 2.50E−07 | 0.00034 | 3/40 | Genes encoding structural components of basement membranes |
| HALLMARK_ESTROGEN_RESPONSE_LATE | 2.90E−07 | 0.0004 | 5/200 | Genes defining late response to estrogen. |
| KEGG_FOCAL_ADHESION | 3.00E−07 | 0.00041 | 5/201 | Focal adhesion |
| PID_INTEGRIN4_PATHWAY | 3.60E−07 | 0.0005 | 2/11 | Alpha6 beta4 integrin-ligand interactions |
| BIOCARTA_ACE2_PATHWAY | 6.30E−07 | 0.00087 | 2/13 | Angiotensin-converting enzyme 2 regulates heart function |
| PID_INTEGRIN1_PATHWAY | 1.90E−06 | 0.0026 | 3/66 | Beta1 integrin cell surface interactions |

Figure 12:
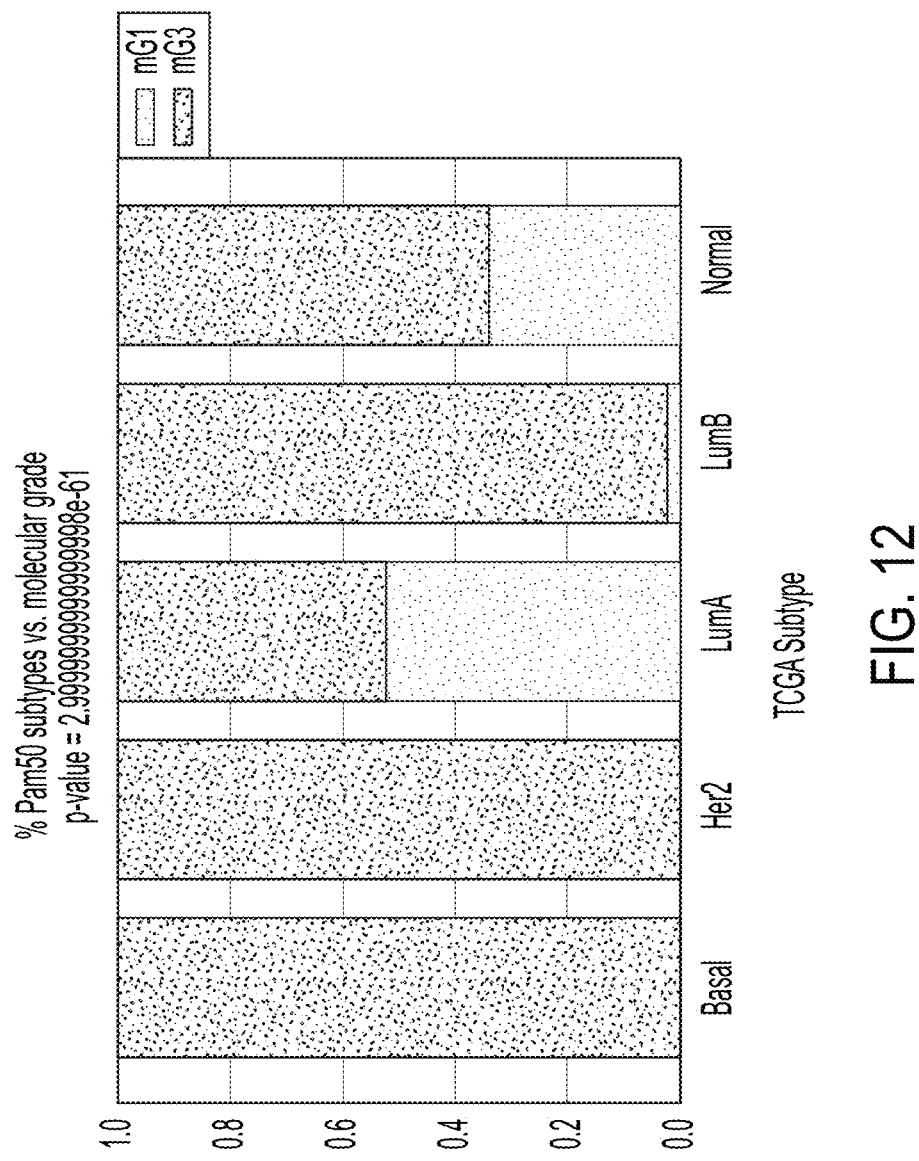
FIG. 12 is an exemplary distribution of molecular cancer grade among PAM50 subtypes.
Figure 13:
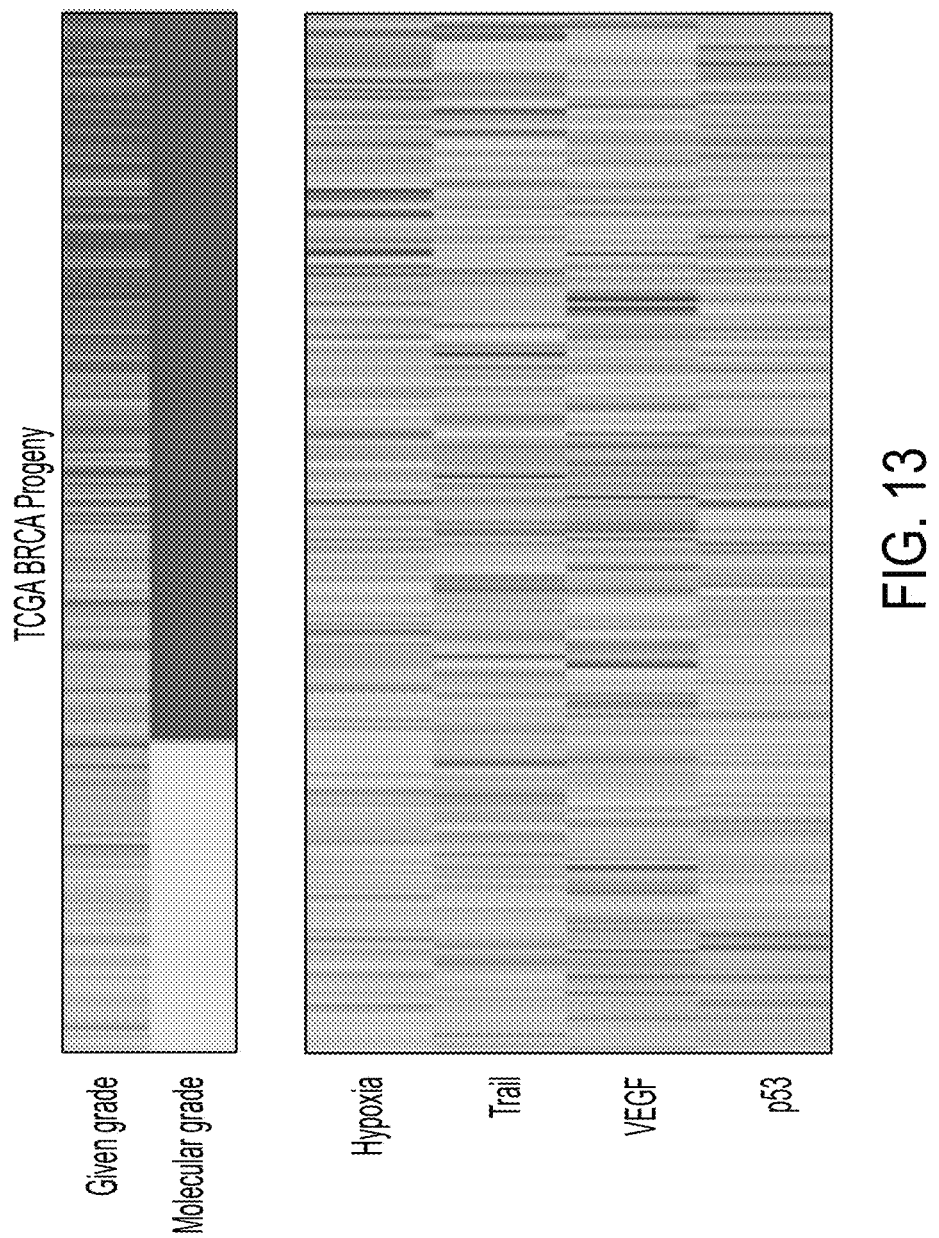
FIG. 13 are illustrative data sets and enrichment signatures showing how progeny process scores correspond to given and predicted cancer grades in TCGA BRCA.
Figure 14:
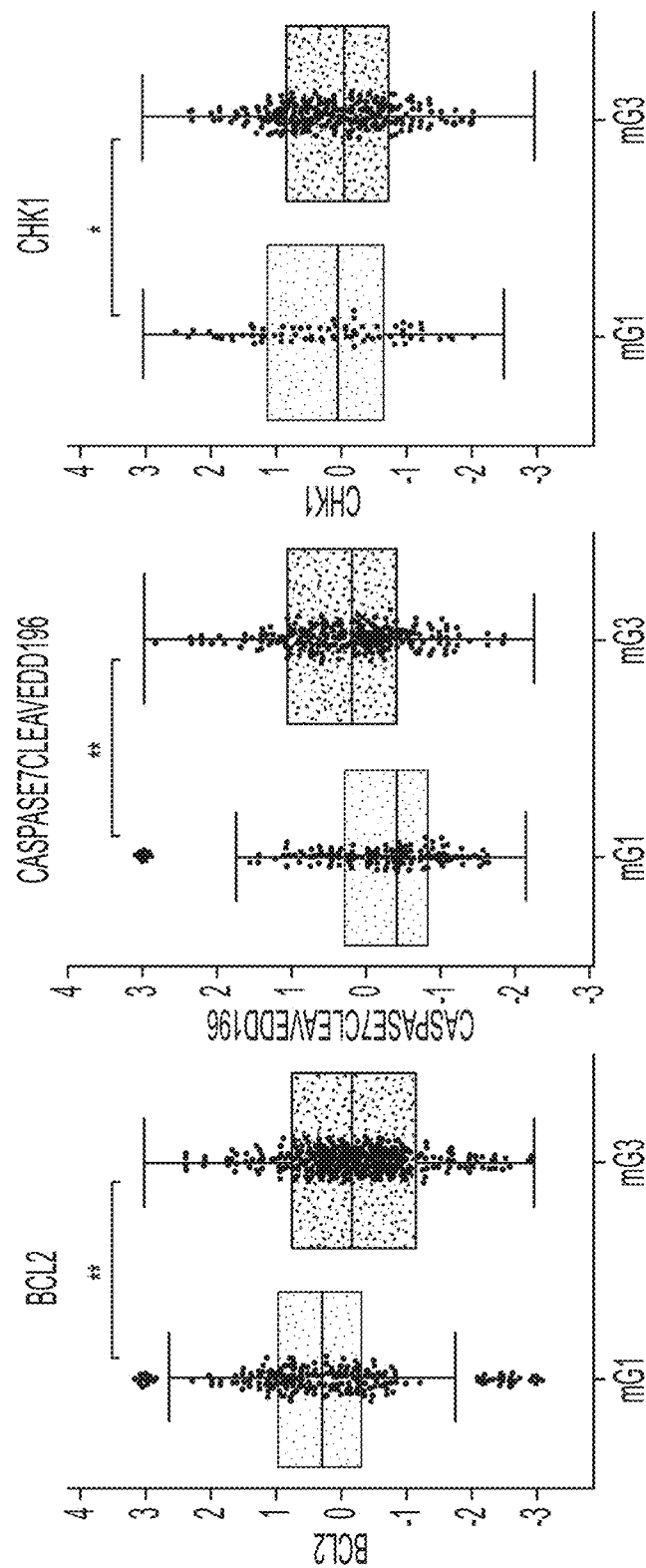
FIG. 14 are exemplary plots comparing different protein expression levels for different predicted cancer grades.
Figure 14:
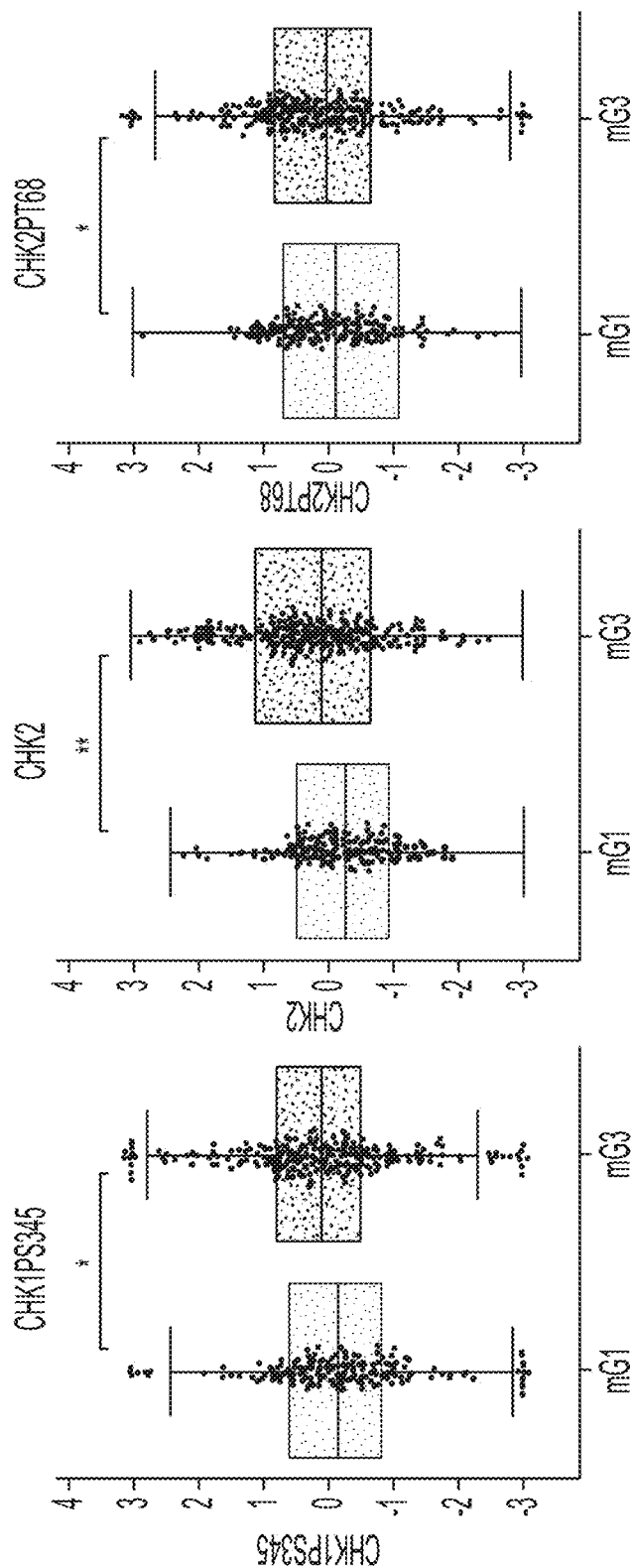
Figure 14:
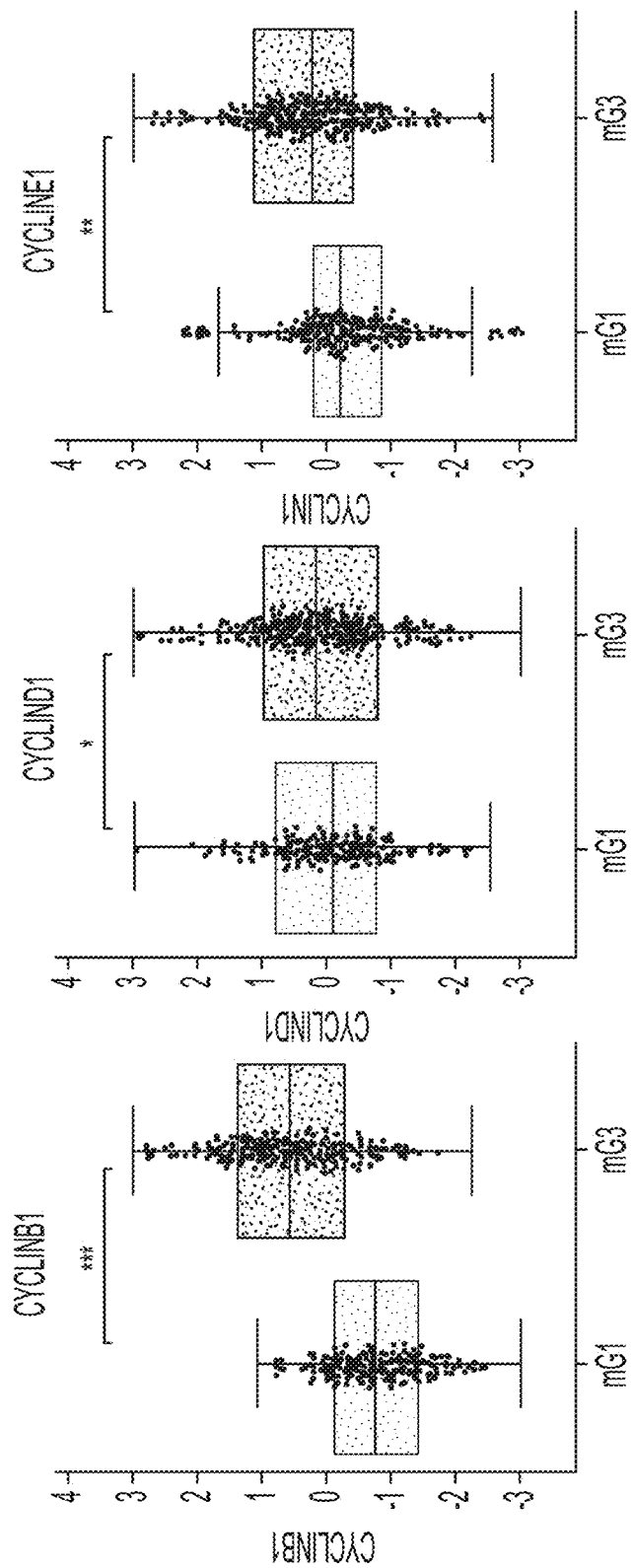
Figure 15:
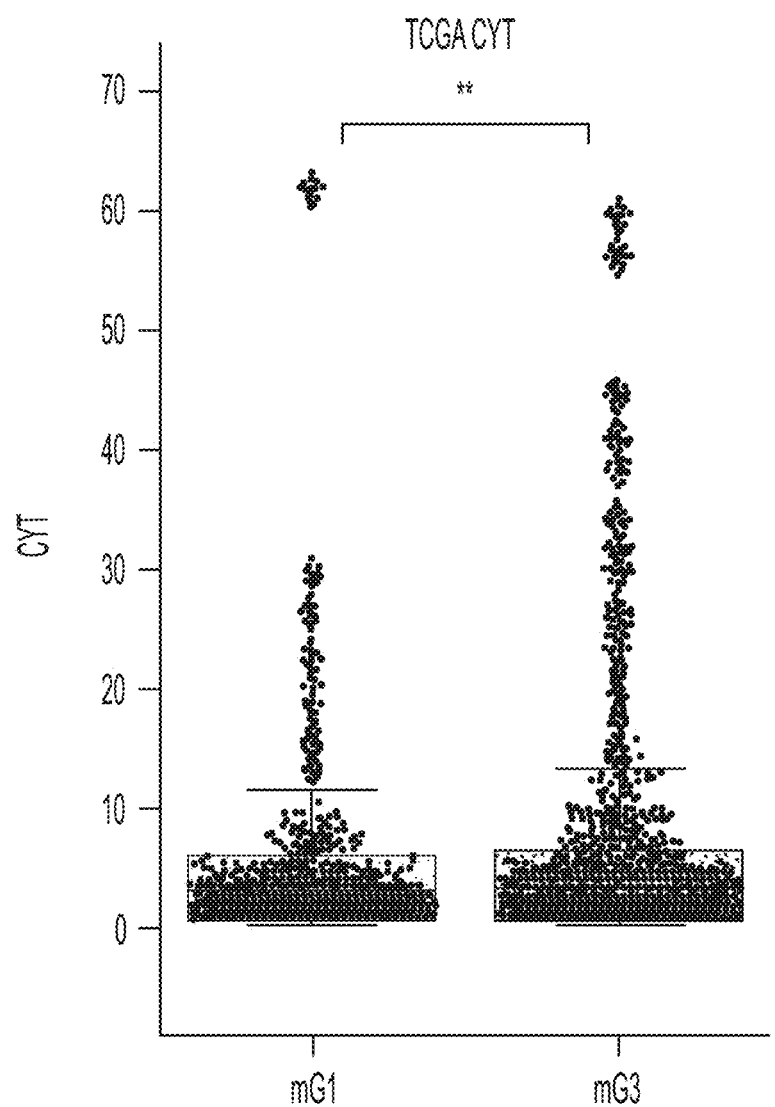
FIG. 15 is an exemplary plot of cytolitic score for different predicted cancer grades.
Figure 16:
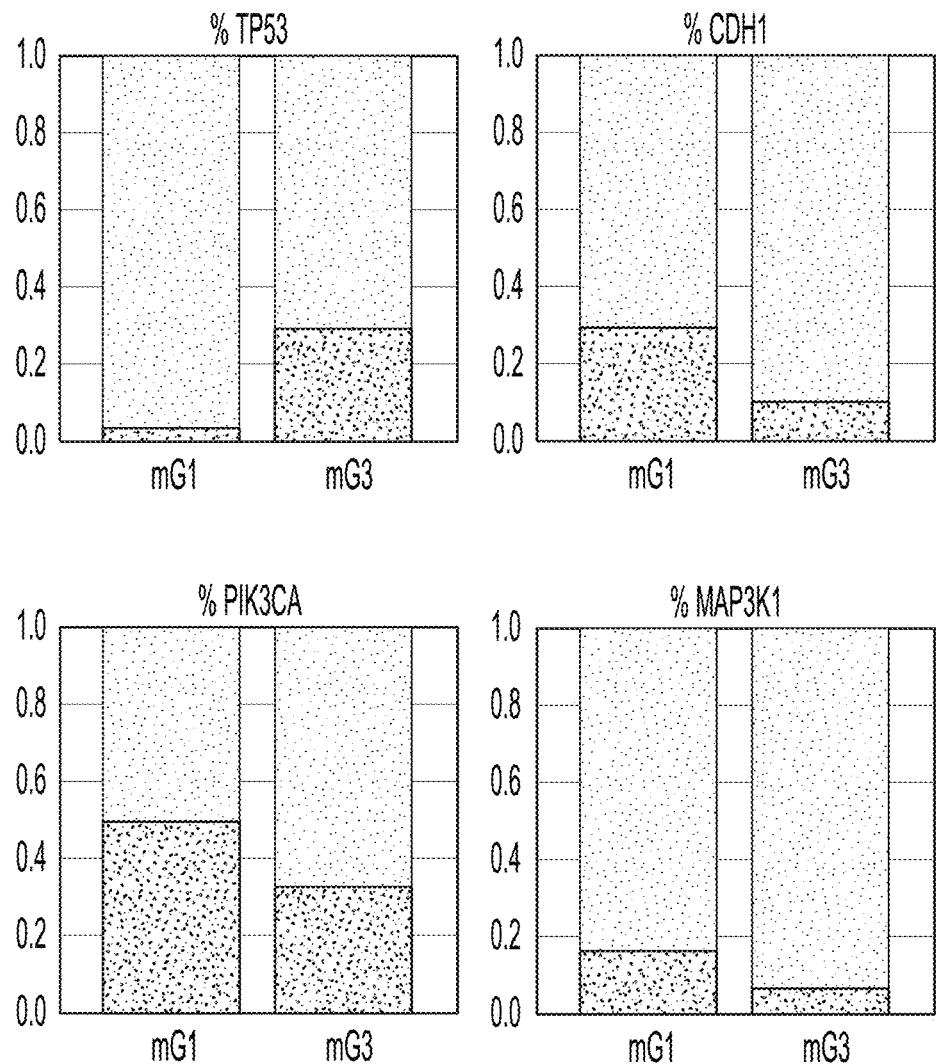
FIG. 16 are illustrative plots showing the difference in mutations between different cancer grades, according to WES data.
Figure 17:
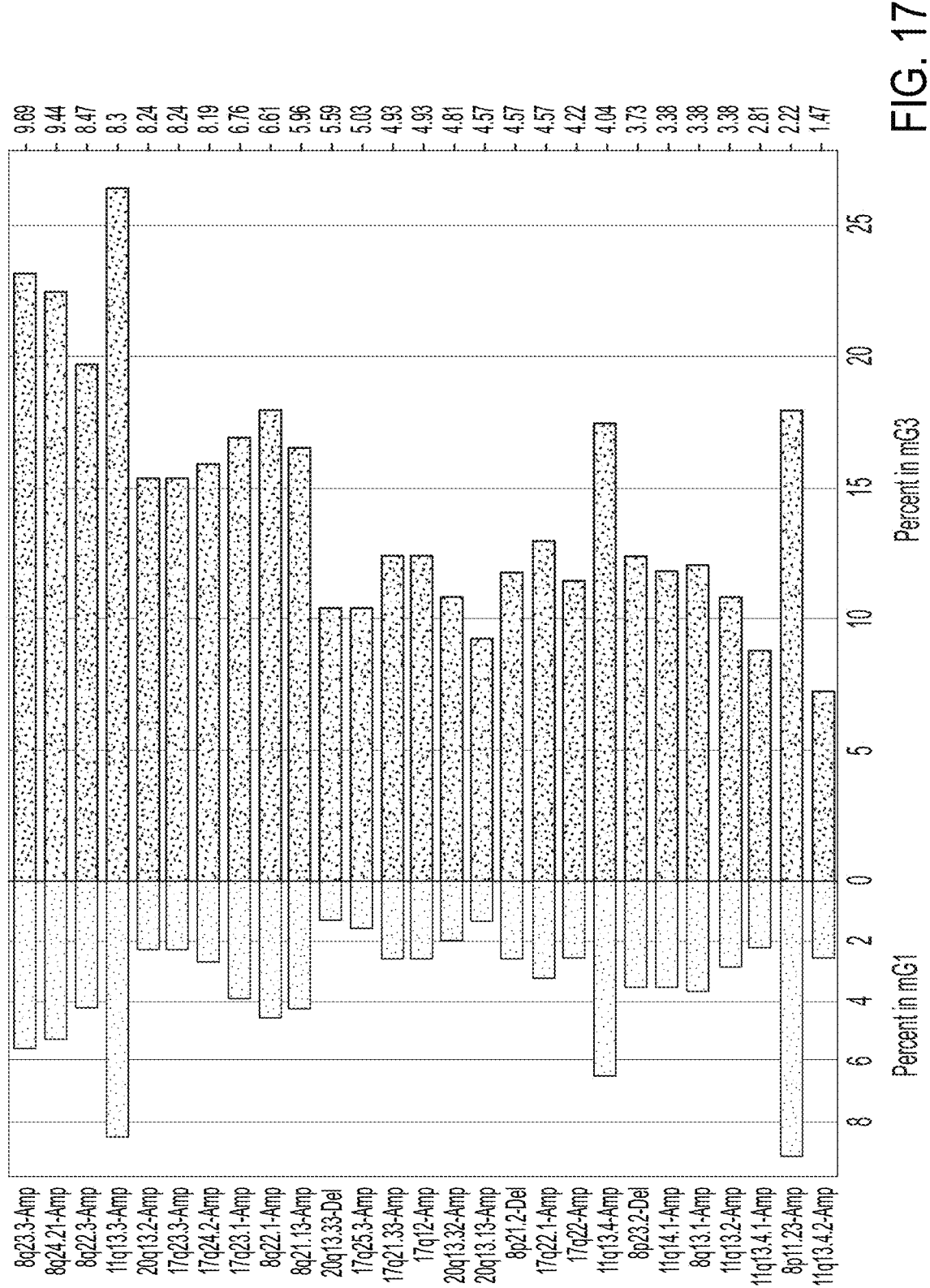
FIG. 17 shows example segments that are differentially amplified or deleted between predicted cancer grades, according to WES data.

FIGS. 12, 13, 14, 15, 16, and 17 illustrate relationships between biological features and different breast cancer grades. In particular, these figures describe the biology of molecular grades (Grade 1 and Grade 3) for breast cancer, where the data depicted is for TCGA BRCA, and the predicted breast cancer grades were obtained using the techniques described herein. FIG. 12 is a distribution of molecular cancer grade among PAM50 subtypes. FIG. 12 illustrates the majority of molecular Grade 1 samples belong to luminal subtypes. Further comparisons on breast cancer datasets for FIGS. 13-17 are for only luminal subtypes. FIG. 13 shows how progeny process scores correspond to given and predicted cancer grades in TCGA BRCA. The progeny process scores are calculated from expression data. FIG. 14 shows plots comparing different protein expression for different predicted cancer grades. The protein expression is according to RPPA data. FIG. 15 is a plot of cytolitic score (CYT) for different predicted cancer grades. FIG. 16 are plots showing the difference in mutations between different cancer grades. FIG. 16 illustrates genes, according to WES data, that are significantly differentially mutated between predicted cancer grades. FIG. 17 shows segments that are differentially amplified or deleted between predicted cancer grades. The segments shown in FIG. 17 are according to WES data.

Figure 6C:
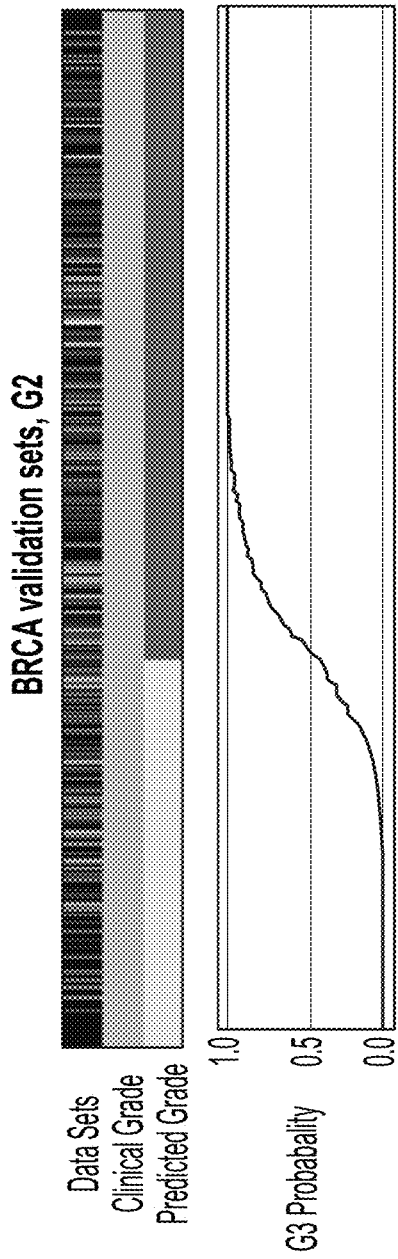
FIG. 6C shows example different data sets, associated clinical cancer grade for samples of the data sets, and predicted cancer grade, using the machine learning techniques described herein, for determining breast cancer grade.
Figure 6D:
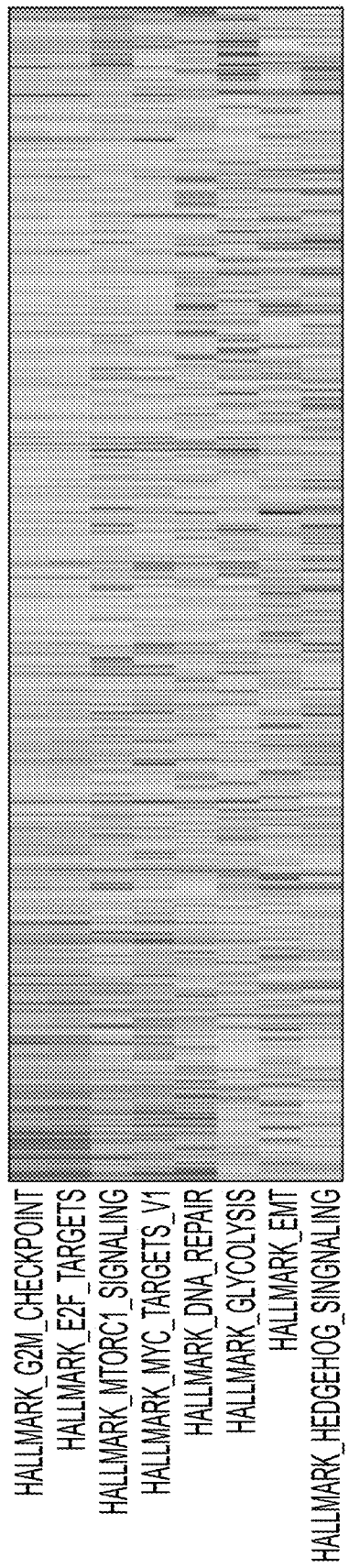
FIG. 6D shows example the enrichment signatures for different pathways, illustrating gene expression profiles associated with breast cancer Grade 1 and Grade 3.

To compare with the computational techniques described herein, FIG. 6A shows the predicted grade (lower panel) using the expression data and a statistical model according to the techniques described herein. The predicted grade shows how the different samples are predicted as being Grade 1 ("G1") for the left portion of samples and as being Grade 3 ("G3") for the right portion of samples. This is further shown in the plot of "G3 probability" over the different samples below the bottom panel of FIG. 6A, where the probability of the Grade 3 is higher for the right portion of samples than the left portion of samples. FIGS. 6C and 6D show similar data as that shown in FIGS. 6A and 6B, respectively, except that the samples and pathway signatures are associated with predicting breast cancer as being Grade 1 or Grade 3 for Grade 2 samples. Here, FIGS. 6C and 6D show how the biological features associated with Grade 2 is similar to the biological features associated with Grade 1 and Grade 3.

Figure 7:
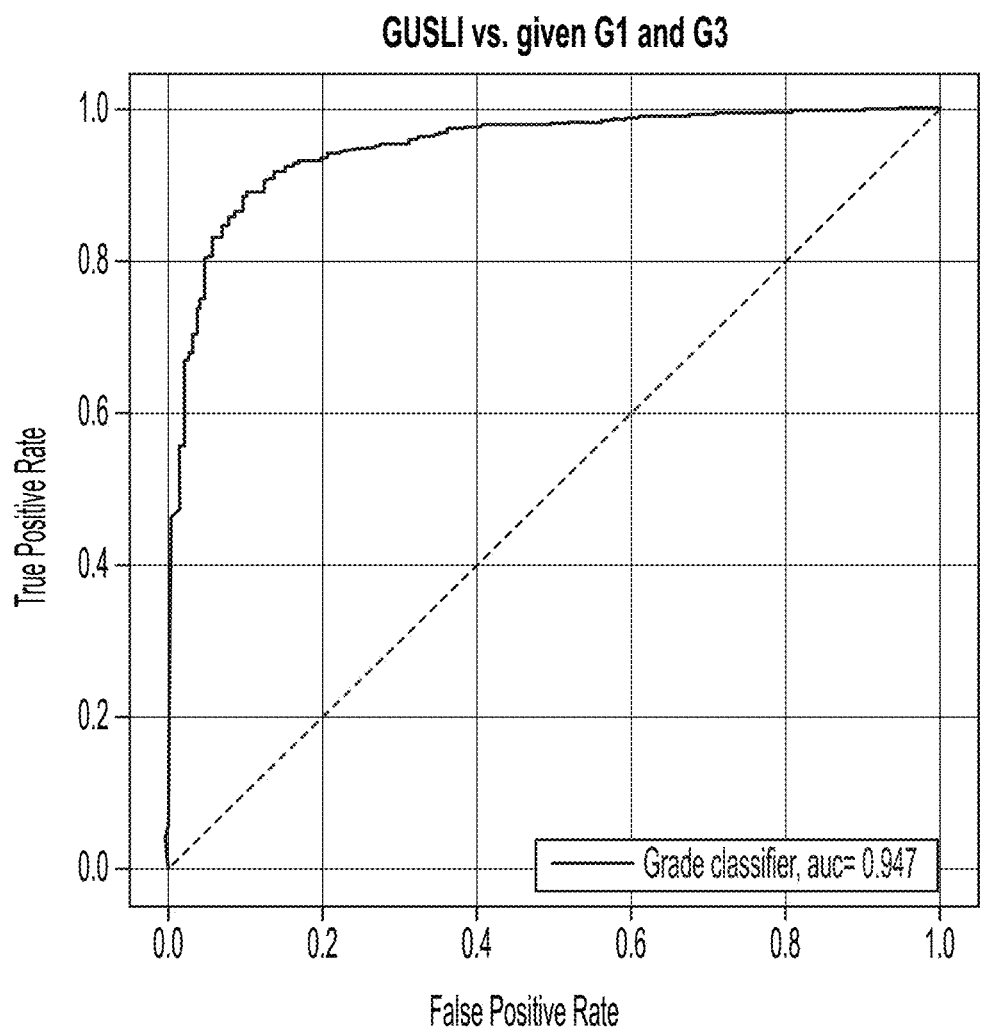
FIG. 7 is an illustrative plot of true positive rate versus false positive rate for predicting breast cancer grade of different biological samples using the machine learning techniques described herein.

FIG. 7 is a plot of true positive rate versus false positive rate for a number of biological samples (shown in the solid line). The plot shows that the predicted cancer grade using the techniques described herein have a high true positive rate while maintaining a low false positive rate.

As another example, pathways associated with cancer grade classification for kidney clear cell are in Table 5, below. In particular the different pathways that are enriched in a set of genes that are upregulated for Grade 4 ("G4") and for Grade 1 ("G1") are listed in Table 5.

TABLE 5

Grade classifier for kidney clear cell cancer gene set enrichment (according to MsigDB 6-1)
Pathway enrichment

| Pathway | P-value | FDR | Genes in/all genes | Description |
|---|---|---|---|---|
| Molecular G4 upregulated | | | | |
| HALLMARK_KRAS_SIGNALING_UP | 1.70E−14 | 2.40E−11 | 9/200 | Genes up-regulated by KRAS activation. |
| HALLMARK_EPITHELIAL_MESENCHYMAL_TRANSITION | 1.00E−12 | 1.40E−09 | 8/200 | Genes defining epithelial-mesenchymal transition, as in wound healing, fibrosis and metastasis. |
| NABA_MATRISOME | 3.20E−12 | 4.40E−09 | 13/1028 | Ensemble of genes encoding extracellular matrix and extracellular matrix-associated proteins |
| NABA_ECM_REGULATORS | 4.80E−12 | 6.60E−09 | 8/238 | Genes encoding enzymes and their regulators involved in the remodeling of the extracellular matrix |
| KEGG_COMPLEMENT_AND_COAGULATION_CASCADES | 1.40E−10 | 1.90E−07 | 5/69 | Complement and coagulation cascades |
| HALLMARK_COAGULATION | 1.70E−10 | 2.30E−07 | 6/138 | Genes encoding components of blood coagulation system; also up-regulated in platelets. |
| REACTOME_IMMUNE_SYSTEM | 4.10E−09 | 5.70E−06 | 10/933 | Genes involved in Immune System |
| NABA_MATRISOME_ASSOCIATED | 7.50E−09 | 1.00E−05 | 9/753 | Ensemble of genes encoding ECM-associated proteins including ECM-affilaited proteins, ECM regulators and secreted factors |
| PID_AVB3_OPN_PATHWAY | 3.80E−08 | 5.30E−05 | 3/31 | Osteopontin-mediated events |
| PID_FRA_PATHWAY | 8.00E−08 | 0.00011 | 3/37 | Validated transcriptional targets of AP1 family members Fra1 and Fra2 |
| HALLMARK_COMPLEMENT | 8.50E−08 | 0.00012 | 5/200 | Genes encoding components of the complement system, which is part of the innate immune system. |
| PID_AMB2_NEUTROPHILS_PATHWAY | 1.20E−07 | 0.00017 | 3/41 | amb2 Integrin signaling |
| PID_UPA_UPAR_PATHWAY | 1.30E−07 | 0.00019 | 3/42 | Urokinase-type plasminogen activator (uPA) and uPAR-mediated signaling |
| PID_FGF_PATHWAY | 4.10E−07 | 0.00056 | 3/55 | FGF signaling pathway |
| BIOCARTA_CLASSIC_PATHWAY | 4.40E−07 | 0.0006 | 2/14 | Classical Complement Pathway |
| REACTOME_INNATE_IMMUNE_SYSTEM | 6.00E−07 | 0.00083 | 5/279 | Innate Immune System |
| PID_INTEGRIN5_PATHWAY | 8.20E−07 | 0.0011 | 2/17 | Beta5 beta6 beta7 and beta8 integrin cell surface interactions |
| BIOCARTA_COMP_PATHWAY | 1.20E−06 | 0.0016 | 2/19 | Complement Pathway |
| NABA_ECM_GLYCOPROTEINS | 2.40E−06 | 0.0034 | 4/196 | Genes encoding structural ECM glycoproteins |
| HALLMARK_INTERFERON_GAMMA_RESPONSE | 2.70E−06 | 0.0037 | 4/200 | Genes up-regulated in response to IFNG [GeneID = 3458]. |
| HALLMARK_G2M_CHECKPOINT | 2.70E−06 | 0.0037 | 4/200 | Genes involved in the G2/M checkpoint, as in progression through the cell division cycle. |
| HALLMARK_GLYCOLYSIS | 2.70E−06 | 0.0037 | 4/200 | Genes encoding proteins involved in glycolysis and gluconeogenesis. |

TABLE 5-continued

Grade classifier for kidney clear cell cancer gene set enrichment (according to MsigDB 6-1)
Pathway enrichment

| Pathway | P-value | FDR | Genes in/all genes | Description |
|---|---|---|---|---|
| HALLMARK_HYPOXIA | 2.70E−06 | 0.0037 | 4/200 | Genes up-regulated in response to low oxygen levels (hypoxia). |
| HALLMARK_TNFA_SIGNALING_VIA_NFKB | 2.70E−06 | 0.0037 | 4/200 | Genes regulated by NF-kB in response to TNF [GeneID = 7124]. |
| PID_TOLL_ENDOGENOUS_PATHWAY | 2.70E−06 | 0.0038 | 2/25 | Endogenous TLR signaling |
| Molecular G1 upregulated | | | | |
| REACTOME_TRANSMEMBRANE_TRANSPORT_OF_SMALL_MOLECULES | 1.20E−08 | 1.70E−05 | 6/413 | |
| REACTOME_SLC_MEDIATED_TRANSMEMBRANE_TRANSPORT | 1.60E−08 | 2.20E−05 | 5/241 | SLC-mediated transmembrane transport |
| REACTOME_TRANSPORT_OF_GLUCOSE_AND_OTHER_SUGARS_BILE_SALTS_AND_ORGANIC_ACIDS_METAL_IONS_AND_AMINE_COMPOUNDS | 4.50E−07 | 0.00063 | 3/89 | |
| KEGG_PROXIMAL_TUBULE_BICARBONATE_RECLAMATION | 5.40E−07 | 0.00074 | 2/23 | Proximal tubule bicarbonate reclamation |
| REACTOME_GLUCONEOGENESIS | 1.80E−06 | 0.0025 | 2/34 | Gluconeogenesis |

Figure 18:
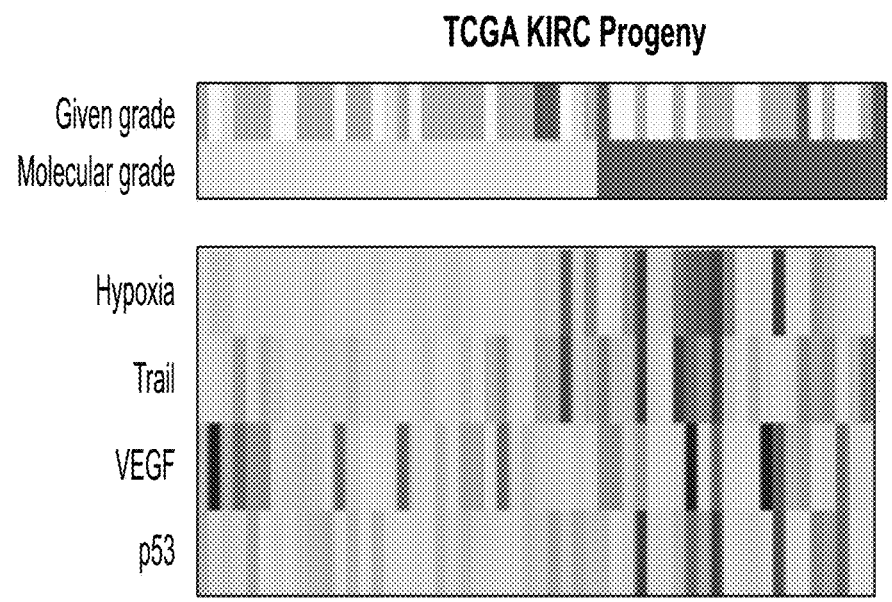
FIG. 18 are illustrative data sets and enrichment signatures showing how progeny process scores correspond to given and predicted cancer grades in TCGA KIRC.
Figure 19:
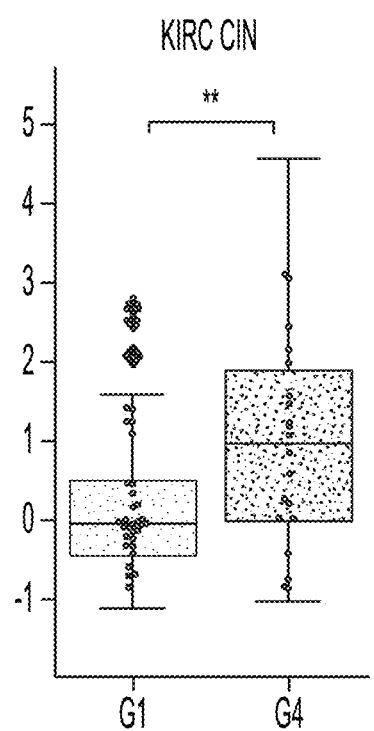
FIG. 19 is a plot illustrating chromosomal instability for different cancer grades.
Figure 20:
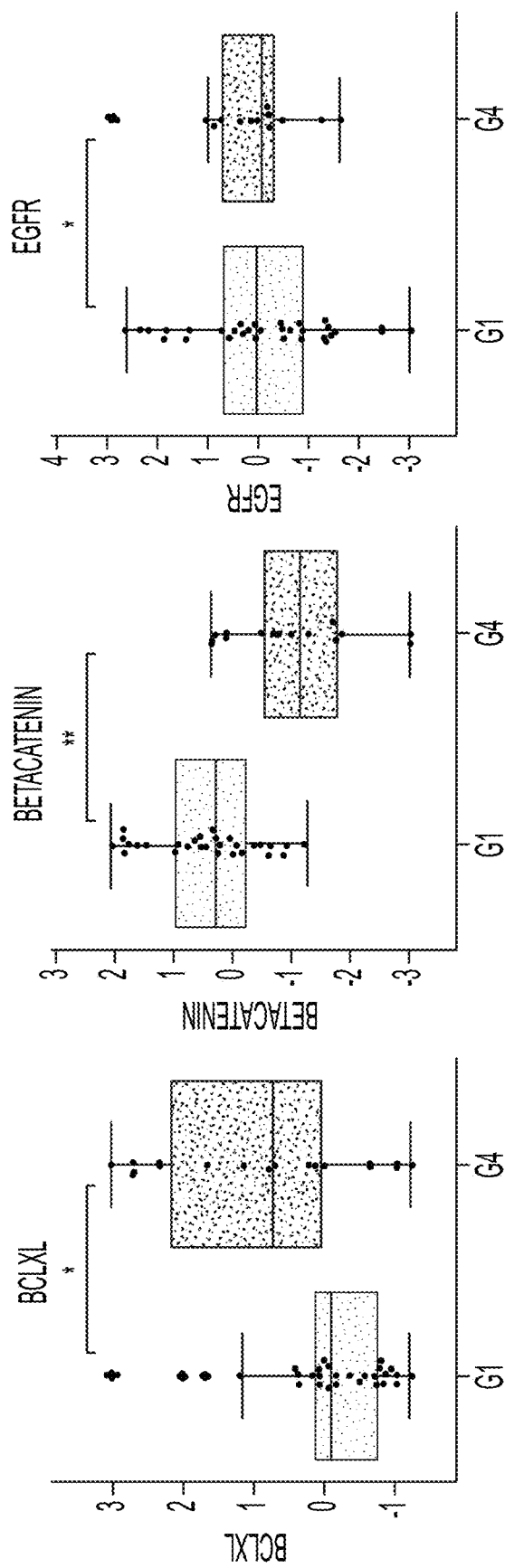
FIG. 20 are plots comparing different protein expression for different predicted cancer grades.
Figure 20:
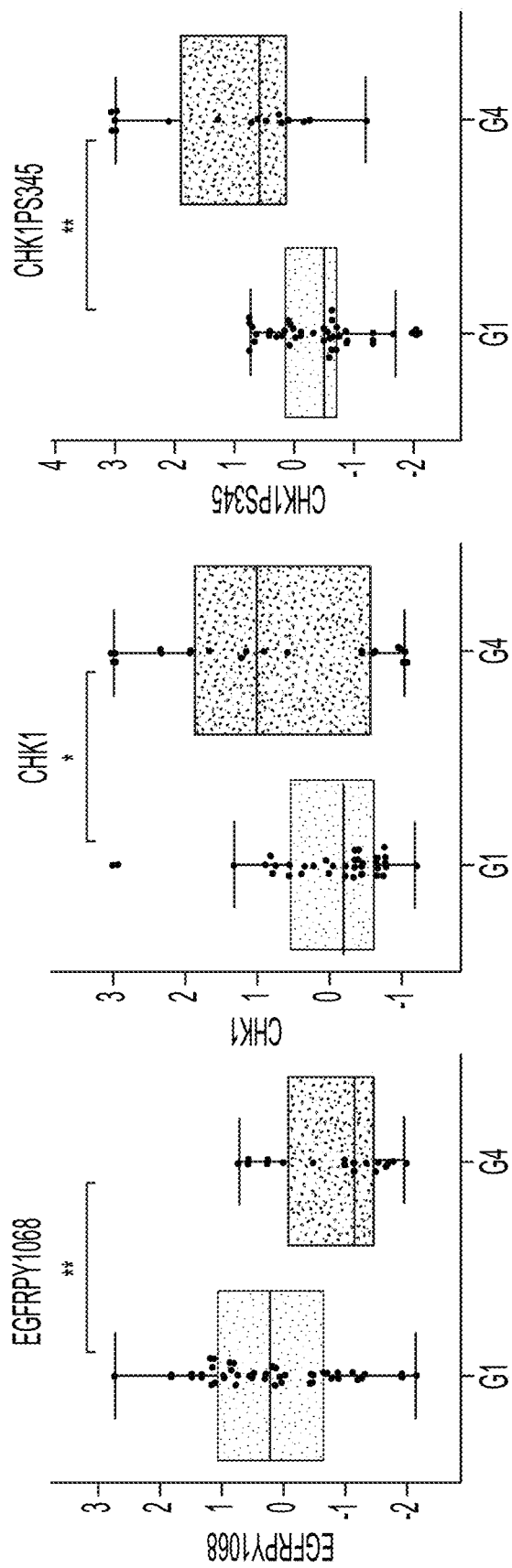
Figure 20:
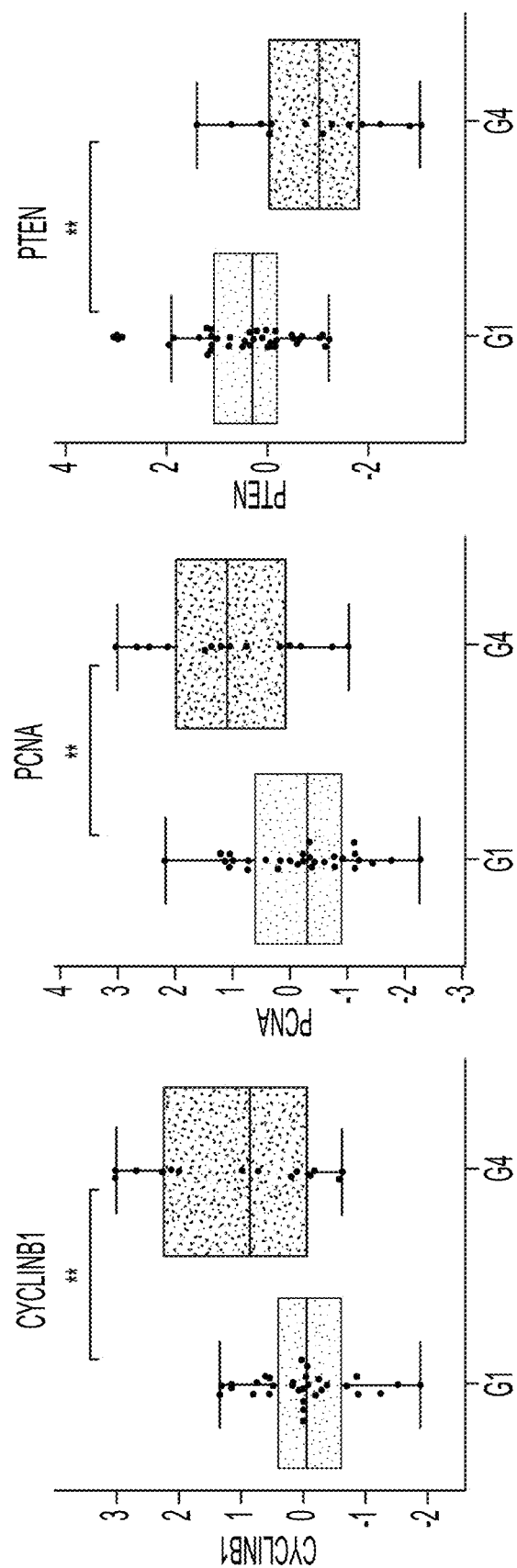
Figure 20:
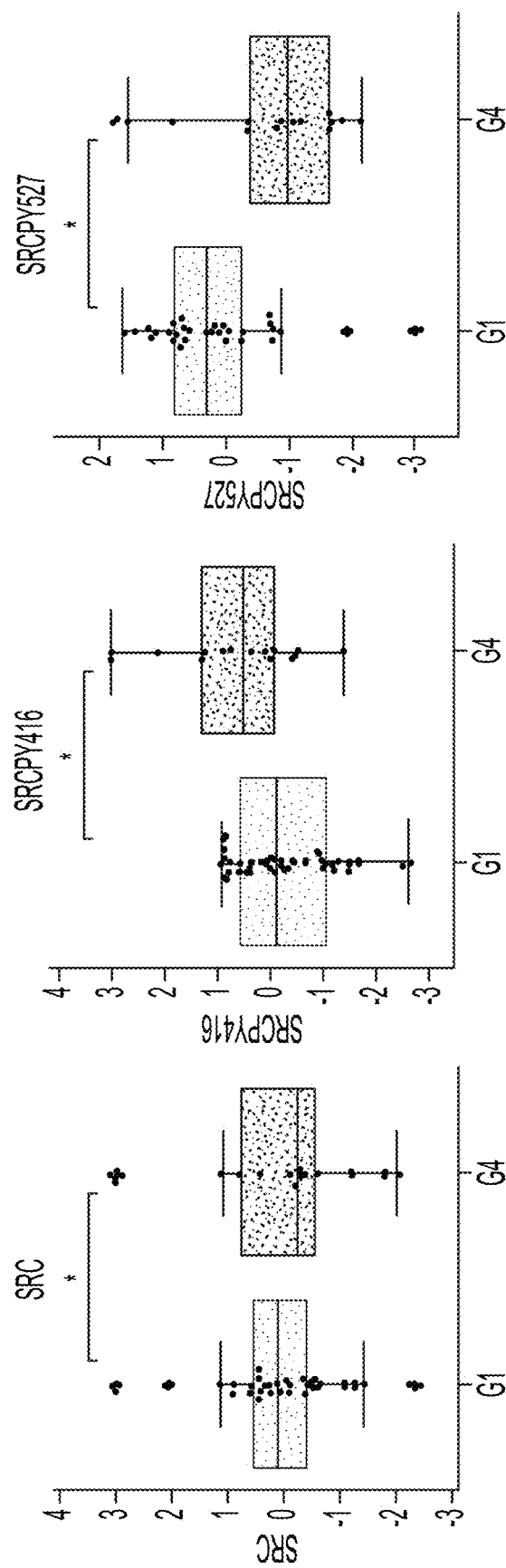
Figure 21:
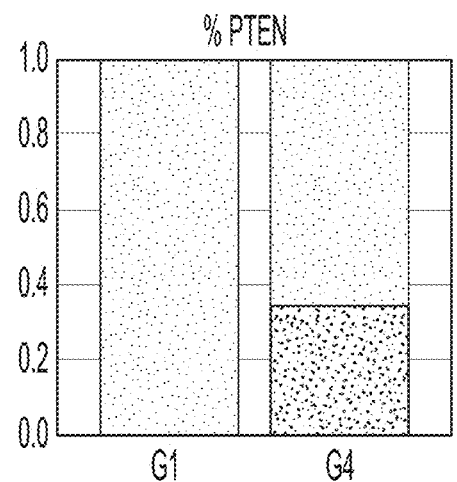
FIG. 21 illustrates genes, according to WES data, that are differentially amplified or deleted between predicted cancer grades.
Figure 22:
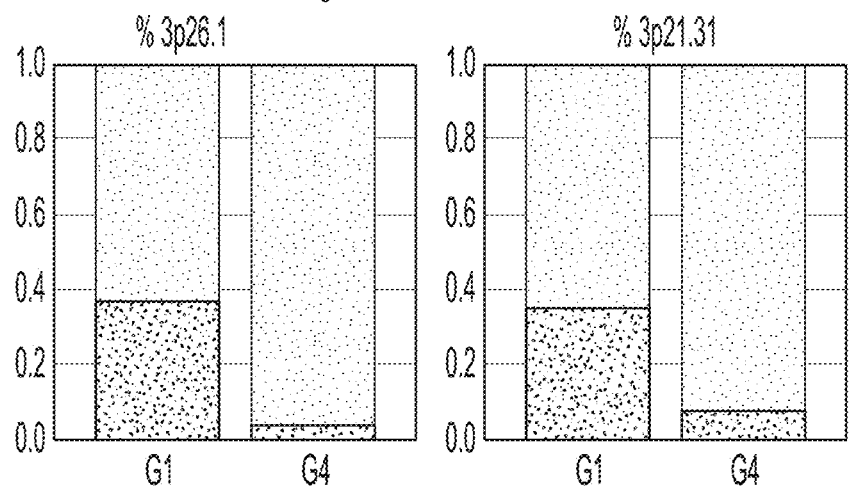
FIG. 22 illustrates genes, according to WES data, that are differentially amplified or deleted between predicted cancer grades.

FIGS. 18, 19, 20, 21, and 22 illustrate relationships between biological features and different kidney clear cell grades. In particular, these figures describe the biology of molecular grades (Grade 1 and Grade 4) for kidney renal clear cell cancer, where the data depicted is for TCGA KIRC, and the predicted breast cancer grades were obtained using the techniques described herein. FIG. 18 shows how progeny process scores correspond to given and predicted cancer grades in TCGA KIRC. The progeny process scores are calculated from expression data. FIG. 19 is a plot illustrating chromosomal instability (CIN) for different cancer grades. FIG. 20 are plots comparing different protein expression, according to RPPA data, for different predicted cancer grades. FIGS. 21 and 22 illustrate genes, according to WES data, that are differentially amplified or deleted between predicted cancer grades.

Some embodiments involve using the techniques described herein for determining cancer grade for lung adenocarcinoma. Examples of genes that may be included in a gene set for determining cancer grade for lung adenocarcinoma are listed in Table 6, below. The set of genes may include at least 3, 5, 10, or 20 genes selected from the group of genes listed in Table 6. In some embodiments, the set of genes may include all the genes listed in Table 6. In some embodiments, the set of genes may include 3-25 genes, 5-25 genes, 10-25 genes, 20-25 genes listed in Table 6. In some embodiments, the set of genes may include 25 or fewer genes, 20 or fewer genes, 15 or fewer genes, 10 or fewer genes listed in Table 6.

TABLE 6

Cancer Grade Classifier for Lung Adenocarcinoma

| Gene | NCBI Gene ID | NCBI Accession Number(s) |
|---|---|---|
| AADAC | 13 | NM_001086 |
| ALDOB | 229 | NM_000035 |
| ANXA10 | 11199 | NM_007193 |
| ASPM | 259266 | NM_001206846; NM_018136 |
| BTNL8 | 79908 | NM_001040462; NM_001159707; NM_001159708; NM_001159709; NM_001159710; NM_024850 |
| CEACAM8 | 1088 | NM_001816; XM_017026195; NM_001816 |
| CENPA | 1058 | NM_001042426; NM_001809 |
| CHGB | 1114 | NM_001819 |
| CHRNA9 | 55584 | NM_017581 |
| COL11A1 | 1301 | NM_001190709; NM_001854; NM_080629; NM_080630 |
| CRABP1 | 1381 | NM_004378; NM_004378 |
| F11 | 2160 | NM_000128 |
| GGTLC1 | 92086 | NM_178311; NM_178312; XM_005260865; XM_017028126 |
| HJURP | 55355 | NM_001282962; NM_001282963; NM_018410 |
| IGF2BP3 | 10643 | NM_006547 |
| IHH | 3549 | NM_002181 |
| KCNE2 | 9992 | NM_172201 |
| KIF14 | 9928 | NM_001305792; NM_014875; XM_011510231; XM_011510232; XM_017003005 |
| LRRC31 | 79782 | NM_001277127; NM_001277128; NM_024727; XM_011513160 |
| MYBL2 | 4605 | NM_001278610; NM_002466 |
| MYOZ1 | 58529 | NM_021245 |
| PCSK2 | 5126 | NM_001201528; NM_001201529; NM_002594 |

TABLE 6-continued

Cancer Grade Classifier for Lung Adenocarcinoma

| Gene | NCBI Gene ID | NCBI Accession Number(s) |
| --- | --- | --- |
| PI15 | 51050 | NM_001324403; NM_015886 |
| SCTR | 6344 | NM_002980 |
| SHH | 6469 | NM_000193 |
| SLC22A3 | 6581 | NM_021977 |
| SLC7A5 | 8140 | NM_003486 |
| SPOCK1 | 6695 | NM_004598 |
| TM4SF4 | 7104 | NM_004617 |
| TRPM8 | 79054 | NM_024080 |
| YBX2 | 51087 | NM_015982 |

The techniques described herein may be implemented in predicting cancer grade for lung adenocarcinoma and are discussed in connection with FIGS. 23A, 23B, and 23C. In particular, a cancer grade classifier for lung adenocarcinoma may distinguish between molecular grade 1 (mG1), a low grade, and molecular grade 3 (mG3), a high grade. Such a classifier may be developed by using samples from TCGA LUAD (from the National Cancer Institute) and CPTAC3 (from NCBI) lung adenocarcinoma expression data as training data. For the classifier discussed in connection with FIGS. 23A, 23B, and 23C 117 samples of TCGA LUAD were excluded from the training data set and included as validation data. An initial gene set was formed from differentially expressed genes between grade 1 and grade 3. A genomic grade index (DOI: 10.1093/jnci/djj052) based on the initial gene set was calculated and training data set samples were split into high and low cancer grade based on survival mode. Through selection of the gene set used for the classifier, the number of genes was reduced. For example, the classifier discussed in connection with FIGS. 23A, 23B, and 23C, the initial gene set included 321 genes and the gene set used in the classifier included 31 genes. Validation data sets included 117 samples from TCGA LUAD and Series GSE68465. After hyperparameter tuning, the classifier's performance on the validation data set reached a 0.89AUC score in distinguishing between grade 1 and grade 3. These results demonstrated the capability of lung molecular grades to be statistically significant in predicting survival.

Figure 23A:
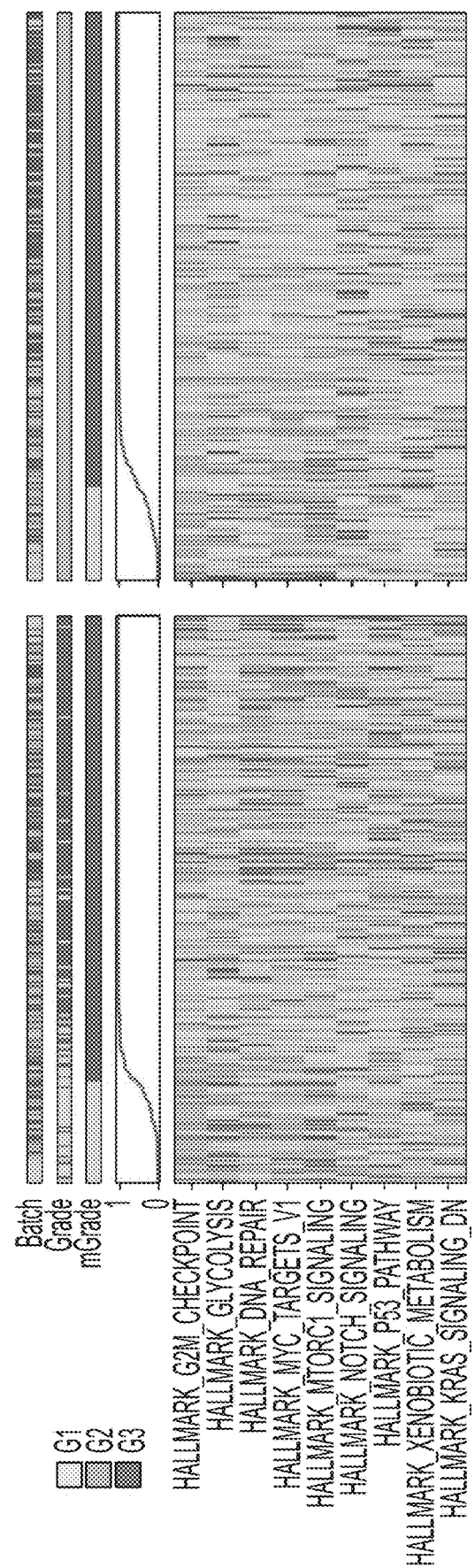
FIG. 23A shows example validation data sets, associated cancer grade reported for samples of the data sets, predicted cancer grade obtained using the machine learning techniques described herein, for determining lung adenocarcinoma cancer grade, and the enrichment signatures for different pathways, illustrating gene expression profiles associated with grade 1 and grade 3.
Figure 23B:
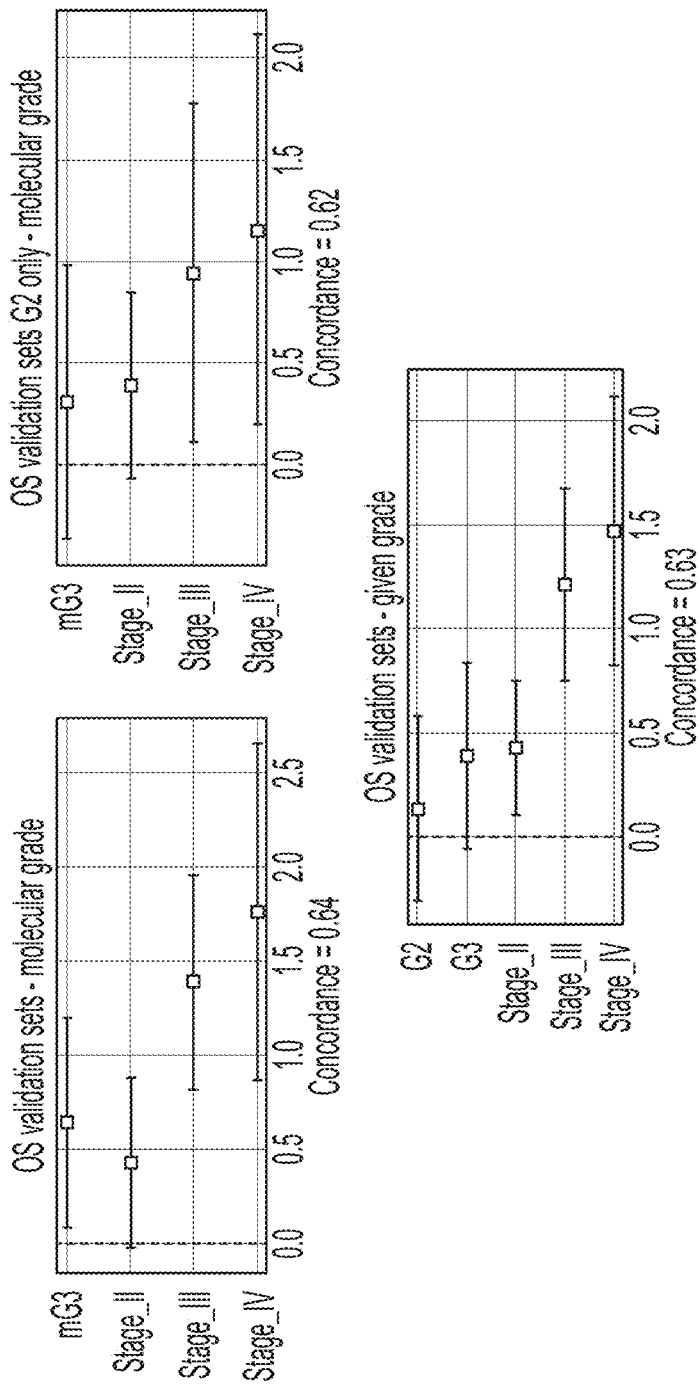
FIG. 23B shows example results of applying validation data sets to a lung adenocarcinoma cancer grade classifier, using the machine learning techniques described herein.
Figure 23C:
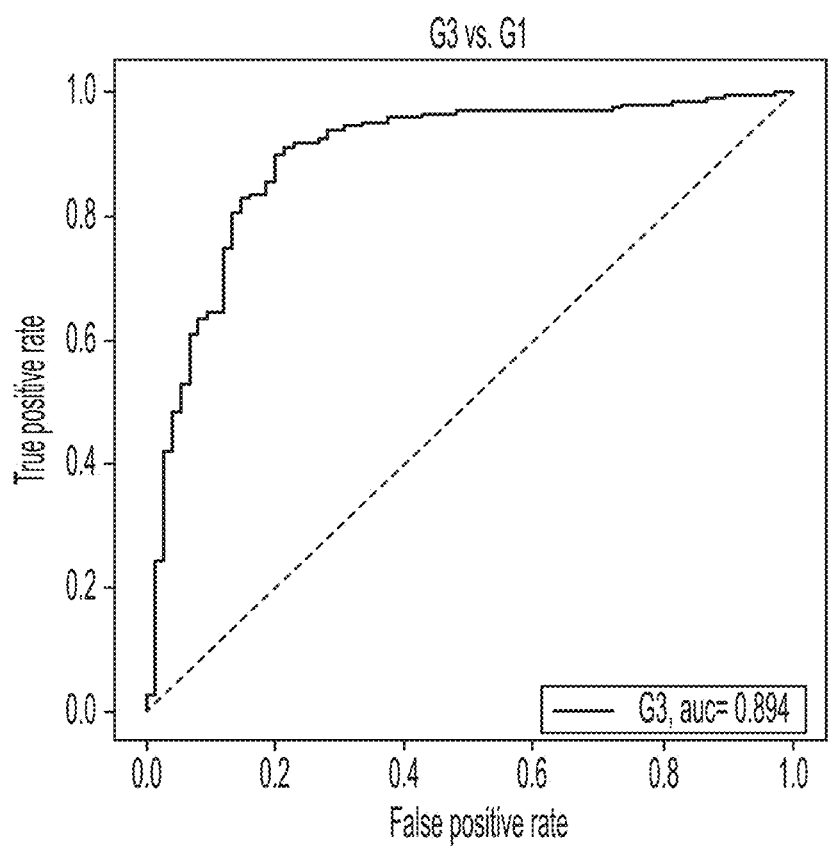
FIG. 23C is an example plot of true positive rate versus false positive rate for predicting cancer grade of different biological samples using the machine learning techniques described herein.

FIG. 23A shows validation data sets, associated cancer grade reported for samples of the data sets, predicted cancer grade obtained using the machine learning techniques described herein, for determining lung adenocarcinoma cancer grade, and the enrichment signatures for different pathways, illustrating gene expression profiles associated with grade 1 and grade 3. The validation data sets shown in FIG. 23A vary in vary in sample preparation, sequencing platform, and data processing used to obtain expression data. FIG. 23A shows data sets (top panels) where each vertical line corresponds to a different sample, where the shading of the line corresponds to different data sets. The cancer grade associated with samples of the data sets is shown, where the lighter shade indicates grade 1 and the darker shade indicates grade 3. The cancer grade associated with the samples may be a determination by a physician (e.g., pathologist) using microscopy to visually inspect the samples. The probability of molecular grade 3 predicted using the cancer grade classifier is also shown. FIG. 23A also shows the enrichment signatures for different pathways, illustrating gene expression profiles associated with lung adenocarcinoma grade 1 and grade 3. Genes in one or more of these pathways may be used for determining lung adenocarcinoma grade according to the techniques described herein. As an example, the HALLMARK_G2M_CHECKPOINT signature is shown in the top panel and has a majority of upregulated genes for the right portion of samples and a majority of downregulated genes for the left portion of samples. FIG. 23B shows results of applying validation data sets to lung adenocarcinoma cancer grade classifier. FIG. 23C is a plot of true positive rate versus false positive rate for predicting cancer grade of different biological samples where the classifier had a 0.894 AUC score.

Figure 8A:
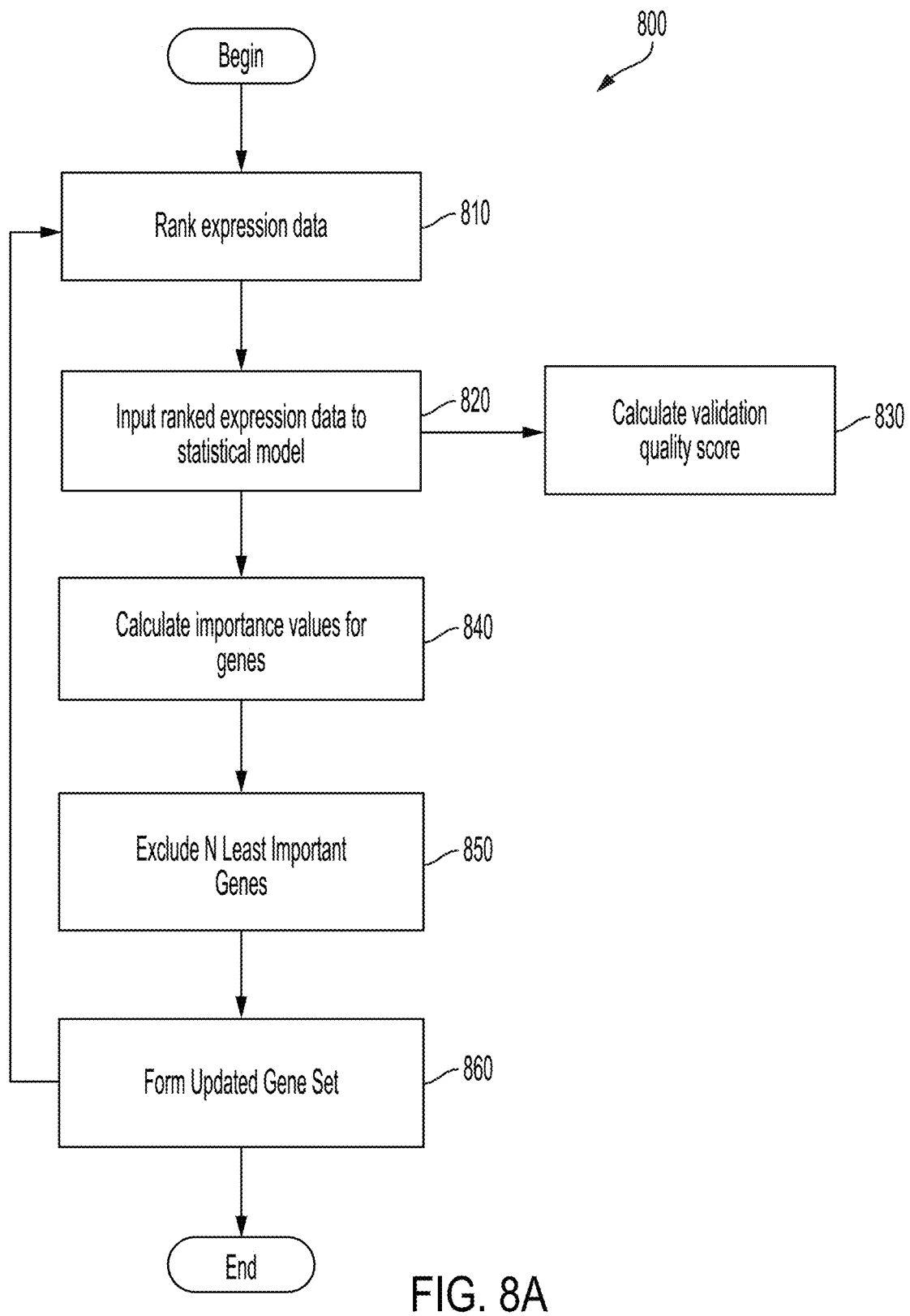
FIG. 8A is a flowchart of an illustrative process for selecting a gene set, using the machine learning techniques described herein.

FIG. 8A is a flow chart of an illustrative process 800 for selecting a gene set, in accordance with some embodiments of the technology described herein. Process 800 may be performed on any suitable computing device(s) (e.g., a single computing device, multiple computing devices co-located in a single physical location or located in multiple physical locations remote from one another, one or more computing devices part of a cloud computing system, etc.), as aspects of the technology described herein are not limited in this respect. In some embodiments, ranking process 108 and statistical model 112 may perform some or all of process 800 to select a gene set, which may be implemented in determining one or more characteristics of a biological sample, such as a tissue of origin, a cancer grade, and a PTCL subtype.

Process 800 begins at act 810, where expression data is ranked to obtain a gene ranking for the genes represented by the expression levels in the expression data. Ranking process 108 may be used in ranking the expression data to obtain the gene ranking.

The expression data used in selecting a gene set may include available expression data obtained through research organizations, including the National Cancer Institute (NCI) (e.g., Gene Expression Omnibus (GEO)), National Center for Biotechnology Information (NCBI), and The Cancer Imaging Archive (TCIA). For example, a gene set used for predicting breast cancer grade may be obtained by using expression data from Series GSE2990 available through the NCI. As another example, a gene set used for determining cancer grade for kidney clear cell cancer may be obtained by using expression data from Series GSE40435. As another example, a gene set used for determining tissue of origin and histological information (e.g., tissue type) for cancer may be obtained by using expression data from The Cancer Genome Atlas Program (TCGAP). As another example, a gene set used for predicting PTCL subtype may be obtained using expression data listed in Table 9.

Next, process 800 proceeds to act 820, where the ranked expression data is input into a statistical model, such as statistical model 112. An output indicating one or more desired characteristics may be obtained as a result of inputting the ranked expression data into the statistical model. Process 800 may proceed to act 830, where a validation quality score is calculated based on the output obtained by inputting the ranked expression data into the statistical model of act 820. A validation quality score may be calculated using one or more suitable metrics, including negative log loss, AUC, F-score (micro, macro, weighted), accuracy, balanced accuracy, precision, and recall.

Next, process 800 proceeds to act 840, where importance value(s) for different genes included in the ranking are calculated. An example of an importance value is a Shapley Additive Explanations (SHAP) value, which is described in "A Unified Approach to Interpreting Model Predictions" by Scott M. Lundberg and Su-In Lee, which is incorporated by reference in its entirety. Example SHAP values are shown in Table 7 in connection with a cell of origin classifier for DLBCL.

Next, process 800 proceeds to act 850, where the N (e.g., 1, 2, 3, 4) least important genes are excluded based on the importance values. Next process 800 proceeds to act 860, where a gene set updated based on excluding the N least important genes. In some embodiments, at least the gene have the lowest importance value is removed from the gene set.

Process 800 may initialize with a larger number of genes (e.g., ~3,000 genes) in the gene set and decrease the number of genes in the set through subsequent iterations. Process 800 may continue by repeating the acts with the gene set selected in act 860 of the prior iteration until a desired quality score is achieved (e.g., a quality score higher than a threshold value). In some instances, an initial gene set may be ranked at act 810 and narrowed by process 800 to achieve a limited gene set used for a classifier as described herein.

Figure 8B:
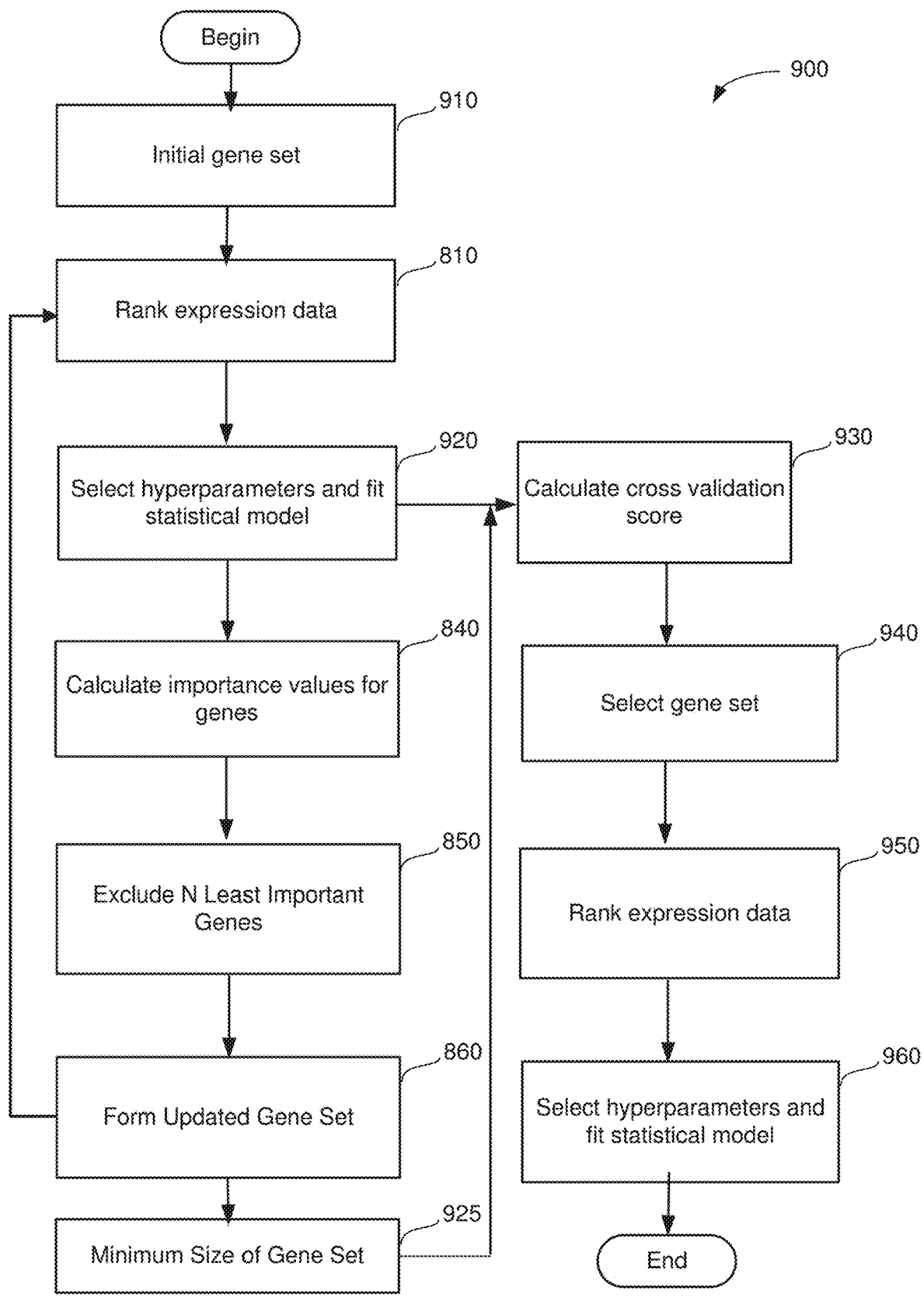
FIG. 8B is a flowchart of an illustrative process for selecting a gene set, using the machine learning techniques described herein.

FIG. 8B is a flow chart of an illustrative process 800 for selecting a gene set, in accordance with some embodiments of the technology described herein. Process 900 may be performed on any suitable computing device(s) (e.g., a single computing device, multiple computing devices co-located in a single physical location or located in multiple physical locations remote from one another, one or more computing devices part of a cloud computing system, etc.), as aspects of the technology described herein are not limited in this respect. In some embodiments, ranking process 108 and statistical model 112 may perform some or all of process 900 to select a gene set, which may be implemented in determining one or more characteristics of a biological sample, such as a tissue of origin, a cancer grade, and a PTCL subtype.

Process 900 begins at act 910, where an initial gene set is selected. The initial gene set selected may include a set of genes selected from Table 1, Table 2, Table 3, Table 6, and Table 8. The number of initial genes may be at least 1,000 genes, at least 3,000 genes, or at least 5,000 genes.

Next, process 900 proceeds to act 810, as discussed above in connection with process 800. Next process 900 proceeds to act 920, where hyperparameters for the statistical model are selected and fit to the statistical model.

Next process proceeds to acts 840, 850, and 860 as discussed above in connection with process 800. As discussed in connection with process 800, the initial set of genes may decrease in number though subsequent iterations of these steps. As a result of these iterative steps, process 900 proceeds to act 925, where a minimum size of gene set is reached.

As part of these iterative steps, process 900 proceeds to act 930, where a cross validation score is calculated based on inputting the ranked expression data into the statistical model of act 820. A cross validation score may be calculated by performing k-fold cross validation.

Process 900 proceeds to act 940, where a gene set is selected based on the cross validation score calculated in act 930. In some embodiments, the gene set selected has the highest cross validation score from a group of gene sets.

Next process 900 proceeds to act 950, where expression data is ranked to obtain a gene ranking for the genes represented by the expression levels in the expression data. Ranking process 108 may be used in ranking the expression data to obtain the gene ranking.

Next process 900 proceeds to act 960, where hyperparameters for the statistical model are selected and fit to the statistical model for the gene set selected in act 940.

Figure 9A:
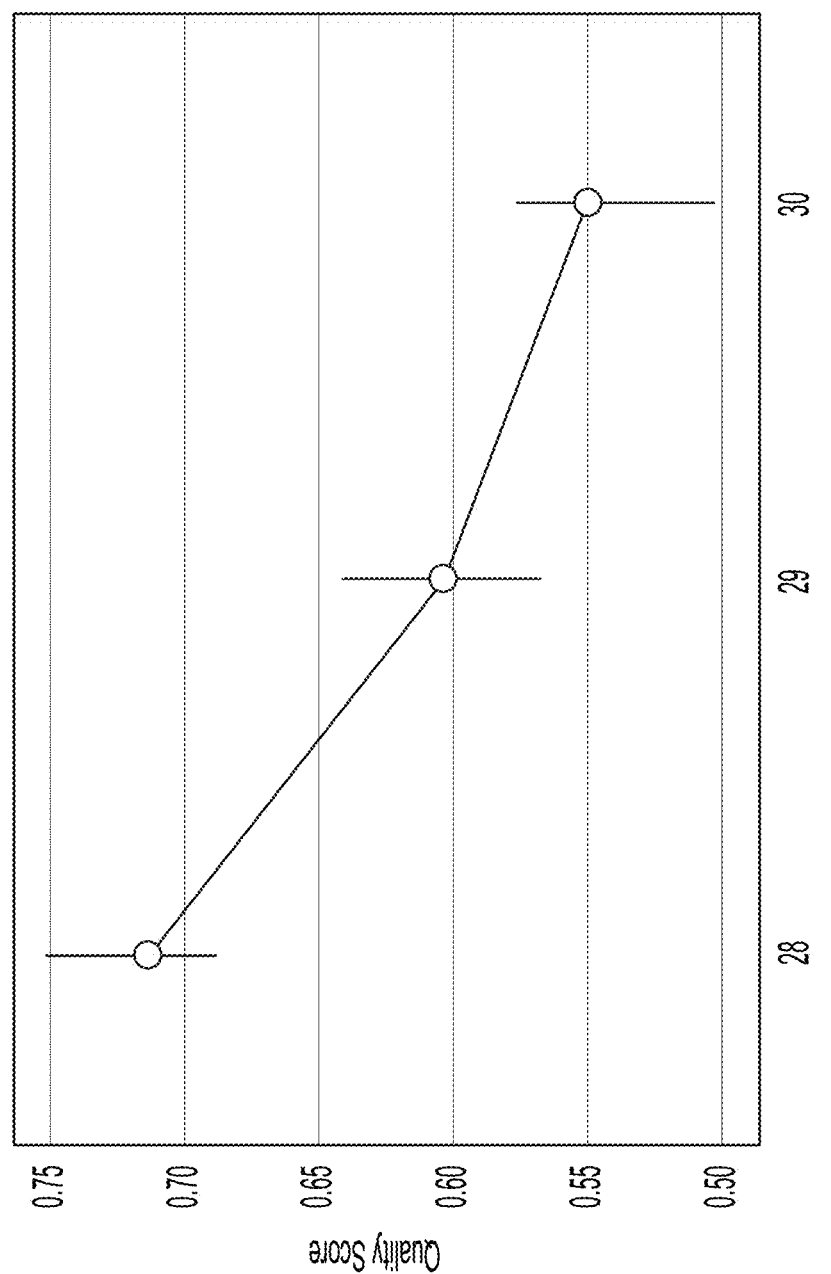
FIG. 9A is an exemplary plot of quality score versus number of genes used for determining tissue of origin, using the machine learning techniques described herein.
Figure 9B:
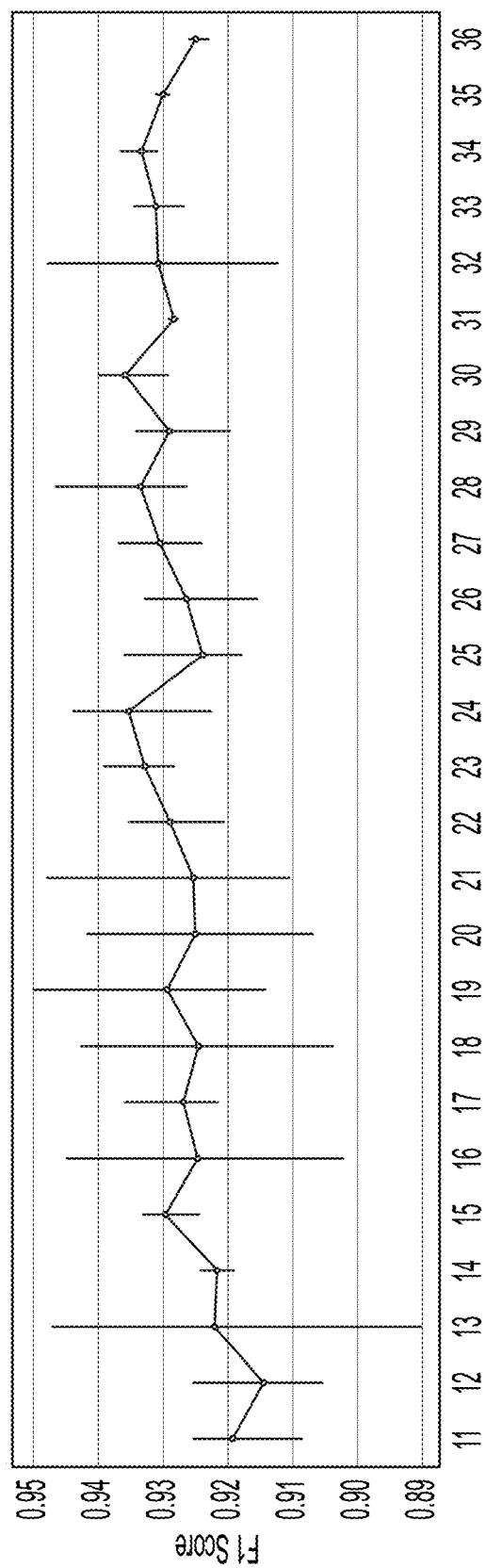
FIG. 9B is an exemplary plot of F1 score versus number of genes used for determining tissue of origin for Diffuse Large B-Cell Lymphoma (DLBCL), such as germinal center B-cell (GCB) and activated B-cell (ABC), using the machine learning techniques described herein.

For example, FIG. 9A is a plot of quality score versus number of genes, which illustrates how decreasing the number of genes to 28 from 30 increases the quality score. FIG. 9B is an exemplary plot of F1 score versus number of genes used in ranking for ABC/GCB tissue of origin prediction, in accordance with some embodiments of the technology described herein.

Cell of Origin DLBCL Classifier

As discussed herein, some embodiments involve using the techniques described herein for determining cell of origin for DLBCL. In particular, a cell of origin DLBCL classifier may categorize samples as being either germinal center B-cell (GCB) and activated B-cell (ABC). Such a classifier may be developed by using samples from Series GSE117556, Leipzig Lymphoma data set (10.1186/s13073-019-0637-7), Series GSE31312, Series GSE10846, Series GSE87371, Series GSE11318, Series GSE32918, Series GSE23501, Lymphoma/Leukemia Molecular Profiling Project (LLMPP), and Series GSE93984 as training data. For each data set, samples were selected to have a balanced cell of origin ratio ABC:GCB ratio of 40:60 per data set. For example, this may involve selecting samples having cell of origin labeling followed by a round of random selection of samples to obtained a desired ABC:GCB ratio. An example cell of origin DLBCL classifier is discussed in connection with FIGS. 24A, 24B, 24C, 24D, and 24E. For this classifier, the training data set includes 1,968 samples.

Suitable data sets may be used to validate the trained cell of origin DLBCL classifier. Validation of a cell of origin DLBCL may involve using data from Series GSE34171 (GPL96+GPL97), Series GSE22898, Series GSE64555, Series GSE145043, Series GSE19246, and the National Cancer Institute Center for Cancer Research (NCICCR) "Genetics and Pathogenesis of Diffuse Large B Cell Lymphoma" data set. Validation of the classifier described in connection with FIGS. 24A, 24B, 24C, 24D, and 24E involved using a validation data set of 928 samples.

A classifier may be further validated using data sets of unknown and unclassified samples. A cell of origin DLBCL classifier may be validated using data from Series GSE69051, Series GSE69049, E-TABM-346, Series GSE68895, Series GSE38202, Series GSE2195, International Cancer Genome Consortium Malignant Lymphoma—DE (ICGC_MALY_DE) data set, and National Cancer Institute Cancer Genome Characterization Initiative (NCICGCI) Non-Hodgkin Lymphoma data set. For the cell of origin DLBCL classifier discussed in connection with FIGS. 24A, 24B, 24C, 24D, and 24E, 1,169 unknown and unclassified samples were used in validation of the classifier.

The cell of origin classifier discussed in connection with FIGS. 24A, 24B, 24C, 24D, and 24E may involve identifying a gene set, such as by process 800 shown in FIG. 8. In particular, an initial gene set may be identified from genes discussed in Wright G, et al., A gene expression-based method to diagnose clinically distinct subgroups of diffuse large B cell lymphoma, PNAS, 2003; 100:9991-9996 (doi: 10.1073/pnas.1732008100), which is incorporated by reference herein in its entirety. The initial gene set was curated down to 30 genes to be used in the classifier. After hyperparameter tuning, the classifier's performance on a validation data set reached 0.93 f1-score and 0.978 AUC score.

In this example classifier, binary classification was performed using a gradient booster decision tree classifier in LightGBM. Feature selection was performed by estimating feature importance in the model using SHAP package. Example SHAP importance values calculated for possible genes to include in a cell of origin classifier for DLBCL are shown in Table 7, below.

TABLE 7

Genes for DLBCL cell of origin classifier and SHAP importance values

| Cell of origin genes | SHAP importance |
|---|---|
| ITPKB | 1.198 |
| MYBL1 | 1.15 |
| LMO2 | 0.93 |
| IRF4 | 0.94 |
| LRMP | 0.71 |
| CCND2 | 0.7 |
| BATF | 0.66 |
| SP140 | 0.52 |
| SPINK2 | 0.54 |
| TCF4 | 0.41 |
| CSTB | 0.41 |
| PIM1 | 0.32 |
| VCL | 0.3 |
| GPR18 | 0.24 |
| FUT8 | 0.22 |
| BCL2 | 0.28 |
| SLA | 0.24 |
| RPL21 | 0.2 |
| P2RX5 | 0.11 |
| REL | 0.12 |
| HLA-DQA1 | 0.13 |
| CSNK1E | 0.16 |
| PTPN1 | 0.05 |
| KRT8 | 0.15 |
| IGHM | 0.13 |
| PRKCB1 | 0.11 |
| GOT2 | 0.11 |
| FAM3C | 0.07 |
| SPIB | 0.09 |
| ACP1 | 0.06 |
| PIM2 | 0.04 |
| PLEK | 0.06 |

Figure 24A:
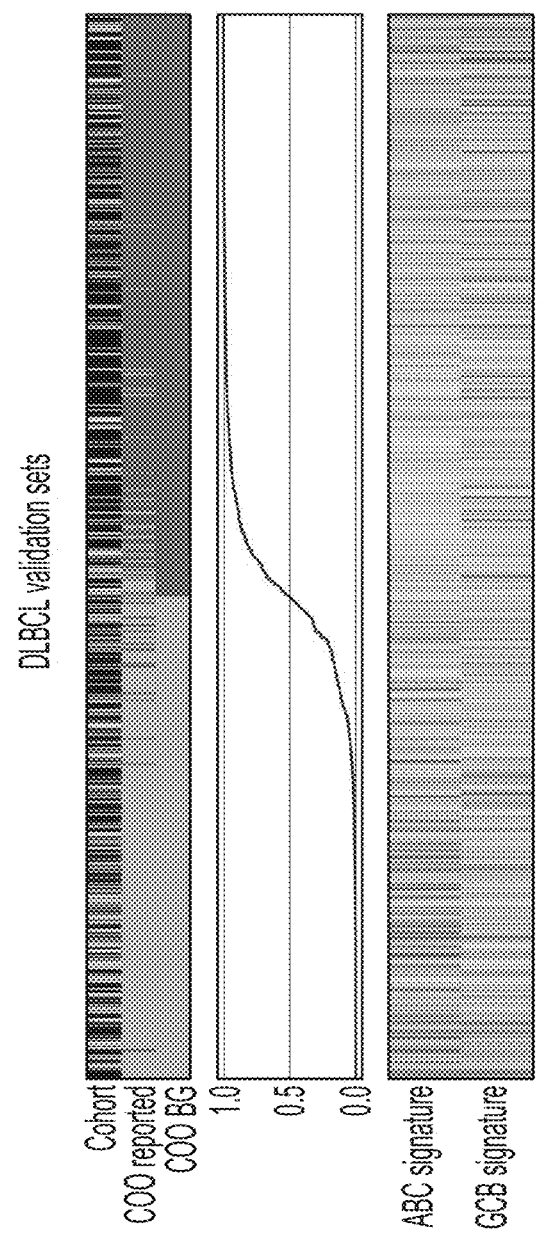
FIG. 24A shows example validation data sets, associated cell of origin reported for samples of the data sets, predicted cell of origin obtained using the machine learning techniques described herein, for determining DLBCL subtype, and the enrichment signatures for ABC and GCB subtypes.
Figure 24B:
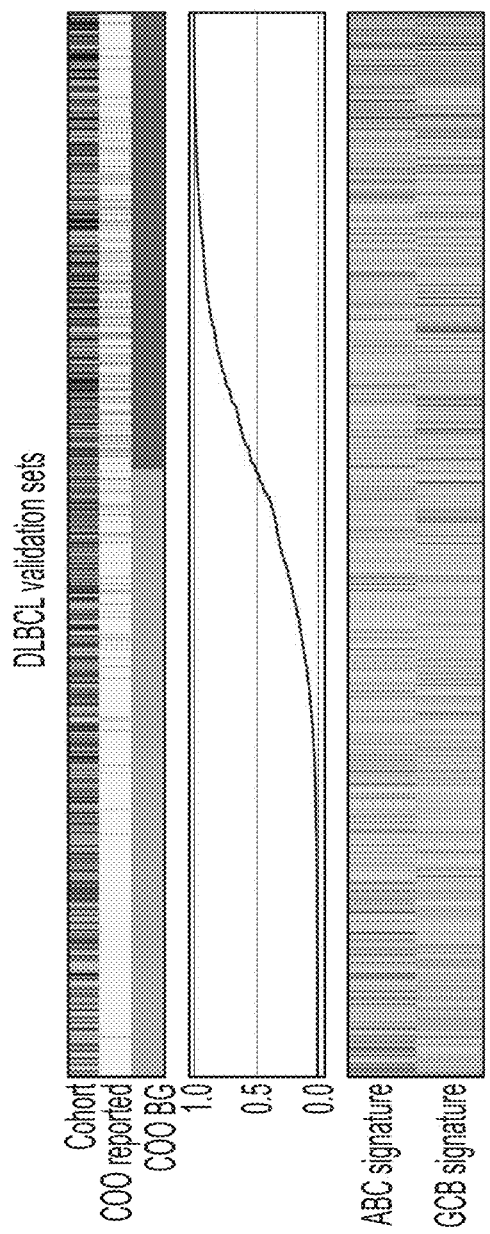
FIG. 24B shows example validation data sets, associated cell of origin reported for samples of the data sets, predicted cell of origin obtained using the machine learning techniques described herein, for determining DLBCL subtype, and the enrichment signatures for ABC and GCB subtypes.
Figure 24C:
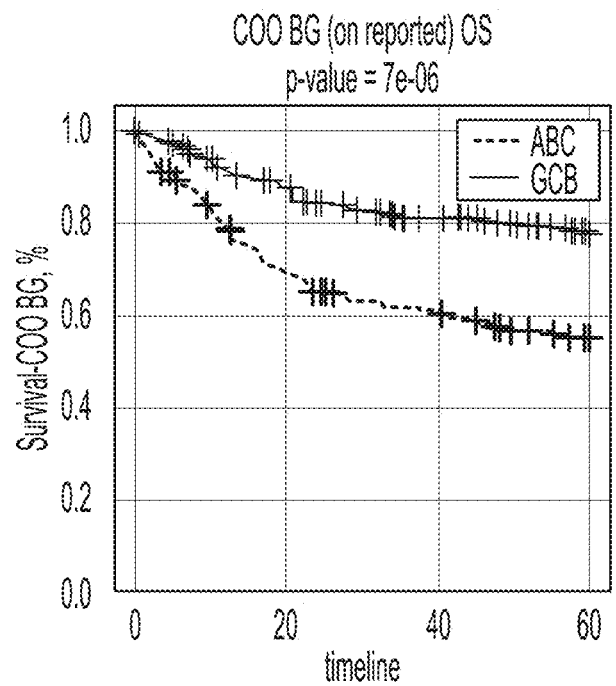
FIGS. 24C and 24D are example plots of survival rates for different groups (ABC, GCB).
Figure 24D:
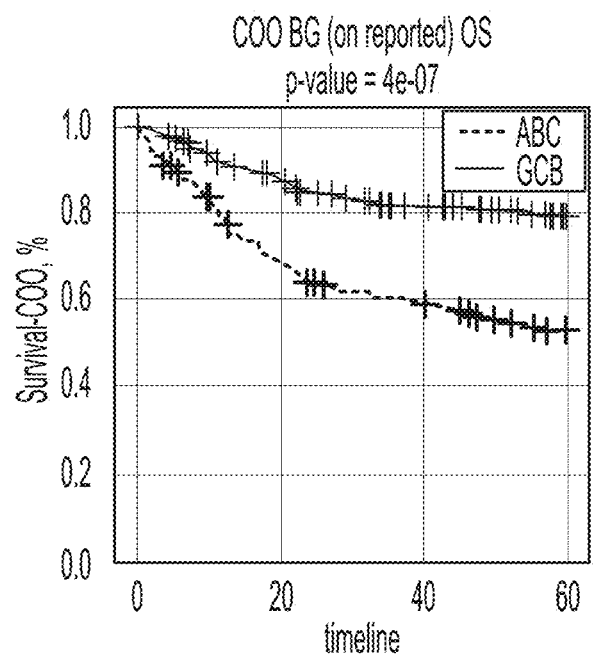
Figure 24E:
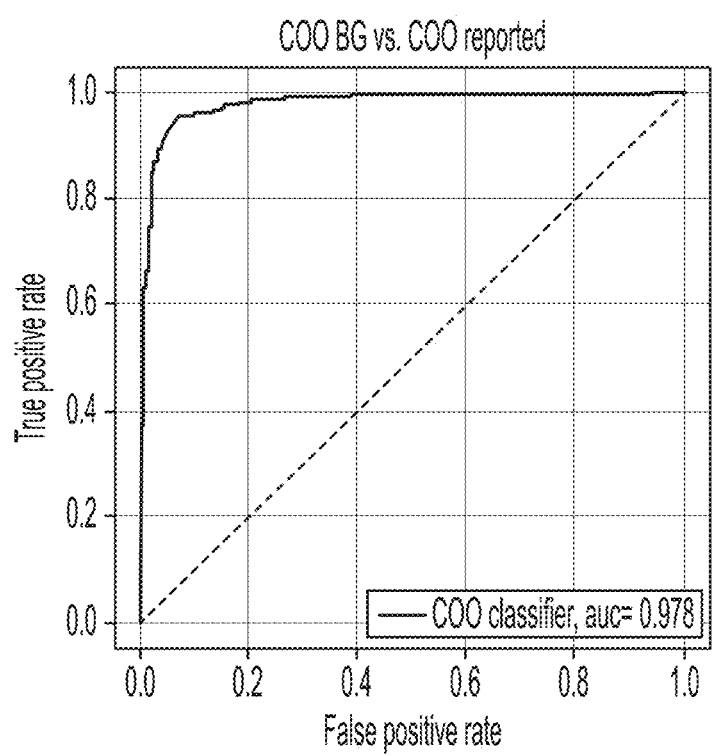
FIG. 24E is an example plot of true positive rate versus false positive rate for predicting DLBCL subtype of different biological samples using the machine learning techniques described herein.

FIG. 24A shows validation data sets, associated cell of origin reported for samples of the data sets, predicted cell of origin obtained using the machine learning techniques described herein, for determining DLBCL subtype, and the enrichment signatures for ABC and GCB subtypes. FIG. 24B shows validation data sets, associated cell of origin reported for samples of the data sets, predicted cell of origin obtained using the machine learning techniques described herein, for determining DLBCL subtype, and the enrichment signatures for ABC and GCB subtypes. The validation data sets shown in FIGS. 24A and 24B vary in sample preparation, sequencing platform, and data processing used to obtain expression data. Both FIGS. 24A and 24B shows data sets (top panel) where each vertical line corresponds to a different sample, where the shading of the line corresponds to different data sets. The cell of origin associated with samples of the data sets is shown, where the lighter shade indicates GCB subtype and the darker shade indicates ABC subtype. The cell of origin associated with the samples may be a determination by a physician (e.g., pathologist) using microscopy to visually inspect the samples. The enrichment signatures for ABC signature and GCB signature are shown in FIGS. 24A and 24B. The ABC signature generally has a majority of upregulated genes on the right portion of samples and the GBC signature has a majority of upregulated genes for the left portion of samples. FIGS. 24C and 24D are plots of survival rates for different groups (ABC, GCB). FIG. 24E is a plot of true positive rate versus false positive rate for predicting DLBCL subtype of different biological samples where the classifier had a 0.978 AUC score.

Human Papillomavirus (HPV) Head and Neck Squamous Cell Carcinoma Classifier

Some embodiments involve using the techniques described herein for predicting HPV status (HPV-positive, HPV-negative). Such embodiments may involve determining a sample as having an HPV-positive status or HPV-negative status. In some embodiments, the HPV status may be determined for a subject having, suspected of having, or at risk of having head and neck squamous cell carcinoma. Examples of genes that may be included in agene set for determining HPV status for head and neck squamous cell carcinoma are listed in Table 8, below. The set of genes may include at least 3, 5, 10, or 20 genes selected from the group of genes listed in Table 8. In some embodiments, the set of genes may include all the genes listed in Table 8. In some embodiments, the set of genes may include 3-130 genes, 5-130 genes, 20-130 genes, 50-130 genes, 80-130 genes listed in Table 8. In some embodiments, the set of genes may include 130 or fewer genes, 100 or fewer genes, 80 or fewer genes, 50 or fewer genes, 20 or fewer genes listed in Table 8.

TABLE 8

HPV Status Classifier for Head and Neck Squamous Cell Carcinoma

| Gene | NCBI Gene ID | NCBI Accession Number(s) |
|---|---|---|
| APOBEC3B | 9582 | NM_001270411; NM_004900 |
| ATAD2 | 29028 | NM_014109; NM_014109 |
| BIRC5 | 332 | NM_001168; NM_001012271; NM_001012270; NM_001168 |
| CCL20 | 6364 | NM_001130046; NM_004591 |
| CCND1 | 595 | NM_053056; NM_053056 |
| CDC45 | 8318 | NM_001178010; NM_001178011; NM_003504; XM_011530417; XM_011530416; NR_161281; XM_017028966; ; XR_002958716; NM_001178010; XM_011530418; XM_017028967; XM_024452277; NM_001369291 |
| CDC7 | 8317 | NM_001134419; NM_001134420; NM_003503; XM_005271241 |
| CDK1 | 983 | NM_001320918; NM_001786; NM_033379; XM_005270303 |

TABLE 8-continued

HPV Status Classifier for Head and Neck Squamous Cell Carcinoma

| Gene | NCBI Gene ID | NCBI Accession Number(s) |
|---|---|---|
| CDKN2A | 1029 | NM_000077; NM_000077; NM_001195132; NM_058197; XM_005251343; XM_011517676; ; NM_058196; NM_058195; XM_011517675; NM_001363763; XR_929159 |
| CDKN2C | 1031 | NM_001262; NM_078626; NM_001262 |
| CDKN3 | 1018 | NM_001258 |
| CENPF | 1063 | NM_016343; XM_017000086 |
| CENPN | 55839 | NM_001100624; NM_001100625; NM_001270473; NM_001270474; NM_018455; XM_006721236; XM_017023456 |
| CXCL14 | 9547 | NM_004887 |
| DCN | 1634 | NM_133505; NM_001920; NM_133503; NM_133504; NM_133505; NM_133506; NM_133507; |
| DHFR | 1719 | NM_000791; NM_001290357; NM_000791; NM_001290354 |
| DKK3 | 27122 | NM_001330220; XM_017017554; XM_017017555; NM_001018057; NM_001330220; NM_013253; NM_015881; XM_006718178 |
| DLGAP5 | 9787 | NM_001146015; NM_014750; XM_017021840 |
| EPCAM | 4072 | NM_002354 |
| FANCI | 55215 | NM_001113378; NM_018193; XM_011521756; NM_001113378; NM_001376910; NM_001376911; ; XM_011521764 |
| FEN1 | 2237 | NM_004111; NM_004111 |
| GMNN | 51053 | NM_001251989; NM_001251990; NM_001251991; NM_015895; XM_005249159; NM_001251989 |
| GPX3 | 2878 | NM_001329790; NM_002084 |
| ID4 | 3400 | NM_001546 |
| IGLC1 | 3537 | NG_000002.1 |
| IL18 | 3606 | NM_001243211; XM_011542805; NM_001243211; NM_001562; ; NM_001386420 |
| IL1R2 | 7850 | NM_001261419; NM_004633; XM_006712734; XM_011511804 |
| KIF18B | 146909 | NM_001264573; NM_001265577; NM_001264573 |
| KIF20A | 10112 | NM_005733 |
| KIF4A | 24137 | NM_012310 |
| KLK13 | 26085 | NM_001348177; NM_001348178; NM_001348177; NM_015596 |
| KLK7 | 5650 | NM_005046; NM_139277; NM_001207053; NM_001243126; NM_005046 |
| KLK8 | 11202 | NM_001281431; NM_001281431; NM_007196; NM_144505; NM_144506; NM_144507 |
| KNTC1 | 9735 | NM_014708; XM_006719706 |
| KRT19 | 3880 | NM_002276 |
| LAMP3 | 27074 | NM_014398 |
| LMNB1 | 4001 | NM_005573 |
| MCM2 | 4171 | NM_004526 |
| MCM4 | 4173 | NM_005914; NM_182746 |
| MCM5 | 4174 | NM_006739; NM_006739 |
| ME1 | 4199 | NM_002395; XM_011535836 |
| MELK | 9833 | NM_001256685; NM_001256687; NM_001256688; NM_001256689; NM_001256690; NM_001256692; NM_001256693; NM_014791; XM_011518076; XM_011518077; XM_011518078; XM_011518079; XM_011518081; XM_011518082; XM_011518083; XM_011518084 |
| MKI67 | 4288 | NM_001145966; NM_002417 |
| MLF1 | 4291 | NM_022443; NM_001130156; NM_001130157; NM_001195432; NM_001195433; NM_001195434; NM_022443; NM_001369782; NM_001378848; NM_001378853; ; NM_001369784; NM_001369785; NM_001369781; NM_001378846; NM_001378855; NM_001378845; NM_001378847; NM_001378850; NM_001378852; NM_001369783; NM_001378851 |
| MMP12 | 4321 | NM_002426 |
| MTHFD2 | 10797 | NM_006636; XM_006711924 |
| NDN | 4692 | NM_002487; NM_002487 |
| NEFH | 4744 | NM_021076 |
| NEK2 | 4751 | NM_001204182; NM_001204182; NM_001204183; NM_002497; XM_005273147 |
| NUP155 | 9631 | NM_153485; NM_001278312; NM_004298; NM_153485 |
| NUP210 | 23225 | NM_024923 |
| NUSAP1 | 51203 | NM_001243142; NM_001243143; NM_001243144; NM_001301136; NM_016359; NM_018454; XM_005254430 |
| PDGFD | 80310 | NM_025208; NM_033135 |
| PLAGL1 | 5325 | NM_001080951; NM_001080952; NM_001080953; NM_001080954; NM_001289042; NM_001289043; NM_001289044; NM_001289047; NM_001289048; NM_001289049; NM_001317157; NM_001317159; NM_006718; NM_001080955; NM_001289037; NM_001289038; NM_001289039; NM_001289040; NM_001080951; NM_001080956; NM_001289041; NM_001289045; NM_001289046; NM_001317156; NM_001317158; NM_001317160; NM_001317161; NM_001317162 |
| PLOD2 | 5352 | NM_000935; NM_182943 |
| PPP1R3C | 5507 | NM_005398 |
| PRIM1 | 5557 | NM_000946 |

TABLE 8-continued

HPV Status Classifier for Head and Neck Squamous Cell Carcinoma

| Gene | NCBI Gene ID | NCBI Accession Number(s) |
|---|---|---|
| PRKDC | 5591 | NM_001081640; NM_006904 |
| PSIP1 | 11168 | NM_001128217; NM_001317898; NM_001317900; NM_021144; NM_033222 |
| RAD51AP1 | 10635 | NM_001130862; NM_006479 |
| RASIP1 | 54922 | NM_017805; NM_017805 |
| RFC5 | 5985 | NM_001130112; NM_001130113; NM_007370; NM_181578; XM_011538643; XM_011538645 |
| RNASEH2A | 10535 | NM_006397 |
| RPA2 | 6118 | NM_001286076; NM_001297558; NM_002946 |
| RPL39L | 116832 | NM_052969 |
| RSRC1 | 51319 | NM_001271834; NM_001271838; NM_016625 |
| RYR1 | 6261 | NM_000540; NM_001042723 |
| SLC35G2 | 80723 | NM_001097599; NM_001097600; NM_025246; XM_006713773; XM_011513214; XM_017007289; XM_017007290; XM_017007291 |
| SMC2 | 10592 | NM_001265602; NM_001042550; NM_001042551; NM_001265602; NM_006444; XM_006716933; XM_011518148; XM_011518149; XM_011518153; XM_017014206; XM_017014207; XM_017014208 |
| SPARCL1 | 8404 | NM_001128310; NM_001291976; NM_001291977; NM_004684 |
| STMN1 | 3925 | NM_001145454; NM_005563; NM_203399; NM_203401 |
| SYCP2 | 10388 | NM_014258; XM_011528489 |
| SYNGR3 | 9143 | NM_004209 |
| TIMELESS | 8914 | NM_001330295; NM_003920 |
| TMPO | 7112 | NM_001032283; NM_001032284; NM_001307975; NM_003276; NM_001032283 |
| TPX2 | 22974 | NM_012112; XM_011528697; XM_011528699; NM_012112 |
| TRIP13 | 9319 | NM_004237; XM_011514163 |
| TYMS | 7298 | NM_001071; NM_001071 |
| UCP2 | 7351 | NM_003355; NM_003355 |
| UPF3B | 65109 | NM_023010; NM_080632 |
| USP1 | 7398 | NM_001017415; NM_001017416; NM_003368 |
| ZSCAN18 | 65982 | NM_001145542; NM_001145543; NM_001145544; NM_023926; XM_005259174; XM_006723335; XM_011527238; XM_011527239; XM_017027169; XM_017027170; XM_017027171 |
| APOBEC3B | 9582 | NM_001270411; NM_004900 |
| ATAD2 | 29028 | NM_014109; NM_014109 |
| BIRC5 | 332 | NM_001168; NM_001012271; NM_001012270; NM_001168 |
| CCL20 | 6364 | NM_001130046; NM_004591 |
| CCND1 | 595 | NM_053056; NM_053056 |
| CDC45 | 8318 | NM_001178010; NM_001178011; NM_003504; XM_011530417; XM_011530416; NR_161281; XM_017028966; ; XR_002958716; NM_001178010; XM_011530418; XM_017028967; XM_024452277; NM_001369291 |
| CDC7 | 8317 | NM_001134419; NM_001134420; NM_003503; XM_005271241 |
| CDK1 | 983 | NM_001320918; NM_001786; NM_033379; XM_005270303 |
| CDKN2A | 1029 | NM_000077; NM_000077; NM_001195132; NM_058197; XM_005251343; XM_011517676; ; NM_058196; NM_058195; XM_011517675; NM_001363763; XR_929159 |
| CDKN2C | 1031 | NM_001262; NM_078626; NM_001262 |
| CDKN3 | 1018 | NM_001258 |
| CENPF | 1063 | NM_016343; XM_017000086 |
| CENPN | 55839 | NM_001100624; NM_001100625; NM_001270473; NM_001270474; NM_018455; XM_006721236; XM_017023456 |
| CXCL14 | 9547 | NM_004887 |
| DCN | 1634 | NM_133505; NM_001920; NM_133503; NM_133504; NM_133505; NM_133506; NM_133507; |
| DHFR | 1719 | NM_000791; NM_001290357; NM_000791; NM_001290354 |
| DKK3 | 27122 | NM_001330220; XM_017017554; XM_017017555; NM_001018057; NM_001330220; NM_013253; NM_015881; XM_006718178 |
| DLGAP5 | 9787 | NM_001146015; NM_014750; XM_017021840 |
| EPCAM | 4072 | NM_002354 |
| FANCI | 55215 | NM_001113378; NM_018193; XM_011521756; NM_001113378; NM_001376910; NM_001376911; XM_011521764 |
| FEN1 | 2237 | NM_004111; NM_004111 |
| GMNN | 51053 | NM_001251989; NM_001251990; NM_001251991; NM_015895; XM_005249159; NM_001251989 |
| GPX3 | 2878 | NM_001329790; NM_002084 |
| ID4 | 3400 | NM_001546 |
| IGLC1 | 3537 | NG_000002.1 |
| IL18 | 3606 | NM_001243211; XM_011542805; NM_001243211; NM_001562; NM_001386420 |
| IL1R2 | 7850 | NM_001261419; NM_004633; XM_006712734; XM_011511804 |
| KIF18B | 146909 | NM_001264573; NM_001265577; NM_001264573 |
| KIF20A | 10112 | NM_005733 |
| KIF4A | 24137 | NM_012310 |
| KLK13 | 26085 | NM_001348177; NM_001348178; NM_001348177; NM_015596 |

TABLE 8-continued

HPV Status Classifier for Head and Neck Squamous Cell Carcinoma

| Gene | NCBI Gene ID | NCBI Accession Number(s) |
|---|---|---|
| KLK7 | 5650 | NM_005046; NM_139277; NM_001207053; NM_001243126; NM_005046 |
| KLK8 | 11202 | NM_001281431; NM_001281431; NM_007196; NM_144505; NM_144506; NM_144507 |
| KNTC1 | 9735 | NM_014708; XM_006719706 |
| KRT19 | 3880 | NM_002276 |
| LAMP3 | 27074 | NM_014398 |
| LMNB1 | 4001 | NM_005573 |
| MCM2 | 4171 | NM_004526 |
| MCM4 | 4173 | NM_005914; NM_182746 |
| MCM5 | 4174 | NM_006739; NM_006739 |
| ME1 | 4199 | NM_002395; XM_011535836 |
| MELK | 9833 | NM_001256685; NM_001256687; NM_001256688; NM_001256689; NM_001256690; NM_001256692; NM_001256693; NM_014791; XM_011518076; XM_011518077; XM_011518078; XM_011518079; XM_011518081; XM_011518082; XM_011518083; XM_011518084 |
| MKI67 | 4288 | NM_001145966; NM_002417 |
| MLF1 | 4291 | NM_022443; NM_001130156; NM_001130157; NM_001195432; NM_001195433; NM_001195434; NM_022443; NM_001369782; NM_001378848; NM_001378853; ; NM_001369784; NM_001369785; NM_001369781; NM_001378846; NM_001378855; NM_001378845; NM_001378847; NM_001378850; NM_001378852; NM_001369783; NM_001378851 |
| MMP12 | 4321 | NM_002426 |
| MTHFD2 | 10797 | NM_006636; XM_006711924 |
| NDN | 4692 | NM_002487; NM_002487 |
| NEFH | 4744 | NM_021076 |
| NEK2 | 4751 | NM_001204182; NM_001204182; NM_001204183; NM_002497; XM_005273147 |
| NUP155 | 9631 | NM_153485; NM_001278312; NM_004298; NM_153485 |
| NUP210 | 23225 | NM_024923 |
| NUSAP1 | 51203 | NM_001243142; NM_001243143; NM_001243144; NM_001301136; NM_016359; NM_018454; XM_005254430 |
| PDGFD | 80310 | NM_025208; NM_033135 |
| PLAGL1 | 5325 | NM_001080951; NM_001080952; NM_001080953; NM_001080954; NM_001289042; NM_001289043; NM_001289044; NM_001289047; NM_001289048; NM_001289049; NM_001317157; NM_001317159; NM_006718; NM_001080955; NM_001289037; NM_001289038; NM_001289039; NM_001289040; NM_001080951; NM_001080956; NM_001289041; NM_001289045; NM_001289046; NM_001317156; NM_001317158; NM_001317160; NM_001317161; NM_001317162 |
| PLOD2 | 5352 | NM_000935; NM_182943 |

Such a classifier may be developed by using samples from Series GSE65858, Series GSE41613, E-TABM-302 (from EMBL-EBI), Series GSE25727, Series GSEE3292, Series GSE6791, Series GSE10300, TCGA HNSC (from The Cancer Imaging Archive (TCIA)) data sets as training data. For classifier discussed in connection with FIGS. 25A, 25B, 25C, 25D, 25E, and 25F, 60 samples of the TCGA HNSC data set were excluded from the training data and used in validation data sets. Validation data sets included the 60 samples from the TCGA HNSC data set and Series GSE40774. Series GSE74927 was used as an additional validation data set where different strains of HPV virus are represented, allowing for assessment of the classifier's performance across different HPV strains. A gene set for the classifier was identified from genes discussed in Chakravarthy et al., Human Papillomavirus Drives Tumor Development Throughout the Head and Neck: Improved Prognosis Is Associated With an Immune Response Largely Restricted to the Oropharynx, Journal of Clinical Oncology, 34, no. 34 (Dec. 1, 2016) 4132-4141 (DOI: 10.1200/JCO.2016.68.2955), which is incorporated by reference herein in its entirety. The initial gene set was curated down to 82 genes, such as by using process 800 shown in FIG. 8. After hyperparameter tuning, the classifier's performance on the validation data set with the TCGA HNSC data set and Series GSE40774 reached a 0.975 AUC score and 0.9 f1 score. The classifier's performance on the validation data set with Series GSE74927 reached a 1.0 AUC score and 1.0 f1 score. It is noted that that classifier successfully recognized several HPV strains, including HPV16 strain, HPV18 strain, HPV33 strain, and HPV55.

Figure 25A:
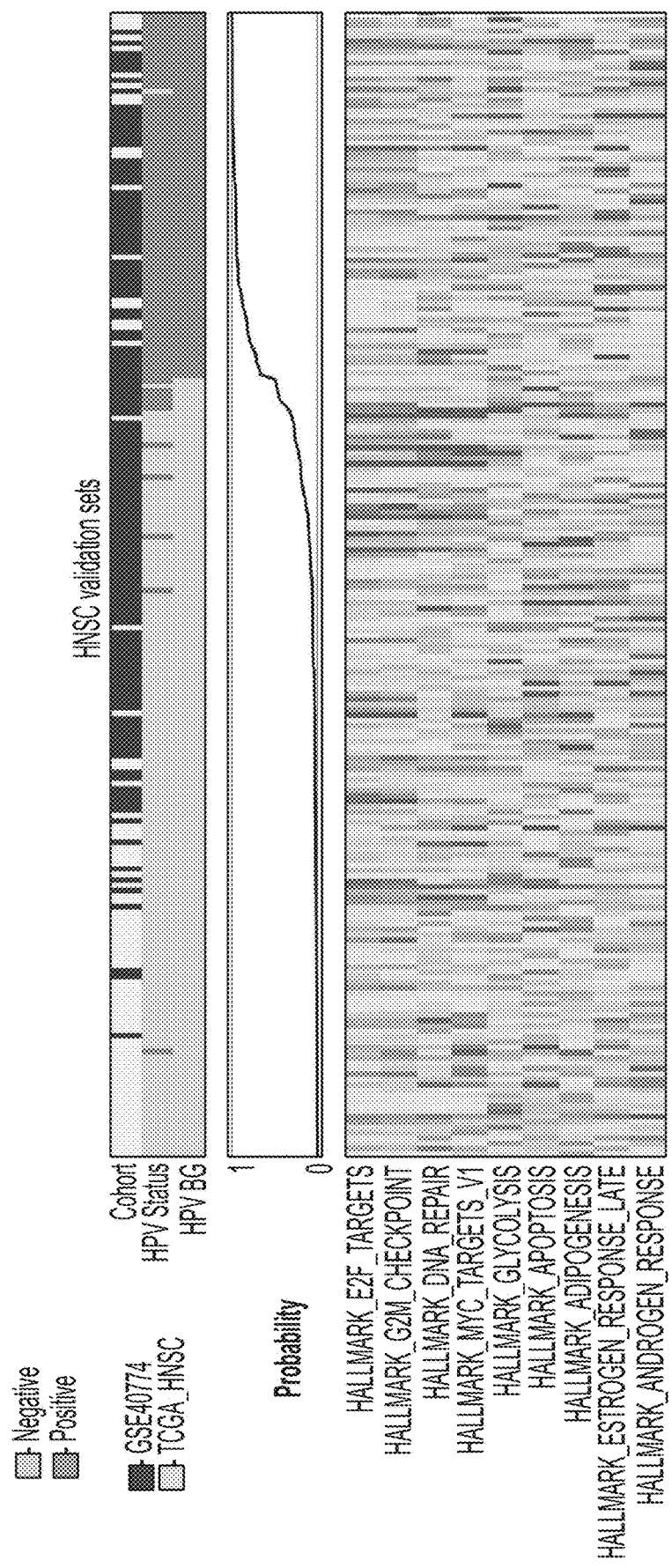
FIG. 25A shows example validation data sets, associated HPV status reported for samples of the data sets, predicted HPV status obtained using the machine learning techniques described herein, for determining HPV status, and the enrichment signatures for different pathways, illustrating gene expression profiles associated with HPV status.
Figure 25B:
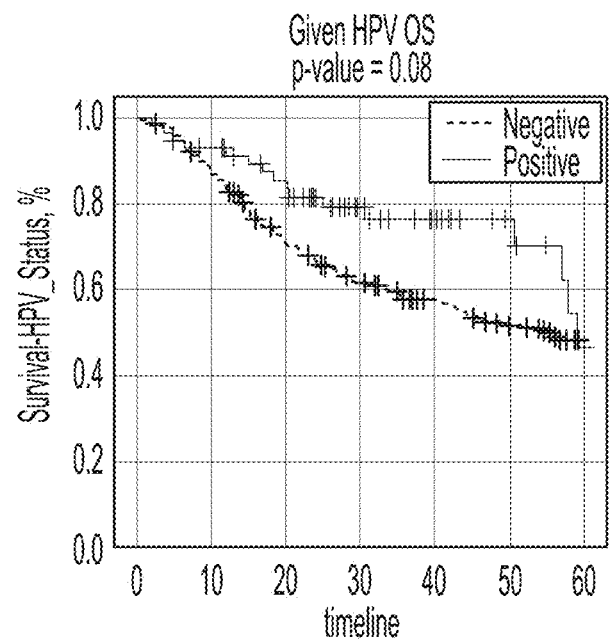
FIGS. 25B and 25C are example plots of survival rates for different groups of HPV status (positive HPV and negative HPV).
Figure 25C:
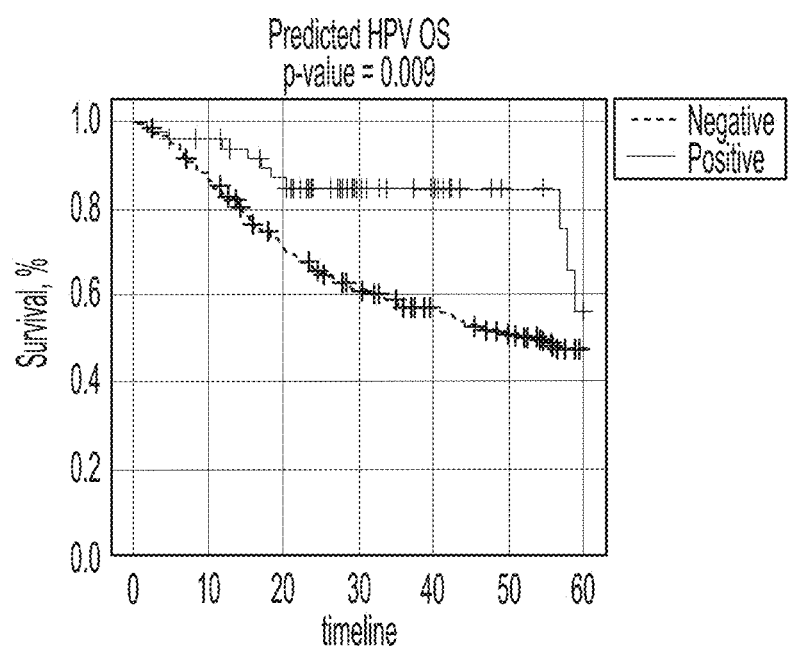
Figure 25D:
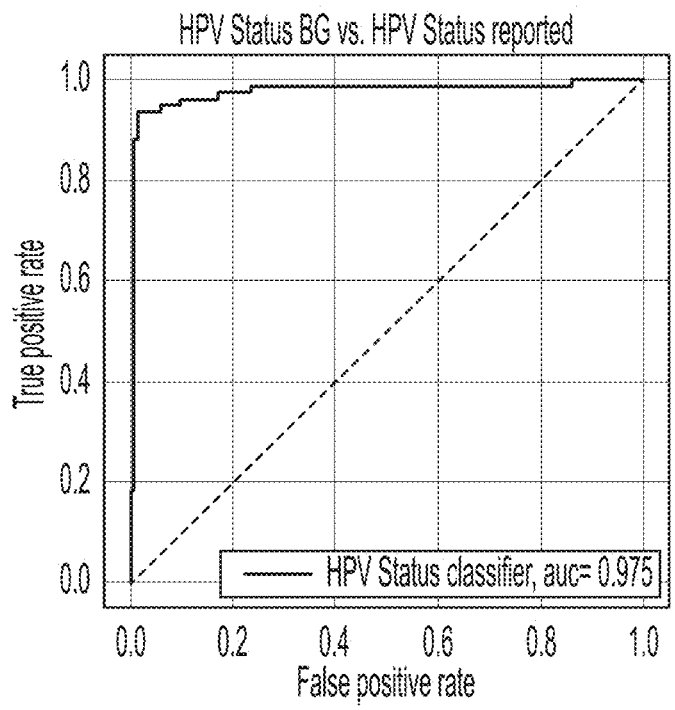
FIG. 25D is an example plot of true positive rate versus false positive rate for predicting HPV status of different biological samples using the machine learning techniques described herein.
Figure 25E:
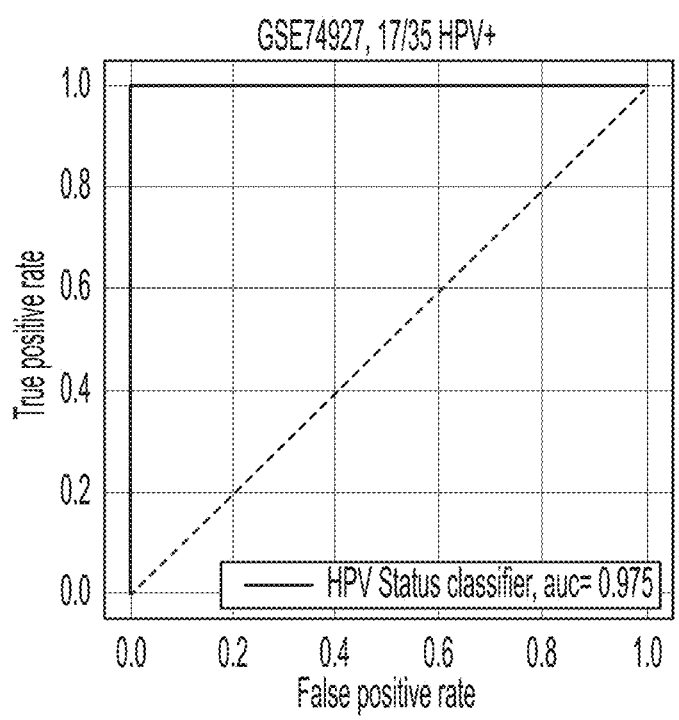
FIG. 25E is an example plot of true positive rate versus false positive rate for predicting HPV status of different biological samples using the machine learning techniques described herein.
Figure 25F:
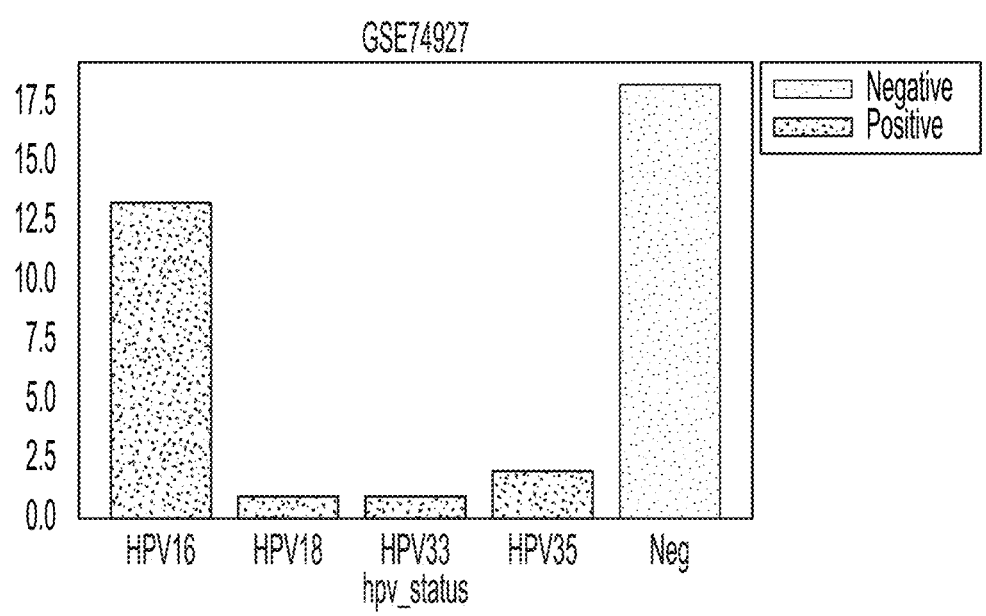
FIG. 25F is an example plot illustrating the performance of a classifier for different HPV strains, using the machine learning techniques described herein.

FIG. 25A shows validation data sets, associated HPV status reported for samples of the data sets, predicted HPV status obtained using the machine learning techniques described herein, for determining HPV status, and the enrichment signatures for different pathways, illustrating gene expression profiles associated with HPV status. Both FIG. 25A shows data sets (top panel) where each vertical line corresponds to a different sample, where the shading of the line corresponds to different data sets. The HPV status associated with samples of the data sets is shown, where the lighter shade indicates negative HPV status and the darker shade indicates positive HPV status. The probability of the sample having a positive HPV status is shown in the middle panel of FIG. 25A. The enrichment signatures for different pathways, illustrating gene expression profiles associated with HPV status are shown in FIG. 25A (bottom panel). As an example, the HALLMARK_E2F_TARGETS signature is shown in FIG. 25A and has a majority of upregulated genes for the right portion of samples and a majority of downregulated genes for the left portion of samples. FIGS. 25B and 25C are plots of survival rates for different groups of HPV status (positive HPV and negative HPV). FIG. 25D is a plot of true positive rate versus false positive rate for predicting HPV status of different biological samples (from the TCGA HNSC data set and Series GSE40774 validation data) where the classifier had a 0.975 AUC score. FIG. 25E is a plot of true positive rate versus false positive rate for predicting HPV status of different biological samples (from the Series GSE74927 validation data) where the classifier had a 1.0 AUC score. FIG. 25F is a plot of illustrating the performance of the classifier for different HPV strains in the Series GSE74927 validation data.

Peripheral T-Cell Lymphoma (PTCL) Classifier

Aspects of the present application relate to techniques, developed by the inventors, for analyzing gene expression data to determine a subtype of peripheral T-cell lymphoma (PTCL) for a biological sample. These techniques involve ranking a set of genes based on gene expression levels and using the ranking and one or more statistical models to determine the PTCL subtype. The set of genes may be associated with biological features (e.g., cell morphology, cell migration, cell cycle), expression pathways, or otherwise associated with one or more subtypes of peripheral T-cell lymphoma (PTCL).

Peripheral T-cell lymphomas accounts for approximately 10% of all non-Hodgkin lymphomas. Peripheral T-cell lymphomas are a heterogeneous group of diseases, which includes more than 20 subtypes, the exact definition of which is limited to modern methods of laboratory diagnosis. Examples of PTCL subtypes include but are not limited to Peripheral T-Cell Lymphoma, Not Otherwise Specified (PTCL-NOS), anaplastic large cell lymphoma (ALCL), angioimmunoblastic T-cell lymphoma (AITL), cutaneous T-cell lymphoma (CTCL), Natural killer/T-cell lymphoma (NKTCL), Sezary syndrome, adult T-cell leukemia/lymphoma (ATLL), enteropathy-type T-cell lymphoma, nasal NK/T-cell lymphoma, hepatosplenic gamma-delta T-cell lymphoma, T-cell lymphomas of Follicular T-cell (TFH) origin, T-cell lymphomas of the gastrointestinal tract (e.g., EATL, MEITL), cutaneous T-cell lymphomas, etc.

The most frequent subgroups among PTCL are adult T-cell leukemia/lymphoma (ATLL), angioimmunoblastic T-cell lymphoma (AITL), NK/T-cell lymphoma (NKTCL), anaplastic large cell lymphoma (ALCL), and cases belong to the Not Otherwise Specified (PTCL-NOS), which correspond to approximately to 35% of the total PTCL patients. Other PTCL subtypes are rare and mostly represented by extranodal tumors. It is anticipated that more effective annotation of the PTCL will eventually lead to the design and implementation of personalized treatments. As discussed herein, the inventors have recognized certain benefits from using the ranking of a set of genes in contrast to particular values for gene expression levels. In some embodiments, the technology described herein involves determining a subtype of peripheral T-cell lymphoma (PTCL) for a biological sample.

For example, in some embodiments, rankings of genes based on the gene expression levels (in a biological sample) as determined by a sequencing platform may be provided as input to a statistical model trained to predict PTCL subtype for the biological sample. The statistical model may include a multi-class classifier and have multiple outputs corresponding to different PTCL subtypes. As another example, in some embodiments, rankings of genes based on the gene expression levels (in a biological sample) as determined by a sequencing platform may be provided as input to multiple statistical models trained to predict different PTCL subtypes. For example, one statistical model may be trained to predict anaplastic large cell lymphoma (ALCL) for the biological sample and another statistical model may be trained to predict angioimmunoblastic T-cell lymphoma (AITL) for the biological sample. In such embodiments, the statistical models may be binary classifiers, each being trained for a different PTCL subtype, or regression type classifiers estimating a likelihood of a particular PTCL subtype.

Different PTCL subtype(s) may have different molecular signatures. In some embodiments, the set of genes being ranked depends on the particular PTCL subtype(s) of interest. In some embodiments, one set of genes may be used for determining a group of PTCL subtype(s) and another set of genes may be used for determining a different group of PTCL subtype(s). For example, one set of genes may be used for determining a group of PTCL subtype(s) that include anaplastic large cell lymphoma (ALCL), and another set of genes may angioimmunoblastic T-cell lymphoma (AITL), natural killer/T-cell lymphoma (NKTCL), and adult T-cell leukemia/lymphoma (ATLL). Another set of genes may be used for determining a group of PTCL subtype(s) that include enteropathy-type T-cell lymphoma, nasal NK/T-cell lymphoma, and hepatosplenic gamma-delta T-cell lymphoma. As another example, one set of genes may be used for determining anaplastic large cell lymphoma (ALCL), and another set of genes may be used for determining natural killer/T-cell lymphoma (NKTCL).

Some embodiments described herein address all of the above-described issues that the inventors have recognized with determining PTCL subtype of a biological sample using gene expression data. However, not every embodiment described herein addresses every one of these issues, and some embodiments may not address any of them. As such, it should be appreciated that embodiments of the technology described herein are not limited to addressing all or any of the above-discussed issues with determining PTCL subtype of a biological sample using gene expression data.

Some embodiments involve obtaining gene expression data for a biological sample of a subject, ranking genes in set(s) of genes based on their expression levels in the expression data to obtain one or more gene rankings. The one or more gene rankings may be used, along with one or more statistical models, to determine a subtype of PTCL for cells in the biological sample. The statistical model may be trained using rankings of expression levels for some or all genes in the set(s) of genes.

In some embodiments, the gene ranking(s) may be obtained by ranking genes in one or more sets of genes based on their expression levels in the expression data. In some embodiments, the expression data includes values, each representing an expression level for a gene in the set(s) of genes. Determining the gene ranking(s) may involve determining a relative rank for each gene in the set(s) of genes based on the values. For example, a first gene ranking may be obtained by ranking genes in a first set of genes based on their expression levels.

In some embodiments, the expression data may be obtained for cells in the biological sample, where the subject has or is suspected of having cancer. In some embodiments, the expression data may be obtained for cells in the biological sample, where the subject has or is suspected of having lymphoma. In some embodiments, the subject has or is suspected of having PTCL.

In some embodiments, processing pipeline 100 shown in FIG. 1 may be used for determining one or more PTCL subtypes. In such embodiments, a gene ranking and a statistical model may be used to determine one or more PTCL subtypes of a biological sample. In some embodiments, one set of genes may be used for determining PTCL subtype for the biological sample and another set of genes may be used for determining tissue of origin. For example, statistical model 112a and gene set 1 106a may be used for determining PTCL subtype for cells in the biological sample and statistical model 112b and gene set 2 106b may be used for determining tissue of origin for cells in the biological sample. In some embodiments, different gene sets may be used for determining different PTCL subtypes. For example, gene set 1 106a may be used for determining whether the biological sample has the AITL subtype and gene set 2 106b may be used for determining whether the biological sample has the ATLL subtype.

In some embodiments, different gene sets and different statistical models may be used for determining different PTCL subtypes. For example, statistical model 112a and gene set 1 106a may be used for determining one PTCL subtype (e.g., AITL) for cells in the biological sample and statistical model 112b and gene set 2 106b may be used for another PTCL subtype (e.g., ATLL) for cells in the biological sample.

A statistical model used for determining PTCL subtype may be trained using data from one or more of Series GSE58445, Series GSE45712, Series GSE1906, Series GSE90597, Series GSE6338, Series GSE36172, Series GSE65823, Series GSE118238, Series GSE78513, Series GSE51521, Series GSE14317, Series GSE80631, Series GSE19067, and Series GSE20874 available through the GEO database. As another example, a statistical model used for determining PTCL subtype may be trained using data from one or more of the cohorts listed in Table 9, below.

TABLE 9

Cohorts of patients with gene expression data for training statistical model(s) for PTCL subtype classification.

| Cohort | Database | Platform | Year |
|---|---|---|---|
| GSE58445 n = 191 | GEO | GPL570 | 2014 |
| GSE45712 n = 101 | GEO | GPL8432 GPL14591 | 2018 |
| GSE19069 n = 100 | GEO | GPL570 | 2015 |
| GSE90597 n = 66 | GEO | GPL10739 | 2018 |

TABLE 9-continued

Cohorts of patients with gene expression data for training statistical model(s) for PTCL subtype classification.

| Cohort | Database | Platform | Year |
|---|---|---|---|
| GSE6338 n = 40 | GEO | GPL570 | 2007 |
| GSE36172 n = 38 | GEO | GPL6480 | 2013 |
| E-TABM-783 n = 33 | ArrayExpress | GPL570 | 2009 |
| GSE65823 n = 31 | GEO | GPL570 | 2015 |
| GSE118238 n = 29 | GEO | GPL570 | 2018 |
| E-TABM-702 n = 23 | ArrayExpress | GPL570 | 2014 |
| GSE78513 n = 23 | GEO | GPL570 | 2016 |
| GSE51521 n = 20 | GEO | GPL17811 | 2018 |
| GSE14317 n= 19 | GEO | GPL571 | 2009 |
| GSE80631 n = 19 | GEO | GPL6883 | 2016 |
| GSE19067 n = 18 | GEO | GPL570 | 2010 |
| GSE20874 n= 18 | GEO | GPL10175 | 2011 |
| SRP049695 n = 17 | SRA | RNASeq | |
| SRP029591 n= 10 | SRA | RNASeq | 2014 |

In some embodiments, PTCL subtype may be determined using the techniques described herein for cells in a biological sample. PTCL subtype may include Peripheral T-Cell Lymphoma, Not Otherwise Specified (PTCL-NOS), anaplastic large cell lymphoma (ALCL), angioimmunoblastic T-cell lymphoma (AITL), cutaneous T-cell lymphoma (CTCL), Natural killer/T-cell lymphoma (NKTCL), Sezary syndrome, adult T-cell leukemia/lymphoma (ATLL), enteropathy-type T-cell lymphoma, nasal NK/T-cell lymphoma, hepatosplenic gamma-delta T-cell lymphoma, T-cell lymphomas of Follicular T-cell (TFH) origin, T-cell lymphomas of the gastrointestinal tract, and cutaneous T-cell lymphomas.

In some embodiments, a set of genes used to obtain a gene ranking may include genes associated with biological features, expression pathways, or otherwise associated with determining one or more PTCL subtypes. Examples of genes that may be included in such a gene set are listed in Table 10, below.

TABLE 10

Gene Set for PTCL Subtype Classifier

| Gene | NCBI Gene ID | NCBI Accession Number(s) |
|---|---|---|
| EFNB2 | 1948 | NM_004093 |
| ROBO1 | 6091 | NM_133631; NM_001145845; NM_002941; XM_006713277; XM_017006983 |
| S1PR3 | 1903 | NM_005226 |
| ANK2 | 287 | NM_001127493; NM_001148; NM_020977 |
| LPAR1 | 1902 | NM_001401; NM_057159; NM_001351414; NM_001351415; NM_001387481; NM_001387505; XM_005251782; NM_001351401; NM_001387470; NM_001387480; NM_001387486; NM_001387498; NM_001387502; NM_001387503; NM_001387509; NM_001387511; NM_001387521; NM_001351398; NM_001351399; NM_001351400; NM_001351419; NM_001387478; NM_001387493; NM_001387497; NM_001387506; NM_001387507; NM_001387508; NM_001387520; NM_001351416; NM_001387476; NM_001387491; NM_001387471; NM_001387472; NM_001387477; NM_001387485; NM_001387492; |

TABLE 10-continued

Gene Set for PTCL Subtype Classifier

| Gene | NCBI Gene ID | NCBI Accession Number(s) |
|---|---|---|
| | | NM_001387494; NM_001387510; NM_001387517; NM_001351397; NM_001351405; NM_001351406; NM_001351407; NM_001351413; NM_001351418; NM_001387475; NM_001387483; NM_001387484; NM_001387488; NM_001387490; NM_001387496; NM_001387516; NM_001387519; NM_001351404; NM_001351408; NM_001351410; NM_001351420; NM_001387473; NM_001387474; NM_001387487; NM_001387489; NM_001387495; NM_001387514; NM_001387518; NM_001351402; NM_001351403; NM_001351409; NM_001351411; NM_001351412; NM_001351417; NM_001387479; NM_001387482; NM_001387501; NM_001387504; NM_001387512; NM_001387513; NM_001387515 |
| SNAP91 | 9892 | XM_011536269; XM_017011557; XM_017011558; XM_017011559; XM_017011560; XM_005248770; XM_017011564; XM_017011571; NM_001376687; NM_001376688; NM_001376698; NM_001376700; NM_001376709; NM_001376715; NM_001376716; NM_001376723; NM_001376728; NM_001376731; NM_001376734; XM_011536266; XM_017011575; XM_017011586; NM_001376676; NM_001376682; NM_001376685; NM_001376702; NM_001376711; NM_001376736; NM_001376738; NR_164844; XM_006715615; XM_011536265; XM_017011570; XM_017011582; XM_024446600; NM_001376691; NM_001376699; NM_001376720; NM_001376735; NM_001376740; NM_014841; NR_164843; NR_164845; XM_011536275; XM_017011562; XM_017011565; XM_017011569; XM_017011580; NR_026669; NM_001256717; NM_001376677; NM_001376680; NM_001376683; NM_001376708; NM_001376718; NM_001376726; NM_001376737; XM_011536273; XM_011536276; XM_017011567; XM_017011583; XM_017011584; NM_001242794; NM_001376679; NM_001376694; NM_001376695; NM_001376697; NM_001376710; NM_001376714; NM_001376717; NM_001376742; XM_017011572; XM_017011577; XM_017011581; XM_017011590; NM_001256718; NM_001363677; NM_001376678; NM_001376686; NM_001376690; NM_001376693 |
| SOX8 | 30812 | NM_014587 |
| RAMP3 | 10268 | NM_005856 |
| TUBB2B | 347733 | NM_178012 |
| ARHGEF10 | 9639 | NM_001308152; NM_001308153; NM_014629; XM_017014003 |
| NOTCH1 | 4851 | NM_017617 |
| ZBTB17 | 7709 | NM_001242884; NM_001287603; NM_003443; XM_011542088 |
| CCNE1 | 898 | NM_001238; NM_001322262; NM_001322259; NM_001322261 |
| FGF18 | 8817 | NM_003862 |
| MYCN | 4613 | NM_001293231; NM_001293228; NM_001293233; NM_005378 |
| PTHLH | 5744 | NM_198965; NM_198966; XM_011520774; NM_002820; XM_017019675; NM_198964 |
| SMARCA2 | 6595 | NM_001289400; NM_001289399; NM_001289398; NM_001289397; NM_001289396; NM_003070; NM_139045 |
| WNK1 | 65125 | NM_014823; NM_018979; NM_001184985; NM_213655; XM_017019837; XM_017019838 |
| NKX2-1 | 7080 | NM_001079668; NM_003317 |
| CYP26A1 | 1592 | NM_000783; NM_057157 |
| HPSE | 10855 | NM_001098540; NM_001166498; NM_001199830; NM_006665 |
| CTLA4 | 1493 | NM_001037631; NM_005214 |
| PELI1 | 57162 | NM_020651; XM_011532994; XM_017004520 |
| PRKCB | 5579 | NM_002738; NM_212535 |
| SPAST | 6683 | NM_014946; NM_199436 |
| ALS2 | 57679 | NM_001135745; NM_020919; XM_006712654 |
| KIF3B | 9371 | NM_004798 |
| ZFYVE27 | 118813 | XM_005269509; XM_011539254; XR_945597; NM_001002262; NM_001174120; NM_001385878; NM_001385889; NM_001385895; NM_001385901; NM_001385918; NR_169800; XM_005269508; XR_945594; NM_001385877; NM_001385902; NM_001385903; NM_001385904; NR_169794; NR_169795; NR_169797; NR_169803; NR_169805; NR_169809; XM_011539253; XM_017015644; XR_002956957; NM_001174121; NM_001174122; NM_001385879; NM_001385881; NM_001385883; NM_001385900; XM_017015645; NM_001385875; NM_001385886; NM_001385896; NR_169796; XM_011539252; NM_001385876; NM_001385880; NM_001385887; NM_001385894; NM_001385898; NM_001385915; NM_001385919; XM_017015646; NM_001385882; NM_001385884; NM_001385890; NM_001385897; NM_001385899; NR_169804; NR_169810; NM_001002261; NM_001385871; NM_001385892; NM_001385905; NM_144588; NR_169802; NR_169806; NR_169808; NR_169811; XR_002956956; NM_001174119; NM_001385885; NM_001385888; NM_001385891; NM_001385893; NM_001385906; NM_001385908; NM_001385911; NM_001385916; NR_169798; NR_169799; NR_169801 |

TABLE 10-continued

Gene Set for PTCL Subtype Classifier

| Gene | NCBI Gene ID | NCBI Accession Number(s) |
|---|---|---|
| FGF18 | 8817 | NM_003862 |
| FNTB | 2342 | NM_001202558; NM_002028 |
| REL | 5966 | NM_001291746; NM_002908 |
| DMRT1 | 1761 | NM_021951 |
| SLC19A2 | 10560 | NM_001319667; NM_006996 |
| STK3 | 6788 | NM_001256313; NM_001256312; NM_006281 |
| PERP | 64065 | NM_022121 |
| TNFRSF8 | 943 | NM_001243; NM_001281430 |
| TMOD1 | 7111 | NM_001166116; NM_003275 |
| BATF3 | 55509 | NM_018664 |
| CDC14B | 8555 | NM_001077181; NM_003671; NM_033331; XM_011519153; XM_017015240; XM_017015247; XR_001746407; XR_001746409; NM_001351567; XM_017015248; XM_017015249; XR_929865; XM_011519147; XM_017015242; XM_017015244; XM_017015245; XR_929864; NM_001351568; XM_011519149; XM_011519152; XR_001746408; NM_001351570; NM_033332; XM_011519148; XM_011519151; XR_929868; NR_147239; XM_011519156; XR_002956814; XM_011519159; XM_017015241; XR_001746406; NM_001351569 |
| WDFEY3 | N/A | N/A |
| AGT | 183 | NM_000029 |
| ALK | 238 | NM_004304 |
| ANXA3 | 306 | NM_005139 |
| BTBD11 | 121551 | NM_001017523; NM_001018072; NM_001347943 |
| CCNA1 | 8900 | NM_001111045; NM_001111046; NM_001111047; NM_003914; XM_011535294; XM_011535295; XM_011535296 |
| DNER | 92737 | NM_139072 |
| GAS1 | 2619 | NM_002048 |
| HS6ST2 | 90161 | NM_001077188; NM_147175; XM_011531407; XM_017029945; XM_011531408; XM_017029946; XM_005262491; XM_011531406 |
| IL1RAP | 3556 | NM_001167928; NM_001167929; NM_001167930; NM_001167931; NM_002182; NM_134470 |
| PCOLCE2 | 26577 | NM_013363 |
| PDE4DIP | 9659 | XM_011510175; NM_001195261; NM_001002810; NM_001002811; NM_001002812; NM_001195260; NM_001198832; NM_001198834; NM_014644; NM_022359 |
| SLC16A3 | 9123 | NM_001042422; NM_001042423; NM_001206950; NM_001206951; NM_001206952; NM_004207; XM_024451023 |
| TIAM2 | 26230 | NM_001010927; NM_012454 |
| TUBB6 | 84617 | NM_001303527; NM_001303525; NM_001303524; NM_001303526; NM_001303528; NM_001303529; NM_001303530; NM_032525 |
| WNT7B | 7477 | XM_011530366; NM_058238 |
| SMOX | 54498 | NM_001270691; NM_175839; NM_175840; NM_175841; NM_175842; XM_011529261 |
| TMEM158 | 25907 | NM_015444 |
| NLRP7 | 199713 | NM_001127255; NM_139176; NM_206828; XM_006723075; XM_006723076; XM_011526599 |
| ADRB2 | 154 | NM_000024 |
| GALNT2 | 2590 | NM_004481; NM_001291866 |
| HRASLS | 57110 | NM_020386; NM_001366112; XM_011513034; XM_011513035 |
| CD244 | 51744 | NM_001166663; NM_001166664; NM_016382; XM_011509622 |
| FASLG | 356 | NM_000639; NM_001302746 |
| KIR2DL4 | 3805 | NM_001080772; NM_001080770; NM_002255 |
| LOC100287534 | 100287534 | HF584483.1 |
| KLRD1 | 3824 | NM_007334; XM_006719067; XR_001748697; XM_017019289; NM_001351062; NR_147038; XM_017019287; NM_001351063; XM_011520650; XM_017019286; XM_024448974; XR_001748696; NR_147040; XM_017019285; NM_001114396; NM_001351060; NR_147039; XM_011520651; XM_017019288; NM_002262 |
| SH2D1B | 117157 | NM_053282 |
| KLRC2 | 3822 | NM_002260 |
| NCAM1 | 4684 | NM_001242607; NM_000615; NM_001076682; NM_001242608; NM_181351 |
| CXCR5 | 643 | NM_001716; NM_032966 |
| IL6 | 3569 | NM_001318095; NM_000600; XM_011515390 |
| ICOS | 29851 | NM_012092 |
| CD40LG | 959 | NM_000074 |
| CD84 | 8832 | NM_001184879; NM_001184881; NM_001184882; NM_001330742; NM_003874 |
| IL21 | 59067 | NM_021803; NM_001207006 |
| BCL6 | 604 | NM_001134738; NM_001130845; NM_001706; XM_005247694; XM_011513062 |
| MAF | 4094 | XM_017023233; XM_017023234; XM_017023235; NM_001031804; NM_005360 |
| SH2D1A | 4068 | NM_001114937; NM_002351 |

TABLE 10-continued

Gene Set for PTCL Subtype Classifier

| Gene | NCBI Gene ID | NCBI Accession Number(s) |
|---|---|---|
| IL4 | 3565 | NM_000589; NM_172348 |
| PTPN1 | 5770 | NM_002827; NM_001278618 |
| PIM1 | 5292 | NM_002648; NM_001243186 |
| ENTPD1 | 953 | NM_001098175; NM_001164178; NM_001164181; NM_001164182; NM_001164183; NM_001312654; NM_001320916; NM_001776; XM_011540371; XM_011540377; XM_017016959 |
| IRF4 | 3662 | NM_001195286; NM_002460 |
| CCND2 | 894 | NM_001759 |
| IL16 | 3603 | NM_001172128; NM_004513; NM_172217; NR_148035; NM_001352685; NM_001352686; NM_001352684 |
| ETV6 | 2120 | NM_001987 |
| BLNK | 29760 | NM_001258441; NM_001258442; NM_001114094; NM_001258440; NM_013314 |
| SH3BP5 | 9467 | NM_001018009; XM_017007522; XM_017007523; XM_017007524; XM_017007525; NM_004844 |
| FUT8 | 2530 | NM_004480; NM_178155; NM_178156 |
| CCR4 | 1233 | NM_005508; XM_017005687 |
| GATA3 | 2625 | NM_001002295; NM_002051; XM_005252442; XM_005252443 |
| IL5 | 3567 | NM_000879; XM_011543373; XM_011543374 |
| IL10 | 3586 | NM_000572 |
| IL13 | 3596 | NM_002188 |
| MMEITPKB | N/A | N/A |
| MYBL1 | 4603 | NM_001080416; NM_001144755; NM_001294282 |
| LRMP | 16970 | NM_001204126; NM_001204127; NM_006152; NM_001366543; NM_001366544; NM_001366546; NM_001366549; NM_001366545; NR_159367; NR_159368; NM_001366541; NR_159366; NM_001366540; NM_001366542; NM_001366547; NR_159369; NM_001366548 |
| KIAA0870 | 22898 | NM_014957 |
| LMO2 | 4005 | NM_001142315; NM_001142316; NM_005574; XM_005252921; XM_017017727; XM_017017728; XM_017017729; XM_017017730; XM_017017731; XM_017017732; XM_017017733 |
| CR1 | 1378 | NM_000651; NM_000573 |
| LTBR | 4055 | NM_001270987; NM_002342 |
| PDPN | 10630 | NM_001006624; NM_001006625; NM_006474; NM_198389; XM_006710295 |
| TNFRSF1A | 7132 | NM_001346091; NM_001065; NM_001346092 |
| FCER2 | 2208 | NM_001207019; NM_001220500; NM_002002; XM_005272462 |
| ICAM1 | 3383 | NM_000201 |
| FCGR2B | 2213 | NM_001002273; NM_001002274; NM_001002275; NM_001190828; NM_004001; XM_024454043; NM_001386004; NR_169827; NM_001386001; NM_001386002; NM_001386006; NM_001386003; XM_017000670; NM_001386000; NM_001386005; XM_024454047 |
| IKZF2 | 22807 | NM_001079526; NM_016260; XM_005246384; XM_005246385; XM_011510818; NM_001371277; XM_011510809; NM_001387220; XM_005246386; XM_011510810; NM_001371275; XM_011510804; XM_011510812; XM_011510815; XM_011510817; XM_017003592; NM_001371275; XM_011510808; NM_001371274; XM_011510802; XM_011510807; XM_011510819; NM_001371276; XM_011510805; XM_011510811; XM_017003591; XM_011510816 |
| CCR8 | 1237 | NM_005201 |
| TNFRSF18 | 8784 | XM_017002722; NM_004195; NM_148901; NM_148902 |
| IKZF4 | 64375 | NM_022465; XM_005269089; XM_017019813; XM_017019815; XM_024449128; XM_024449129; NM_001351090; XM_017019807; XM_017019812; XM_024449131; NM_001351089; XM_011538664; XM_011538669; XM_017019814; XM_017019808; XM_024449130; NM_001351092; XM_017019806; XM_017019809; XM_017019810; XM_005269086; XM_017019811; XM_017019816; NM_001351091 |
| FOXP3 | 50943 | XM_006724533; NM_001114377; NM_014009 |
| IL2 | 3558 | NM_000586 |
| TBX21 | 30009 | NM_013351 |
| IFNG | 3458 | NM_000619 |
| GZMH | 2999 | NM_001270781; NM_033423 |
| GNLY | 10578 | NM_001302758; NM_006433; NM_012483 |
| EOMES | 8320 | NM_001278182; NM_001278183; NM_005442 |
| NCR1 | 9437 | NM_004829; NM_001145458; NM_001145457; NM_001242356; NM_001242357 |
| GZMB | 3002 | NM_001346011; NM_004131 |
| NKG7 | 4818 | NM_005601 |
| FGFBP2 | 83888 | NM_031950 |
| KLRF1 | 51348 | NM_001291822; NM_001291823; NM_016523 |
| CD160 | 11126 | NM_007053; XM_005272929; XM_011509104 |
| KLRK1 | 22914 | NM_001199805; NM_007360 |
| CD226 | 10666 | NM_001303619; XM_005266643; XM_017025525; NM_006566; XM_006722374; XM_017025526; NM_001303618; XM_005266642; XM_017025527 |

TABLE 10-continued

Gene Set for PTCL Subtype Classifier

| Gene | NCBI Gene ID | NCBI Accession Number(s) |
| --- | --- | --- |
| NCR3 | 259197 | NM_001145466; NM_001145467; NM_147130; XM_006715049; XM_011514459 |
| TNFRSF8 | 943 | NM_001243; NM_001281430 |
| BATF3 | 55509 | NM_018664 |
| TMOD1 | 7111 | NM_001166116; NM_003275 |
| TMEM158 | 25907 | NM_015444 |
| MSC | 9242 | NM_005098 |
| POPDC3 | 64208 | NM_022361; XM_011536067; XM_017011194; XM_017011195 |

Some embodiments involve using a gene set that includes genes associated with a molecular signature of one or more PTCL subtypes. Examples of genes that may be included in such a gene set are listed in Table 11, below, which shows different genes and their corresponding PTCL subtype. In some embodiments, one or more genes listed in Table 11 may be combined with one or more genes listed in Table 10 to form a gene set used for determining PTCL subtype according to the techniques described herein.

TABLE 11

Functional annotation of the representative genes in the molecular signatures of the common PTCL subtypes.

| PTCL subgroups | Major functional category | Gene symbols |
| --- | --- | --- |
| AITL | Cell morphology/Intracellular signaling | EFNB2, ROBO1, S1PR3, ANK2, LPAR1, SNAP91, SOX8 |
| | Cell migration/Vascularization | LPAR1, RAMP3, S1PR3, ROBO1, EFNB2, TUBB2B, SOX8 |
| | Cell cycle | SOX8, ARHGEF10 |
| ATLL | T-cell homeostasis/activation/ differentiation | NOTCH1, ZBTB17, CCNE1, FGF18, MYCN, PTHLH, SMARCA2, WNK1, NKX2-1, CYP26A1, HPSE, CTLA4, MYCN, PELI1, PRKCB, SPAST, ALS2, KIF3B, ZFYVE27 |
| | Cell cycle/Proliferation | FGF18, MYCN, NKX2-1, NOTCH1, PTHLH, SMARCA2, CCNE1, GF18, WNK1, CTLA4, PELI1, PRKCB, ZBTB17, HPSE, FNTB, REL-1 |
| ALCL | Cell morphology/Intracellular signaling and interaction | DMRT1, SLC19A21, STK3, PERP, TNFRSF8, TMOD1, BATF3, DNER, ADRB2, AGT, TIAM2, HS6ST2, GAS1, IL1RAP, WNT7B, ARHGEF10, HRASLS |
| | P53-induced genes | CDC14B, PERP, WDFEY3, TMOD1 |
| | Cell cycle/Proliferation | AGT, ALK, ANXA3, BTBD11, CCNA1, DNER, GAS1, HS6ST2, IL1RAP, PCOLCE2, PDE4DIP, SLC16A3, TIAM2, TUBB6, WNT7B, SMOX, TMEM158, NLRP7, ADRB2, GALNT2 |
| NKTCL | NK-cell activation/survival | CD244, FASLG, KIR2DL4, KLRD1, SH2D1B |
| | NK cell markers | CD244, FASLG, KLRC2, KLRD1, NCAM1 |

Further examples of genes that may be included in a gene set used for determining PTCL subtype according to the techniques described herein are described and listed in Iqbal J, Wright G, Wang C, et al., Gene expression signatures delineate biological and prognostic subgroups in peripheral T-cell lymphoma, Blood, 2014; 123(19):2915-2923 (doi: 10.1182/blood-2013-11-536359), which is incorporated herein by reference in its entirety.

Some embodiments may involve using a gene set that includes genes that are up-regulated in angioimmunoblastic T-cell lymphoma (AITL) compared to normal T lymphocytes, which may be referred to herein as "up-regulated in AITL genes". For example, one or more genes in the gene set PICCALUGA_ANGIOIMMUNOBLASTIC_LYM-PHOMA_UP, with the systematic name M12225 in the Gene Set Enrichment Analysis (GSEA) database, may be used in determining PTCL subtype according to the techniques described herein. In some embodiments, the gene set may include one or more genes selected from the group consisting of: A2M, ABCC3, ABI3BP, ACKR1, ACTA2, ACVRL1, ADAMDEC1, ADAMTS1, ADAMTS9, ADGRF5, ADGRL4 ADRA2A, ANK2, ANKRD29, ANTXR1, APOC1, APOE, ARHGAP29, ARHGAP42, ARHGEF10, ASPM, ATOX1, C1QA, C1QB, C1QC, C1R, C1S, C2, C3, C4A, C7, CALD1, CARMN, CAV2, CAVIN1, CCDC102B, CCDC80, CCL14, CCL19, CCL2, CCL21, CCN4, CD63, CD93, CDH11, CDH5, CETP, CFB, CFH, CHI3L1, CLMP, CLU, CMKLR1, COL12A1, COL15A1, COL1A1, COL1A2, COL3A1, COL4A1, COL4A2, COL6A1, COL8A2, COX7A1, CP, CSRP2, CTHRC1, CTSC, CTSL, CTTNBP2NL, CXCL10, CXCL12, CXCL9, CYBRD1, CYFIP1, CYP1B1, CYP26B1, CYP27A1, DAB2, DCLK1, DDR2, DEPP1, DHRS7B, DOCK4, DPYSL3, EMCN, EMILIN1, ENG, ENPP2, EPHX1, FAM107A, FAM114A1, FAM20A, FBN1, FCHO2, FERMT2, FLRT2, FN1, FSTL1, FUCA1, GABBR1, GASK1B, GJA1, GJC1, GPNMB, GPRC5B, GUCY1B1, HNMT, HSPB8, HSPG2, IDH1, IFI27, IGFBP5, IGFBP7, IL18, IL33, IRAK3, ITGA9, ITPRIPL2, KCNJ10, KCNMA1, KCTD12, LAMA4, LAMB1, LAMC1, LIFR, LOXL1, LPAR1, LUM, MARCKS, MFAP4, MIR1245A, MIR34AHG, MMP9, MXRA5, MYL9, MYLK, NAGK, NEXN, NFIB, NNMT, NPL, NR1H3, NR2F2, OSMR, P2RY13, PAPSS2, PARVA, PCOLCE, PDGFRA, PDLIM5, PDPN, PGF, PLA2G2D, PLA2G4C, PLD1, PLPP3, PMP22, PPIC, PRRX1, PTGDS, RAB13, RAI14, RARRES2, RASSF4, RBP5, RBPMS, RGL1, RGS5, RHOBTB3, RND3, RPE, RRAS, RSPO3, S1PR3, SAMD9L, SEPTIN10, SERPING1, SERPINH1, SLAMF8, SLC1A3, SLC40A1, SLCO2B1, SMOC2, SPARC, SPARCL1, SPRED1, SULF1, TAGLN, TANC1, TCIM, TDO2, TEAD2, THY1, TJP1, TLR4, TMEM163, TMEM176A, TMEM176B, TNC, TNS1, TNS3, TPM1, TRIM47, VCAM1, VWF, WDFY3, WLS, WWTR1, YAP1, and ZNF226.

Some embodiments may involve using a gene set that includes genes that are down-regulated in angioimmunoblastic lymphoma (AITL) compared to normal T lymphocytes, which may be referred to herein as "down-regulated in AITL genes". For example, one or more genes in the gene set PICCALUGA_ANGIOIMMUNOBLASTIC_LYMPHOMA_DN, with the systematic name M4781 in the Gene Set Enrichment Analysis (GSEA) database, may be used in determining PTCL subtype according to the techniques described herein. In some embodiments, the gene set may include one or more genes selected from the group consisting of: AMD1, AREG, ATP2B1-AS1, B3GNT2, BOLA2, BTG1, C16orf72, CBX4, CCDC59, CCNL1, CD6, CD69, CHD1, CLK1, CNOT6L, CNST, COG3, CREM, CSGALNACT2, CSRNP1, DDX3X, DNAJB6, DUSP10, DUSP2, DUSP4, EIF1, EIF4E, EIF4G3, EIF5, EPC1, ETNK1, FBXO33, FBXW7, FOSB, FOSL2, FOXP1, G3BP2, GABARAPL1, GADD45A, GADD45B, GATA3, H2AC18, H3-3B, HAUS3, HECA, HIPK1, ID2, IDS, IER5, IFRD1, IKZF5, ING3, IRF2BP2, IRS2, JMJD1C, JMY, JUN, JUND, KDM3A, KDM6B, KLF10, KLF4, KLF6, LINC-PINT, LINC01578, LY9, MAP3K8, MCL1, MEX3C, MGAT4A, MOAP1, MPZL3, MXD1, MYLIP, NAMPT, NDUFA10, NR4A2, NR4A3, PCIF1, PDE4D, PELI1, PER1, PHF1, PIGA, PMAIP1, PNPLA8, PPP1R15A, PPP1R15B, PRNP, PTGER4, PTP4A1, PTP4A2, RAPGEF6, REL, RGCC, RGS1, RGS2, RNF103, RNF11, RNF139, RSRC2, SARAF, SBDS, SETD2, SIK1, SIK3, SLC2A3, SLC30A1, SMURF2, SNORD22, SNORD3B-1, SON, SRSF5, STK17B, SUCO, THAP2, TIPARP, TMX4, TNFAIP3, TOB1, TP53INP2, TRA2B, TSC22D2, TSC22D3, TSPYL2, TTC7A, TUBB2A, WIPF1, YPEL5, ZBTB10, ZBTB24, ZFAND2A, ZFAND5, ZFC3H1, ZFP36, and ZNF331.

Some embodiments may involve using a gene set that includes genes associated with a molecular functional (MF) profile of a subject, which may be referred to herein as "MF profile genes". In some embodiments, genes associated with a MF profile may include genes in one or more modules of the MF profile. Examples of genes associated with a MF profile and modules of a MF profile are described and listed in U.S. Pat. No. 10,311,967, titled "SYSTEMS AND METHODS FOR GENERATING, VISUALIZING AND CLASSIFYING MOLECULAR FUNCTION PROFILES," issued on Jun. 4, 2019, which is incorporated herein by reference in its entirety. In some embodiments, one or more of the genes associated with a MF profile and one or more of the genes listed in Table 10 may be used in combination as a gene set for determining a PTCL subtype.

Figure 26:
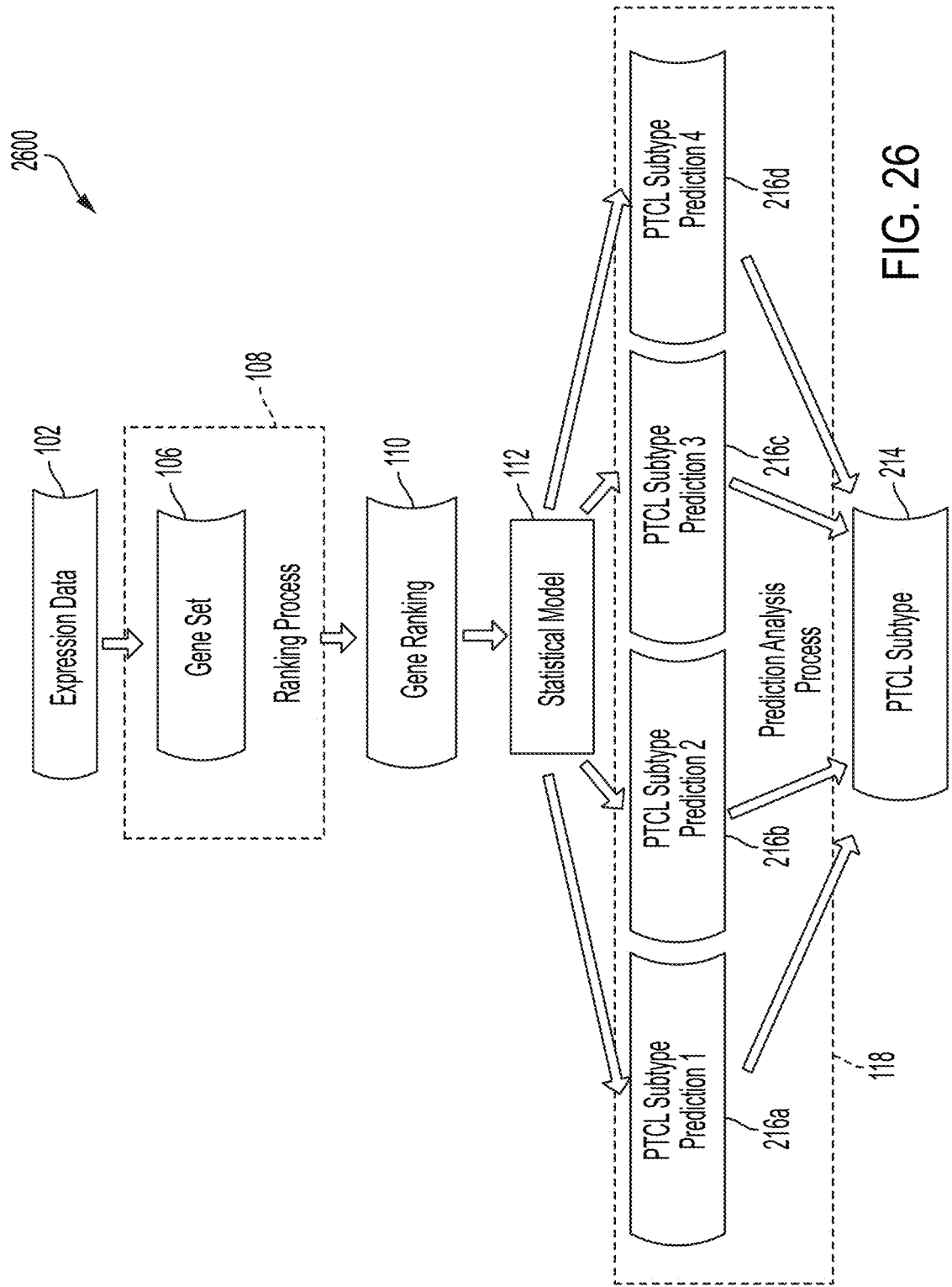
FIG. 26 is a diagram of an illustrative process for determining peripheral T-cell lymphoma (PTCL) subtype of a biological sample using the machine learning techniques described herein.

Some embodiments may involve determining a PTCL subtype for cells in a biological sample by using a statistical model that outputs multiple PTCL subtype predictions corresponding to different PTCL subtypes, which are used to determine a PTCL subtype for the biological sample. FIG. 26 is a diagram of an illustrative processing pipeline 2600 for determining a PTCL subtype of a biological sample, which may include ranking genes based on their gene expression levels and using the ranking and statistical model to determine the PTCL subtype, in accordance with some embodiments of the technology described herein. Processing pipeline 2600 may be performed on any suitable computing device(s) (e.g., a single computing device, multiple computing devices co-located in a single physical location or located in multiple physical locations remote from one another, one or more computing devices part of a cloud computing system, etc.), as aspects of the technology described herein are not limited in this respect. In some embodiments, processing pipeline 2600 may be performed by a desktop computer, a laptop computer, a mobile computing device. In some embodiments, processing pipeline 2600 may be performed within one or more computing devices that are part of a cloud computing environment.

In some embodiments, gene expression data 102 and ranking process 108 are used to rank genes based on their expression levels in gene expression data 102 to obtain gene ranking 110. Gene ranking 110 may be input to statistical model 112. Statistical model 112 may be trained using training data indicating rankings of expression levels for some or all genes in the gene set.

In some embodiments, statistical model 112 may output predictions of the biological sample having particular PTCL subtypes. In some instances, a prediction output by a statistical model may include a probability of the biological sample having the PTCL subtype. As shown in FIG. 26, statistical model 112 outputs PTCL Subtype Prediction 1 216a, PTCL Subtype Prediction 2 216b, PTCL Subtype Prediction 1 216c, and PTCL Subtype Prediction 1 216d. The predictions output by statistical model 112 may be analyzed using prediction analysis process 118 to determine PTCL subtype 214 for the biological sample. Prediction analysis process 118 may involve selecting a particular PTCL subtype for the biological sample from among the different PTCL subtype predictions. In some embodiments, a PTCL subtype prediction may include a probability that the biological sample has the particular PTCL subtype. In such embodiments, prediction analysis process 118 may involve selecting a PTCL subtype based on the probabilities. In some embodiments, selecting the PTCL subtype may involve selecting the PTCL subtype having the highest probability as being PTCL subtype 214.

In some embodiments, statistical model 112 may provide outputs, each corresponding to a different PTCL subtype. For example, PTCL Subtype Prediction 1 216a may correspond to anaplastic large cell lymphoma (ALCL), PTCL Subtype Prediction 2 216b may correspond to angioimmunoblastic T-cell lymphoma (AITL), PTCL Subtype Prediction 3 216c may correspond to natural killer/T-cell lymphoma (NKTCL), and PTCL Subtype Prediction 4 216d may correspond to adult T-cell leukemia/lymphoma (ATLL). In some embodiments, statistical model 112 may include a multi-class classifier. In some embodiments, a class weight may be implemented for one or more of the classes in the multi-class classifier. Examples of classifiers that statistical model 112 may include are a gradient boosted decision tree classifier, a decision tree classifier, a gradient boosted classifier, a random forest classifier, a clustering-based classifier, a Bayesian classifier, a Bayesian network classifier, a neural network classifier, a kernel-based classifier, and a support vector machine classifier.

Although four outputs from statistical model 112 are shown in FIG. 26, it should be appreciated that a statistical model having any suitable number of outputs for PTCL subtype predictions may be implemented using the techniques described above in determining a PTCL subtype of a biological sample. In some embodiments, the outputs may be in the range of 3 to 5, 3 to 10, 3 to 15, or 3 to 20.

Figure 27:
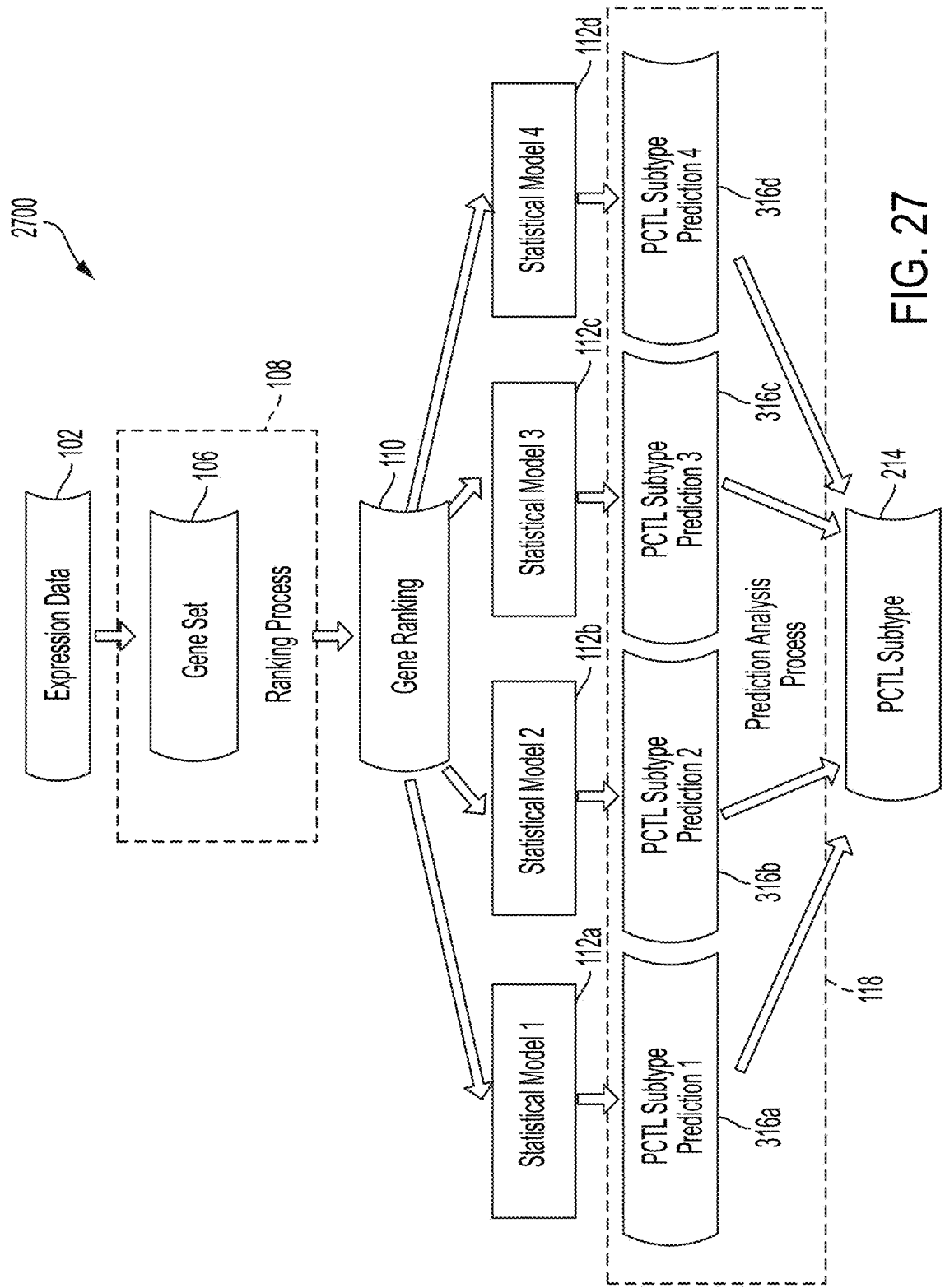
FIG. 27 is a diagram of an illustrative process for determining peripheral T-cell lymphoma (PTCL) subtype of a biological sample using the machine learning techniques described herein.

Some embodiments may involve determining a PTCL subtype for cells in a biological sample by using multiple statistical models that correspond to different PTCL subtypes and output predictions for the PTCL subtypes, which are used to determine a PTCL subtype for the biological sample. FIG. 27 is a diagram of an illustrative processing pipeline 2700 for determining a PTCL subtype of a biological sample, which may include ranking genes based on their gene expression levels and using the ranking and statistical models to determine the PTCL subtype, in accordance with some embodiments of the technology described herein. Processing pipeline 2700 may be performed on any suitable computing device(s) (e.g., a single computing device, multiple computing devices co-located in a single physical location or located in multiple physical locations remote from one another, one or more computing devices part of a cloud computing system, etc.), as aspects of the technology described herein are not limited in this respect. In some embodiments, processing pipeline 2700 may be performed by a desktop computer, a laptop computer, a mobile computing device. In some embodiments, processing pipeline 2700 may be performed within one or more computing devices that are part of a cloud computing environment.

In some embodiments, gene expression data 102 and ranking process 108 are used to rank genes based on their expression levels in gene expression data 102 to obtain gene ranking 110. Gene ranking 110 may be input to statistical model 1 112a, statistical model 2 112b, statistical model 3 112c, and statistical model 4 112d. Each of statistical model 1 112a, statistical model 2 112b, statistical model 3 112c, and statistical model 4 112d may be trained using training data indicating rankings of expression levels for some or all genes in the gene set. Statistical model 1 112a, statistical model 2 112b, statistical model 3 112c, and statistical model 4 112d may each correspond to a different PTCL subtype and output a prediction of the biological sample having its particular PTCL subtype. In some instances, the prediction output by a statistical model may include a probability of the biological sample having the PTCL subtype.

As shown in FIG. 27, statistical model 1 112a outputs PTCL Subtype Prediction 1 316a, statistical model 2 112b outputs PTCL Subtype Prediction 2 316b, statistical model 3 112c outputs PTCL Subtype Prediction 3 316c, and statistical model 4 112d outputs PTCL Subtype Prediction 4 316d. Each of statistical model 1 112a, statistical model 2 112b, statistical model 3 112c, and statistical model 4 112d may correspond to a different PTCL subtype. For example, statistical model 1 112a and PTCL Subtype Prediction 1 316a may correspond to anaplastic large cell lymphoma (ALCL) and statistical model 1 112a may be trained using rankings of expression levels for one or more genes associated with ALCL, such as those listed in Table 11. As another example, statistical model 2 112b and PTCL Subtype Prediction 2 316b may correspond to angioimmunoblastic T-cell lymphoma (AITL) and statistical model 2 112b may be trained using rankings of expression levels for one or more genes associated with AITL, such as those listed in Table 11. As yet another example, statistical model 3 112c and PTCL Subtype Prediction 3 316c may correspond to natural killer/T-cell lymphoma (NKTCL) and statistical model 3 112c may be trained using rankings of expression levels for one or more genes associated with NKTCL, such as those listed in Table 11. As another example, statistical model 4 112d and PTCL Subtype Prediction 4 316d may correspond to adult T-cell leukemia/lymphoma (ATLL) and statistical model 4 112d may be trained using rankings of expression levels for one or more genes associated with ATLL, such as those listed in Table 11.

The predictions output by statistical model 1 112a, statistical model 2 112b, statistical model 3 112c, and statistical model 4 112d may be analyzed using prediction analysis process 118 to determine PTCL subtype 214 for the biological sample. Prediction analysis process 118 may involve selecting a particular PTCL subtype for the biological sample from among the different PTCL subtype predictions. In some embodiments, a PTCL subtype prediction may include a probability that the biological sample has the particular PTCL subtype. In such embodiments, prediction analysis process 118 may involve selecting a PTCL subtype based on the probabilities. In some embodiments, selecting the PTCL subtype may involve selecting the PTCL subtype having the highest probability as being PTCL subtype 214.

In some embodiments, one or more of statistical model 1 112a, statistical model 2 112b, statistical model 3 112c, and statistical model 4 112d may include a binary classifier. In some embodiments, each of statistical model 1 112a, statistical model 2 112b, statistical model 3 112c, and statistical model 4 112d includes a binary classifier. In such embodiments, if none of the binary classifiers used are not determinative as to which class the biological sample belongs, then the sample may be determined to be unclassified. In some embodiments, statistical model 1 112a, statistical model 2 112b, statistical model 3 112c, and statistical model 4 112d may have a hierarchical classifier configuration.

Some embodiments may involve a hierarchical configuration of four classifiers in the order of a first classifier for the NKTCL PTCL subtype, a second classifier for the ATLL PTCL subtype, a third classifier for the AITL PTCL subtype, a fourth classifier for the ALCL PTCL subtype. In some embodiments, each of the first, second, third, and fourth classifiers is a binary classifier.

Although four statistical models and corresponding outputs are shown in FIG. 27, it should be appreciated that any number of statistical models may be implemented using the techniques described above in determining a PTCL subtype of a biological sample. In some embodiments, the number of statistical models may be in the range of 3 to 5, 3 to 10, 3 to 15, or 3 to 20.

Figure 28:
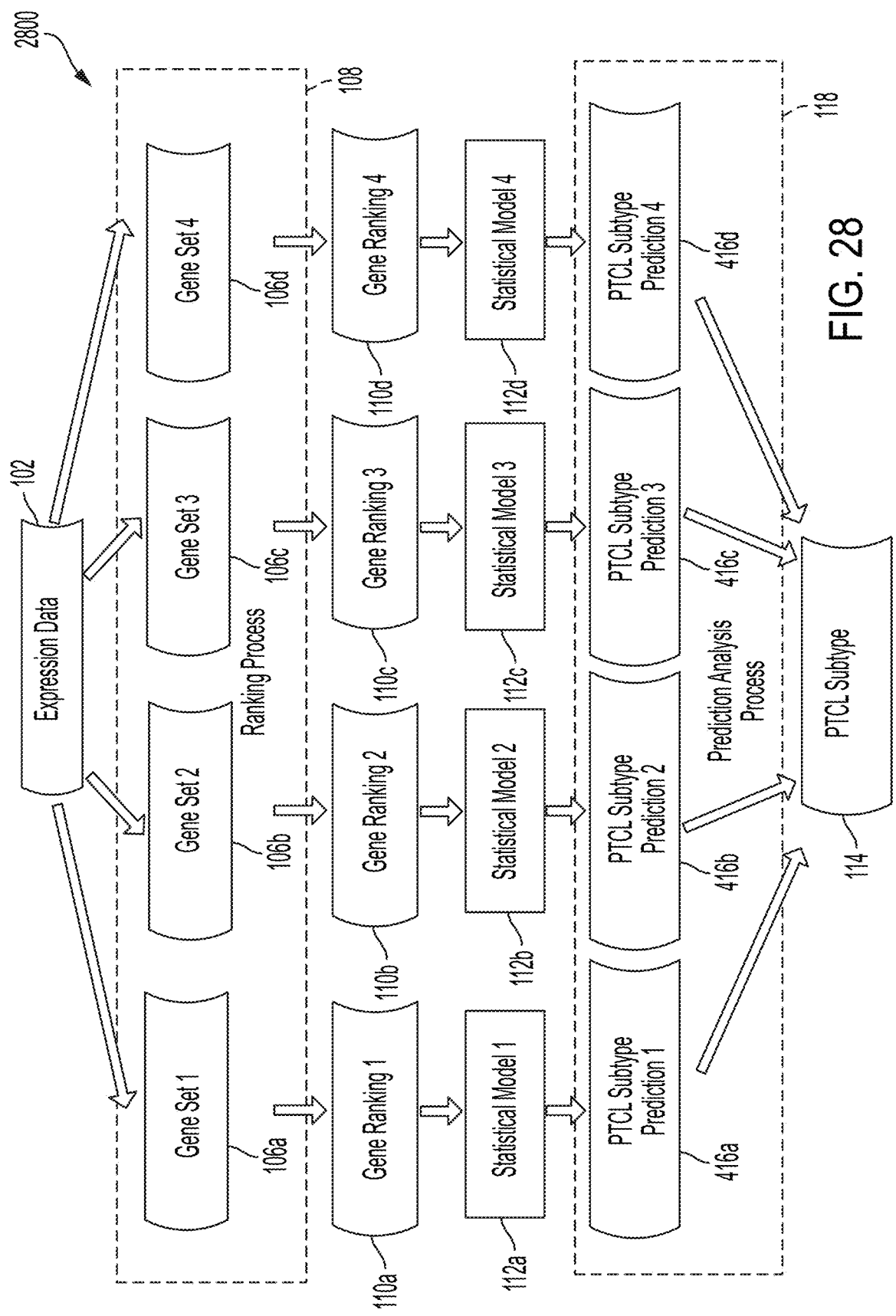
FIG. 28 is a diagram of an illustrative process for determining a characteristic of a biological sample based on using multiple statistical models to determine peripheral T-cell lymphoma (PTCL) subtype of the biological sample using the machine learning techniques described herein.

Some embodiments may involve determining a PTCL subtype of a biological sample by using different gene sets and statistical models corresponding to the different gene sets to obtain PTCL subtype predictions, which are used to determine the PTCL subtype. FIG. 28 is a diagram of an illustrative processing pipeline 2800 for determining a PTCL subtype of a biological sample, which may include ranking genes based on their gene expression levels and using the rankings and statistical models to determine the PTCL subtype, in accordance with some embodiments of the technology described herein. Processing pipeline 2800 may be performed on any suitable computing device(s) (e.g., a single computing device, multiple computing devices co-located in a single physical location or located in multiple physical locations remote from one another, one or more computing devices part of a cloud computing system, etc.), as aspects of the technology described herein are not limited in this respect. In some embodiments, processing pipeline 2800 may be performed by a desktop computer, a laptop computer, a mobile computing device. In some embodiments, processing pipeline 2800 may be performed within one or more computing devices that are part of a cloud computing environment.

In some embodiments, gene expression data 102 is used to rank genes in different sets of genes based on their expression levels in gene expression data 102 to obtain multiple gene rankings. For example, a gene ranking may be obtained for each gene set and the gene ranking may be input to a statistical model trained using training data indicating rankings of expression levels for some or all genes in the gene set. As shown in FIG. 28, ranking process 108 may involve using expression data 102 to rank genes in different gene sets, including Gene Set 1 106*a*, Gene Set 2 106*b*, Gene Set 3 106*c*, and Gene Set 4 106*d*, to obtain Gene Ranking 1 110*a*, Gene Ranking 2 110*b*, Gene Ranking 3 110*c*, and Gene Ranking 4 110*d*, respectively. Ranking process 108 may involve ranking genes in a set of genes based on numerical values of their expression levels. Different gene rankings may be obtained by ranking expression levels for different gene sets, and each gene ranking may be input to its respective statistical model to obtain a PTCL subtype prediction. As shown in FIG. 28, Gene Ranking 1 110*a*, Gene Ranking 2 110*b*, Gene Ranking 3 110*c*, and Gene Ranking 4 110*d* is provided as input to Statistical Model 1 112*a*, Statistical Model 2 112*b*, Statistical Model 3 112*c*, and Statistical Model 4 112*d*, respectively.

In some embodiments, the different statistical models and their respective gene sets may correspond to a particular PTCL subtypes of the biological sample. In such embodiments, each of the statistical models may output a prediction of the biological sample having a particular PTCL subtype. In some instances, the prediction output by a statistical model may include a probability of the biological sample having the PTCL subtype.

As shown in FIG. 28, Statistical Model 1 112*a* outputs PTCL Subtype Prediction 1 416*a*, Statistical Model 2 112*b* outputs PTCL Subtype Prediction 2 416*b*, Statistical Model 3 112*c* outputs PTCL Subtype Prediction 3 416*c*, and PTCL Subtype Prediction 4 116*d* outputs PTCL Subtype Prediction 4 416*d*. The predictions output by the different statistical models may be analyzed using prediction analysis process 118 to determine PTCL subtype 114 for the biological sample.

Although four gene sets and four statistical models are shown in FIG. 28, it should be appreciated that any suitable number of gene sets and corresponding statistical models may be implemented using the techniques described above in determining PTCL subtype predictions to obtain a PTCL subtype of a biological sample. In some embodiments, the number of gene sets and corresponding statistical models may be in the range of 3 to 100, 3 to 70, 3 to 50, 3 to 40, 3 to 30, 5 to 50, 10 to 60, or 10 to 70.

In some embodiments, the number of gene sets and corresponding statistical models is equal to or less than the number of classes for the PTCL subtype. Such embodiments may involve a different gene set and corresponding statistical model for each PTCL subtype. For example, Gene Set 1 106*a* and Statistical Model 1 112*a* may be used for generating a prediction of the PTCL subtype being anaplastic large cell lymphoma (ALCL) (as PTCL Subtype Prediction 1 416*a*), Gene Set 2 106*b* and Statistical Model 2 112*b* may be used for generating a prediction of the PTCL subtype being angioimmunoblastic T-cell lymphoma (AITL) (as PTCL Subtype Prediction 2 416*b*), Gene Set 3 106*c* and Statistical Model 3 112*c* may be used for generating a prediction of the PTCL subtype being natural killer/T-cell lymphoma (NKTCL) (as PTCL Subtype Prediction 3 416*c*), and Gene Set 4 106*d* and Statistical Model 4 112*d* may be used for generating a prediction of the PTCL subtype being adult T-cell leukemia/lymphoma (ATLL) (as PTCL Subtype Prediction 4 416*d*). It should be appreciated that additional gene sets and their corresponding statistical models may be implemented for different tissue types.

Figure 29:
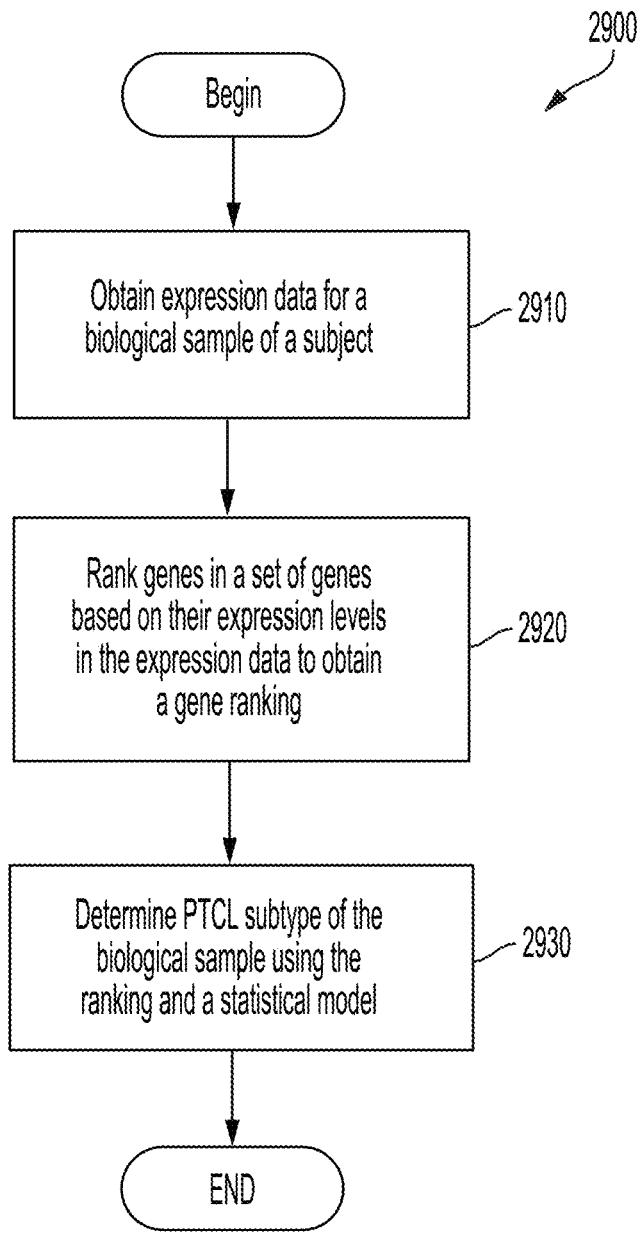
FIG. 29 is a flow chart of an illustrative process for determining a subtype of peripheral T-cell lymphoma (PTCL) for a biological sample using a gene ranking and a statistical model using the machine learning techniques described herein.

FIG. 29 is a flow chart of an illustrative process 2900 for determining one or more characteristics of a biological sample using a gene ranking and a statistical model, in accordance with some embodiments of the technology described herein. Process 2900 may be performed on any suitable computing device(s) (e.g., a single computing device, multiple computing devices co-located in a single physical location or located in multiple physical locations remote from one another, one or more computing devices part of a cloud computing system, etc.), as aspects of the technology described herein are not limited in this respect. In some embodiments, ranking process 108 and statistical model 112 may perform some or all of process 2900 to determine PTCL subtype.

Process 2900 begins at act 2910, where expression data for a biological sample of a subject is obtained. In some embodiments, the expression data may be obtained using a gene expression microarray. In some embodiments, the expression data may be obtained by performing next generation sequencing. In some embodiments, the expression data may be obtained by using a hybridization-based expression assay. Some embodiments involve performing a sequencing process of the biological sample (e.g., a gene expression microarray, next generation sequencing) prior to obtaining expression data 102. In some embodiments, obtaining gene expression data 102 may involve obtaining gene expression data 102 in silico, such as by accessing, using a computing device, expression data (e.g., expression data that has been previously obtained from a biological sample) in one or more data stores, receiving the expression data from one or more other device, or any other way. In some embodiments, obtaining gene expression data 102 may involve analyzing a biological sample (in vitro) and accessing (e.g., by a computing device, processor) the expression data. Further aspects relating to obtaining expression data are provided in the section titled "Obtaining Expression Data".

Next, process 2900 proceeds to act 2920, where genes in a set of genes are ranked based on their expression levels in the expression data to obtain a gene ranking, such as by using ranking process 108. The expression data may include values, each representing an expression level for a gene in the set of genes, and determining the gene ranking may involve determining a relative rank for each gene in the set of genes based on the values.

In some embodiments, the subject has, is suspected of having, or is at risk of having breast cancer. The set of genes may be selected from the group of genes listed in Table 10. The set of genes may include at least 3, 5, 10, or 20 genes selected from the group of genes listed in Table 10. In some embodiments, the set of genes may include all the genes listed in Table 10. In some embodiments, the set of genes may include 3-120 genes, 5-120 genes, 20-120 genes, 50-120 genes, 80-120 genes listed in Table 10. In some embodiments, the set of genes may include 120 or fewer genes, 100 or fewer genes, 80 or fewer genes, 50 or fewer genes, 20 or fewer genes listed in Table 10.

In some embodiments, the subject has, is suspected of having, or is at risk of having lymphoma. In some embodiments, the subject has, is suspected of having, or is at risk of having PTCL.

Next process 2900 proceeds to act 2920, where PTCL subtype of the biological sample is determined using the gene ranking and a statistical model, such as statistical model 112. The statistical model may be trained using rankings of expression levels for one or more genes in the set of genes. In some embodiments, the gene ranking may be used as an input to the statistical model to obtain an output indicating the PTCL subtype. In some embodiments, the statistical model comprises one or more classifiers selected from the group consisting of: a statistical model may include are a gradient boosted decision tree classifier, a decision tree classifier, a gradient boosted classifier, a random forest classifier, a clustering-based classifier, a Bayesian classifier, a Bayesian network classifier, a neural network classifier, a kernel-based classifier, and a support vector machine classifier. In some embodiments, a statistical model may involve using a machine learning algorithm that implements of a gradient boosting framework, such as a gradient boosting decision tree (GBDT) and a gradient boosted regression tree (GBRT). Examples of software packages that implement machine learning algorithms that may be used according to the techniques described herein include the LightGBM package, the XGBoost package, and the pGBRT package.

In some embodiments, the statistical model may include a multi-class classifier. The multi-class classifier may provide at least four outputs each corresponding to a different PTCL subtype. For example, a first output may correspond to anaplastic large cell lymphoma (ALCL), a second output may correspond to angioimmunoblastic T-cell lymphoma (AITL), a third output may correspond to natural killer/T-cell lymphoma (NKTCL), and a fourth output may correspond to adult T-cell leukemia/lymphoma (ATLL).

In some embodiments, the statistical model may include multiple classifiers corresponding to different PTCL subtypes. For example, a first classifier may correspond anaplastic large cell lymphoma (ALCL), a second classifier may correspond to angioimmunoblastic T-cell lymphoma (AITL), a third classifier may correspond to natural killer/T-cell lymphoma (NKTCL), and a fourth classifier may correspond to adult T-cell leukemia/lymphoma (ATLL). In some embodiments, the multiple classifiers may be binary classifiers. The binary classifiers may have a hierarchical classification. For example, a statistical mode may include four binary classifiers having a hierarchical configuration in the order of a first classifier for the NKTCL PTCL subtype, a second classifier for the ATLL PTCL subtype, a third classifier for the AITL PTCL subtype, a fourth classifier for the ALCL PTCL subtype.

In some embodiments, the subtype of PTCL is selected from the group consisting of: anaplastic large cell lymphoma (ALCL), angioimmunoblastic T-cell lymphoma (AITL), natural killer/T-cell lymphoma (NKTCL), and adult T-cell leukemia/lymphoma (ATLL). In some embodiments, the subtype of PTCL is selected from the group consisting of: Peripheral T-Cell Lymphoma, Not Otherwise Specified (PTCL-NOS), anaplastic large cell lymphoma (ALCL), angioimmunoblastic T-cell lymphoma (AITL), cutaneous T-cell lymphoma (CTCL), Natural killer/T-cell lymphoma (NKTCL), Sezary syndrome, adult T-cell leukemia/lymphoma (ATLL), enteropathy-type T-cell lymphoma, nasal NK/T-cell lymphoma, hepatosplenic gamma-delta T-cell lymphoma, T-cell lymphomas of Follicular T-cell (TFH) origin, T-cell lymphomas of the gastrointestinal tract, and cutaneous T-cell lymphomas.

In some embodiments, process 2900 may include outputting the PTCL subtype to a user (e.g., physician), such as by displaying the PTCL subtype to the user on a graphical user interface (GUI), including the PTCL subtype in a report, sending an email to the user, and in any other suitable way.

In some embodiments, process 2900 may include administering a treatment to the subject based on the determined PTCL subtype of the biological sample. For example, a physician may administer a treatment for the subject associated with treating lymphomas of the determined PTCL subtype. Further examples where PTCL subtype of a biological sample determined using the techniques described herein are used for administering a treatment are provided in the section titled "Methods of Treatment".

In some embodiments, process 2900 may include identifying a treatment for the subject based on the determined PTCL subtype. For example, the determined PTCL subtype may be used to identify a treatment for the subject associated with treating lymphomas of the determined PTCL subtype.

In some embodiments, process 2900 may include determining a prognosis for the subject based on the determined PTCL subtype. For example, the determined PTCL subtype may be used to determine a prognosis for the subject associated with treating lymphomas of the determined PTCL subtype.

Further aspects relating to other applications where PTCL subtype of a biological sample determined using the techniques described herein are provided in the section titled "Applications".

Figure 30:
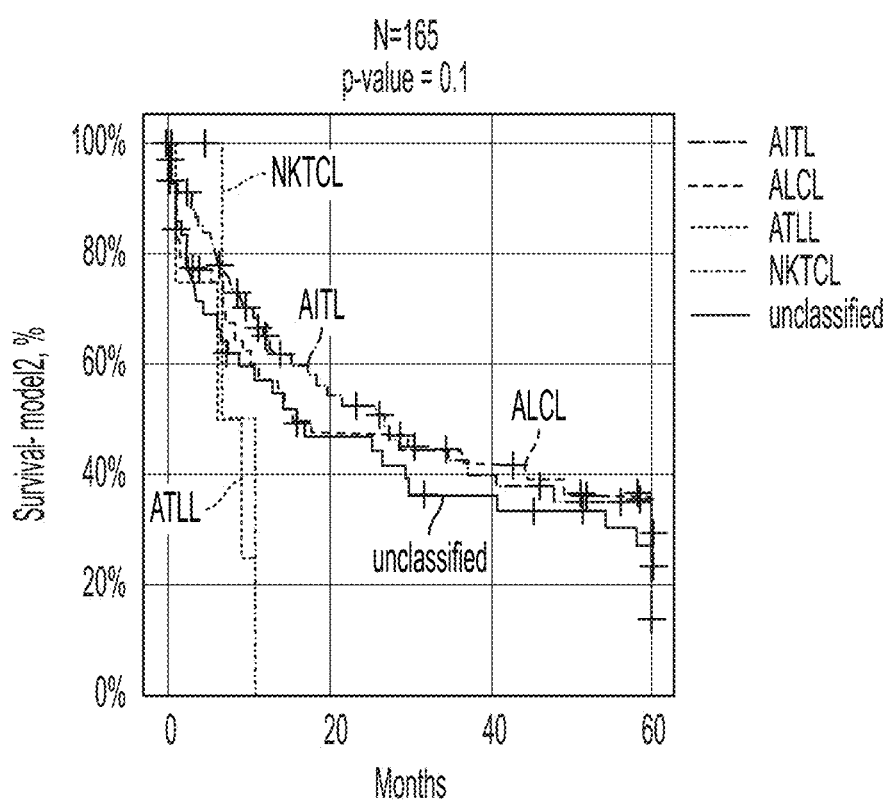
FIG. 30 is an example plot of survival rates for the different peripheral T-cell lymphoma (PTCL) subtypes.

In some embodiments, a trained statistical model used for determining PTCL subtype may be evaluated using existing clinical data to determine its performance in identifying PTCL subtype. As an example, a gene set having the genes listed in Table 10 was used for rank process 108 and a multi-class classifier was used for determining whether samples belong to AITL, ATLL, ALCL, NKTCL, or PTCL NOS subtypes. The clinical data listed in Table 9 was used for this evaluation process and Table 12, below, shows the PTCL subtypes identified using this process. The statistical model used achieved a 0.84 f1 score. FIG. 30 is a plot of survival rates for the different PTCL subtypes (ATLL, ALCL, NKTCL, and PTCL NOS).

TABLE 12

PTCL Subtype Classification Performance.

| Cohort | AITL | ATLL | ALCL | NKTCL | PTCL NOS |
|---|---|---|---|---|---|
| GSE58445<br>n = 191 | 15 | 0 | 9 | 7 | 160 |
| GSE45712<br>n = 101 | 10 | 0 | 12 | 0 | 80 |
| GSE19069<br>n = 100 | 29 | 11 | 24 | 0 | 36 |
| GSE90597<br>n = 66 | 0 | 0 | 0 | 66 | 0 |
| GSE6338<br>n = 40 | 6 | 0 | 6 | 0 | 28 |
| GSE36172<br>n = 38 | 0 | 0 | 0 | 0 | 38 |
| E-TABM-783<br>n = 33 | 17 | 0 | 0 | 0 | 16 |
| GSE65823<br>n = 31 | 0 | 0 | 31 | 0 | 0 |
| GSE118238<br>n = 29 | 0 | 0 | 29 | 0 | 0 |

TABLE 12-continued

PTCL Subtype Classification Performance.

| Cohort | AITL | ATLL | ALCL | NKTCL | PTCL NOS |
|---|---|---|---|---|---|
| E-TABM-702 n = 23 | 0 | 0 | 0 | 7 | 16 |
| GSE78513 n = 23 | 0 | 0 | 23 | 0 | 0 |
| GSE51521 n = 20 | 20 | 0 | 0 | 0 | 0 |
| GSE14317 n = 19 | 0 | 19 | 0 | 0 | 0 |
| GSE80631 n = 19 | 0 | 0 | 0 | 19 | 0 |
| GSE19067 n = 18 | 0 | 0 | 0 | 18 | 0 |
| GSE20874 n = 18 | 8 | 0 | 0 | 4 | 6 |
| SRP049695 n = 17 | 0 | 0 | 0 | 17 | 0 |
| SRP029591 n = 10 | 10 | 0 | 0 | 0 | 0 |

In some aspects, methods for characterization of cancers as described herein may be applied to any lymphoma. "Lymphoma" generally refers to a cancer (e.g., neoplasm) that originates from lymph node and lymphoid cells. Lymphomas are typically classified according to the normal cell type from which the tumor cells originate, for example T-cell lymphomas, B-cell lymphomas, Hodgkin (lymphocyte) lymphomas, and histiocytic and dendritic cell neoplasms. Classification of lymphomas is described, for example, by Jiang et al. Expert Rev. Hematol. 2017 March; 10(3):239-249. Classification of PTCL lymphomas is described, for example, by Iqbal J, Wright G, Wang C, et al., Gene expression signatures delineate biological and prognostic subgroups in peripheral T-cell lymphoma, Blood, 2014; 123(19):2915-2923 (doi:10.1182/blood-2013-11-536359), which is incorporated herein by reference in its entirety.

In some embodiments, a lymphoma is a B-cell lymphoma. In some embodiments, a B-cell lymphoma is a diffuse large B-cell lymphoma (DLBCL). Classification of DLBCL is described, for example, Alizadeh et al., Distinct types of diffuse large B-cell lymphoma identified by gene expression profiling, Nature 403, 503-511 (2000) (doi:10.1038/35000501). Examples of DLBCLs include but are not limited to germinal center B-cell (GCB) subtype and activated B-cell (ABC) subtype.

In some embodiments, a lymphoma is a T-cell lymphoma. In some embodiments, a T-cell lymphoma is a mature T-cell lymphoma, such as a peripheral T-cell lymphoma (PTCL). Over 25 mature T-cell lymphomas have been identified. Examples of PTCLs include but are not limited to Peripheral T-Cell Lymphoma, Not Otherwise Specified (PTCL-NOS), anaplastic large cell lymphoma (ALCL), angioimmunoblastic T-cell lymphoma (AITL), cutaneous T-cell lymphoma (CTCL), Natural killer/T-cell lymphoma (NKTCL), Sezary syndrome, adult T-cell leukemia/lymphoma (ATLL), enteropathy-type T-cell lymphoma, nasal NK/T-cell lymphoma, hepatosplenic gamma-delta T-cell lymphoma, T-cell lymphomas of Follicular T-cell (TFH) origin, T-cell lymphomas of the gastrointestinal tract (e.g., EATL, MEITL), cutaneous T-cell lymphomas, etc.

In some embodiments, the lymphoma is an anaplastic large cell lymphoma (ALCL). In some embodiments, the ALCL is systemic ALCL. In some embodiments, the ALCL is cutaneous ALCL (e.g., ALCL affecting the skin). In some embodiments, the ALCL is ALK-positive ALCL. In some embodiments, the ALCL is ALK-negative ALCL.

In some embodiments, the lymphoma is an angioimmunoblastic T-cell lymphoma (AITL). In some embodiments, AITL tumor cells express one or more follicular T cell markers, for example CD10 and CD279 (PD-1, PDCD1), CXCL13, BCL6, CD40L, or NFATC1.

In some embodiments, the lymphoma is an adult T-cell leukemia/lymphoma (ATLL). In some embodiments, ATLL results from infection with HTLV-1 virus.

In some embodiments, the lymphoma is a Natural killer/T-cell lymphoma (NKTCL). In some embodiments, NKTCL tumors are located in the palate and/or sinuses of a subject. In some embodiments, NKTCL tumors are located in the nasal cavity of a subject.

Obtaining Expression Data

Expression data (e.g., microarray data, next-generation sequencing (NGS) data) as described herein may be obtained from a variety of sources. In some embodiments, expression data may be obtained by analyzing a biological sample of a subject. The biological sample may be analyzed prior to performance of the techniques described herein, including the techniques for ranking genes based on their expression levels and using the ranking(s) to determine one or more characteristics of the biological sample. In some such embodiments, data obtained from the biological sample may be stored (e.g., in a database) and accessed during performance of the techniques described herein. Thus, "obtaining expression data" as described herein may involve obtaining gene expression data in silico, such as by accessing, using a computing device, expression data (e.g., expression data that has been previously obtained from a biological sample) in one or more data stores, receiving the expression data from one or more other device, or any other way, analyzing a biological sample (in vitro), or a combination thereof. Examples of additional techniques relating to how expression data is obtained are described in U.S. Pat. No. 10,311,967, titled "SYSTEMS AND METHODS FOR GENERATING, VISUALIZING AND CLASSIFYING MOLECULAR FUNCTION PROFILES," issued on Jun. 4, 2019, which is incorporated herein by reference in its entirety.

In some embodiments, expression data may include expression levels for the entire cellular RNA, for all mRNAs in a cell, or a subset of RNAs in a cell (e.g., for a subset of RNAs expressed from a group of genes comprising or consisting of one or more gene sets described in this application, or at least some of the genes in those gene sets). RNA levels can be obtained using any appropriate technique including sequencing and/or hybridization based techniques (e.g., whole exome sequencing data, target specific sequencing data for a subset of RNAs, microarray data, etc.).

Biological Samples

Any of the methods, systems, assays, or other suitable techniques may be used to analyze any biological sample from a subject (e.g., a patient). In some embodiments, the biological sample may be any sample from a subject known or suspected of having cancer, including cancerous cells or pre-cancerous cells.

The biological sample may be any type of sample including, for example, a sample of a bodily fluid, one or more cells, a piece of tissue, or some or all of an organ. In some embodiments, the sample may be from a cancerous tissue or organ or a tissue or organ suspected of having one or more cancerous cells. In some embodiments, the sample may be from a healthy (e.g., non-cancerous) tissue or organ. In some embodiments, a sample from a subject (e.g., a biopsy from a subject) may include both healthy and cancerous cells and/or tissue. In certain embodiments, one sample will be taken from a subject for analysis.

Any of the biological samples described herein may be obtained from the subject using any known technique. In some embodiments, the biological sample may be obtained from a surgical procedure (e.g., laparoscopic surgery, microscopically controlled surgery, or endoscopy), bone marrow biopsy, punch biopsy, endoscopic biopsy, or needle biopsy (e.g., a fine-needle aspiration, core needle biopsy, vacuum-assisted biopsy, or image-guided biopsy). In some embodiments, each of the biological samples is a bodily fluid sample, a cell sample, or a tissue biopsy. In some embodiments, one or more than one cell (a cell sample) is obtained from a subject using a scrape or brush method. The cell sample may be obtained from any area in or from the body of a subject including, for example, from one or more of the following areas: the cervix, esophagus, stomach, bronchus, or oral cavity. In some embodiments, one or more than one piece of tissue (e.g., a tissue biopsy) from a subject may be used. In certain embodiments, the tissue biopsy may comprise one or more than one (e.g., 2, 3, 4, 5, 6, 7, 8, 9, 10, or more than 10) samples from one or more tumors or tissues known or suspected of having cancerous cells.

Sample Analysis

Methods described herein are based, at least in part, on the identification and characterization of certain biological processes and/or molecular and cellular compositions that are present within and/or surrounding the cancer (e.g., the tumor).

Biological processes within and/or surrounding cancer (e.g., a tumor) include, but are not limited to, angiogenesis, metastasis, proliferation, cell activation (e.g., T cell activation), tumor invasion, immune response, cell signaling (e.g., HER2 signaling), and apoptosis.

Molecular and cellular compositions within and/or surrounding cancer (e.g., a tumor) include, but are not limited to, nucleic acids (e.g., DNA and/or RNA), molecules (e.g., hormones), proteins (e.g., wild-type and/or mutant proteins), and cells (e.g., malignant and/or non-malignant cells). The cancer microenvironment, as used herein, refers to the molecular and cellular environment in which the cancer (e.g., a tumor) exists including, but not limited to, blood vessels that surround and/or are internal to a tumor, immune cells, fibroblasts, bone marrow-derived inflammatory cells, lymphocytes, signaling molecules, and the extracellular matrix (ECM).

The molecular and cellular composition and biological processes present within and/or surrounding the tumor may be directed toward promoting cancer (e.g., tumor) growth and survival (e.g., pro-tumor) and/or inhibiting cancer (e.g., tumor) growth and survival (e.g., anti-tumor).

The cancer (e.g., tumor) microenvironment may comprise cellular compositions and biological processes directed toward promoting cancer (e.g., tumor) growth and survival (e.g., pro-tumor microenvironment) and/or inhibiting cancer (e.g., tumor) growth and survival (e.g., anti-tumor microenvironment). In some embodiments, the cancer (e.g., tumor) microenvironment comprises a pro-cancer (e.g., tumor) microenvironment. In some embodiments, the cancer (e.g., tumor) microenvironment comprises an anti-cancer (e.g., tumor) microenvironment. In some embodiments, the cancer (e.g., tumor) microenvironment comprises a pro-cancer (e.g., tumor) microenvironment and an anti-cancer (e.g., tumor) microenvironment.

Any information relating to molecular and cellular compositions, and biological processes that are present within and/or surrounding cancer (e.g., a tumor) may be used in methods for characterization of cancers (e.g., tumors) as described herein. In some embodiments, cancer (e.g., a tumor) may be characterized based on gene group expression level (e.g., on gene group RNA expression level). In some embodiments, cancer (e.g., a tumor) is characterized based on protein expression.

Methods for characterization of cancers as described herein may be applied to any cancer (e.g., any tumor). Exemplary cancers include, but are not limited to, adrenocortical carcinoma, bladder urothelial carcinoma, breast invasive carcinoma, cervical squamous cell carcinoma, endocervical adenocarcinoma, colon adenocarcinoma, esophageal carcinoma, kidney renal clear cell carcinoma, kidney renal papillary cell carcinoma, liver hepatocellular carcinoma, lung adenocarcinoma, lung squamous cell carcinoma, ovarian serous cystadenocarcinoma, pancreatic adenocarcinoma, prostate adenocarcinoma, rectal adenocarcinoma, skin cutaneous melanoma, stomach adenocarcinoma, thyroid carcinoma, uterine corpus endometrial carcinoma, and cholangiocarcinoma.

Expression Data

Expression data (e.g., indicating expression levels) for a plurality of genes may be used for any of the methods described herein. The number of genes which may be examined may be up to and inclusive of all the genes of the subject.

Any method may be used on a sample from a subject in order to acquire expression data (e.g., indicating expression levels) for the plurality of genes. As a set of non-limiting examples, the expression data may be RNA expression data, DNA expression data, or protein expression data.

DNA expression data, in some embodiments, refers to a level of DNA in a sample from a subject. The level of DNA in a sample from a subject having cancer may be elevated compared to the level of DNA in a sample from a subject not having cancer, e.g., a gene duplication in a cancer patient's sample. The level of DNA in a sample from a subject having cancer may be reduced compared to the level of DNA in a sample from a subject not having cancer, e.g., a gene deletion in a cancer patient's sample.

DNA expression data, in some embodiments, refers to data for DNA (or gene) expressed in a sample, for example, sequencing data for a gene that is expressed in a patient's sample. Such data may be useful, in some embodiments, to determine whether the patient has one or more mutations associated with a particular cancer.

RNA expression data may be acquired using any method known in the art including, but not limited to: whole transcriptome sequencing, total RNA sequencing, mRNA sequencing, targeted RNA sequencing, small RNA sequencing, ribosome profiling, RNA exome capture sequencing, and/or deep RNA sequencing. DNA expression data may be acquired using any method known in the art including any known method of DNA sequencing. For example, DNA sequencing may be used to identify one or more mutations in the DNA of a subject. Any technique used in the art to sequence DNA may be used with the methods described herein. As a set of non-limiting examples, the DNA may be sequenced through single-molecule real-time sequencing, ion torrent sequencing, pyrosequencing, sequencing by synthesis, sequencing by ligation (SOLiD sequencing), nanopore sequencing, or Sanger sequencing (chain termination sequencing). Protein expression data may be acquired using any method known in the art including, but not limited to: N-terminal amino acid analysis, C-terminal amino acid analysis, Edman degradation (including though use of a machine such as a protein sequenator), or mass spectrometry.

In some embodiments, the expression data comprises next-generation sequencing (NGS) data. In some embodiments, the expression data comprises microarray data. In some embodiments, the expression data comprises whole exome sequencing (WES) data. In some embodiments, the expression data comprises whole genome sequencing (WGS) data. In some embodiments, expression data comprises RNA Seq data (e.g., by performing RNA sequencing). In some embodiments, expression data comprises a combination of RNA Seq data and WGS data. In some embodiments, expression data comprises a combination of RNA Seq data and WES data.

Assays

Any of the biological samples described herein can be used for obtaining expression data using conventional assays or those described herein. Expression data, in some embodiments, includes gene expression levels. Gene expression levels may be detected by detecting a product of gene expression such as mRNA and/or protein.

In some embodiments, gene expression levels are determined by detecting a level of a protein in a sample and/or by detecting a level of activity of a protein in a sample. As used herein, the terms "determining" or "detecting" may include assessing the presence, absence, quantity and/or amount (which can be an effective amount) of a substance within a sample, including the derivation of qualitative or quantitative concentration levels of such substances, or otherwise evaluating the values and/or categorization of such substances in a sample from a subject.

The level of a protein may be measured using an immunoassay. Examples of immunoassays include any known assay (without limitation), and may include any of the following: immunoblotting assay (e.g., Western blot), immunohistochemical analysis, flow cytometry assay, immunofluorescence assay (IF), enzyme linked immunosorbent assays (ELISAs) (e.g., sandwich ELISAs), radioimmunoassays, electrochemiluminescence-based detection assays, magnetic immunoassays, lateral flow assays, and related techniques. Additional suitable immunoassays for detecting a level of a protein provided herein will be apparent to those of skill in the art.

Such immunoassays may involve the use of an agent (e.g., an antibody) specific to the target protein. An agent such as an antibody that "specifically binds" to a target protein is a term well understood in the art, and methods to determine such specific binding are also well known in the art. An antibody is said to exhibit "specific binding" if it reacts or associates more frequently, more rapidly, with greater duration and/or with greater affinity with a particular target protein than it does with alternative proteins. It is also understood by reading this definition that, for example, an antibody that specifically binds to a first target peptide may or may not specifically or preferentially bind to a second target peptide. As such, "specific binding" or "preferential binding" does not necessarily require (although it can include) exclusive binding. Generally, but not necessarily, reference to binding means preferential binding. In some examples, an antibody that "specifically binds" to a target peptide or an epitope thereof may not bind to other peptides or other epitopes in the same antigen. In some embodiments, a sample may be contacted, simultaneously or sequentially, with more than one binding agent that binds different proteins (e.g., multiplexed analysis).

It will be apparent to those of skill in the art that this disclosure is not limited to immunoassays. Detection assays that are not based on an antibody, such as mass spectrometry, are also useful for the detection and/or quantification of a protein and/or a level of protein as provided herein. Assays that rely on a chromogenic substrate can also be useful for the detection and/or quantification of a protein and/or a level of protein as provided herein.

Alternatively, the level of nucleic acids encoding a gene in a sample can be measured via a conventional method. In some embodiments, measuring the expression level of nucleic acid encoding the gene comprises measuring mRNA. In some embodiments, the expression level of mRNA encoding a gene can be measured using real-time reverse transcriptase (RT) Q-PCR or a nucleic acid microarray. Methods to detect nucleic acid sequences include, but are not limited to, polymerase chain reaction (PCR), reverse transcriptase-PCR (RT-PCR), in situ PCR, quantitative PCR (Q-PCR), real-time quantitative PCR (RT Q-PCR), in situ hybridization, Southern blot, Northern blot, sequence analysis, microarray analysis, detection of a reporter gene, or other DNA/RNA hybridization platforms.

In some embodiments, the level of nucleic acids encoding a gene in a sample can be measured via a hybridization assay. In some embodiments, the hybridization assay comprises at least one binding partner. In some embodiments, the hybridization assay comprises at least one oligonucleotide binding partner. In some embodiments, the hybridization assay comprises at least one labeled oligonucleotide binding partner. In some embodiments, the hybridization assay comprises at least one pair of oligonucleotide binding partners. In some embodiments, the hybridization assay comprises at least one pair of labeled oligonucleotide binding partners.

Any binding agent that specifically binds to a desired nucleic acid or protein may be used in the methods and kits described herein to measure an expression level in a sample. In some embodiments, the binding agent is an antibody or an aptamer that specifically binds to a desired protein. In other embodiments, the binding agent may be one or more oligonucleotides complementary to a nucleic acid or a portion thereof. In some embodiments, a sample may be contacted, simultaneously or sequentially, with more than one binding agent that binds different proteins or different nucleic acids (e.g., multiplexed analysis).

To measure an expression level of a protein or nucleic acid, a sample can be in contact with a binding agent under suitable conditions. In general, the term "contact" refers to an exposure of the binding agent with the sample or cells collected therefrom for suitable period sufficient for the formation of complexes between the binding agent and the target protein or target nucleic acid in the sample, if any. In some embodiments, the contacting is performed by capillary action in which a sample is moved across a surface of the support membrane.

In some embodiments, an assay may be performed in a low-throughput platform, including single assay format. In some embodiments, an assay may be performed in a high-throughput platform. Such high-throughput assays may comprise using a binding agent immobilized to a solid support (e.g., one or more chips). Methods for immobilizing a binding agent will depend on factors such as the nature of the binding agent and the material of the solid support and may require particular buffers. Such methods will be evident to one of ordinary skill in the art.

Genes

The various genes recited herein are, in general, named using human gene naming conventions. The various genes, in some embodiments, are described in publicly available resources such as published journal articles. The gene names may be correlated with additional information (including sequence information) through use of, for example, the NCBI GenBank® databases; the HUGO (Human Genome Organization) Gene Nomination Committee (HGNC) databases; the DAVID Bioinformatics Resource. The gene names may also be correlated with additional information through printed publications from the foregoing organizations, which are incorporated by reference herein for this purpose. It should be appreciated that a gene may encompass all variants of that gene. For organisms or subjects other than human subjects, corresponding specific-specific genes may be used. Synonyms, equivalents, and closely related genes (including genes from other organisms) may be identified using similar databases including the NCBI GenBank® databases described above.

Some embodiments involve using a gene set for predicting breast cancer grade, including the genes listed in Table 1. Some embodiments involve using a gene set for predicting kidney clear cell cancer grade, including the genes listed in Table 2. Some embodiments involve using a gene set for predicting tissue of origin for Diffuse Large B-Cell Lymphoma (DLBCL), such as germinal center B-cell (GCB) and activated B-cell (ABC), including the genes listed in Table 3. Some embodiments involve using a gene set for predicting PTCL subtype, including the genes listed in Table 10.

Applications

Methods for biological sample characterization, which may include tumor type characterization, as described herein may be used for various clinical purposes including, but not limited to, monitoring the progress of cancer in a subject, assessing the efficacy of a treatment for cancer, identifying patients suitable for a particular treatment, evaluating suitability of a patient for participating in a clinical trial and/or predicting relapse in a subject. Accordingly, described herein are diagnostic and prognostic methods for cancer treatment based on tumor type described herein.

Methods described herein can be used to evaluate the efficacy of a cancer treatment, such as those described herein, given the correlation between cancer type (e.g., tumor types) and cancer prognosis. For example, multiple biological samples, such as those described herein, can be collected from a subject to whom a treatment is performed either before and after the treatment or during the course of the treatment. The cancer type (e.g., the tumor type) in the biological sample from the subject can be determined using any of the methods described herein. For example, if the cancer type indicates that the subject has a poor prognosis and the cancer type changes to a cancer type indicative of a favorable prognosis after the treatment or over the course of treatment, it indicates that the treatment is effective.

In some embodiments, cancer types can also be used to identify a cancer that may be treatable using a specific anti-cancer therapeutic agent (e.g., a chemotherapy). To practice this method, the cancer type in a sample (e.g., a tumor biopsy) collected from a subject having cancer can be determined using methods described herein. If the cancer type is identified as being susceptible to treatment with an anti-cancer therapeutic agent, the method may further comprise administering to the subject having the cancer an effective amount of the anti-cancer therapeutic agent.

In some embodiments, the methods for cancer type characterization as described herein may be relied on in the development of new therapeutics for cancer. In some embodiments, the cancer type may indicate or predict the efficacy of a new therapeutic or the progression of cancer in a subject prior to, during, or after the administration of the new therapy.

In some embodiments, methods for cancer type characterization as described herein may be used to evaluate suitability of a patient for participating in a clinical trial. In some embodiments, the cancer type may be used to include patients in a clinical trial. In some embodiments, patients having a specified cancer grade (e.g., Grade 1) are included in a clinical trial. In some embodiments, patients having a specified tissue of origin for the cancer are included in a clinical trial. In some embodiments, the cancer type may be used to exclude patients in a clinical trial. In some embodiments, patients having a specified cancer grade (e.g., Grade 3) are excluded from a clinical trial. In some embodiments, patients having a specified tissue of origin are excluded from a clinical trial. In some embodiments, patients having a specified PTCL subtype are excluded from a clinical trial.

In some embodiments, the methods described herein may be used in monitoring progression of a patient's disease and identifying one or more treatments based on a stage of disease determined using the techniques described herein. In some embodiments, the monitoring occurs over a period of time where a first disease stage is identified for the patient at a first time and a second disease stage is identified for the patient at a second time. The second disease stage may be used to identify a different type of treatment. For example, in the context of using the techniques described herein for predicting cancer grade, monitoring a patient's disease and identifying different treatments based on stage of disease may involve obtaining first expression data obtained by sequencing a first biological sample of a subject (e.g., a subject having kidney cancer), determining a first cancer grade using the first expression data and a statistical model described herein, identifying or recommending a first treatment for the subject based on the first cancer grade, and optionally, administering the first treatment. Monitoring the patient's disease may further involve obtaining second expression data obtained by sequencing a second biological sample of the subject (e.g., a biological sample obtained from the subject at a different time than the first biological sample), determining a second cancer grade using the second expression data, identifying or recommending a second treatment for the subject based on the second cancer grade, and optionally, administering the second treatment. In some embodiments, the first cancer grade is different from the first cancer grade and the first treatment is different from the second treatment. In some embodiments, monitoring may be performed multiple times (e.g., along with multiple medical visits) to evaluate progress of a treatment, determine how a patient is responding to a particular treatment, or a combination thereof.

In some embodiments, the methods described herein may be used in assessing how a subject has responded to a treatment. For example, these techniques described herein may be used in determining whether a subject is responding to a line of treatment or not, whether a subject is in remission, and whether there is a recurrence of a disease.

In some embodiments, characteristic(s) for cells of a biological sample of a subject determined using the techniques described herein may be used in identifying a diagnosis for the subject. In some embodiments, the characteristic(s) may provide information for a physician or other user to determine a diagnosis for the subject. For example, the characteristic(s) alone may be sufficient to allow a physician to determine the diagnosis. In some embodiments, a combination of the characteristic(s) and other patient medical data may be used by a physician or other user in determining a diagnosis for the subject.

In some embodiments, characteristic(s) for cells of a biological sample of a subject determined using the techniques described herein may be used in identifying a prognosis for the subject. In some embodiments, the characteristic(s) may provide information for a physician or other user to determine a prognosis for the subject. For example, the characteristic(s) alone may be sufficient to allow a physician to determine the prognosis. In some embodiments, a combination of the characteristic(s) and other patient medical data may be used by a physician or other user in determining a prognosis for the subject.

In some embodiments, a diagnosis or prognosis determined using the techniques described herein may be used in recommending a treatment or therapy for the subject. The therapy may be a drug treatment, radiation, surgery, diet or lifestyle change, or other therapy. A treatment may be chemotherapy, immunotherapy, hormone therapy, or other treatment. In some embodiments, recommending a treatment or therapy may include a change in treatment (e.g., a different treatment, an additional treatment, or a different frequency or dose).

In some embodiments, a diagnosis or prognosis determined using the techniques described herein may be used in generating a recommendation for further analysis of the patient. For example, a recommendation for further diagnostic intervention (e.g., more extensive CAT scan, MRI, more extensive or invasive biopsies, more detailed genetic, proteomic, or histological analysis of one or more tissue samples, etc.).

In some embodiments, a diagnosis or prognosis determined using the techniques described herein may be used in generating a recommendation to change the frequency of follow up medical checks. For example, a recommendation to have more frequent medical checks if the analysis suggests a higher risk, or less frequent medical checks if the analysis suggests a lower risk or that the subject is in remission.

In some embodiments, characteristic(s) for cells of a biological sample of a subject determined using the techniques described herein may be using in generating a report specific to the subject. For example, the report may be a patient-specific cancer characteristics report. Generating the report may involve generating a file comprising information indicative of disease characteristics determined using the techniques described herein (e.g., cancer grade, tissue of origin, tissue subtype).

In the context of providing a recommendation or other information to a physician or other user, providing such information may involve transmitting electronic information to the physician or other user. In some embodiments, the electronic information may be transmitted to a medical center or to a computer system that hosts the patient medical information, and the physician or other user may access the information using a computing device.

Examples of additional applications for how characteristics of a biological sample, as determined using the techniques described herein, may be used are described in in U.S. Pat. No. 10,311,967, titled "SYSTEMS AND METHODS FOR GENERATING, VISUALIZING AND CLASSIFYING MOLECULAR FUNCTION PROFILES," issued on Jun. 4, 2019, which is incorporated herein by reference in its entirety.

Methods of Treatment

In certain methods described herein, an effective amount of anti-cancer therapy described herein may be administered or recommended for administration to a subject (e.g., a human) in need of the treatment via a suitable route (e.g., intravenous administration).

The subject to be treated by the methods described herein may be a human patient having, suspected of having, or at risk for a cancer. A subject having, suspected of having, or at risk of having cancer may be a subject exhibiting one or more signs or symptoms of cancer, subject that is diagnosed as having cancer, a subject that has a family history and/or a genetic predisposition to having cancer, and/or a subject that has one or more other risk factors for cancer (e.g., age, exposure to carcinogens, environmental exposure, exposure to a virus associated with a higher likelihood of developing cancer, etc.). Examples of a cancer include, but are not limited to, melanoma, lung cancer, brain cancer, breast cancer, colorectal cancer, pancreatic cancer, liver cancer, prostate cancer, skin cancer, kidney cancer, bladder cancer, or prostate cancer. The subject to be treated by the methods described herein may be a mammal (e.g., may be a human). Mammals include, but are not limited to: farm animals (e.g., livestock), sport animals, laboratory animals, pets, primates, horses, dogs, cats, mice, and rats.

"An effective amount" as used herein refers to the amount of each active agent required to confer therapeutic effect on the subject, either alone or in combination with one or more other active agents. Effective amounts vary, as recognized by those skilled in the art, depending on the particular condition being treated, the severity of the condition, the individual patient parameters including age, physical condition, size, gender and weight, the duration of the treatment, the nature of concurrent therapy (if any), the specific route of administration and like factors within the knowledge and expertise of the health practitioner. These factors are well known to those of ordinary skill in the art and can be addressed with no more than routine experimentation. It is generally preferred that a maximum dose of the individual components or combinations thereof be used, that is, the highest safe dose according to sound medical judgment. It will be understood by those of ordinary skill in the art, however, that a patient may insist upon a lower dose or tolerable dose for medical reasons, psychological reasons, or for virtually any other reasons.

Examples of additional methods of treatment are described in U.S. Pat. No. 10,311,967, titled "SYSTEMS AND METHODS FOR GENERATING, VISUALIZING AND CLASSIFYING MOLECULAR FUNCTION PROFILES," issued on Jun. 4, 2019, which is incorporated herein by reference in its entirety.

Quality Control Analysis

In some embodiments, the techniques described herein may be used in performing quality control. One application is quality control analysis in a laboratory setting. For example, a sequencing laboratory may receive a biological sample together with information about the biological sample. Aside from an identifier and/or tracking number, such information may include information about the characteristics of the biological sample (e.g., the tissue source, cancer type, cancer grade, etc.). However, due to laboratory errors, it is possible that the biological sample provided does not actually have these characteristics (e.g., due to an error where patient samples are switched, mislabeled, wrong information is provided, etc.).

Another application is to quality control analysis in data analysis setting. For example, a patient's sequencing data (e.g., reads, aligned reads, expression levels, etc.) may be provided as input to a data processing pipeline. However, if that sequencing data does not correspond to the alleged source (e.g., it comes from a different patient due to an error), the results of the analysis are likely meaningless.

In some embodiments, quality control may be performed by comparing an asserted characteristic of a biological sample to a predicted characteristic determined using the techniques described herein. When the asserted characteristic and the predicted characteristic match (e.g., are the same or are within a tolerated difference), then it may be determined that a quality control check has been satisfied. On the other hand, if the predicted and asserted characteristics do not match, then further action may need to be taken. For example, further analysis of the biological sample may be performed, the biological sample may be rejected, a data processing pipeline may be stopped or not executed (thereby saving valuable and costly computational resources), a laboratory operator and/or other party (e.g., clinician, staff, etc.) may be notified of a potential discrepancy (e.g., by an e-mail alert, a message, a report, an entry in a log-file, etc.).

For example, a classifier for determining cancer grade may be used to predict cancer grade from gene expression data of a sample, and the predicted cancer grade may be compared to an asserted cancer grade for the sample. If the predicted and asserted cancer grades match, then it may be determined that the sample analysis has met quality control standards. However, if the predicted and asserted cancer grades do not match, then further analysis may be performed. As another example, a classifier for determining tissue of origin may be used to predict a type of tissue for a sample and the predicted tissue type may be compared to an asserted tissue type for the sample. If the predicted and asserted tissue types do not match, then further analysis of the biological sample may be performed to identify the tissue type for the sample. Any of the classification techniques described herein may be used in this manner, either alone or in combination with one another to provide multiple quality control checkpoints.

Examples of additional quality control analysis are described in U.S. patent application Ser. No. 16/920,636, titled "TECHNIQUES FOR BIAS CORRECTION IN SEQUENCE DATA," filed Jul. 3, 2020, which is incorporated herein by reference in its entirety.

Computational System

Figure 10:
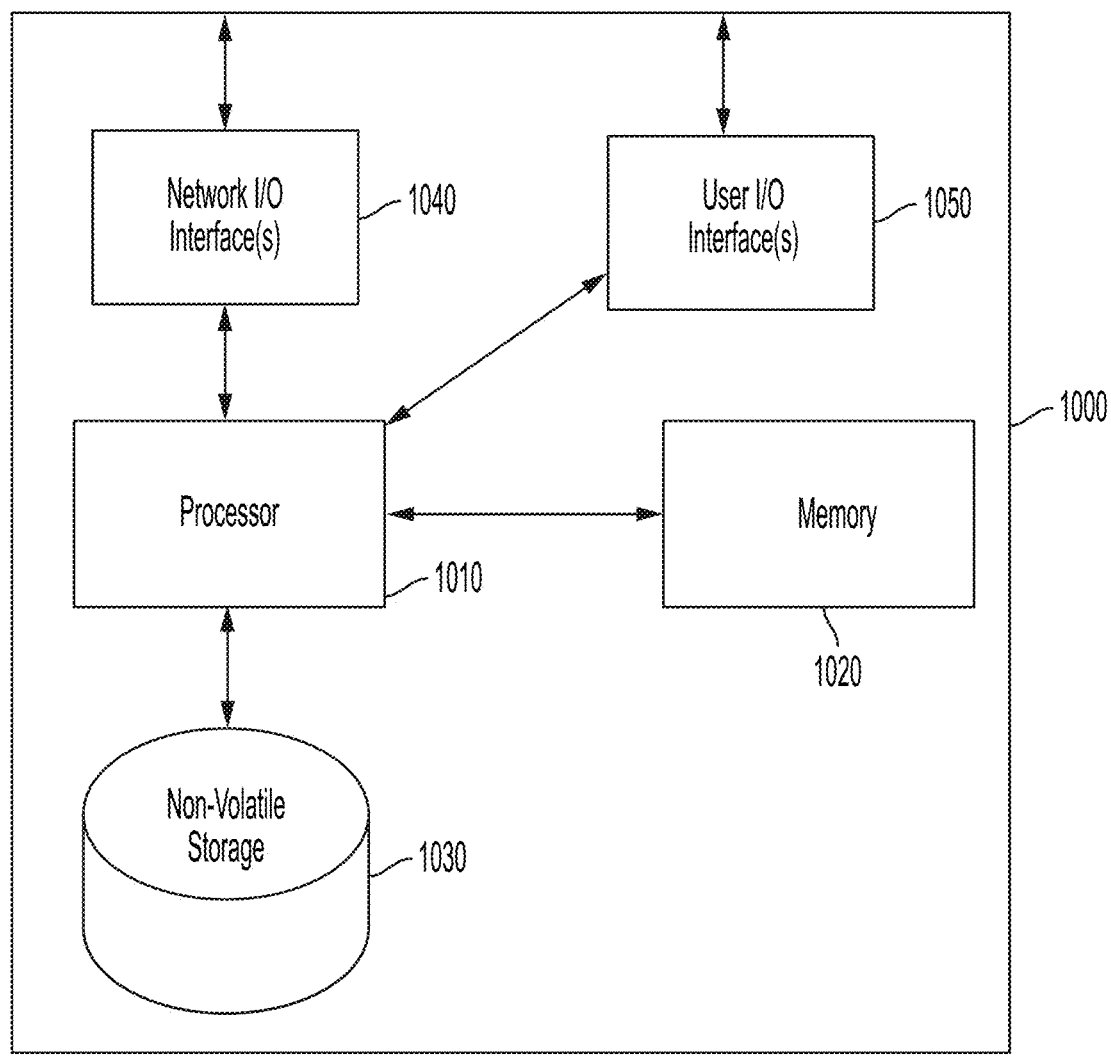
FIG. 10 is a block diagram of an illustrative computer system that may be used in implementing the machine learning techniques described herein.

An illustrative implementation of a computer system 1000 that may be used in connection with any of the embodiments of the technology described herein is shown in FIG. 10. The computer system 1000 includes one or more processors 1010 and one or more articles of manufacture that comprise non-transitory computer-readable storage media (e.g., memory 1020 and one or more non-volatile storage media 1030). The processor 1010 may control writing data to and reading data from the memory 1020 and the non-volatile storage device 1030 in any suitable manner, as the aspects of the technology described herein are not limited in this respect. To perform any of the functionality described herein, the processor 1010 may execute one or more processor-executable instructions stored in one or more non-transitory computer-readable storage media (e.g., the memory 1020), which may serve as non-transitory computer-readable storage media storing processor-executable instructions for execution by the processor 1010.

Computing device 1000 may also include a network input/output (I/O) interface 1040 via which the computing device may communicate with other computing devices (e.g., over a network), and may also include one or more user I/O interfaces 1050, via which the computing device may provide output to and receive input from a user. The user I/O interfaces may include devices such as a keyboard, a mouse, a microphone, a display device (e.g., a monitor or touch screen), speakers, a camera, and/or various other types of I/O devices.

The above-described embodiments can be implemented in any of numerous ways. For example, the embodiments may be implemented using hardware, software or a combination thereof. When implemented in software, the software code can be executed on any suitable processor (e.g., a microprocessor) or collection of processors, whether provided in a single computing device or distributed among multiple computing devices. It should be appreciated that any component or collection of components that perform the functions described above can be generically considered as one or more controllers that control the above-discussed functions. The one or more controllers can be implemented in numerous ways, such as with dedicated hardware, or with general purpose hardware (e.g., one or more processors) that is programmed using microcode or software to perform the functions recited above.

In this respect, it should be appreciated that one implementation of the embodiments described herein comprises at least one computer-readable storage medium (e.g., RAM, ROM, EEPROM, flash memory or other memory technology, CD-ROM, digital versatile disks (DVD) or other optical disk storage, magnetic cassettes, magnetic tape, magnetic disk storage or other magnetic storage devices, or other tangible, non-transitory computer-readable storage medium) encoded with a computer program (e.g., a plurality of executable instructions) that, when executed on one or more processors, performs the above-discussed functions of one or more embodiments. The computer-readable medium may be transportable such that the program stored thereon can be loaded onto any computing device to implement aspects of the techniques discussed herein. In addition, it should be appreciated that the reference to a computer program which, when executed, performs any of the above-discussed functions, is not limited to an application program running on a host computer. Rather, the terms computer program and software are used herein in a generic sense to reference any type of computer code (e.g., application software, firmware, microcode, or any other form of computer instruction) that can be employed to program one or more processors to implement aspects of the techniques discussed herein.

The terms "program" or "software" are used herein in a generic sense to refer to any type of computer code or set of processor-executable instructions that can be employed to program a computer or other processor to implement various aspects of embodiments as discussed above. Additionally, it should be appreciated that according to one aspect, one or more computer programs that when executed perform methods of the disclosure provided herein need not reside on a single computer or processor, but may be distributed in a modular fashion among different computers or processors to implement various aspects of the disclosure provided herein.

Processor-executable instructions may be in many forms, such as program modules, executed by one or more computers or other devices. Generally, program modules include routines, programs, objects, components, data structures, etc. that perform particular tasks or implement particular abstract data types. Typically, the functionality of the program modules may be combined or distributed as desired in various embodiments.

Also, data structures may be stored in one or more non-transitory computer-readable storage media in any suitable form. For simplicity of illustration, data structures may be shown to have fields that are related through location in the data structure. Such relationships may likewise be achieved by assigning storage for the fields with locations in a non-transitory computer-readable medium that convey relationship between the fields. However, any suitable mechanism may be used to establish relationships among information in fields of a data structure, including through the use of pointers, tags or other mechanisms that establish relationships among data elements.

Also, various inventive concepts may be embodied as one or more processes, of which examples have been provided. The acts performed as part of each process may be ordered in any suitable way. Accordingly, embodiments may be constructed in which acts are performed in an order different than illustrated, which may include performing some acts simultaneously, even though shown as sequential acts in illustrative embodiments.

Aspects of the technology described herein provide computer implemented methods for generating, visualizing and classifying biological characteristic(s) (e.g., cancer grade, tissue of origin) of cancer patients.

In some embodiments, a software program may provide a user with a visual representation of a patient's characteristic(s) and/or other information related to a patient's cancer using an interactive graphical user interface (GUI). Such a software program may execute in any suitable computing environment including, but not limited to, a cloud-computing environment, a device co-located with a user (e.g., the user's laptop, desktop, smartphone, etc.), one or more devices remote from the user (e.g., one or more servers), etc.

Figure 11:
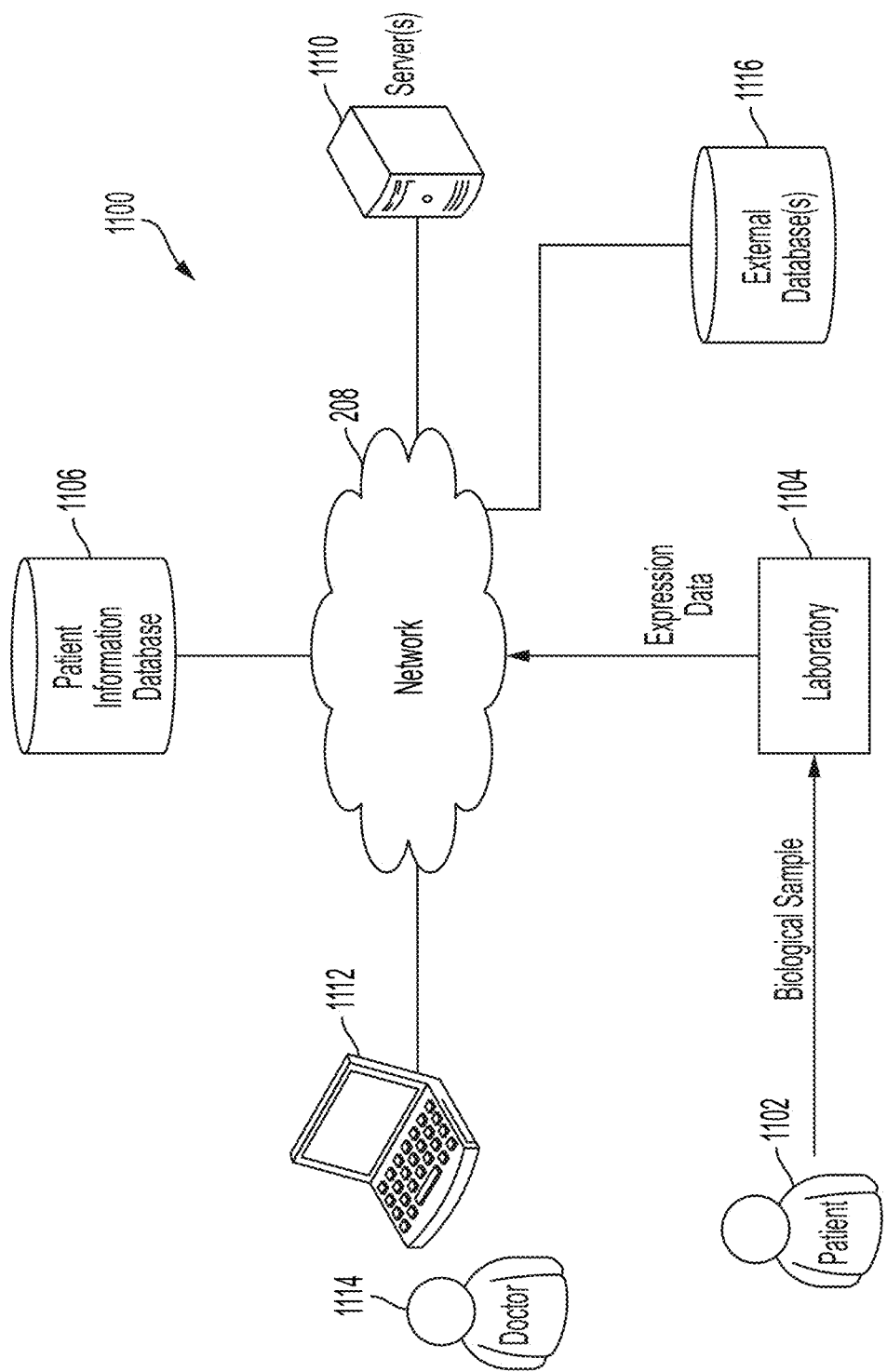
FIG. 11 is a block diagram of an illustrative environment 1100 in which the machine learning techniques described herein may be implemented.

For example, in some embodiments, the techniques described herein may be implemented in the illustrative environment 1100 shown in FIG. 11. As shown in FIG. 11, within illustrative environment 1100, one or more biological samples of a patient 1102 may be provided to a laboratory 1104. Laboratory 1104 may process the biological sample(s) to obtain expression data (e.g., DNA, RNA, and/or protein expression data) and provide it, via network 1108, to at least one database 1106 that stores information about patient 1102.

Network 1108 may be a wide area network (e.g., the Internet), a local area network (e.g., a corporate Intranet), and/or any other suitable type of network. Any of the devices shown in FIG. 11 may connect to the network 1108 using one or more wired links, one or more wireless links, and/or any suitable combination thereof.

In the illustrated embodiment of FIG. 11, the at least one database 1106 may store expression data for the patient, medical history data for the patient, test result data for the patient, and/or any other suitable information about the patient 1102. Examples of stored test result data for the patient include biopsy test results, imaging test results (e.g., MRI results), and blood test results. The information stored in at least one database 1106 may be stored in any suitable format and/or using any suitable data structure(s), as aspects of the technology described herein are not limited in this respect. The at least one database 1106 may store data in any suitable way (e.g., one or more databases, one or more files). The at least one database 1106 may be a single database or multiple databases.

As shown in FIG. 11, illustrative environment 1100 includes one or more external databases 1116, which may store information for patients other than patient 1102. For example, external databases 1116 may store expression data (of any suitable type) for one or more patients, medical history data for one or more patients, test result data (e.g., imaging results, biopsy results, blood test results) for one or more patients, demographic and/or biographic information for one or more patients, and/or any other suitable type of information. In some embodiments, external database(s) 1116 may store information available in one or more publicly accessible databases such as TCGA (The Cancer Genome Atlas), one or more databases of clinical trial information, and/or one or more databases maintained by commercial sequencing suppliers. The external database(s) 1116 may store such information in any suitable way using any suitable hardware, as aspects of the technology described herein are not limited in this respect.

In some embodiments, the at least one database 1106 and the external database(s) 1116 may be the same database, may be part of the same database system, or may be physically co-located, as aspects of the technology described herein are not limited in this respect.

For example, in some embodiments, server(s) 1110 may access information stored in database(s) 1106 and/or 1116 and use this information to perform process 300, described with reference to FIG. 3, for determining one or more characteristics of a biological sample.

As another example, in some embodiments, server(s) 1110 may access information stored in database(s) 1106 and/or 1116 and use this information to perform process 400, described with reference to FIG. 4, for determining tissue of origin for some or all cells in a biological sample.

As another example, in some embodiments, server(s) 1110 may access information stored in database(s) 1106 and/or 1116 and use this information to perform process 500, described with reference to FIG. 5, for determining cancer grade for some or all cells in a biological sample.

As another example, in some embodiments, server(s) 1110 may access information stored in database(s) 1106 and/or 1116 and use this information to perform process 800, described with reference to FIG. 8, for selecting a gene set.

As another example, in some embodiments, server(s) 1110 may access information stored in database(s) 1106 and/or 1116 and use this information to perform process 2900, described with reference to FIG. 29, for determining PTCL subtype of a biological sample. In some embodiments, server(s) 1110 may include one or multiple computing devices. When server(s) 1110 include multiple computing devices, the device(s) may be physically co-located (e.g., in a single room) or distributed across multi-physical locations. In some embodiments, server(s) 1110 may be part of a cloud computing infrastructure. In some embodiments, one or more server(s) 1110 may be co-located in a facility operated by an entity (e.g., a hospital, research institution) with which doctor 1114 is affiliated. In such embodiments, it may be easier to allow server(s) 1110 to access private medical data for the patient 1102.

As shown in FIG. 11, in some embodiments, the results of the analysis performed by server(s) 1110 may be provided to doctor 1114 through a computing device 1112 (which may be a portable computing device, such as a laptop or smartphone, or a fixed computing device such as a desktop computer). The results may be provided in a written report, an e-mail, a graphical user interface, and/or any other suitable way. It should be appreciated that although in the embodiment of FIG. 11, the results are provided to a doctor, in other embodiments, the results of the analysis may be provided to patient 1102 or a caretaker of patient 1102, a healthcare provider such as a nurse, or a person involved with a clinical trial.

In some embodiments, the results may be part of a graphical user interface (GUI) presented to the doctor 1114 via the computing device 1112. In some embodiments, the GUI may be presented to the user as part of a webpage displayed by a web browser executing on the computing device 1112. In some embodiments, the GUI may be presented to the user using an application program (different from a web-browser) executing on the computing device 1112. For example, in some embodiments, the computing device 1112 may be a mobile device (e.g., a smartphone) and the GUI may be presented to the user via an application program (e.g., "an app") executing on the mobile device.

The GUI presented on computing device 1112 may provide a wide range of oncological data relating to both the patient and the patient's cancer in a new way that is compact and highly informative. Previously, oncological data was obtained from multiple sources of data and at multiple times making the process of obtaining such information costly from both a time and financial perspective. Using the techniques and graphical user interfaces illustrated herein, a user can access the same amount of information at once with less demand on the user and with less demand on the computing resources needed to provide such information. Low demand on the user serves to reduce clinician errors associated with searching various sources of information. Low demand on the computing resources serves to reduce processor power, network bandwidth, and memory needed to provide a wide range of oncological data, which is an improvement in computing technology. All definitions, as defined and used herein, should be understood to control over dictionary definitions, and/or ordinary meanings of the defined terms.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

Use of ordinal terms such as "first," "second," "third," etc., in the claims to modify a claim element does not by itself connote any priority, precedence, or order of one claim element over another or the temporal order in which acts of a method are performed. Such terms are used merely as labels to distinguish one claim element having a certain name from another element having a same name (but for use of the ordinal term).

The phraseology and terminology used herein is for the purpose of description and should not be regarded as limiting. The use of "including," "comprising," "having," "containing", "involving", and variations thereof, is meant to encompass the items listed thereafter and additional items.

Having described several embodiments of the techniques described herein in detail, various modifications, and improvements will readily occur to those skilled in the art. Such modifications and improvements are intended to be within the spirit and scope of the disclosure. Accordingly, the foregoing description is by way of example only, and is not intended as limiting. The techniques are limited only as defined by the following claims and the equivalents thereto.

What is claimed is:

1. A system, comprising:
   at least one computer hardware processor; and
   at least one computer-readable storage medium storing processor-executable instructions configured to perform a method comprising:
   accessing a trained statistical model comprising parameters estimated using training data, the training data indicating a plurality of gene rankings of at least some genes in a set of genes, the parameters being estimated after the at least some genes in the set of genes were selected;
   obtaining expression data for a biological sample of a subject having, suspected of having or at risk of having cancer, the expression data previously obtained at least in part by sequencing the biological sample and comprising first expression levels for the set of genes;
   ranking the at least some genes in the set of genes based on their first expression levels in the expression data to obtain a gene ranking, the gene ranking including values identifying relative ranks of the at least some genes in the gene ranking, wherein the values are different from the first expression levels; and
   determining at least one characteristic of the biological sample by providing the gene ranking as an input to the trained statistical model and processing the gene ranking with the trained statistical model to obtain an output indicating the at least one characteristic of the biological sample,
   the processing of the gene ranking with the trained statistical model comprises using the parameters and the gene ranking provided as the input to obtain the output indicating the at least one characteristic of the biological sample; and
   the at least one characteristic of the biological sample is a physiological characteristic of cells in the biological sample or a physiological characteristic of a tissue from which the cells in the biological sample originate.

2. The system of claim 1, wherein the at least one characteristic is selected from the group consisting of cancer grade for the biological sample, tissue of origin for the biological sample, tissue type for the biological sample, and cancer subtype for the biological sample.

3. The system of claim 1, wherein the at least one characteristic includes cancer grade for the cells in the biological sample, and the cancer grade is selected from the group consisting of Grade 1, Grade 2, Grade 3, Grade 4, and Grade 5.

4. The system of claim 1, wherein the at least one characteristic includes tissue of origin for the cells in the biological sample, and the tissue of origin is selected from the group consisting of lung tissue, pancreas tissue, stomach tissue, colon tissue, liver tissue, bladder tissue, kidney tissue, thyroid tissue, lymph node tissue, adrenal gland tissue, skin tissue, breast tissue, ovary tissue, prostate tissue, urothelial tissue, cervical tissue, esophagus tissue, brain tissue, soft tissue, connective tissue, head tissue, and neck tissue.

5. The system of claim 1, wherein the at least one characteristic includes tissue type for the cells in the biological sample, and the tissue type is selected from the group consisting of adenocarcinoma, squamous cell carcinoma, carcinoma, cystadenocarcinoma, sarcoma, and glioma.

6. The system of claim 1, wherein the at least one characteristic includes human papillomavirus (HPV) status for the cells in the biological sample, and wherein the set of genes includes at least 5 genes selected from the group of genes listed in Table 8, wherein Table 8 is:

| Gene | NCBI Gene ID | NCBI Accession Number(s) |
|---|---|---|
| APOBEC3B | 9582 | NM_001270411; NM_004900 |
| ATAD2 | 29028 | NM_014109; NM_014109 |
| BIRC5 | 332 | NM_001168; NM_001012271; NM_001012270; NM_001168 |
| CCL20 | 6364 | NM_001130046; NM_004591 |
| CCND1 | 595 | NM_053056; NM_053056 |
| CDC45 | 8318 | NM_001178010; NM_001178011; NM_003504; XM_011530417; XM_011530416; NR_161281; XM_017028966; ; XR_002958716; NM_001178010; XM_011530418; XM_017028967; XM_024452277; NM_001369291 |
| CDC7 | 8317 | NM_001134419; NM_001134420; NM_003503; XM_005271241 |
| CDK1 | 983 | NM_001320918; NM_001786; NM_033379; XM_005270303 |
| CDKN2A | 1029 | NM_000077; NM_000077; NM_001195132; NM_058197; XM_005251343; XM_011517676; ; NM_058196; NM_058195; XM_011517675; NM_001363763; XR_929159 |
| CDKN2C | 1031 | NM_001262; NM_078626; NM_001262 |
| CDKN3 | 1018 | NM_001258 |
| CENPF | 1063 | NM_016343; XM_017000086 |
| CENPN | 55839 | NM_001100624; NM_001100625; NM_001270473; NM_001270474; NM_018455; XM_006721236; XM_017023456 |
| CXCL14 | 9547 | NM_004887 |
| DCN | 1634 | NM_133505; NM_001920; NM_133503; NM_133504; NM_133505; NM_133506; NM_133507; |
| DHFR | 1719 | NM_000791; NM_001290357; NM_000791; NM_001290354 |
| DKK3 | 27122 | NM_001330220; XM_017017554; XM_017017555; NM_001018057; NM_001330220; NM_013253; NM_015881; XM_006718178 |
| DLGAP5 | 9787 | NM_001146015; NM_014750; XM_017021840 |
| EPCAM | 4072 | NM_002354 |
| FANCI | 55215 | NM_001113378; NM_018193; XM_011521756; NM_001113378; NM_001376910; NM_001376911; ; XM_011521764 |
| FEN1 | 2237 | NM_004111; NM_004111 |
| GMNN | 51053 | NM_001251989; NM_001251990; NM_001251991; NM_015895; XM_005249159; NM_001251989 |
| GPX3 | 2878 | NM_001329790; NM_002084 |
| ID4 | 3400 | NM_001546 |
| IGLC1 | 3537 | NG_000002.1 |
| IL18 | 3606 | NM_001243211; XM_011542805; NM_001243211; NM_001562; ; NM_001386420 |
| IL1R2 | 7850 | NM_001261419; NM_004633; XM_006712734; XM_011511804 |
| KIF18B | 146909 | NM_001264573; NM_001265577; NM_001264573 |
| KIF20A | 10112 | NM_005733 |
| KIF4A | 24137 | NM_012310 |
| KLK13 | 26085 | NM_001348177; NM_001348178; NM_001348177; NM_015596 |
| KLK7 | 5650 | NM_005046; NM_139277; NM_001207053; NM_001243126; NM_005046 |
| KLK8 | 11202 | NM_001281431; NM_001281431; NM_007196; NM_144505; NM_144506; NM_144507 |
| KNTC1 | 9735 | NM_014708; XM_006719706 |
| KRT19 | 3880 | NM_002276 |
| LAMP3 | 27074 | NM_014398 |
| LMNB1 | 4001 | NM_005573 |
| MCM2 | 4171 | NM_004526 |
| MCM4 | 4173 | NM_005914; NM_182746 |
| MCM5 | 4174 | NM_006739; NM_006739 |
| ME1 | 4199 | NM_002395; XM_011535836 |
| MELK | 9833 | NM_001256685; NM_001256687; NM_001256688; NM_001256689; NM_001256690; NM_001256692; NM_001256693; NM_014791; XM_011518076; XM_011518077; XM_011518078; XM_011518079; XM_011518081; XM_011518082; XM_011518083; XM_011518084 |

-continued

| Gene | NCBI Gene ID | NCBI Accession Number(s) |
|---|---|---|
| MKI67 | 4288 | NM_001145966; NM_002417 |
| MLF1 | 4291 | NM_022443; NM_001130156; NM_001130157; NM_001195432; NM_001195433; NM_001195434; NM_022443; NM_001369782; NM_001378848; NM_001378853; ; NM_001369784; NM_001369785; NM_001369781; NM_001378846; NM_001378855; NM_001378845; NM_001378847; NM_001378850; NM_001378852; NM_001369783; NM_001378851 |
| MMP12 | 4321 | NM_002426 |
| MTHFD2 | 10797 | NM_006636; XM_006711924 |
| NDN | 4692 | NM_002487; NM_002487 |
| NEFH | 4744 | NM_021076 |
| NEK2 | 4751 | NM_001204182; NM_001204182; NM_001204183; NM_002497; XM_005273147 |
| NUP155 | 9631 | NM_153485; NM_001278312; NM_004298; NM_153485 |
| NUP210 | 23225 | NM_024923 |
| NUSAP1 | 51203 | NM_001243142; NM_001243143; NM_001243144; NM_001301136; NM_016359; NM_018454; XM_005254430 |
| PDGFD | 80310 | NM_025208; NM_033135 |
| PLAGL1 | 5325 | NM_001080951; NM_001080952; NM_001080953; NM_001080954; NM_001289042; NM_001289043; NM_001289044; NM_001289047; NM_001289048; NM_001289049; NM_001317157; NM_001317159; NM_006718; NM_001080955; NM_001289037; NM_001289038; NM_001289039; NM_001289040; NM_001080951; NM_001080956; NM_001289041; NM_001289045; NM_001289046; NM_001317156; NM_001317158; NM_001317160; NM_001317161; NM_001317162 |
| PLOD2 | 5352 | NM_000935; NM_182943 |
| PPP1R3C | 5507 | NM_005398 |
| PRIM1 | 5557 | NM_000946 |
| PRKDC | 5591 | NM_001081640; NM_006904 |
| PSIP1 | 11168 | NM_001128217; NM_001317898; NM_001317900; NM_021144; NM_033222 |
| RAD51AP1 | 10635 | NM_001130862; NM_006479 |
| RASIP1 | 54922 | NM_017805; NM_017805 |
| RFC5 | 5985 | NM_001130112; NM_001130113; NM_007370; NM_181578; XM_011538643; XM_011538645 |
| RNASEH2A | 10535 | NM_006397 |
| RPA2 | 6118 | NM_001286076; NM_001297558; NM_002946 |
| RPL39L | 116832 | NM_052969 |
| RSRC1 | 51319 | NM_001271834; NM_001271838; NM_016625 |
| RYR1 | 6261 | NM_000540; NM_001042723 |
| SLC35G2 | 80723 | NM_001097599; NM_001097600; NM_025246; XM_006713773; XM_011513214; XM_017007289; XM_017007290; XM_017007291 |
| SMC2 | 10592 | NM_001265602; NM_001042550; NM_001042551; NM_001265602; NM_006444; XM_006716933; XM_011518148; XM_011518149; XM_011518153; XM_017014206; XM_017014207; XM_017014208 |
| SPARCL1 | 8404 | NM_001128310; NM_001291976; NM_001291977; NM_004684 |
| STMN1 | 3925 | NM_001145454; NM_005563; NM_203399; NM_203401 |
| SYCP2 | 10388 | NM_014258; XM_011528489 |
| SYNGR3 | 9143 | NM_004209 |
| TIMELESS | 8914 | NM_001330295; NM_003920 |
| TMPO | 7112 | NM_001032283; NM_001032284; NM_001307975; NM_003276; NM_001032283 |
| TPX2 | 22974 | NM_012112; XM_011528697; XM_011528699; NM_012112 |
| TRIP13 | 9319 | NM_004237; XM_011514163 |
| TYMS | 7298 | NM_001071; NM_001071 |
| UCP2 | 7351 | NM_003355; NM_003355 |
| UPF3B | 65109 | NM_023010; NM_080632 |
| USP1 | 7398 | NM_001017415; NM_001017416; NM_003368 |
| ZSCAN18 | 65982 | NM_001145542; NM_001145543; NM_001145544; NM_023926; XM_005259174; XM_006723335; XM_011527238; XM_011527239; XM_017027169; XM_017027170; XM_017027171 |
| APOBEC3B | 9582 | NM_001270411; NM_004900 |
| ATAD2 | 29028 | NM_014109; NM_014109 |
| BIRC5 | 332 | NM_001168; NM_001012271; NM_001012270; NM_001168 |
| CCL20 | 6364 | NM_001130046; NM_004591 |
| CCND1 | 595 | NM_053056; NM_053056 |
| CDC45 | 8318 | NM_001178010; NM_001178011; NM_003504; XM_011530417; XM_011530416; NR_161281; XM_017028966; ; XR_002958716; NM_001178010; XM_011530418; XM_017028967; XM_024452277; NM_001369291 |
| CDC7 | 8317 | NM_001134419; NM_001134420; NM_003503; XM_005271241 |
| CDK1 | 983 | NM_001320918; NM_001786; NM_033379; XM_005270303 |
| CDKN2A | 1029 | NM_000077; NM_000077; NM_ 001195132; NM_058197; XM_005251343; XM_011517676; ; NM_058196; NM_058195; XM_011517675; NM_001363763; XR_929159 |
| CDKN2C | 1031 | NM_001262; NM_078626; NM_001262 |
| CDKN3 | 1018 | NM_001258 |

-continued

| Gene | NCBI Gene ID | NCBI Accession Number(s) |
| --- | --- | --- |
| CENPF | 1063 | NM_016343; XM_017000086 |
| CENPN | 55839 | NM_001100624; NM_001100625; NM_001270473; NM_001270474; NM_018455; XM_006721236; XM_017023456 |
| CXCL14 | 9547 | NM_004887 |
| DCN | 1634 | NM_133505; NM_001920; NM_133503; NM_133504; NM_133505; NM_133506; NM_133507; |
| DHFR | 1719 | NM_000791; NM_001290357; NM_000791; NM_001290354 |
| DKK3 | 27122 | NM_001330220; XM_017017554; XM_017017555; NM_001018057; NM_001330220; NM_013253; NM_015881; NM_006718178 |
| DLGAP5 | 9787 | NM_001146015; NM_014750; XM_017021840 |
| EPCAM | 4072 | NM_002354 |
| FANCI | 55215 | NM_001113378; NM_018193; XM_011521756; NM_001113378; NM_001376910; NM_001376911; XM_011521764 |
| FEN1 | 2237 | NM_004111; NM_004111 |
| GMNN | 51053 | NM_001251989; NM_001251990; NM_001251991; NM_015895; XM_005249159; NM_001251989 |
| GPX3 | 2878 | NM_001329790; NM_002084 |
| ID4 | 3400 | NM_001546 |
| IGLC1 | 3537 | NG_000002.1 |
| IL18 | 3606 | NM_001243211; XM_011542805; NM_001243211; NM_001562; NM_001386420 |
| IL1R2 | 7850 | NM_001261419; NM_004633; XM_006712734; XM_011511804 |
| KIF18B | 146909 | NM_001264573; NM_001265577; NM_001264573 |
| KIF20A | 10112 | NM_005733 |
| KIF4A | 24137 | NM_012310 |
| KLK13 | 26085 | NM_001348177; NM_001348178; NM_001348177; NM_015596 |
| KLK7 | 5650 | NM_005046; NM_139277; NM_001207053; NM_001243126; NM_005046 |
| KLK8 | 11202 | NM_001281431; NM_001281431; NM_007196; NM_144505; NM_144506; NM_144507 |
| KNTC1 | 9735 | NM_014708; XM_006719706 |
| KRT19 | 3880 | NM_002276 |
| LAMP3 | 27074 | NM_014398 |
| LMNB1 | 4001 | NM_005573 |
| MCM2 | 4171 | NM_004526 |
| MCM4 | 4173 | NM_005914; NM_182746 |
| MCM5 | 4174 | NM_006739; NM_006739 |
| ME1 | 4199 | NM_002395; XM_011535836 |
| MELK | 9833 | NM_001256685; NM_001256687; NM_001256688; NM_001256689; NM_001256690; NM_001256692; NM_001256693; NM_014791; XM_011518076; XM_011518077; XM_011518078; XM_011518079; XM_011518081; XM_011518082; XM_011518083; XM_011518084 |
| MKI67 | 4288 | NM_001145966; NM_002417 |
| MLF1 | 4291 | NM_022443; NM_001130156; NM_001130157; NM_001195432; NM_001195433; NM_001195434; NM_022443; NM_001369782; NM_001378848; NM_001378853; ; NM_001369784; NM_001369785; NM_001369781; NM_001378846; NM_001378855; NM_001378845; NM_001378847; NM_001378850; NM_001378852; NM_001369783; NM_001378851 |
| MMP12 | 4321 | NM_002426 |
| MTHFD2 | 10797 | NM_006636; XM_006711924 |
| NDN | 4692 | NM_002487; NM_002487 |
| NEFH | 4744 | NM_021076 |
| NEK2 | 4751 | NM_001204182; NM_001204182; NM_001204183; NM_002497; XM_005273147 |
| NUP155 | 9631 | NM_153485; NM_001278312; NM_004298; NM_153485 |
| NUP210 | 23225 | NM_024923 |
| NUSAP1 | 51203 | NM_001243142; NM_001243143; NM_001243144; NM_001301136; NM_016359; NM_018454; XM_005254430 |
| PDGFD | 80310 | NM_025208; NM_033135 |
| PLAGL1 | 5325 | NM_001080951; NM_001080952; NM_001080953; NM_001080954; NM_001289042; NM_001289043; NM_001289044; NM_001289047; NM_001289048; NM_001289049; NM_001317157; NM_001317159; NM_006718; NM_001080955; NM_001289037; NM_001289038; NM_001289039; NM_001289040; NM_001080951; NM_001080956; NM_001289041; NM_001289045; NM_001289046; NM_001317156; NM_001317158; NM_001317160; NM_001317161; NM_001317162 |
| PLOD2 | 5352 | NM_000935; NM_182943. |

7. The system of claim 1, wherein the at least one characteristic includes a subtype of peripheral T-cell lymphoma (PTCL) for the cells in the biological sample, and wherein the set of genes includes at least 5 genes selected from the group of genes listed in Table 10, wherein Table 10 is:

| Gene | NCBI Gene ID | NCBI Accession Number(s) |
|---|---|---|
| EFNB2 | 1948 | NM_004093 |
| ROBO1 | 6091 | NM_133631; NM_001145845; NM_002941; XM_006713277; XM_017006983 |
| S1PR3 | 1903 | NM_005226 |
| ANK2 | 287 | NM_001127493; NM_001148; NM_020977 |
| LPAR1 | 1902 | NM_001401; NM_057159; NM_001351414; NM_001351415; NM_001387481; NM_001387505; XM_005251782; NM_001351401; NM_001387470; NM_001387480; NM_001387486; NM_001387498; NM_001387502; NM_001387503; NM_001387509; NM_001387511; NM_001387521; NM_001351398; NM_001351399; NM_001351400; NM_001351419; NM_001387478; NM_001387493; NM_001387497; NM_001387506; NM_001387507; NM_001387493; NM_001387520; NM_001351416; NM_001387476; NM_001387491; NM_001387471; NM_001387472; NM_001387477; NM_001387485; NM_001387492; NM_001387494; NM_001387510; NM_001387517; NM_001351397; NM_001351405; NM_001351406; NM_001351407; NM_001351413; NM_001351418; NM_001387475; NM_001387483; NM_001387484; NM_001387488; NM_001387490; NM_001387496; NM_001387516; NM_001387519; NM_001351404; NM_001351408; NM_001351410; NM_001351420; NM_001387473; NM_001387474; NM_001387487; NM_001387489; NM_001387495; NM_001387514; NM_001387518; NM_001351402; NM_001351403; NM_001351409; NM_001351411; NM_001351412; NM_001351417; NM_001387479; NM_001387482; NM_001387501; NM_001387504; NM_001387512; NM_001387513; NM_001387515 |
| SNAP91 | 9892 | XM_011536269; XM_017011557; XM_017011558; XM_017011559; XM_017011560; XM_005248770; XM_017011564; XM_017011571; NM_001376687; NM_001376688; NM_001376698; NM_001376700; NM_001376709; NM_001376715; NM_001376716; NM_001376723; NM_001376728; NM_001376731; NM_001376734; XM_011536266; XM_017011575; XM_017011586; NM_001376676; NM_001376682; NM_001376685; NM_001376702; NM_001376711; NM_001376736; NM_001376738; NR_164844; XM_006715615; XM_011536265; XM_017011570; XM_017011582; XM_024446600; NM_001376691; NM_001376699; NM_001376720; NM_001376735; NM_001376740; NM_014841; NR_164843; NR_164845; XM_011536275; XM_017011562; XM_017011565; XM_017011569; XM_017011580; NR_026669; NM_001256717; NM_001376677; NM_001376680; NM_001376683; NM_001376708; NM_001376718; NM_001376726; NM_001376737; XM_011536273; XM_011536276; XM_017011567; XM_017011583; XM_017011584; NM_001242794; NM_001376679; NM_001376694; NM_001376695; NM_001376697; NM_001376710; NM_001376714; NM_001376717; NM_001376742; XM_017011572; XM_017011577; XM_017011581; XM_017011590; NM_001256718; NM_001363677; NM_001376678; NM_001376686; NM_001376690; NM_001376693 |
| SOX8 | 30812 | NM_014587 |
| RAMP3 | 10268 | NM_005856 |
| TUBB2B | 347733 | NM_178012 |
| ARHGEF10 | 9639 | NM_001308152; NM_001308153; NM_014629; XM_017014003 |
| NOTCH1 | 4851 | NM_017617 |
| ZBTB17 | 7709 | NM_001242884; NM_001287603; NM_003443; XM_011542088 |
| CCNE1 | 898 | NM_001238; NM_001322262; NM_001322259; NM_001322261 |
| FGF18 | 8817 | NM_003862 |
| MYCN | 4613 | NM_001293231; NM_001293228; NM_001293233; NM_005378 |
| PTHLH | 5744 | NM_198965; NM_198966; XM_011520774; NM_002820; XM_017019675; NM_198964 |
| SMARCA2 | 6595 | NM_001289400; NM_001289399; NM_001289398; NM_001289397; NM_001289396; NM_003070; NM_139045 |
| WNK1 | 65125 | NM_014823; NM_018979; NM_001184985; NM_213655; XM_017019837; XM_017019838 |
| NKX2-1 | 7080 | NM_001079668; NM_003317 |
| CYP26A1 | 1592 | NM_000783; NM_057157 |
| HPSE | 10855 | NM_001098540; NM_001166498; NM_001199830; NM_006665 |
| CTLA4 | 1493 | NM_001037631; NM_005214 |
| PELI1 | 57162 | NM_020651; XM_011532994; XM_017004520 |
| PRKCB | 5579 | NM_002738; NM_212535 |
| SPAST | 6683 | NM_014946; NM_199436 |
| ALS2 | 57679 | NM_001135745; NM_020919; XM_006712654 |
| KIF3B | 9371 | NM_004798 |
| ZFYVE27 | 118813 | XM_005269509; XM_011539254; XR_945597; NM_001002262; NM_001174120; NM_001385878; NM_001385889; NM_001385895; NM_001385901; NM_001385918; NR_169800; XM_005269508; XR_945594; NM_001385877; NM_001385902; NM_001385903; NM_001385904; NR_169794; NR_169795; NR_169797; NR_169803; NR_169805; NR_169809; XM_011539253; XM_017015644; XR_002956957; NM_001174121; NM_001174122; NM_001385879; NM_001385881; NM_001385883; NM_001385900; XM_017015645; NM_001385875; NM_001385886; NM_001385896; NR_169796; XM_011539252; NM_001385876; NM_001385880; NM_001385887; |

| Gene | NCBI Gene ID | NCBI Accession Number(s) |
|---|---|---|
| | | NM_001385894; NM_001385898; NM_001385915; NM_001385919; XM_017015646; NM_001385882; NM_001385884; NM_001385890; NM_001385897; NM_001385899; NR_169804; NR_169810; NM_001002261; NM_001385871; NM_001385892; NM_001385905; NM_144588; NR_169802; NR_169806; NR_169808; NR_169811; XR_002956956; NM_001174119; NM_001385885; NM_001385888; NM_001385891; NM_001385893; NM_001385906; NM_001385908; NM_001385911; NM_001385916; NR_169798; NR_169799; NR_169801 |
| FGF18 | 8817 | NM_003862 |
| FNTB | 2342 | NM_001202558; NM_002028 |
| REL | 5966 | NM_001291746; NM_002908 |
| DMRT1 | 1761 | NM_021951 |
| SLC19A2 | 10560 | NM_001319667; NM_006996 |
| STK3 | 6788 | NM_001256313; NM_001256312; NM_006281 |
| PERP | 64065 | NM_022121 |
| TNFRSF8 | 943 | NM_001243; NM_001281430 |
| TMOD1 | 7111 | NM_001166116; NM_003275 |
| BATF3 | 55509 | NM_018664 |
| CDC14B | 8555 | NM_001077181; NM_003671; NM_033331; XM_011519153; XM_017015240; XM_017015247; XR_001746407; XR_001746409; NM_001351567; XM_017015248; XM_017015249; XR_929865; XM_011519147; XM_017015242; XM_017015244; XM_017015245; XR_929864; NM_001351568; XM_011519149; XM_011519152; XR_001746408; NM_001351570; NM_033332; XM_011519148; XM_011519151; XR_929868; NR_147239; XM_011519156; XR_002956814; XM_011519159; XM_017015241; XR_001746406; NM_001351569 |
| WDFEY3 | N/A | N/A |
| AGT | 183 | NM_000029 |
| ALK | 238 | NM_004304 |
| ANXA3 | 306 | NM_005139 |
| BTBD11 | 121551 | NM_001017523; NM_001018072; NM_001347943 |
| CCNA1 | 8900 | NM_001111045; NM_001111046; NM_001111047; NM_003914; XM_011535294; XM_011535295; XM_011535296 |
| DNER | 92737 | NM_139072 |
| GAS1 | 2619 | NM_002048 |
| HS6ST2 | 90161 | NM_001077188; NM_147175; XM_011531407; XM_017029945; XM_011531408; XM_017029946; XM_005262491; XM_011531406 |
| IL1RAP | 3556 | NM_001167928; NM_001167929; NM_001167930; NM_001167931; NM_002182; NM_134470 |
| PCOLCE2 | 26577 | NM_013363 |
| PDE4DIP | 9659 | XM_011510175; NM_001195261; NM_001002810; NM_001002811; NM_001002812; NM_001195260; NM_001198832; NM_001198834; NM_014644; NM_022359 |
| SLC16A3 | 9123 | NM_001042422; NM_001042423; NM_001206950; NM_001206951; NM_001206952; NM_004207; XM_024451023 |
| TIAM2 | 26230 | NM_001010927; NM_012454 |
| TUBB6 | 84617 | NM_001303527; NM_001303525; NM_001303524; NM_001303526; NM_001303528; NM_001303529; NM_001303530; NM_032525 |
| WNT7B | 7477 | XM_011530366; NM_058238 |
| SMOX | 54498 | NM_001270691; NM_175839; NM_175840; NM_175841; NM_175842; XM_011529261 |
| TMEM158 | 25907 | NM_015444 |
| NLRP7 | 199713 | NM_001127255; NM_139176; NM_206828; XM_006723075; XM_006723076; XM_011526599 |
| ADRB2 | 154 | NM_000024 |
| GALNT2 | 2590 | NM_004481; NM_001291866 |
| HRASLS | 57110 | NM_020386; NM_001366112; XM_011513034; XM_011513035 |
| CD244 | 51744 | NM_001166663; NM_001166664; NM_016382; XM_011509622 |
| FASLG | 356 | NM_000639; NM_001302746 |
| KIR2DL4 | 3805 | NM_001080772; NM_001080770; NM_002255 |
| LOC100287534 | 100287534 | HF584483.1 |
| KLRD1 | 3824 | NM_007334; XM_006719067; XR_001748697; XM_017019289; NM_001351062; NR_147038; XM_017019287; NM_001351063; XM_011520650; XM_017019286; XM_024448974; XR_001748696; NR_147040; XM_017019285; NM_001114396; NM_001351060; NR_147039; XM_011520651; XM_017019288; NM_002262 |
| SH2D1B | 117157 | NM_053282 |
| KLRC2 | 3822 | NM_002260 |
| NCAM1 | 4684 | NM_001242607; NM_000615; NM_001076682; NM_001242608; NM_181351 |
| CXCR5 | 643 | NM_001716; NM_032966 |
| IL6 | 3569 | NM_001318095; NM_000600; XM_011515390 |
| ICOS | 29851 | NM_012092 |
| CD40LG | 959 | NM_000074 |
| CD84 | 8832 | NM_001184879; NM_001184881; NM_001184882; NM_001330742; NM_003874 |

| Gene | NCBI Gene ID | NCBI Accession Number(s) |
|---|---|---|
| IL21 | 59067 | NM_021803; NM_001207006 |
| BCL6 | 604 | NM_001134738; NM_001130845; NM_001706; XM_005247694; XM_011513062 |
| MAF | 4094 | XM_017023233; XM_017023234; XM_017023235; XM_001031804; NM_005360 |
| SH2D1A | 4068 | NM_001114937; NM_002351 |
| IL4 | 3565 | NM_000589; NM_172348 |
| PTPN1 | 5770 | NM_002827; NM_001278618 |
| PIM1 | 5292 | NM_002648; NM_001243186 |
| ENTPD1 | 953 | NM_001098175; NM_001164178; NM_001164181; NM_001164182; NM_001164183; NM_001312654; NM_001320916; NM_001776; XM_011540371; XM_011540377; XM_017016959 |
| IRF4 | 3662 | NM_001195286; NM_002460 |
| CCND2 | 894 | NM_001759 |
| IL16 | 3603 | NM_001172128; NM_004513; NM_172217; NR_148035; NM_001352685; NM_001352686; NM_001352684 |
| ETV6 | 2120 | NM_001987 |
| BLNK | 29760 | NM_001258441; NM_001258442; NM_001114094; NM_001258440; NM_013314 |
| SH3BP5 | 9467 | NM_001018009; XM_017007522; XM_017007523; XM_017007524; XM_017007525; NM_004844 |
| FUT8 | 2530 | NM_004480; NM_178155; NM_178156 |
| CCR4 | 1233 | NM_005508; XM_017005687 |
| GATA3 | 2625 | NM_001002295; NM_002051; XM_005252442; XM_005252443 |
| IL5 | 3567 | NM_000879; XM_011543373; XM_011543374 |
| IL10 | 3586 | NM_000572 |
| IL13 | 3596 | NM_002188 |
| MMEITPKB | N/A | N/A |
| MYBL1 | 4603 | NM_001080416; NM_001144755; NM_001294282 |
| LRMP | 16970 | NM_001204126; NM_001204127; NM_006152; NM_001366543; NM_001366544; NM_001366546; NM_001366549; NM_001366545; NR_159367; NR_159368; NM_001366541; NR_159366; NM_001366540; NM_001366542; NM_001366547; NR_159369; NM_001366548 |
| KIAA0870 | 22898 | NM_014957 |
| LMO2 | 4005 | NM_001142315; NM_001142316; NM_005574; XM_005252921; XM_017017727; XM_017017728; XM_017017729; XM_017017730; XM_017017731; XM_017017732; XM_017017733 |
| CR1 | 1378 | NM_000651; NM_000573 |
| LTBR | 4055 | NM_001270987; NM_002342 |
| PDPN | 10630 | NM_001006624; NM_001006625; NM_006474; NM_198389; XM_006710295 |
| TNFRSF1A | 7132 | NM_001346091; NM_001065; NM_001346092 |
| FCER2 | 2208 | NM_001207019; NM_001220500; NM_002002; XM_005272462 |
| ICAM1 | 3383 | NM_000201 |
| FCGR2B | 2213 | NM_001002273; NM_001002274; NM_001002275; NM_001190828; NM_004001; XM_024454043; NM_001386004; NR_169827; NM_001386001; NM_001386002; NM_001386006; NM_001386003; XM_017000670; NM_001386000; NM_001386005; XM_024454047 |
| IKZF2 | 22807 | NM_001079526; NM_016260; XM_005246384; XM_005246385; XM_011510818; NM_001371277; XM_011510809; NM_001387220; XM_005246386; XM_011510810; XM_011510803; XM_011510804; XM_011510812; XM_011510815; XM_011510817; XM_017003592; NM_001371275; XM_011510808; NM_001371274; XM_011510802; XM_011510807; XM_011510819; NM_001371276; XM_011510805; XM_011510811; XM_017003591; XM_011510816 |
| CCR8 | 1237 | NM_005201 |
| TNFRSF18 | 8784 | XM_017002722; NM_004195; NM_148901; NM_148902 |
| IKZF4 | 64375 | NM_022465; XM_005269089; XM_017019813; XM_017019815; XM_024449128; XM_024449129; NM_001351090; XM_017019807; XM_017019812; XM_024449131; NM_001351089; XM_011538664; XM_011538669; XM_017019814; XM_017019808; XM_024449130; NM_001351092; XM_017019806; XM_017019809; XM_017019810; XM_005269086; XM_017019811; XM_017019816; NM_001351091 |
| FOXP3 | 50943 | XM_006724533; NM_001114377; NM_014009 |
| IL2 | 3558 | NM_000586 |
| TBX21 | 30009 | NM_013351 |
| IFNG | 3458 | NM_000619 |
| GZMH | 2999 | NM_001270781; NM_033423 |
| GNLY | 10578 | NM_001302758; NM_006433; NM_012483 |
| EOMES | 8320 | NM_001278182; NM_001278183; NM_005442 |
| NCR1 | 9437 | NM_004829; NM_001145458; NM_001145457; NM_001242356; NM_001242357 |
| GZMB | 3002 | NM_001346011; NM_004131 |
| NKG7 | 4818 | NM_005601 |
| FGFBP2 | 83888 | NM_031950 |
| KLRF1 | 51348 | NM_001291822; NM_001291823; NM_016523 |
| CD160 | 11126 | NM_007053; XM_005272929; XM_011509104 |

-continued

| Gene | NCBI Gene ID | NCBI Accession Number(s) |
| --- | --- | --- |
| KLRK1 | 22914 | NM_001199805; NM_007360 |
| CD226 | 10666 | NM_001303619; XM_005266643; XM_017025525; NM_006566; XM_006722374; XM_017025526; NM_001303618; XM_005266642; XM_017025527 |
| NCR3 | 259197 | NM_001145466; NM_001145467; NM_147130; XM_006715049; XM_011514459 |
| TNFRSF8 | 943 | NM_001243; NM_001281430 |
| BATF3 | 55509 | NM_018664 |
| TMOD1 | 7111 | NM_001166116; NM_003275 |
| TMEM158 | 25907 | NM_015444 |
| MSC | 9242 | NM_005098 |
| POPDC3 | 64208 | NM_022361; XM_011536067; XM_017011194; XM_017011195. |

8. The system of claim 7, wherein the subtype of PTCL is selected from the group consisting of: anaplastic large cell lymphoma (ALCL), angioimmunoblastic T-cell lymphoma (AITL), natural killer/T-cell lymphoma (NKTCL), and adult T-cell leukemia/lymphoma (ATLL).

9. The system of claim 1, wherein the method further comprises: presenting, to a user, an indication of the at least one characteristic via a graphical user interface (GUI).

10. The system of claim 1, wherein the gene ranking does not include the first expression levels.

11. The system of claim 1, wherein the values identifying relative ranks of the at least some genes in the gene ranking include ordinal numbers.

12. The system of claim 1, wherein the values identifying relative ranks of the at least some genes in the gene ranking include whole numbers.

13. The system of claim 1, wherein the values identifying relative ranks of the at least some genes in the gene ranking include a list of genes sorted according to their relative ranks.

14. The system of claim 1, wherein the method further comprises: training a statistical model to obtain the trained statistical model, the training comprising:
   selecting the at least some genes in the set of genes; and
   after the selecting, estimating the plurality of parameters using the training data.

15. A method, comprising:
   using at least one computer hardware processor to perform:
      accessing a trained statistical model comprising parameters estimated using training data, the training data indicating a plurality of gene rankings of at least some genes in a set of genes, the parameters being estimated after the at least some genes in the set of genes were selected;
      obtaining expression data for a biological sample of a subject having, suspected of having or at risk of having cancer, the expression data previously obtained at least in part by sequencing the biological sample and comprising first expression levels for the set of genes;
      ranking the at least some genes in the set of genes based on their first expression levels in the expression data to obtain a gene ranking, the gene ranking including values identifying relative ranks of the at least some genes in the gene ranking, wherein the values are different from the first expression levels; and
      determining at least one characteristic of the biological sample by providing the gene ranking as an input to the trained statistical model and processing the gene ranking with the trained statistical model to obtain an output indicating the at least one characteristic of the biological sample,
      the processing of the gene ranking with the trained statistical model comprises using the parameters and the gene ranking provided as the input to obtain the output indicating the at least one characteristic of the biological sample; and
      the at least one characteristic of the biological sample is a physiological characteristic of cells in the biological sample or a physiological characteristic of a tissue from which the cells in the biological sample originate.

16. The method of claim 15, wherein the at least one characteristic includes cancer grade for the cells in the biological sample.

17. The method of claim 16, wherein the subject has, is suspected of having, or is at risk of having breast cancer, and wherein the set of genes comprises at least 5 genes selected from the group of genes listed in Table 1, wherein Table 1 is:

| Gene | NCBI Gene ID | NCBI Accession Number(s) |
| --- | --- | --- |
| UBE2C | 11065 | NM_001281741; NM_001281742; NM_007019; NM_181799; NM_181800; NM_181801 |
| MYBL2 | 4605 | NM_001278610; NM_002466 |
| PRAME | 23532 | NM_001291715; NM_001291716; NM_006115; NM_206953; NM_206954; NM_206955; NM_206956; NM_001291717; NM_001291719; NM_001318126; NM_001318127 |
| LMNB1 | 4001 | NM_005573 |
| CXCL9 | 4283 | NM_002416 |
| KPNA2 | 3838 | NM_001320611; NM_002266 |
| TPX2 | 22974 | NM_012112; XM_011528697; XM_011528699 |
| PLCH1 | 23007 | NM_001130960; NM_001130961; NM_014996; XM_011512561; XM_017005923; XM_017005926; NM_001349251; XM_011512560; XM_011512562; XM_011512565; XM_017005925; NM_001349250; NM_001349252; XM_005247238; XM_005247239; XM_011512567; XM_017005927; XM_011512566 |

-continued

| Gene | NCBI Gene ID | NCBI Accession Number(s) |
| --- | --- | --- |
| CCL18 | 6362 | NM_002988 |
| CDK1 | 983 | NM_001320918; NM_001786; NM_033379; XM_005270303 |
| MELK | 9833 | NM_001256685; NM_001256687; NM_001256688; NM_001256689; NM_001256690; NM_001256692; NM_001256693; NM_014791; XM_011518076; XM_011518077; XM_011518078; XM_011518079; XM_011518081; XM_011518082; XM_011518083; XM_011518084 |
| CCNB2 | 9133 | NM_004701 |
| RRM2 | 6241 | NM_001034; NM_001165931 |
| CCNB1 | 891 | NM_031966 |
| NUSAP1 | 51203 | NM_001243142; NM_001243143; NM_001243144; NM_001301136; NM_016359; NM_018454; XM_005254430 |
| SLC7A5 | 8140 | NM_003486 |
| TYMS | 7298 | NM_001071 |
| GZMK | 3003 | NM_002104 |
| SQLE | 6713 | NM_003129 |
| C1orf106 | 55765 | NM_001142569; NM_018265; XM_011509754; XM_011509755 |
| CDC25B | 994 | NM_001287519; NM_001287520; NM_004358; NM_021872; NM_021873; NM_001287516; NM_001287522; NM_001287518; NM_001287524 |
| ATAD2 | 29028 | NM_014109 |
| QPRT | 23475 | NM_001318249; NM_001318250; NM_014298 |
| CCNA2 | 890 | NM_001237 |
| NEK2 | 4751 | NM_001204182; NM_001204183; NM_002497; XM_005273147 |
| IDO1 | 3620 | NM_002164 |
| NDC80 | 10403 | NM_006101 |
| ZWINT | 11130 | NM_001005413; NM_007057; NM_032997 |
| ABCA12 | 26154 | NM_015657; NM_173076 |
| TOP2A | 7153 | NM_001067 |
| TDO2 | 6999 | NM_005651 |
| S100A8 | 6279 | NM_001319197; NM_001319198; NM_001319201; NM_002964 |
| LAMP3 | 27074 | NM_014398 |
| MMP1 | 4312 | NM_002421 |
| GZMB | 3002 | NM_001346011; NM_004131 |
| BIRC5 | 332 | NM_001168; NM_001012271; NM_001012270 |
| TRIP13 | 9319 | NM_004237; XM_011514163 |
| RACGAP1 | 29127 | NM_001126103; NM_001126104; NM_001319999; NM_001320000; NM_001320001; NM_001320002; NM_001320003; NM_001320004; NM_013277; XM_006719359; XM_011538238; XM_017019220; NM_001320005; NM_001320006; NM_001320007 |
| ASPM | 259266 | NM_001206846; NM_018136 |
| ESRP1 | 54845 | NM_001122827; NM_001034915; NM_001122825; NM_001122826; NM_017697; XM_005250991 |
| MAD2L1 | 4085 | NM_002358 |
| CENPF | 1063 | NM_016343; XM_017000086 |
| CDC20 | 991 | NM_001255 |
| MCM4 | 4173 | NM_005914; NM_182746 |
| MKI67 | 4288 | NM_001145966; NM_002417 |
| PBK | 55872 | NM_001278945; NM_018492; NM_001363040 |
| CKS2 | 1164 | NM_001827 |
| KIF2C | 11004 | NM_001297655; NM_001297656; NM_001297657; NM_006845 |
| MRPL13 | 28998 | NM_014078 |
| TTK | 7272 | NM_001166691; NM_003318; XM_011536099; XM_011536100 |
| BUB1 | 699 | NM_001278617; NM_004336 |
| TK1 | 7083 | NM_001346663; NM_003258 |
| FOXM1 | 2305 | NM_001243088; NM_202003; NM_202002; NM_001243089; NM_021953 |
| CEP55 | 55165 | NM_001127182; NM_018131 |
| EZH2 | 2146 | NM_004456; XM_011515884; NM_001203247; NM_001203248; NM_001203249; NM_152998 |
| ECT2 | 1894 | NM_001258315; NM_001258316; NM_018098; XM_011512514 |
| PRC1 | 9055 | NM_003981; NM_001267580 |
| CENPU | 79682 | NM_024629 |
| CCNE2 | 9134 | NM_057749; XM_011517366; NM_004702; XM_017013959; XM_017013958; NM_057735 |
| AURKA | 6790 | NM_001323303; NM_001323304; NM_001323305; NM_003600; NM_198433; NM_198434; NM_198435; NM_198436; NM_198437; XM_017028035 |
| HMGB3 | 3149 | NM_001301228; NM_001301229; NM_001301231; NM_005342 |
| APOBEC3B | 9582 | NM_001270411; NM_004900 |
| LAGE3 | 8270 | NM_006014 |
| CDKN3 | 1033 | NM_001258 |
| DTL | 51514 | NM_001286229; NM_016448 |
| ATP6V1C1 | 528 | NM_001695 |
| KIAA0101 | 9768 | NM_001029989; NM_014736 |
| CD2 | 914 | NM_001328609; NM_001767 |
| KIF11 | 3832 | NM_004523 |

-continued

| Gene | NCBI Gene ID | NCBI Accession Number(s) |
|---|---|---|
| KIF20A | 10112 | NM_005733 |
| CDCA8 | 55143 | NM_001256875; NM_018101 |
| NCAPG | 64151 | NM_022346 |
| CENPN | 55839 | NM_001100624; NM_001100625; NM_001270473; NM_001270474; NM_018455; XM_006721236; XM_017023456 |
| MTFR1 | 9650 | NM_014637; NM_001145838 |
| MCM2 | 4171 | NM_004526 |
| DSCC1 | 79075 | NM_024094 |
| WDR19 | 57728 | NM_001317924; NM_025132 |
| SEMA3G | 56920 | NM_020163 |
| KCND3 | 3752 | NM_172198; XM_011541425; XM_006710632; XM_011541428; NM_001378969; NM_004980; NM_001378970; XM_006710629; XM_006710631; XM_017001245; XM_011541426; XM_011541427; XM_017001244 |
| SETBP1 | 26040 | NM_001130110; NM_015559 |
| KIF13B | 23303 | NM_015254 |
| NR4A2 | 4929 | NM_006186; XM_017004219; XM_017004220; XR_001738751; XR_001738752; NM_173173; NM_173171; XM_011511246; NM_173172; XR_427087; XM_005246621; XM_006712553 |
| NAV3 | 89795 | XM_017020172; NM_001024383; NM_014903; XM_011538944 |
| PDZRN3 | 23024 | NM_001303140; NM_001303142; NM_001303139; NM_001303141; NM_015009 |
| MAGI2 | 9863 | NM_001301128; NM_012301 |
| CACNA1D | 776 | XM_005265448; NM_000720; NM_001128839; NM_001128840 |
| STC2 | 8614 | NM_003714 |
| CHAD | 1101 | NM_001267 |
| PDGFD | 80310 | NM_025208; NM_033135 |
| ARMCX2 | 9823 | NM_001282231; NM_014782; NM_177949; XM_005278109; XM_005278110; XM_005278111; XM_005278113; XM_005278114; XM_005278115; XM_005278116; XM_005278117; XM_011531071; XM_011531072; XM_017029987; XM_017029988; XM_017029989; XM_017029990; XM_017029991; XM_017029992; XM_017029993; XM_017029994; XM_017029995; XM_017029996; XM_017029997 |
| FRY | 10129 | NM_023037 |
| AGTR1 | 185 | NM_032049; NM_004835; NM_031850; NM_000685; NM_009585 |
| MARCH8 | 220972 | NM_001002266; NM_145021; XM_011539495; XM_006717704; NM_001002265; XR_246519; NM_001282866; XM_005271804; XM_011539492 |
| ANG | 283 | NM_001097577; NM_001145 |
| ABAT | 18 | NM_000663; NM_001127448; NM_020686; NM_001386602; NM_001386609; NM_001386611; NM_001386612; NM_001386613; NM_001386605; NM_001386610; NM_001386616; NM_001386601; NM_001386603; NM_001386604; NM_001386606; NM_001386615; NM_001386600; NM_001386607; NM_001386614; NM_001386608 |
| THBD | 7056 | NM_000361 |
| RAI2 | 10742 | NM_001172739; NM_001172743; NM_021785; NM_001172732; XM_006724459; XM_006724460; XM_011545439; XM_011545440; XM_011545441 |
| HSPA2 | 3306 | NM_021979 |
| ERBB4 | 2066 | NM_001042599; NM_005235; XM_005246376; XM_005246377 |
| ECHDC2 | 55268 | NM_001198962; NM_001198961; NM_018281; XM_011541722; XM_011541726; XM_017001638; XM_024448158; XM_011541719; XM_011541723; XM_024448164; XR_002957011; NM_001319958; XR_002957012; XM_011541709; XM_024448153; XM_024448157; XR_002957014; XM_011541713; XM_024448163; XM_011541715; XM_017001640; XM_024448160; XM_011541720; XM_011541727; XM_024448159; XM_024448161; XR_002957013; XM_017001639; XM_024448152 |
| FST | 10468 | NM_013409; NM_006350 |
| EPHX2 | 2053 | NM_001256482; NM_001256483; NM_001256484; NM_001979 |
| FOSB | 2354 | NM_006732; XM_005258691; NM_001114171 |
| STARD13 | 90627 | NM_178006; NM_052851; NM_001243466; NM_001243474; NM_001243476; NM_178007 |
| ID4 | 3400 | NM_001546 |
| FAM129A | 116496 | NM_052966 |
| FCGBP | 8857 | NM_003890 |
| LAMA2 | 3908 | NM_000426; NM_001079823 |
| FGFR2 | 2263 | NM_001144919; NM_023029; NM_000141; NM_001144913; NM_001144914; NM_001144915; NM_001144916; NM_001144917; NM_001144918; NM_001320654; NM_001320658; NM_022970 |
| PTGER3 | 5733 | NM_198718; NM_001126044; NM_198714; NM_198715; NM_198716; NM_198717; NM_198719 |
| NME5 | 8382 | NM_003551 |
| LRRC17 | 10234 | NM_001031692; NM_005824; XM_005250108 |
| OSBPL1A | 114876 | NM_080597; NM_018030; XM_017025533; XR_002958162; XM_006722380; XM_017025530; NM_133268; XM_017025532; XR_001753139; NM_001242508; XM_006722382; XM_017025531 |

| Gene | NCBI Gene ID | NCBI Accession Number(s) |
| --- | --- | --- |
| ADRA2A | 150 | NM_000681 |
| LRP2 | 4036 | NM_004525 |
| C1orf115 | 79762 | NM_024709 |
| COL4A5 | 1287 | NM_000495; NM_033380 |
| DIXDC1 | 85458 | NM_001037954; NM_001278542; NM_033425 |
| KIAA1324 | 57535 | NM_001267048; NM_020775; XM_011541825 |
| HPN | 3249 | NM_002151; NM_182983; XM_017026732; NM_001384133; XM_017026731; NM_001375441 |
| KLF4 | 9314 | NM_001314052; NM_004235 |
| SCUBE2 | 57758 | NM_001170690; NM_001330199; NM_020974 |
| FMO5 | 2330 | NM_001461; XM_005272946; XM_005272947; XM_005272948; XM_011509350; NM_001144829; NM_001144830; XM_006711245 |
| SORBS2 | 8470 | NM_001145670; NM_001145671; NM_001145672; NM_001145673; NM_001145674; NM_001270771; NM_003603; NM_021069; XM_005263312; XM_006714390; XM_017008771 |
| CARD10 | 29775 | NM_014550 |
| CITED2 | 10370 | NM_001168389; NM_001168388; NM_006079 |
| MUC1 | 4582 | NM_001204292; NM_001204286; NM_001204291; NM_001204285; NM_001204287; NM_001204288; NM_001204289; NM_001204290; NM_001204295; NM_001204297; NM_001204296; NM_001018016; NM_001018017; NM_001044390; NM_001044391; NM_001044392; NM_001044393; NM_001204293; NM_001204294; NM_002456 |
| BCL2 | 596 | NM_000633; NM_000657 |
| RGS5 | 8490 | NM_003617; NM_001195303; NM_001254748; NM_001254749 |
| CYBRD1 | 79901 | NM_001127383; NM_001256909; NM_024843 |
| OMD | 4958 | NM_005014 |
| IGFBP4 | 3487 | NM_001552 |
| LAMB2 | 3913 | NM_002292; XM_005265127 |
| DUSP4 | 1846 | NM_001394; NM_057158; XM_011544428 |
| PDLIM5 | 10611 | NM_006457; NM_001011515; NM_001011516; NM_001256429 |
| IRS2 | 8660 | NM_003749 |
| CX3CR1 | 1524 | NM_001171171; NM_001171172; NM_001171174; NM_001337. |

18. The method of claim 16, wherein the subject has, is suspected of having, or is at risk of having kidney cancer, and wherein the set of genes comprises at least 5 genes selected from the group of genes listed in Table 2, wherein Table 2 is:

| Gene | NCBI Gene ID | NCBI Accession Number(s) |
| --- | --- | --- |
| PLTP | 5360 | NM_001242920; NM_001242921; NM_006227; NM_182676 |
| C1S | 716 | NM_001346850; NM_001734; NM_201442; XM_005253760 |
| LY96 | 23643 | NM_001195797; NM_015364 |
| TSKU | 25987 | NM_001258210; NM_001318477; NM_001318478; NM_001318479; NM_015516 |
| TPST2 | 8459 | NM_001008566; NM_003595 |
| SERPINF1 | 5176 | NM_001329903; NM_002615 |
| SRPX2 | 27286 | NM_014467 |
| SAA1 | 6288 | NM_000331; NM_001178006; NM_199161 |
| CTHRC1 | 115908 | NM_001256099; NM_138455 |
| GFPT2 | 9945 | NM_005110 |
| CKAP4 | 10970 | NM_006825 |
| SERPINA3 | 12 | NM_001085 |
| CFH | 3075 | NM_001014975; NM_000186 |
| PLAU | 5328 | NM_002658; NM_001145031; NM_001319191 |
| BASP1 | 10409 | NM_001271606; NM_006317 |
| PTTG1 | 9232, 10744 | NM_001282382; NM_001282383; NM_004219 |
| MOCOS | 55034 | NM_017947 |
| LEF1 | 51176 | NM_001130713; NM_001130714; NM_001166119; NM_016269 |
| SLPI | 6590 | NM_003064 |
| PRAME | 23532 | NM_001291715; NM_001291716; NM_006115; NM_206953; NM_206954; NM_206955; NM_206956; NM_001291717; NM_001291719; NM_001318126; NM_001318127 |
| STEAP3 | 55240 | NM_001008410; NM_018234; XM_006712614; XM_006712615; XM_011511403; NM_138637; NM_182915 |
| LGALS2 | 3957 | NM_006498 |
| CD44 | 960 | NM_000610; NM_001001389; NM_001001390; NM_001001391; NM_001001392; NM_001202555; NM_001202556; NM_001202557; XM_011520488 |
| FLNC | 2318 | NM_001127487; NM_001458 |
| UBE2C | 11065 | NM_001281741; NM_001281742; NM_007019; NM_181799; NM_181800; NM_181801 |

-continued

| Gene | NCBI Gene ID | NCBI Accession Number(s) |
|---|---|---|
| CTSK | 1513 | NM_000396 |
| SULF2 | 55959 | NM_001161841; NM_018837; NM_198596; NM_001387053; XM_006723830; NM_001387051; NM_001387055; NM_001387048; NM_001387049; NM_001387054; XM_011528914; NM_001387050; NM_001387052 |
| TMEM45A | 55076 | XM_005247569; NM_018004; XM_024453614; XM_024453615; NM_001363876 |
| FCGR1A | 2209, 100132417 | NM_000566 |
| PLOD2 | 5352 | NM_000935; NM_182943 |
| C19orf80 | 55908 | NM_018687 |
| PDGFRL | 5157 | NM_006207 |
| IGF2BP3 | 10643 | NM_006547 |
| SLC7A5 | 8140 | NM_003486 |
| PRRX1 | 5396 | NM_006902; NM_022716 |
| RARRES1 | 5918 | NM_002888; NM_206963 |
| LHFPL2 | 10184 | NM_005779; XM_006714515 |
| KDELR3 | 11015 | NM_006855; NM_016657 |
| TRIB3 | 57761 | NM_001301201; XM_017027989; NM_001301188; NM_001301190; NM_001301193; NM_001301196; NM_021158 |
| IL20RB | 53833 | NM_144717 |
| FBLN1 | 2192 | NM_001996; NM_006485; NM_006486; NM_006487 |
| KMO | 8564 | NM_003679 |
| C1R | 715 | NM_001733 |
| CYP1B1 | 1545 | NM_000104 |
| KIF2A | 3796 | NM_001098511; NM_001243952; NM_004520 |
| PLAUR | 5329 | NM_001301037; NM_001005376; NM_001005377; NM_002659 |
| CKS2 | 1164 | NM_001827 |
| CDCP1 | 64866 | NM_022842; NM_178181 |
| SFRP4 | 6424 | NM_003014 |
| HAMP | 57817 | NM_021175 |
| MMP9 | 4318 | NM_004994 |
| SLC3A1 | 6519 | NM_000341; XM_011533047 |
| NAT8 | 9027, 51471 | NM_003960 |
| FRMD3 | 257019 | NM_001244959; NM_001244960; NM_001244961; NM_001244962; NM_174938 |
| NPR3 | 4883 | NM_000908; NM_001204375; NM_001204376 |
| NAT8B | 9027, 51471 | NM_016347 |
| BBOX1 | 8424 | NM_003986; NM_001376258; NM_001376259; NM_001376260; NM_001376261; XM_011520402 |
| SLC5A1 | 6523 | NM_000343; NM_001256314 |
| GBA3 | 57733 | NM_020973; NM_001128432; NM_001277225 |
| EMCN | 51705 | NM_016242; XM_011532024; NM_001159694 |
| SLC47A1 | 55244 | NM_018242 |
| AQP1 | 358 | NM_198098 |
| PCK1 | 5105 | NM_002591 |
| UGT2A3 | 79799 | NM_024743 |
| BHMT | 635 | NM_001713 |
| FMO1 | 2326 | NM_001282693; NM_002021; NM_001282692; NM_001282694 |
| ACAA2 | 10449, 648603 | NM_006111 |
| SLC5A8 | 160728 | NM_145913 |
| SLC16A9 | 220963 | NM_001323981; NM_194298; XM_017015884 |
| TSPAN18 | 90139 | NM_130783; XM_006718373; XM_011520459 |
| SLC17A3 | 10786 | NM_006632; NM_001098486 |
| STK32B | 55351 | NM_001306082; NM_018401 |
| MAP7 | 9053 | NM_001198609; NM_001198608; NM_001388350; NM_001198614; NM_001198617; NM_001388331; NM_001388333; NM_001388336; NM_001388340; NM_001388344; NM_001388345; NM_001388347; NM_001388348; NM_001388349; XM_011536246; NM_001198616; NM_001388330; NM_001388335; NM_003980; XM_011536243; NM_001388341; NM_001388342; NM_001388343; NM_001198611; NM_001388338; NM_001388346; NM_001198615; NM_001198618; NM_001198619; NM_001388329; NM_001388334; NM_001388339; NM_001388328; NM_001388332; NM_001388337; NM_001388351; NM_001388352; NM_001388353 |
| MYLIP | 29116 | XM_005249033; NM_013262 |
| SLC22A12 | 116085 | NM_001276326; NM_001276327; NM_144585; NM_153378 |
| LRP2 | 4036 | NM_004525 |
| CD34 | 947 | NM_001025109; NM_001773 |
| PODXL | 5420 | NM_001018111; NM_005397 |
| ZBTB42 | 100128927 | NM_001137601; NM_001370342 |
| TEK | 7010 | NM_000459; NM_001290077; NM_001290078 |
| FBP1 | 2203 | NM_000507; NM_001127628 |
| BCL2 | 596 | NM_000633; NM_000657. |

19. The method of claim 16, wherein the subject has, is suspected of having, or is at risk of having lymphoma, and wherein the set of genes comprises at least 5 genes selected from the group of genes listed in Table 3, wherein Table 3 is:

| Gene | NCBI Gene ID | NCBI Accession Number(s) |
| --- | --- | --- |
| ITPKB | 3707 | NM_002221; NM_001388404; XM_017001211 |
| MYBL1 | 4603 | NM_001080416; NM_001144755; NM_001294282 |
| LMO2 | 4005 | NM_001142315; NM_001142316; NM_005574; XM_005252921; XM_017017727; XM_017017728; XM_017017729; XM_017017730; XM_017017731; XM_017017732; XM_017017733 |
| BATF | 10538 | NM_006399 |
| IRF4 | 3662 | NM_001195286; NM_002460 |
| LRMP | 4033 | NM_001204126; NM_001204127; NM_006152; NM_001366543; NM_001366544; NM_001366546; NM_001366549; NM_001366545; NR_159367; NR_159368; NM_001366541; NR_159366; NM_001366540; NM_001366542; NM_001366547; NR_159369; NM_001366548 |
| CCND2 | 894 | NM_001759 |
| SLA | 6503 | NM_001045556; NM_001045557; NM_001282964; NM_001282965; NM_006748; XM_017013739 |
| SP140 | 11262 | NM_001278452; NM_001005176; NM_001278451; NM_001278453; NM_007237 |
| PIM1 | 5292 | NM_002648; NM_001243186 |
| CSTB | 1476 | NM_000100 |
| BCL2 | 596 | NM_000633; NM_000657 |
| TCF4 | 6925 | NM_003199; XM_017025956; NM_001348220; NM_001369581; NM_001369582; NM_001369585; XM_005266749; XM_005266761; XM_017025950; NM_001083962; NM_001243235; NM_001348211; NM_001348214; NM_001369583; XM_017025951; XM_024451241; NM_001369578; NM_001243227; NM_001243231; NM_001348218; NM_001369571; NM_001369575; NM_001369586; XM_005266755; XM_006722538; XM_017025954; NM_001243230; NM_001243233; NM_001306207; NM_001306208; NM_001330604; NM_001348212; XM_005266752; NM_001243236; NM_001330605; NM_001348213; NM_001348215; NM_001348217; NM_001348219; NM_001369577; NM_001369580; XM_017025952; XM_017025953; NM_001243226; NM_001348216; NM_001369567; NM_001369569; NM_001369573; NM_001369574; NM_001369579; NM_001243228; NM_001243232; NM_001243234; NM_001369568; NM_001369570; NM_001369572; NM_001369576; NM_001369584 |
| P2RX5 | 5026 | NM_001204519; NM_001204520; NM_002561; NM_175080 |
| SPINK2 | 6691 | NM_021114; NM_001271722; NM_001271720; NM_001271718; NM_001271721 |
| VCL | 7414 | NM_003373; NM_014000 |
| PTPN1 | 5770 | NM_002827; NM_001278618 |
| REL | 5966 | NM_001291746; NM_002908 |
| FUT8 | 2530 | NM_004480; NM_178155; NM_178156 |
| RPL21 | 6144 | NM_000982 |
| PRKCB1 | 5579 | NM_002738; NM_212535 |
| CSNK1E | 1454 | NM_001289912; NM_001894; NM_152221 |
| GPR18 | 2841 | NM_001098200; NM_005292; XM_006719946 |
| IGHM | 3500, 3492, 28396, 3502, 3507, 28450, 28452 | NG_001019.6 |
| ACP1 | 52 | NM_004300; NM_007099 |
| SPIB | 6689 | NM_003121; NM_001243998; NM_001243999; NM_001244000 |
| HLA-DQA1 | 3117, 731682, 100133678 | NM_002122 |
| KRT8 | 390601, 149501, 3856 | NM_001256293; NM_002273 |
| FAM3C | 10447 | NM_001040020; NM_014888; XM_011515736; XM_011515737 |
| HLA-DMB | 3109 | NM_002118 |
| GOT2 | 2806 | NM_001286220; NM_002080 |
| PIM2 | 11040 | NM_006875 |
| PLEK | 5341 | NM_002664. |

20. The method of claim 19, wherein the subject has, is suspected of having, or is at risk of having Diffuse Large B-Cell Lymphoma (DLBCL), the set of genes comprises at least 10 genes selected from the group of genes listed in Table 3, and the at least one characteristic is a cell of origin selected from the group consisting of germinal center B-cell (GCB) and activated B-cell (ABC), wherein Table 3 is:

| Gene | NCBI Gene ID | NCBI Accession Number(s) |
| --- | --- | --- |
| ITPKB | 3707 | NM_002221; NM_001388404; XM_017001211 |
| MYBL1 | 4603 | NM_001080416; NM_001144755; NM_001294282 |
| LMO2 | 4005 | NM_001142315; NM_001142316; NM_005574; XM_005252921; XM_017017727; XM_017017728; XM_017017729; XM_017017730; XM_017017731; XM_017017732; XM_017017733 |
| BATF | 10538 | NM_006399 |
| IRF4 | 3662 | NM_001195286; NM_002460 |
| LRMP | 4033 | NM_001204126; NM_001204127; NM_006152; NM_001366543; NM_001366544; NM_001366546; NM_001366549; NM_001366545; NR_159367; NR_159368; NM_001366541; NR_159366; NM_001366540; NM_001366542; NM_001366547; NR_159369; NM_001366548 |
| CCND2 | 894 | NM_001759 |
| SLA | 6503 | NM_001045556; NM_001045557; NM_001282964; NM_001282965; NM_006748; XM_017013739 |
| SP140 | 11262 | NM_001278452; NM_001005176; NM_001278451; NM_001278453; NM_007237 |
| PIM1 | 5292 | NM_002648; NM_001243186 |
| CSTB | 1476 | NM_000100 |
| BCL2 | 596 | NM_000633; NM_000657 |
| TCF4 | 6925 | NM_003199; XM_017025956; NM_001348220; NM_001369581; NM_001369582; NM_001369585; XM_005266749; XM_005266761; XM_017025950; NM_001083962; NM_001243235; NM_001348211; NM_001348214; NM_001369583; XM_017025951; XM_024451241; NM_001369578; NM_001243227; NM_001243231; NM_001348218; NM_001369571; NM_001369575; NM_001369586; XM_005266755; XM_006722538; XM_017025954; NM_001243230; NM_001243233; NM_001306207; NM_001306208; NM_001330604; NM_001348212; XM_005266752; NM_001243236; NM_001330605; NM_001348213; NM_001348215; NM_001348217; NM_001348219; NM_001369577; NM_001369580; XM_017025952; XM_017025953; NM_001243226; NM_001348216; NM_001369567; NM_001369569; NM_001369573; NM_001369574; NM_001369579; NM_001243228; NM_001243232; NM_001243234; NM_001369568; NM_001369570; NM_001369572; NM_001369576; NM_001369584 |
| P2RX5 | 5026 | NM_001204519; NM_001204520; NM_002561; NM_175080 |
| SPINK2 | 6691 | NM_021114; NM_001271722; NM_001271720; NM_001271718; NM_001271721 |
| VCL | 7414 | NM_003373; NM_014000 |
| PTPN1 | 5770 | NM_002827; NM_001278618 |
| REL | 5966 | NM_001291746; NM_002908 |
| FUT8 | 2530 | NM_004480; NM_178155; NM_178156 |
| RPL21 | 6144 | NM_000982 |
| PRKCB1 | 5579 | NM_002738; NM_212535 |
| CSNK1E | 1454 | NM_001289912; NM_001894; NM_152221 |
| GPR18 | 2841 | NM_001098200; NM_005292; XM_006719946 |
| IGHM | 3500, 3492, 28396, 3502, 3507, 28450, 28452 | NG_001019.6 |
| ACP1 | 52 | NM_004300; NM_007099 |
| SPIB | 6689 | NM_003121; NM_001243998; NM_001243999; NM_001244000 |
| HLA-DQA1 | 3117, 731682, 100133678 | NM_002122 |
| KRT8 | 390601, 149501, 3856 | NM_001256293; NM_002273 |
| FAM3C | 10447 | NM_001040020; NM_014888; XM_011515736; XM_011515737 |
| HLA-DMB | 3109 | NM_002118 |
| GOT2 | 2806 | NM_001286220; NM_002080 |
| PIM2 | 11040 | NM_006875 |
| PLEK | 5341 | NM_002664. |

21. The method of claim 16, wherein the subject has, is suspected of having, or is at risk of having lung adenocarcinoma, and wherein the set of genes comprises at least 5 genes selected from the group of genes listed in Table 6, wherein Table 6 is:

| Gene | NCBI Gene ID | NCBI Accession Number(s) |
|---|---|---|
| AADAC | 13 | NM_001086 |
| ALDOB | 229 | NM_000035 |
| ANXA10 | 11199 | NM_007193 |
| ASPM | 259266 | NM_001206846; NM_018136 |
| BTNL8 | 79908 | NM_001040462; NM_001159707; NM_001159708; NM_001159709; NM_001159710; NM_024850 |
| CEACAM8 | 1088 | NM_001816; XM_017026195; NM_001816 |
| CENPA | 1058 | NM_001042426; NM_001809 |
| CHGB | 1114 | NM_001819 |
| CHRNA9 | 55584 | NM_017581 |
| COL11A1 | 1301 | NM_001190709; NM_001854; NM_080629; NM_080630 |
| CRABP1 | 1381 | NM_004378; NM_004378 |
| F11 | 2160 | NM_000128 |
| GGTLC1 | 92086 | NM_178311; NM_178312; XM_005260865; XM_017028126 |
| HJURP | 55355 | NM_001282962; NM_001282963; NM_018410 |
| IGF2BP3 | 10643 | NM_006547 |
| IHH | 3549 | NM_002181 |
| KCNE2 | 9992 | NM_172201 |
| KIF14 | 9928 | NM_001305792; NM_014875; XM_011510231; XM_011510232; XM_017003005 |
| LRRC31 | 79782 | NM_001277127; NM_001277128; NM_024727; XM_011513160 |
| MYBL2 | 4605 | NM_001278610; NM_002466 |
| MYOZ1 | 58529 | NM_021245 |
| PCSK2 | 5126 | NM_001201528; NM_001201529; NM_002594 |
| PI15 | 51050 | NM_001324403; NM_015886 |
| SCTR | 6344 | NM_002980 |
| SHH | 6469 | NM_000193 |
| SLC22A3 | 6581 | NM_021977 |
| SLC7A5 | 8140 | NM_003486 |
| SPOCK1 | 6695 | NM_004598 |
| TM4SF4 | 7104 | NM_004617 |
| TRPM8 | 79054 | NM_024080 |
| YBX2 | 51087 | NM_015982. |

22. The method of claim 15, wherein the at least one characteristic is selected from the group consisting of cancer grade for the biological sample, tissue of origin for the biological sample, tissue type for the biological sample, and cancer subtype for the biological sample.

23. The method of claim 15, further comprising training a statistical model to obtain the trained statistical model, the training comprising:
selecting the at least some genes in the set of genes; and
after the selecting, estimating the parameters using the training data.

24. At least one non-transitory computer-readable storage medium storing processor-executable instructions that are configured to cause, when executed by at least one computer hardware processor, the at least one computer hardware processor to perform:
accessing a trained statistical model comprising parameters estimated using training data, the training data indicating a plurality of gene rankings of at least some genes in a set of genes, the parameters being estimated after the at least some genes in the set of genes were selected;
obtaining expression data for a biological sample of a subject having, suspected of having or at risk of having cancer, the expression data previously obtained at least in part by sequencing the biological sample and comprising first expression levels for the set of genes;
ranking the at least some genes in the set of genes based on their first expression levels in the expression data to obtain a gene ranking, the gene ranking including values identifying relative ranks of the at least some genes in the gene ranking, wherein the values are different from the first expression levels; and
determining at least one characteristic of the biological sample by providing the gene ranking as an input to the trained statistical model and processing the gene ranking with the trained statistical model to obtain an output indicating the at least one characteristic of the biological sample,
the processing of the gene ranking with the trained statistical model comprises using the parameters and the gene ranking provided as the input to obtain the output indicating the at least one characteristic of the biological sample; and
the at least one characteristic of the biological sample is a physiological characteristic of cells in the biological sample or a physiological characteristic of a tissue from which the cells in the biological sample originate.

25. The at least one non-transitory computer-readable storage medium of claim 24, wherein each gene ranking includes a value identifying a relative rank for each gene in the set of genes.

26. The at least one non-transitory computer-readable storage medium of claim 24, wherein the trained statistical model comprises a gradient-boosted decision tree classifier.

27. The at least one non-transitory computer-readable storage medium of claim 20, wherein the at least one characteristic is selected from the group consisting of cancer grade for the biological sample, tissue of origin for the biological sample, tissue type for the biological sample, and cancer subtype for the biological sample.

28. The at least one non-transitory computer-readable storage medium of claim 24, wherein the cancer is head and neck squamous cell carcinoma, and wherein the set of genes comprises at least 5 genes selected from the group of genes listed in Table 8, wherein Table 8 is:

| Gene | NCBI Gene ID | NCBI Accession Number(s) |
|---|---|---|
| APOBEC3B | 9582 | NM_001270411; NM_004900 |
| ATAD2 | 29028 | NM_014109; NM_014109 |
| BIRC5 | 332 | NM_001168; NM_001012271; NM_001012270; NM_001168 |
| CCL20 | 6364 | NM_001130046; NM_004591 |
| CCND1 | 595 | NM_053056; NM_053056 |
| CDC45 | 8318 | NM_001178010; NM_001178011; NM_003504; XM_011530417; XM_011530416; NR_161281; XM_017028966; ; XR_002958716; NM_001178010; XM_011530418; XM_017028967; XM_024452277; NM_001369291 |
| CDC7 | 8317 | NM_001134419; NM_001134420; NM_003503; XM_005271241 |
| CDK1 | 983 | NM_001320918; NM_001786; NM_033379; XM_005270303 |
| CDKN2A | 1029 | NM_000077; NM_000077; NM_001195132; NM_058197; XM_005251343; XM_011517676; ; NM_058196; NM_058195; XM_011517675; NM_001363763; XR_929159 |
| CDKN2C | 1031 | NM_001262; NM_078626; NM_001262 |
| CDKN3 | 1018 | NM_001258 |
| CENPF | 1063 | NM_016343; XM_017000086 |
| CENPN | 55839 | NM_001100624; NM_001100625; NM_001270473; NM_001270474; NM_018455; XM_006721236; XM_017023456 |
| CXCL14 | 9547 | NM_004887 |
| DCN | 1634 | NM_133505; NM_001920; NM_133503; NM_133504; NM_133505; NM_133506; NM_133507; |
| DHFR | 1719 | NM_000791; NM_001290357; NM_000791; NM_001290354 |
| DKK3 | 27122 | NM_001330220; XM_017017554; XM_017017555; NM_001018057; NM_001330220; NM_013253; NM_015881; XM_006718178 |
| DLGAP5 | 9787 | NM_001146015; NM_014750; XM_017021840 |
| EPCAM | 4072 | NM_002354 |
| FANCI | 55215 | NM_001113378; NM_018193; XM_011521756; NM_001113378; NM_001376910; NM_001376911; ; XM_011521764 |
| FEN1 | 2237 | NM_004111; NM_004111 |
| GMNN | 51053 | NM_001251989; NM_001251990; NM_001251991; NM_015895; XM_005249159; NM_001251989 |
| GPX3 | 2878 | NM_001329790; NM_002084 |
| ID4 | 3400 | NM_001546 |
| IGLC1 | 3537 | NG_000002.1 |
| IL18 | 3606 | NM_001243211; XM_011542805; NM_001243211; NM_001562; ; NM_001386420 |
| IL1R2 | 7850 | NM_001261419; NM_004633; XM_006712734; XM_011511804 |
| KIF18B | 146909 | NM_001264573; NM_001265577; NM_001264573 |
| KIF20A | 10112 | NM_005733 |
| KIF4A | 24137 | NM_012310 |
| KLK13 | 26085 | NM_001348177; NM_001348178; NM_001348177; NM_015596 |
| KLK7 | 5650 | NM_005046; NM_139277; NM_001207053; NM_001243126; NM_005046 |
| KLK8 | 11202 | NM_001281431; NM_001281431; NM_007196; NM_144505; NM_144506; NM_144507 |
| KNTC1 | 9735 | NM_014708; XM_006719706 |
| KRT19 | 3880 | NM_002276 |
| LAMP3 | 27074 | NM_014398 |
| LMNB1 | 4001 | NM_005573 |
| MCM2 | 4171 | NM_004526 |
| MCM4 | 4173 | NM_005914; NM_182746 |
| MCM5 | 4174 | NM_006739; NM_006739 |
| ME1 | 4199 | NM_002395; XM_011535836 |
| MELK | 9833 | NM_001256685; NM_001256687; NM_001256688; NM_001256689; NM_001256690; NM_001256692; NM_001256693; NM_014791; XM_011518076; XM_011518077; XM_011518078; XM_011518079; XM_011518081; XM_011518082; XM_011518083; XM_011518084 |
| MKI67 | 4288 | NM_001145966; NM_002417 |
| MLF1 | 4291 | NM_022443; NM_001130156; NM_001130157; NM_001195432; NM_001195433; NM_001195434; NM_022443; NM_001369782; NM_001378848; NM_001378853; ; NM_001369784; NM_001369785; NM_001369781; NM_001378846; NM_001378855; NM_001378845; NM_001378847; NM_001378850; NM_001378852; NM_001369783; NM_001378851 |
| MMP12 | 4321 | NM_002426 |
| MTHFD2 | 10797 | NM_006636; XM_006711924 |
| NDN | 4692 | NM_002487; NM_002487 |
| NEFH | 4744 | NM_021076 |
| NEK2 | 4751 | NM_001204182; NM_001204182; NM_001204183; NM_002497; XM_005273147 |
| NUP155 | 9631 | NM_153485; NM_001278312; NM_004298; NM_153485 |
| NUP210 | 23225 | NM_024923 |
| NUSAP1 | 51203 | NM_001243142; NM_001243143; NM_001243144; NM_001301136; NM_016359; NM_018454; XM_005254430 |
| PDGFD | 80310 | NM_025208; NM_033135 |
| PLAGL1 | 5325 | NM_001080951; NM_001080952; NM_001080953; NM_001080954; NM_001289042; NM_001289043; NM_001289044; NM_001289047; NM_001289048; NM_001289049; NM_001317157; NM_001317159; |

| Gene | NCBI Gene ID | NCBI Accession Number(s) |
|---|---|---|
| | | NM_006718; NM_001080955; NM_001289037; NM_001289038; NM_001289039; NM_001289040; NM_001080951; NM_001080956; NM_001289041; NM_001289045; NM_001289046; NM_001317156; NM_001317158; NM_001317160; NM_001317161; NM_001317162 |
| PLOD2 | 5352 | NM_000935; NM_182943 |
| PPP1R3C | 5507 | NM_005398 |
| PRIM1 | 5557 | NM_000946 |
| PRKDC | 5591 | NM_001081640; NM_006904 |
| PSIP1 | 11168 | NM_001128217; NM_001317898; NM_001317900; NM_021144; NM_033222 |
| RAD51AP1 | 10635 | NM_001130862; NM_006479 |
| RASIP1 | 54922 | NM_017805; NM_017805 |
| RFC5 | 5985 | NM_001130112; NM_001130113; NM_007370; NM_181578; XM_011538643; XM_011538645 |
| RNASEH2A | 10535 | NM_006397 |
| RPA2 | 6118 | NM_001286076; NM_001297558; NM_002946 |
| RPL39L | 116832 | NM_052969 |
| RSRC1 | 51319 | NM_001271834; NM_001271838; NM_016625 |
| RYR1 | 6261 | NM_000540; NM_001042723 |
| SLC35G2 | 80723 | NM_001097599; NM_001097600; NM_025246; XM_006713773; XM_011513214; XM_017007289; XM_017007290; XM_017007291 |
| SMC2 | 10592 | NM_001265602; NM_001042550; NM_001042551; NM_001265602; NM_006444; XM_006716933; XM_011518148; XM_011518149; XM_011518153; XM_017014206; XM_017014207; XM_017014208 |
| SPARCL1 | 8404 | NM_001128310; NM_001291976; NM_001291977; NM_004684 |
| STMN1 | 3925 | NM_001145454; NM_005563; NM_203399; NM_203401 |
| SYCP2 | 10388 | NM_014258; XM_011528489 |
| SYNGR3 | 9143 | NM_004209 |
| TIMELESS | 8914 | NM_001330295; NM_003920 |
| TMPO | 7112 | NM_001032283; NM_001032284; NM_001307975; NM_003276; NM_001032283 |
| TPX2 | 22974 | NM_012112; XM_011528697; XM_011528699; NM_012112 |
| TRIP13 | 9319 | NM_004237; XM_011514163 |
| TYMS | 7298 | NM_001071; NM_001071 |
| UCP2 | 7351 | NM_003355; NM_003355 |
| UPF3B | 65109 | NM_023010; NM_080632 |
| USP1 | 7398 | NM_001017415; NM_001017416; NM_003368 |
| ZSCAN18 | 65982 | NM_001145542; NM_001145543; NM_001145544; NM_023926; XM_005259174; XM_006723335; XM_011527238; XM_011527239; XM_017027169; XM_017027170; XM_017027171 |
| APOBEC3B | 9582 | NM_001270411; NM_004900 |
| ATAD2 | 29028 | NM_014109; NM_014109 |
| BIRC5 | 332 | NM_001168; NM_001012271; NM_001012270; NM_001168 |
| CCL20 | 6364 | NM_001130046; NM_004591 |
| CCND1 | 595 | NM_053056; NM_053056 |
| CDC45 | 8318 | NM_001178010; NM_001178011; NM_003504; XM_011530417; XM_011530416; NR_161281; XM_017028966; ; XR_002958716; NM_001178010; XM_011530418; XM_017028967; XM_024452277; NM_001369291 |
| CDC7 | 8317 | NM_001134419; NM_001134420; NM_003503; XM_005271241 |
| CDK1 | 983 | NM_001320918; NM_001786; NM_033379; XM_005270303 |
| CDKN2A | 1029 | NM_000077; NM_000077; NM_ 001195132; NM_058197; XM_005251343; XM_011517676; ; NM_058196; NM_058195; XM_011517675; NM_001363763; XR_929159 |
| CDKN2C | 1031 | NM_001262; NM_078626; NM_001262 |
| CDKN3 | 1018 | NM_001258 |
| CENPF | 1063 | NM_016343; XM_017000086 |
| CENPN | 55839 | NM_001100624; NM_001100625; NM_001270473; NM_001270474; NM_018455; XM_006721236; XM_017023456 |
| CXCL14 | 9547 | NM_004887 |
| DCN | 1634 | NM_133505; NM_001920; NM_133503; NM_133504; NM_133505; NM_133506; NM_133507; |
| DHFR | 1719 | NM_000791; NM_001290357; NM_000791; NM_001290354 |
| DKK3 | 27122 | NM_001330220; XM_017017554; XM_017017555; NM_001018057; NM_001330220; NM_013253; NM_015881; XM_006718178 |
| DLGAP5 | 9787 | NM_001146015; NM_014750; XM_017021840 |
| EPCAM | 4072 | NM_002354 |
| FANCI | 55215 | NM_001113378; NM_018193; XM_011521756; NM_001113378; NM_001376910; NM_001376911; XM_011521764 |
| FEN1 | 2237 | NM_004111; NM_004111 |
| GMNN | 51053 | NM_001251989; NM_001251990; NM_001251991; NM_015895; XM_005249159; NM_001251989 |
| GPX3 | 2878 | NM_001329790; NM_002084 |
| ID4 | 3400 | NM_001546 |
| IGLC1 | 3537 | NG_000002.1 |
| IL18 | 3606 | NM_001243211; XM_011542805; NM_001243211; NM_001562; NM_001386420 |

-continued

| Gene | NCBI Gene ID | NCBI Accession Number(s) |
| --- | --- | --- |
| IL1R2 | 7850 | NM_001261419; NM_004633; XM_006712734; XM_011511804 |
| KIF18B | 146909 | NM_001264573; NM_001265577; NM_001264573 |
| KIF20A | 10112 | NM_005733 |
| KIF4A | 24137 | NM_012310 |
| KLK13 | 26085 | NM_001348177; NM_001348178; NM_001348177; NM_015596 |
| KLK7 | 5650 | NM_005046; NM_139277; NM_001207053; NM_001243126; NM_005046 |
| KLK8 | 11202 | NM_001281431; NM_001281431; NM_007196; NM_144505; NM_144506; NM_144507 |
| KNTC1 | 9735 | NM_014708; XM_006719706 |
| KRT19 | 3880 | NM_002276 |
| LAMP3 | 27074 | NM_014398 |
| LMNB1 | 4001 | NM_005573 |
| MCM2 | 4171 | NM_004526 |
| MCM4 | 4173 | NM_005914; NM_182746 |
| MCM5 | 4174 | NM_006739; NM_006739 |
| ME1 | 4199 | NM_002395; XM_011535836 |
| MELK | 9833 | NM_001256685; NM_001256687; NM_001256688; NM_001256689; NM_001256690; NM_001256692; NM_001256693; NM_014791; XM_011518076; XM_011518077; XM_011518078; XM_011518079; XM_011518081; XM_011518082; XM_011518083; XM_011518084 |
| MKI67 | 4288 | NM_001145966; NM_002417 |
| MLF1 | 4291 | NM_022443; NM_001130156; NM_001130157; NM_001195432; NM_001195433; NM_001195434; NM_022443; NM_001369782; NM_001378848; NM_001378853; ; NM_001369784; NM_001369785; NM_001369781; NM_001378846; NM_001378855; NM_001378845; NM_001378847; NM_001378850; NM_001378852; NM_001369783; NM_001378851 |
| MMP12 | 4321 | NM_002426 |
| MTHFD2 | 10797 | NM_006636; XM_006711924 |
| NDN | 4692 | NM_002487; NM_002487 |
| NEFH | 4744 | NM_021076 |
| NEK2 | 4751 | NM_001204182; NM_001204182; NM_001204183; NM_002497; XM_005273147 |
| NUP155 | 9631 | NM_153485; NM_001278312; NM_004298; NM_153485 |
| NUP210 | 23225 | NM_024923 |
| NUSAP1 | 51203 | NM_001243142; NM_001243143; NM_001243144; NM_001301136; NM_016359; NM_018454; XM_005254430 |
| PDGFD | 80310 | NM_025208; NM_033135 |
| PLAGL1 | 5325 | NM_001080951; NM_001080952; NM_001080953; NM_001080954; NM_001289042; NM_001289043; NM_001289044; NM_001289047; NM_001289048; NM_001289049; NM_001317157; NM_001317159; NM_006718; NM_001080955; NM_001289037; NM_001289038; NM_001289039; NM_001289040; NM_001080951; NM_001080956; NM_001289041; NM_001289045; NM_001289046; NM_001317156; NM_001317158; NM_001317160; NM_001317161; NM_001317162 |
| PLOD2 | 5352 | NM_000935; NM_182943. |

29. The at least one non-transitory computer-readable storage medium of claim 28, wherein the set of genes comprises at least 10 genes selected from the group of genes listed in Table 8, wherein Table 8 is:

| Gene | NCBI Gene ID | NCBI Accession Number(s) |
| --- | --- | --- |
| APOBEC3B | 9582 | NM_001270411; NM_004900 |
| ATAD2 | 29028 | NM_014109; NM_014109 |
| BIRC5 | 332 | NM_001168; NM_001012271; NM_001012270; NM_001168 |
| CCL20 | 6364 | NM_001130046; NM_004591 |
| CCND1 | 595 | NM_053056; NM_053056 |
| CDC45 | 8318 | NM_001178010; NM_001178011; NM_003504; XM_011530417; XM_011530416; NR_161281; XM_017028966; ; XR_002958716; NM_001178010; XM_011530418; XM_017028967; XM_024452277; NM_001369291 |
| CDC7 | 8317 | NM_001134419; NM_001134420; NM_003503; XM_005271241 |
| CDK1 | 983 | NM_001320918; NM_001786; NM_033379; XM_005270303 |
| CDKN2A | 1029 | NM_000077; NM_000077; NM_001195132; NM_058197; XM_005251343; XM_011517676; ; NM_058196; NM_058195; XM_011517675; NM_001363763; XR_929159 |
| CDKN2C | 1031 | NM_001262; NM_078626; NM_001262 |
| CDKN3 | 1018 | NM_001258 |
| CENPF | 1063 | NM_016343; XM_017000086 |
| CENPN | 55839 | NM_001100624; NM_001100625; NM_001270473; NM_001270474; NM_018455; XM_006721236; XM_017023456 |

| Gene | NCBI Gene ID | NCBI Accession Number(s) |
|---|---|---|
| CXCL14 | 9547 | NM_004887 |
| DCN | 1634 | NM_133505; NM_001920; NM_133503; NM_133504; NM_133505; NM_133506; NM_133507; |
| DHFR | 1719 | NM_000791; NM_001290357; NM_000791; NM_001290354 |
| DKK3 | 27122 | NM_001330220; XM_017017554; XM_017017555; NM_001018057; NM_001330220; NM_013253; NM_015881; XM_006718178 |
| DLGAP5 | 9787 | NM_001146015; NM_014750; XM_017021840 |
| EPCAM | 4072 | NM_002354 |
| FANCI | 55215 | NM_001113378; NM_018193; XM_011521756; NM_001113378; NM_001376910; NM_001376911; ; XM_011521764 |
| FEN1 | 2237 | NM_004111; NM_004111 |
| GMNN | 51053 | NM_001251989; NM_001251990; NM_001251991; NM_015895; XM_005249159; NM_001251989 |
| GPX3 | 2878 | NM_001329790; NM_002084 |
| ID4 | 3400 | NM_001546 |
| IGLC1 | 3537 | NG_000002.1 |
| IL18 | 3606 | NM_001243211; XM_011542805; NM_001243211; NM_001562; ; NM_001386420 |
| IL1R2 | 7850 | NM_001261419; NM_004633; XM_006712734; XM_011511804 |
| KIF18B | 146909 | NM_001264573; NM_001265577; NM_001264573 |
| KIF20A | 10112 | NM_005733 |
| KIF4A | 24137 | NM_012310 |
| KLK13 | 26085 | NM_001348177; NM_001348178; NM_001348177; NM_015596 |
| KLK7 | 5650 | NM_005046; NM_139277; NM_001207053; NM_001243126; NM_005046 |
| KLK8 | 11202 | NM_001281431; NM_001281431; NM_007196; NM_144505; NM_144506; NM_144507 |
| KNTC1 | 9735 | NM_014708; XM_006719706 |
| KRT19 | 3880 | NM_002276 |
| LAMP3 | 27074 | NM_014398 |
| LMNB1 | 4001 | NM_005573 |
| MCM2 | 4171 | NM_004526 |
| MCM4 | 4173 | NM_005914; NM_182746 |
| MCM5 | 4174 | NM_006739; NM_006739 |
| ME1 | 4199 | NM_002395; XM_011535836 |
| MELK | 9833 | NM_001256685; NM_001256687; NM_001256688; NM_001256689; NM_001256690; NM_001256692; NM_001256693; NM_014791; XM_011518076; XM_011518077; XM_011518078; XM_011518079; XM_011518081; XM_011518082; XM_011518083; XM_011518084 |
| MKI67 | 4288 | NM_001145966; NM_002417 |
| MLF1 | 4291 | NM_022443; NM_001130156; NM_001130157; NM_001195432; NM_001195433; NM_001195434; NM_022443; NM_001369782; NM_001378848; NM_001378853; ; NM_001369784; NM_001369785; NM_001369781; NM_001378846; NM_001378855; NM_001378845; NM_001378847; NM_001378850; NM_001378852; NM_001369783; NM_001378851 |
| MMP12 | 4321 | NM_002426 |
| MTHFD2 | 10797 | NM_006636; XM_006711924 |
| NDN | 4692 | NM_002487; NM_002487 |
| NEFH | 4744 | NM_021076 |
| NEK2 | 4751 | NM_001204182; NM_001204182; NM_001204183; NM_002497; XM_005273147 |
| NUP155 | 9631 | NM_153485; NM_001278312; NM_004298; NM_153485 |
| NUP210 | 23225 | NM_024923 |
| NUSAP1 | 51203 | NM_001243142; NM_001243143; NM_001243144; NM_001301136; NM_016359; NM_018454; XM_005254430 |
| PDGFD | 80310 | NM_025208; NM_033135 |
| PLAGL1 | 5325 | NM_001080951; NM_001080952; NM_001080953; NM_001080954; NM_001289042; NM_001289043; NM_001289044; NM_001289047; NM_001289048; NM_001289049; NM_001317157; NM_001317159; NM_006718; NM_001080955; NM_001289037; NM_001289038; NM_001289039; NM_001289040; NM_001080951; NM_001080956; NM_001289041; NM_001289045; NM_001289046; NM_001317156; NM_001317158; NM_001317160; NM_001317161; NM_001317162 |
| PLOD2 | 5352 | NM_000935; NM_182943 |
| PPP1R3C | 5507 | NM_005398 |
| PRIM1 | 5557 | NM_000946 |
| PRKDC | 5591 | NM_001081640; NM_006904 |
| PSIP1 | 11168 | NM_001128217; NM_001317898; NM_001317900; NM_021144; NM_033222 |
| RAD51AP1 | 10635 | NM_001130862; NM_006479 |
| RASIP1 | 54922 | NM_017805; NM_017805 |
| RFC5 | 5985 | NM_001130112; NM_001130113; NM_007370; NM_181578; XM_011538643; XM_011538645 |
| RNASEH2A | 10535 | NM_006397 |
| RPA2 | 6118 | NM_001286076; NM_001297558; NM_002946 |
| RPL39L | 116832 | NM_052969 |

| Gene | NCBI Gene ID | NCBI Accession Number(s) |
| --- | --- | --- |
| RSRC1 | 51319 | NM_001271834; NM_001271838; NM_016625 |
| RYR1 | 6261 | NM_000540; NM_001042723 |
| SLC35G2 | 80723 | NM_001097599; NM_001097600; NM_025246; XM_006713773; XM_011513214; XM_017007289; XM_017007290; XM_017007291 |
| SMC2 | 10592 | NM_001265602; NM_001042550; NM_001042551; NM_001265602; NM_006444; XM_006716933; XM_011518148; XM_011518149; XM_011518153; XM_017014206; XM_017014207; XM_017014208 |
| SPARCL1 | 8404 | NM_001128310; NM_001291976; NM_001291977; NM_004684 |
| STMN1 | 3925 | NM_001145454; NM_005563; NM_203399; NM_203401 |
| SYCP2 | 10388 | NM_014258; XM_011528489 |
| SYNGR3 | 9143 | NM_004209 |
| TIMELESS | 8914 | NM_001330295; NM_003920 |
| TMPO | 7112 | NM_001032283; NM_001032284; NM_001307975; NM_003276; NM_001032283 |
| TPX2 | 22974 | NM_012112; XM_011528697; XM_011528699; NM_012112 |
| TRIP13 | 9319 | NM_004237; XM_011514163 |
| TYMS | 7298 | NM_001071; NM_001071 |
| UCP2 | 7351 | NM_003355; NM_003355 |
| UPF3B | 65109 | NM_023010; NM_080632 |
| USP1 | 7398 | NM_001017415; NM_001017416; NM_003368 |
| ZSCAN18 | 65982 | NM_001145542; NM_001145543; NM_001145544; NM_023926; XM_005259174; XM_006723335; XM_011527238; XM_011527239; XM_017027169; XM_017027170; XM_017027171 |
| APOBEC3B | 9582 | NM_001270411; NM_004900 |
| ATAD2 | 29028 | NM_014109; NM_014109 |
| BIRC5 | 332 | NM_001168; NM_001012271; NM_001012270; NM_001168 |
| CCL20 | 6364 | NM_001130046; NM_004591 |
| CCND1 | 595 | NM_053056; NM_053056 |
| CDC45 | 8318 | NM_001178010; NM_001178011; NM_003504; XM_011530417; XM_011530416; NR_161281; XM_017028966; ; XR_002958716; NM_001178010; XM_011530418; XM_017028967; XM_024452277; NM_001369291 |
| CDC7 | 8317 | NM_001134419; NM_001134420; NM_003503; XM_005271241 |
| CDK1 | 983 | NM_001320918; NM_001786; NM_033379; XM_005270303 |
| CDKN2A | 1029 | NM_000077; NM_000077; NM_ 001195132; NM_058197; XM_005251343; XM_011517676; ; NM_058196; NM_058195; XM_011517675; NM_001363763; XR_929159 |
| CDKN2C | 1031 | NM_001262; NM_078626; NM_001262 |
| CDKN3 | 1018 | NM_001258 |
| CENPF | 1063 | NM_016343; XM_017000086 |
| CENPN | 55839 | NM_001100624; NM_001100625; NM_001270473; NM_001270474; NM_018455; XM_006721236; XM_017023456 |
| CXCL14 | 9547 | NM_004887 |
| DCN | 1634 | NM_133505; NM_001920; NM_133503; NM_133504; NM_133505; NM_133506; NM_133507; |
| DHFR | 1719 | NM_000791; NM_001290357; NM_000791; NM_001290354 |
| DKK3 | 27122 | NM_001330220; XM_017017554; XM_017017555; NM_001018057; NM_001330220; NM_013253; NM_015881; XM_006718178 |
| DLGAP5 | 9787 | NM_001146015; NM_014750; XM_017021840 |
| EPCAM | 4072 | NM_002354 |
| FANCI | 55215 | NM_001113378; NM_018193; XM_011521756; NM_001113378; NM_001376910; NM_001376911; XM_011521764 |
| FEN1 | 2237 | NM_004111; NM_004111 |
| GMNN | 51053 | NM_001251989; NM_001251990; NM_001251991; NM_015895; XM_005249159; NM_001251989 |
| GPX3 | 2878 | NM_001329790; NM_002084 |
| ID4 | 3400 | NM_001546 |
| IGLC1 | 3537 | NG_000002.1 |
| IL18 | 3606 | NM_001243211; XM_011542805; NM_001243211; NM_001562; NM_001386420 |
| IL1R2 | 7850 | NM_001261419; NM_004633; XM_006712734; XM_011511804 |
| KIF18B | 146909 | NM_001264573; NM_001265577; NM_001264573 |
| KIF20A | 10112 | NM_005733 |
| KIF4A | 24137 | NM_012310 |
| KLK13 | 26085 | NM_001348177; NM_001348178; NM_001348177; NM_015596 |
| KLK7 | 5650 | NM_005046; NM_139277; NM_001207053; NM_001243126; NM_005046 |
| KLK8 | 11202 | NM_001281431; NM_001281431; NM_007196; NM_144505; NM_144506; NM_144507 |
| KNTC1 | 9735 | NM_014708; XM_006719706 |
| KRT19 | 3880 | NM_002276 |
| LAMP3 | 27074 | NM_014398 |
| LMNB1 | 4001 | NM_005573 |
| MCM2 | 4171 | NM_004526 |
| MCM4 | 4173 | NM_005914; NM_182746 |
| MCM5 | 4174 | NM_006739; NM_006739 |
| ME1 | 4199 | NM_002395; XM_011535836 |

-continued

| Gene | NCBI Gene ID | NCBI Accession Number(s) |
|---|---|---|
| MELK | 9833 | NM_001256685; NM_001256687; NM_001256688; NM_001256689; NM_001256690; NM_001256692; NM_001256693; NM_014791; XM_011518076; XM_011518077; XM_011518078; XM_011518079; XM_011518081; XM_011518082; XM_011518083; XM_011518084 |
| MKI67 | 4288 | NM_001145966; NM_002417 |
| MLF1 | 4291 | NM_022443; NM_001130156; NM_001130157; NM_001195432; NM_001195433; NM_001195434; NM_022443; NM_001369782; NM_001378848; NM_001378853; ; NM_001369784; NM_001369785; NM_001369781; NM_001378846; NM_001378855; NM_001378845; NM_001378847; NM_001378850; NM_001378852; NM_001369783; NM_001378851 |
| MMP12 | 4321 | NM_002426 |
| MTHFD2 | 10797 | NM_006636; XM_006711924 |
| NDN | 4692 | NM_002487; NM_002487 |
| NEFH | 4744 | NM_021076 |
| NEK2 | 4751 | NM_001204182; NM_001204182; NM_001204183; NM_002497; XM_005273147 |
| NUP155 | 9631 | NM_153485; NM_001278312; NM_004298; NM_153485 |
| NUP210 | 23225 | NM_024923 |
| NUSAP1 | 51203 | NM_001243142; NM_001243143; NM_001243144; NM_001301136; NM_016359; NM_018454; XM_005254430 |
| PDGFD | 80310 | NM_025208; NM_033135 |
| PLAGL1 | 5325 | NM_001080951; NM_001080952; NM_001080953; NM_001080954; NM_001289042; NM_001289043; NM_001289044; NM_001289047; NM_001289048; NM_001289049; NM_001317157; NM_001317159; NM_006718; NM_001080955; NM_001289037; NM_001289038; NM_001289039; NM_001289040; NM_001080951; NM_001080956; NM_001289041; NM_001289045; NM_001289046; NM_001317156; NM_001317158; NM_001317160; NM_001317161; NM_001317162 |
| PLOD2 | 5352 | NM_000935; NM_182943. |

30. The at least one non-transitory computer-readable storage medium of claim 28, wherein the at least one characteristic includes human papillomavirus (HPV) status for the cells in the biological sample.

31. The at least one non-transitory computer-readable storage medium of claim 24, wherein the at least one characteristic includes a subtype of peripheral T-cell lymphoma (PTCL) for the cells in the biological sample, and wherein the set of genes includes at least 5 genes selected from the group of genes listed in Table 10, wherein Table 10 is:

| Gene | NCBI Gene ID | NCBI Accession Number(s) |
|---|---|---|
| EFNB2 | 1948 | NM_004093 |
| ROBO1 | 6091 | NM_133631; NM_001145845; NM_002941; XM_006713277; XM_017006983 |
| S1PR3 | 1903 | NM_005226 |
| ANK2 | 287 | NM_001127493; NM_001148; NM_020977 |
| LPAR1 | 1902 | NM_001401; NM_057159; NM_001351414; NM_001351415; NM_001387481; NM_001387505; XM_005251782; NM_001351401; NM_001387470; NM_001387480; NM_001387486; NM_001387498; NM_001387502; NM_001387503; NM_001387509; NM_001387511; NM_001387521; NM_001351398; NM_001351399; NM_001351400; NM_001351419; NM_001387478; NM_001387493; NM_001387497; NM_001387506; NM_001387507; NM_001387508; NM_001387520; NM_001351416; NM_001387476; NM_001387491; NM_001387471; NM_001387472; NM_001387477; NM_001387485; NM_001387492; NM_001387494; NM_001387510; NM_001387517; NM_001351397; NM_001351405; NM_001351406; NM_001351407; NM_001351413; NM_001351418; NM_001387475; NM_001387483; NM_001387484; NM_001387488; NM_001387490; NM_001387496; NM_001387516; NM_001387519; NM_001351404; NM_001351408; NM_001351410; NM_001351420; NM_001387473; NM_001387474; NM_001387487; NM_001387489; NM_001387495; NM_001387514; NM_001387518; NM_001351402; NM_001351403; NM_001351409; NM_001351411; NM_001351412; NM_001351417; NM_001387479; NM_001387482; NM_001387501; NM_001387504; NM_001387512; NM_001387513; NM_001387515 |
| SNAP91 | 9892 | XM_011536269; XM_017011557; XM_017011558; XM_017011559; XM_017011560; XM_011536264; XM_017011564; XM_017011571; NM_001376687; NM_001376688; NM_001376698; NM_001376700; NM_001376709; NM_001376715; NM_001376716; NM_001376723; NM_001376728; NM_001376731; NM_001376734; XM_011536266; XM_017011575; XM_017011586; NM_001376676; NM_001376682; NM_001376685; NM_001376702; NM_001376711; NM_001376736; NM_001376738; NR_164844; XM_006715615; XM_011536265; |

-continued

| Gene | NCBI Gene ID | NCBI Accession Number(s) |
|---|---|---|
| | | XM_017011570; XM_017011582; XM_024446600; NM_001376691; NM_001376699; NM_001376720; NM_001376735; NM_001376740; NM_014841; NR_164843; NR_164845; XM_011536275; XM_017011562; XM_017011565; XM_017011569; XM_017011580; NR_026669; NM_001256717; NM_001376677; NM_001376680; NM_001376683; NM_001376708; NM_001376718; NM_001376726; NM_001376737; XM_011536273; XM_011536276; XM_017011567; NM_001376694; XM_017011584; NM_001242794; NM_001376679; NM_001376694; NM_001376695; NM_001376697; NM_001376710; NM_001376714; NM_001376717; NM_001376742; XM_017011572; XM_017011577; XM_017011581; XM_017011590; NM_001256718; NM_001363677; NM_001376678; NM_001376686; NM_001376690; NM_001376693 |
| SOX8 | 30812 | NM_014587 |
| RAMP3 | 10268 | NM_005856 |
| TUBB2B | 347733 | NM_178012 |
| ARHGEF10 | 9639 | NM_001308152; NM_001308153; NM_014629; XM_017014003 |
| NOTCH1 | 4851 | NM_017617 |
| ZBTB17 | 7709 | NM_001242884; NM_001287603; NM_003443; XM_011542088 |
| CCNE1 | 898 | NM_001238; NM_001322262; NM_001322259; NM_001322261 |
| FGF18 | 8817 | NM_003862 |
| MYCN | 4613 | NM_001293231; NM_001293228; NM_001293233; NM_005378 |
| PTHLH | 5744 | NM_198965; NM_198966; XM_011520774; NM_002820; XM_017019675; NM_198964 |
| SMARCA2 | 6595 | NM_001289400; NM_001289399; NM_001289398; NM_001289397; NM_001289396; NM_003070; NM_139045 |
| WNK1 | 65125 | NM_014823; NM_018979; NM_001184985; NM_213655; XM_017019837; XM_017019838 |
| NKX2-1 | 7080 | NM_001079668; NM_003317 |
| CYP26A1 | 1592 | NM_000783; NM_057157 |
| HPSE | 10855 | NM_001098540; NM_001166498; NM_001199830; NM_006665 |
| CTLA4 | 1493 | NM_001037631; NM_005214 |
| PELI1 | 57162 | NM_020651; XM_011532994; XM_017004520 |
| PRKCB | 5579 | NM_002738; NM_212535 |
| SPAST | 6683 | NM_014946; NM_199436 |
| ALS2 | 57679 | NM_001135745; NM_020919; XM_006712654 |
| KIF3B | 9371 | NM_004798 |
| ZFYVE27 | 118813 | XM_005269509; XM_011539254; XR_945597; NM_001002262; NM_001174120; NM_001385878; NM_001385889; NM_001385895; NM_001385901; NM_001385918; NR_169800; XM_005269508; XR_945594; NM_001385877; NM_001385902; NM_001385903; NM_001385904; NR_169794; NR_169795; NR_169797; NR_169803; NR_169805; NR_169809; XM_011539253; XM_017015644; XR_002956957; NM_001174121; NM_001174122; NM_001385879; NM_001385881; NM_001385883; NM_001385900; XM_017015645; NM_001385875; NM_001385886; NM_001385896; NR_169796; XM_011539252; NM_001385876; NM_001385880; NM_001385887; NM_001385894; NM_001385898; NM_001385915; NM_001385919; XM_017015646; NM_001385882; NM_001385884; NM_001385890; NM_001385897; NM_001385899; NR_169804; NR_169810; NM_001002261; NM_001385871; NM_001385892; NM_001385905; NM_144588; NR_169802; NR_169806; NR_169808; NR_169811; XR_002956956; NM_001174119; NM_001385885; NM_001385888; NM_001385891; NM_001385893; NM_001385906; NM_001385908; NM_001385911; NM_001385916; NR_169798; NR_169799; NR_169801 |
| FGF18 | 8817 | NM_003862 |
| FNTB | 2342 | NM_001202558; NM_002028 |
| REL | 5966 | NM_001291746; NM_002908 |
| DMRT1 | 1761 | NM_021951 |
| SLC19A2 | 10560 | NM_001319667; NM_006996 |
| STK3 | 6788 | NM_001256313; NM_001256312; NM_006281 |
| PERP | 64065 | NM_022121 |
| TNFRSF8 | 943 | NM_001243; NM_001281430 |
| TMOD1 | 7111 | NM_001166116; NM_003275 |
| BATF3 | 55509 | NM_018664 |
| CDC14B | 8555 | NM_001077181; NM_003671; NM_033331; XM_011519153; XM_017015240; XM_017015247; XR_001746407; XR_001746409; NM_001351567; XM_017015248; XM_017015249; XR_929865; XM_011519147; XM_017015242; XM_017015244; XM_017015245; XR_929864; NM_001351568; XM_011519149; XM_011519152; XR_001746408; NM_001351570; NM_033332; XM_011519148; XM_011519151; XR_929868; NR_147239; XM_011519156; XR_002956814; XM_011519159; XM_017015241; XR_001746406; NM_001351569 |
| WDFEY3 | N/A | N/A |
| AGT | 183 | NM_000029 |
| ALK | 238 | NM_004304 |
| ANXA3 | 306 | NM_005139 |

-continued

| Gene | NCBI Gene ID | NCBI Accession Number(s) |
|---|---|---|
| BTBD11 | 121551 | NM_001017523; NM_001018072; NM_001347943 |
| CCNA1 | 8900 | NM_001111045; NM_001111046; NM_001111047; NM_003914; XM_011535294; XM_011535295; XM_011535296 |
| DNER | 92737 | NM_139072 |
| GAS1 | 2619 | NM_002048 |
| HS6ST2 | 90161 | NM_001077188; NM_147175; XM_011531407; XM_017029945; XM_011531408; XM_017029946; XM_005262491; XM_011531406 |
| IL1RAP | 3556 | NM_001167928; NM_001167929; NM_001167930; NM_001167931; NM_002182; NM_134470 |
| PCOLCE2 | 26577 | NM_013363 |
| PDE4DIP | 9659 | XM_011510175; NM_001195261; NM_001002810; NM_001002811; NM_001002812; NM_001195260; NM_001198832; NM_001198834; NM_014644; NM_022359 |
| SLC16A3 | 9123 | NM_001042422; NM_001042423; NM_001206950; NM_001206951; NM_001206952; NM_004207; XM_024451023 |
| TIAM2 | 26230 | NM_001010927; NM_012454 |
| TUBB6 | 84617 | NM_001303527; NM_001303525; NM_001303524; NM_001303526; NM_001303528; NM_001303529; NM_001303530; NM_032525 |
| WNT7B | 7477 | XM_011530366; NM_058238 |
| SMOX | 54498 | NM_001270691; NM_175839; NM_175840; NM_175841; NM_175842; XM_011529261 |
| TMEM158 | 25907 | NM_015444 |
| NLRP7 | 199713 | NM_001127255; NM_139176; NM_206828; XM_006723075; XM_006723076; XM_011526599 |
| ADRB2 | 154 | NM_000024 |
| GALNT2 | 2590 | NM_004481; NM_001291866 |
| HRASLS | 57110 | NM_020386; NM_001366112; XM_011513034; XM_011513035 |
| CD244 | 51744 | NM_001166663; NM_001166664; NM_016382; XM_011509622 |
| FASLG | 356 | NM_000639; NM_001302746 |
| KIR2DL4 | 3805 | NM_001080772; NM_001080770; NM_002255 |
| LOC100287534 | 100287534 | HF584483.1 |
| KLRD1 | 3824 | NM_007334; XM_006719067; XR_001748697; XM_017019289; NM_001351062; NR_147038; XM_017019287; NM_001351063; XM_011520650; XM_017019286; XM_024448974; XR_001748696; NR_147040; XM_017019285; NM_001114396; NM_001351060; NR_147039; XM_011520651; XM_017019288; NM_002262 |
| SH2D1B | 117157 | NM_053282 |
| KLRC2 | 3822 | NM_002260 |
| NCAM1 | 4684 | NM_001242607; NM_000615; NM_001076682; NM_001242608; NM_181351 |
| CXCR5 | 643 | NM_001716; NM_032966 |
| IL6 | 3569 | NM_001318095; NM_000600; XM_011515390 |
| ICOS | 29851 | NM_012092 |
| CD40LG | 959 | NM_000074 |
| CD84 | 8832 | NM_001184879; NM_001184881; NM_001184882; NM_001330742; NM_003874 |
| IL21 | 59067 | NM_021803; NM_001207006 |
| BCL6 | 604 | NM_001134738; NM_001130845; NM_001706; XM_005247694; XM_011513062 |
| MAF | 4094 | XM_017023233; XM_017023234; XM_017023235; NM_001031804; NM_005360 |
| SH2D1A | 4068 | NM_001114937; NM_002351 |
| IL4 | 3565 | NM_000589; NM_172348 |
| PTPN1 | 5770 | NM_002827; NM_001278618 |
| PIM1 | 5292 | NM_002648; NM_001243186 |
| ENTPD1 | 953 | NM_001098175; NM_001164178; NM_001164181; NM_001164182; NM_001164183; NM_001312654; NM_001320916; NM_001776; XM_011540371; XM_011540377; XM_017016959 |
| IRF4 | 3662 | NM_001195286; NM_002460 |
| CCND2 | 894 | NM_001759 |
| IL16 | 3603 | NM_001172128; NM_004513; NM_172217; NR_148035; NM_001352685; NM_001352686; NM_001352684 |
| ETV6 | 2120 | NM_001987 |
| BLNK | 29760 | NM_001258441; NM_001258442; NM_001114094; NM_001258440; NM_013314 |
| SH3BP5 | 9467 | NM_001018009; XM_017007522; XM_017007523; XM_017007524; XM_017007525; NM_004844 |
| FUT8 | 2530 | NM_004480; NM_178155; NM_178156 |
| CCR4 | 1233 | NM_005508; XM_017005687 |
| GATA3 | 2625 | NM_001002295; NM_002051; XM_005252442; XM_005252443 |
| IL5 | 3567 | NM_000879; XM_011543373; XM_011543374 |
| IL10 | 3586 | NM_000572 |
| IL13 | 3596 | NM_002188 |
| MMEITPKB | N/A | N/A |
| MYBL1 | 4603 | NM_001080416; NM_001144755; NM_001294282 |

-continued

| Gene | NCBI Gene ID | NCBI Accession Number(s) |
|---|---|---|
| LRMP | 16970 | NM_001204126; NM_001204127; NM_006152; NM_001366543; NM_001366544; NM_001366546; NM_001366549; NM_001366545; NR_159367; NR_159368; NM_001366541; NR_159366; NM_001366540; NM_001366542; NM_001366547; NR_159369; NM_001366548 |
| KIAA0870 | 22898 | NM_014957 |
| LMO2 | 4005 | NM_001142315; NM_001142316; NM_005574; XM_005252921; XM_017017727; XM_017017728; XM_017017729; XM_017017730; XM_017017731; XM_017017732; XM_017017733 |
| CR1 | 1378 | NM_000651; NM_000573 |
| LTBR | 4055 | NM_001270987; NM_002342 |
| PDPN | 10630 | NM_001006624; NM_001006625; NM_006474; NM_198389; XM_006710295 |
| TNFRSF1A | 7132 | NM_001346091; NM_001065; NM_001346092 |
| FCER2 | 2208 | NM_001207019; NM_001220500; NM_002002; XM_005272462 |
| ICAM1 | 3383 | NM_000201 |
| FCGR2B | 2213 | NM_001002273; NM_001002274; NM_001002275; NM_001190828; NM_004001; XM_024454043; NM_001386004; NR_169827; NM_001386001; NM_001386002; NM_001386006; NM_001386003; XM_017000670; NM_001386000; NM_001386005; XM_024454047 |
| IKZF2 | 22807 | NM_001079526; NM_016260; XM_005246384; XM_005246385; XM_011510818; NM_001371277; XM_011510809; NM_001387220; XM_005246386; XM_011510810; XM_011510803; XM_011510804; XM_011510812; XM_011510815; XM_011510817; XM_017003592; NM_001371275; XM_011510808; NM_001371274; XM_011510802; XM_011510807; XM_011510819; NM_001371276; XM_011510805; XM_011510811; XM_017003591; XM_011510816 |
| CCR8 | 1237 | NM_005201 |
| TNFRSF18 | 8784 | XM_017002722; NM_004195; NM_148901; NM_148902 |
| IKZF4 | 64375 | NM_022465; XM_005269089; XM_017019813; XM_017019815; XM_024449128; XM_024449129; NM_001351090; XM_017019807; XM_017019812; XM_024449131; NM_001351089; XM_011538664; XM_011538669; XM_017019814; XM_017019808; XM_024449130; NM_001351092; XM_017019806; XM_017019809; XM_017019810; XM_005269086; XM_017019811; XM_017019816; NM_001351091 |
| FOXP3 | 50943 | XM_006724533; NM_001114377; NM_014009 |
| IL2 | 3558 | NM_000586 |
| TBX21 | 30009 | NM_013351 |
| IFNG | 3458 | NM_000619 |
| GZMH | 2999 | NM_001270781; NM_033423 |
| GNLY | 10578 | NM_001302758; NM_006433; NM_012483 |
| EOMES | 8320 | NM_001278182; NM_001278183; NM_005442 |
| NCR1 | 9437 | NM_004829; NM_001145458; NM_001145457; NM_001242356; NM_001242357 |
| GZMB | 3002 | NM_001346011; NM_004131 |
| NKG7 | 4818 | NM_005601 |
| FGFBP2 | 83888 | NM_031950 |
| KLRF1 | 51348 | NM_001291822; NM_001291823; NM_016523 |
| CD160 | 11126 | NM_007053; XM_005272929; XM_011509104 |
| KLRK1 | 22914 | NM_001199805; NM_007360 |
| CD226 | 10666 | NM_001303619; XM_005266643; XM_017025525; NM_006566; XM_006722374; XM_017025526; NM_001303618; XM_005266642; XM_017025527 |
| NCR3 | 259197 | NM_001145466; NM_001145467; NM_147130; XM_006715049; XM_011514459 |
| TNFRSF8 | 943 | NM_001243; NM_001281430 |
| BATF3 | 55509 | NM_018664 |
| TMOD1 | 7111 | NM_001166116; NM_003275 |
| TMEM158 | 25907 | NM_015444 |
| MSC | 9242 | NM_005098 |
| POPDC3 | 64208 | NM_022361; XM_011536067; XM_017011194; XM_017011195. |

32. The at least one non-transitory computer-readable storage medium of claim 31, wherein the subtype of PTCL is selected from the group consisting of: anaplastic large cell lymphoma (ALCL), angioimmunoblastic T-cell lymphoma (AITL), natural killer/T-cell lymphoma (NKTCL), and adult T-cell leukemia/lymphoma (ATLL).

33. The at least one non-transitory computer-readable storage medium of claim 24, wherein the processor-executable instructions are further configured to cause the at least one computer hardware processor to perform training a statistical model to obtain the trained statistical model, the training comprising:
selecting the at least some genes in the set of genes; and
after the selecting, estimating the parameters using the training data.

* * * * *

UNITED STATES PATENT AND TRADEMARK OFFICE
CERTIFICATE OF CORRECTION

| | | |
|---|---|---|
| PATENT NO. | : 11,482,301 B2 | Page 1 of 1 |
| APPLICATION NO. | : 17/113008 | |
| DATED | : October 25, 2022 | |
| INVENTOR(S) | : Zoia Antysheva et al. | |

It is certified that error appears in the above-identified patent and that said Letters Patent is hereby corrected as shown below:

In the Claims

Column 100, Claim 1, Line 54:
"the biological sample,"

Should read:
--the biological sample, wherein:--

Column 113, Claim 15, Line 33:
"the biological sample,"

Should read:
--the biological sample, wherein:--

Column 128, Claim 24, Line 41:
"the biological sample,"

Should read:
--the biological sample, wherein:--

Signed and Sealed this
Thirteenth Day of December, 2022

Katherine Kelly Vidal
*Director of the United States Patent and Trademark Office*